(12) United States Patent
Spriggs et al.

(10) Patent No.: US 12,168,696 B2
(45) Date of Patent: Dec. 17, 2024

(54) ANTIBODIES TO MUCIN-16 (MUC16), ENCODING POLYNUCLEOTIDES AND METHODS OF TREATING MUC16-POSITIVE CANCER

(71) Applicants: Memorial Sloan Kettering Cancer Center, New York, NY (US); Eureka Therapeutics, Inc., Emeryville, CA (US)

(72) Inventors: David Spriggs, New York, NY (US); Javier Morales, Emeryville, CA (US); Yoko Nakano, Emeryville, CA (US); Hong Liu, Emeryville, CA (US)

(73) Assignees: Memorial Sloan Kettering Cancer Center, New York, NY (US); Eureka Therapeutics, Inc., Emeryville, CA (US)

( * ) Notice: Subject to any disclaimer, the term of this patent is extended or adjusted under 35 U.S.C. 154(b) by 733 days.

(21) Appl. No.: 17/292,749

(22) PCT Filed: Nov. 14, 2019

(86) PCT No.: PCT/US2019/061503
§ 371 (c)(1),
(2) Date: May 11, 2021

(87) PCT Pub. No.: WO2020/102555
PCT Pub. Date: May 22, 2020

(65) Prior Publication Data
US 2021/0403597 A1 Dec. 30, 2021

Related U.S. Application Data

(60) Provisional application No. 62/768,730, filed on Nov. 16, 2018.

(51) Int. Cl.
C07K 16/30 (2006.01)
A61K 39/00 (2006.01)
A61P 35/00 (2006.01)

(52) U.S. Cl.
CPC .......... *C07K 16/3092* (2013.01); *A61P 35/00* (2018.01); *A61K 2039/505* (2013.01); *C07K 2317/21* (2013.01); *C07K 2317/31* (2013.01); *C07K 2317/34* (2013.01); *C07K 2317/622* (2013.01); *C07K 2317/73* (2013.01); *C07K 2317/76* (2013.01)

(58) Field of Classification Search
CPC ............ C07K 16/3092; C07K 2317/21; C07K 2317/31; C07K 2317/34; C07K 2317/622; C07K 2317/73; C07K 2317/76; A61P 35/00; A61K 2039/505
See application file for complete search history.

(56) References Cited

U.S. PATENT DOCUMENTS

| 2006/0246071 A1 | 11/2006 | Green et al. |
| 2009/0142352 A1 | 6/2009 | Jackson et al. |
| 2018/0112001 A1 | 4/2018 | Haber et al. |

FOREIGN PATENT DOCUMENTS

| WO | WO-2011/119979 A2 | 9/2011 |
| WO | WO-2016/149368 A1 | 9/2016 |
| WO | WO-2018/067331 A1 | 4/2018 |
| WO | WO-2020/227538 A1 | 11/2020 |

OTHER PUBLICATIONS

Rao et al., "Antibodies Against Specific MUC16 Glycosylation Sites Inhibit Ovarian Cancer Growth." ACS Chem Biol. 12(8):2085-2096. Epub Jun. 28, 2017.
Rao et al., "Expression of the Carboxy-Terminal Portion of MUC16/CA125 Induces Transformation and Tumor Invasion." PLoS One, 10(5):e0126633 (2015).
International Search Report and Written Opinion on PCT/US2019/061503, mailed Apr. 24, 2020 (11 pages).

*Primary Examiner* — Robert S Landsman
(74) *Attorney, Agent, or Firm* — Foley & Lardner LLP

(57) ABSTRACT

Provided herein are compositions, methods, and uses involving anti-Mucin-16 (MUC16) agents that immunospecifically bind an epitope of Mucin-16 (MUC16). Also provided herein are uses and methods for managing, treating, or preventing disorders, such as cancer and diseases associated with positive MUC16 expression.

15 Claims, 12 Drawing Sheets
Specification includes a Sequence Listing.

Figure 2

|  | | | | | | Section 1 |
|---|---|---|---|---|---|---|
|  | 1 | 10 | 20 | 30 | 40 | 55 |
| Translation of MUC16c114 (1) | NFSPLARRVDRVAIYEEFLRMTRNGTQLQNFTLDRSSVLVDGYSPNRNEPLIGNS |
| Translation of N3mutMUC16c114 (1) | NFSPLARRVDRVAIYEEFLRMTRNGTQLQAFTLDRSSVLVDGYSPNRNEPLIGNS |
| Consensus (1) | NFSPLARRVDRVAIYEEFLRMTRNGTQLQ FTLDRSSVLVDGYSPNRNEPLIGNS |

Section 2

|  | 56 | 70 | 80 | 90 | 100 | 110 |
|---|---|---|---|---|---|---|
| Translation of MUC16c114 (56) | DLPFWAVILIGLAGLLGVITCLICGVLVTIRRKKEGEYNVQQQCPGYYQSHLDL |
| Translation of N3mutMUC16c114 (56) | DLPFWAVILIGLAGLLGVITCLICGVLVTIRRKKEGEYNVQQQCPGYYQSHLDL |
| Consensus (56) | DLPFWAVILIGLAGLLGVITCLICGVLVTIRRKKEGEYNVQQQCPGYYQSHLDL |

Section 3

| 1ffm4 (111) | |
|---|---|
| Translation of MUC16c114 (111) | EDLQ |
| Translation of N3mutMUC16c114 (111) | EDLQ |
| Consensus (111) | EDLQ |

SEQUENCE LISTING

```
<160> NUMBER OF SEQ ID NOS: 33

<210> SEQ ID NO 1
<211> LENGTH: 14507
<212> TYPE: PRT
<213> ORGANISM: Homo sapiens

<400> SEQUENCE: 1

Met Leu Lys Pro Ser Gly Leu Pro Gly Ser Ser Ser Pro Thr Arg Ser
1               5                   10                  15

Leu Met Thr Gly Ser Arg Ser Thr Lys Ala Thr Pro Glu Met Asp Ser
            20                  25                  30

Gly Leu Thr Gly Ala Thr Leu Ser Pro Lys Thr Ser Thr Gly Ala Ile
        35                  40                  45

Val Val Thr Glu His Thr Leu Pro Phe Thr Ser Pro Asp Lys Thr Leu
    50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95

Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser
        115                 120                 125

Pro Arg Thr Arg Thr Ser Ser Thr Glu Gly Asn Phe Thr Lys Glu Ala
    130                 135                 140

Ser Thr Tyr Thr Leu Thr Val Glu Thr Thr Ser Gly Pro Val Thr Glu
```

```
                145                 150                 155                 160
Lys Tyr Thr Val Pro Thr Glu Thr Ser Thr Glu Gly Asp Ser Thr
                    165                 170                 175
Glu Thr Pro Trp Asp Thr Arg Tyr Ile Pro Val Lys Ile Thr Ser Pro
                180                 185                 190
Met Lys Thr Phe Ala Asp Ser Thr Ala Ser Lys Glu Asn Ala Pro Val
                    195                 200                 205
Ser Met Thr Pro Ala Glu Thr Thr Val Thr Asp Ser His Thr Pro Gly
        210                 215                 220
Arg Thr Asn Pro Ser Phe Gly Thr Leu Tyr Ser Ser Phe Leu Asp Leu
225                 230                 235                 240
Ser Pro Lys Gly Thr Pro Asn Ser Arg Gly Glu Thr Ser Leu Glu Leu
                245                 250                 255
Ile Leu Ser Thr Thr Gly Tyr Pro Phe Ser Ser Pro Glu Pro Gly Ser
                260                 265                 270
Ala Gly His Ser Arg Ile Ser Thr Ser Ala Pro Leu Ser Ser Ser Ala
                275                 280                 285
Ser Val Leu Asp Asn Lys Ile Ser Glu Thr Ser Ile Phe Ser Gly Gln
                290                 295                 300
Ser Leu Thr Ser Pro Leu Ser Pro Gly Val Pro Glu Ala Arg Ala Ser
305                 310                 315                 320
Thr Met Pro Asn Ser Ala Ile Pro Phe Ser Met Thr Leu Ser Asn Ala
                    325                 330                 335
Glu Thr Ser Ala Glu Arg Val Arg Ser Thr Ile Ser Ser Leu Gly Thr
                340                 345                 350
Pro Ser Ile Ser Thr Lys Gln Thr Ala Glu Thr Ile Leu Thr Phe His
                355                 360                 365
Ala Phe Ala Glu Thr Met Asp Ile Pro Ser Thr His Ile Ala Lys Thr
            370                 375                 380
Leu Ala Ser Glu Trp Leu Gly Ser Pro Gly Thr Leu Gly Gly Thr Ser
385                 390                 395                 400
Thr Ser Ala Leu Thr Thr Thr Ser Pro Ser Thr Thr Leu Val Ser Glu
                    405                 410                 415
Glu Thr Asn Thr His His Ser Thr Ser Gly Lys Glu Thr Glu Gly Thr
                420                 425                 430
Leu Asn Thr Ser Met Thr Pro Leu Glu Thr Ser Ala Pro Gly Glu Glu
                435                 440                 445
Ser Glu Met Thr Ala Thr Leu Val Pro Thr Leu Gly Phe Thr Thr Leu
            450                 455                 460
Asp Ser Lys Ile Arg Ser Pro Ser Gln Val Ser Ser Ser His Pro Thr
465                 470                 475                 480
Arg Glu Leu Arg Thr Thr Gly Ser Thr Ser Gly Arg Gln Ser Ser Ser
                    485                 490                 495
Thr Ala Ala His Gly Ser Ser Asp Ile Leu Arg Ala Thr Thr Ser Ser
                500                 505                 510
Thr Ser Lys Ala Ser Ser Trp Thr Ser Glu Ser Thr Ala Gln Gln Phe
            515                 520                 525
Ser Glu Pro Gln His Thr Gln Trp Val Glu Thr Ser Pro Ser Met Lys
                530                 535                 540
Thr Glu Arg Pro Pro Ala Ser Thr Ser Val Ala Ala Pro Ile Thr Thr
545                 550                 555                 560
Ser Val Pro Ser Val Val Ser Gly Phe Thr Thr Leu Lys Thr Ser Ser
                    565                 570                 575
```

```
Thr Lys Gly Ile Trp Leu Glu Thr Ser Ala Asp Thr Leu Ile Gly
            580                 585                 590

Glu Ser Thr Ala Gly Pro Thr His Gln Phe Ala Val Pro Thr Gly
            595                 600                 605

Ile Ser Met Thr Gly Gly Ser Ser Thr Arg Gly Ser Gln Gly Thr Thr
            610                 615                 620

His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
                645                 650                 655

Lys Thr Ala Ala Gly Ser Ser Pro Pro Gly Gly Thr Lys Pro Ser Tyr
            660                 665                 670

Thr Met Val Ser Ser Val Ile Pro Glu Thr Ser Ser Leu Gln Ser Ser
            675                 680                 685

Ala Phe Arg Glu Gly Thr Ser Leu Gly Leu Thr Pro Leu Asn Thr Arg
            690                 695                 700

His Pro Phe Ser Ser Pro Glu Pro Asp Ser Ala Gly His Thr Lys Ile
705                 710                 715                 720

Ser Thr Ser Ile Pro Leu Leu Ser Ser Ala Ser Val Leu Glu Asp Lys
                725                 730                 735

Val Ser Ala Thr Ser Thr Phe Ser His His Lys Ala Thr Ser Ser Ile
            740                 745                 750

Thr Thr Gly Thr Pro Glu Ile Ser Thr Lys Thr Lys Pro Ser Ser Ala
            755                 760                 765

Val Leu Ser Ser Met Thr Leu Ser Asn Ala Ala Thr Ser Pro Glu Arg
            770                 775                 780

Val Arg Asn Ala Thr Ser Pro Leu Thr His Pro Ser Pro Ser Gly Glu
785                 790                 795                 800

Glu Thr Ala Gly Ser Val Leu Thr Leu Ser Thr Ser Ala Glu Thr Thr
                805                 810                 815

Asp Ser Pro Asn Ile His Pro Thr Gly Thr Leu Thr Ser Glu Ser Ser
            820                 825                 830

Glu Ser Pro Ser Thr Leu Ser Leu Pro Ser Val Ser Gly Val Lys Thr
            835                 840                 845

Thr Phe Ser Ser Ser Thr Pro Ser Thr His Leu Phe Thr Ser Gly Glu
            850                 855                 860

Glu Thr Glu Glu Thr Ser Asn Pro Ser Val Ser Gln Pro Glu Thr Ser
865                 870                 875                 880

Val Ser Arg Val Arg Thr Thr Leu Ala Ser Thr Ser Val Pro Thr Pro
                885                 890                 895

Val Phe Pro Thr Met Asp Thr Trp Pro Thr Arg Ser Ala Gln Phe Ser
            900                 905                 910

Ser Ser His Leu Val Ser Glu Leu Arg Ala Thr Ser Ser Thr Ser Val
            915                 920                 925

Thr Asn Ser Thr Gly Ser Ala Leu Pro Lys Ile Ser His Leu Thr Gly
            930                 935                 940

Thr Ala Thr Met Ser Gln Thr Asn Arg Asp Thr Phe Asn Asp Ser Ala
945                 950                 955                 960

Ala Pro Gln Ser Thr Thr Trp Pro Glu Thr Ser Pro Arg Phe Lys Thr
                965                 970                 975

Gly Leu Pro Ser Ala Thr Thr Thr Val Ser Thr Ser Ala Thr Ser Leu
            980                 985                 990
```

```
Ser Ala Thr Val Met Val Ser Lys Phe Thr Ser Pro Ala Thr Ser Ser
        995                 1000                1005

Met Glu Ala Thr Ser Ile Arg Glu Pro Ser Thr Thr Ile Leu Thr
1010                1015                1020

Thr Glu Thr Thr Asn Gly Pro Gly Ser Met Ala Val Ala Ser Thr
1025                1030                1035

Asn Ile Pro Ile Gly Lys Gly Tyr Ile Thr Glu Gly Arg Leu Asp
1040                1045                1050

Thr Ser His Leu Pro Ile Gly Thr Thr Ala Ser Ser Glu Thr Ser
1055                1060                1065

Met Asp Phe Thr Met Ala Lys Glu Ser Val Ser Met Ser Val Ser
1070                1075                1080

Pro Ser Gln Ser Met Asp Ala Ala Gly Ser Ser Thr Pro Gly Arg
1085                1090                1095

Thr Ser Gln Phe Val Asp Thr Phe Ser Asp Asp Val Tyr His Leu
1100                1105                1110

Thr Ser Arg Glu Ile Thr Ile Pro Arg Asp Gly Thr Ser Ser Ala
1115                1120                1125

Leu Thr Pro Gln Met Thr Ala Thr His Pro Pro Ser Pro Asp Pro
1130                1135                1140

Gly Ser Ala Arg Ser Thr Trp Leu Gly Ile Leu Ser Ser Ser Pro
1145                1150                1155

Ser Ser Pro Thr Pro Lys Val Thr Met Ser Ser Thr Phe Ser Thr
1160                1165                1170

Gln Arg Val Thr Thr Ser Met Ile Met Asp Thr Val Glu Thr Ser
1175                1180                1185

Arg Trp Asn Met Pro Asn Leu Pro Ser Thr Thr Ser Leu Thr Pro
1190                1195                1200

Ser Asn Ile Pro Thr Ser Gly Ala Ile Gly Lys Ser Thr Leu Val
1205                1210                1215

Pro Leu Asp Thr Pro Ser Pro Ala Thr Ser Leu Glu Ala Ser Glu
1220                1225                1230

Gly Gly Leu Pro Thr Leu Ser Thr Tyr Pro Glu Ser Thr Asn Thr
1235                1240                1245

Pro Ser Ile His Leu Gly Ala His Ala Ser Ser Glu Ser Pro Ser
1250                1255                1260

Thr Ile Lys Leu Thr Met Ala Ser Val Val Lys Pro Gly Ser Tyr
1265                1270                1275

Thr Pro Leu Thr Phe Pro Ser Ile Glu Thr His Ile His Val Ser
1280                1285                1290

Thr Ala Arg Met Ala Tyr Ser Gly Ser Ser Pro Glu Met Thr
1295                1300                1305

Ala Pro Gly Glu Thr Asn Thr Gly Ser Thr Trp Asp Pro Thr Thr
1310                1315                1320

Tyr Ile Thr Thr Thr Asp Pro Lys Asp Thr Ser Ser Ala Gln Val
1325                1330                1335

Ser Thr Pro His Ser Val Arg Thr Leu Arg Thr Thr Glu Asn His
1340                1345                1350

Pro Lys Thr Glu Ser Ala Thr Pro Ala Ala Tyr Ser Gly Ser Pro
1355                1360                1365

Lys Ile Ser Ser Ser Pro Asn Leu Thr Ser Pro Ala Thr Lys Ala
1370                1375                1380

Trp Thr Ile Thr Asp Thr Thr Glu His Ser Thr Gln Leu His Tyr
```

```
        1385                1390                1395

Thr Lys Leu Ala Glu Lys Ser Ser Gly Phe Glu Thr Gln Ser Ala
        1400                1405                1410

Pro Gly Pro Val Ser Val Val Ile Pro Thr Ser Pro Thr Ile Gly
        1415                1420                1425

Ser Ser Thr Leu Glu Leu Thr Ser Asp Val Pro Gly Glu Pro Leu
        1430                1435                1440

Val Leu Ala Pro Ser Glu Gln Thr Thr Ile Thr Leu Pro Met Ala
        1445                1450                1455

Thr Trp Leu Ser Thr Ser Leu Thr Glu Glu Met Ala Ser Thr Asp
        1460                1465                1470

Leu Asp Ile Ser Ser Pro Ser Ser Pro Met Ser Thr Phe Ala Ile
        1475                1480                1485

Phe Pro Pro Met Ser Thr Pro Ser His Glu Leu Ser Lys Ser Glu
        1490                1495                1500

Ala Asp Thr Ser Ala Ile Arg Asn Thr Asp Ser Thr Thr Leu Asp
        1505                1510                1515

Gln His Leu Gly Ile Arg Ser Leu Gly Arg Thr Gly Asp Leu Thr
        1520                1525                1530

Thr Val Pro Ile Thr Pro Leu Thr Thr Thr Trp Thr Ser Val Ile
        1535                1540                1545

Glu His Ser Thr Gln Ala Gln Asp Thr Leu Ser Ala Thr Met Ser
        1550                1555                1560

Pro Thr His Val Thr Gln Ser Leu Lys Asp Gln Thr Ser Ile Pro
        1565                1570                1575

Ala Ser Ala Ser Pro Ser His Leu Thr Glu Val Tyr Pro Glu Leu
        1580                1585                1590

Gly Thr Gln Gly Arg Ser Ser Ser Glu Ala Thr Thr Phe Trp Lys
        1595                1600                1605

Pro Ser Thr Asp Thr Leu Ser Arg Glu Ile Glu Thr Gly Pro Thr
        1610                1615                1620

Asn Ile Gln Ser Thr Pro Pro Met Asp Asn Thr Thr Thr Gly Ser
        1625                1630                1635

Ser Ser Ser Gly Val Thr Leu Gly Ile Ala His Leu Pro Ile Gly
        1640                1645                1650

Thr Ser Ser Pro Ala Glu Thr Ser Thr Asn Met Ala Leu Glu Arg
        1655                1660                1665

Arg Ser Ser Thr Ala Thr Val Ser Met Ala Gly Thr Met Gly Leu
        1670                1675                1680

Leu Val Thr Ser Ala Pro Gly Arg Ser Ile Ser Gln Ser Leu Gly
        1685                1690                1695

Arg Val Ser Ser Val Leu Ser Glu Ser Thr Thr Glu Gly Val Thr
        1700                1705                1710

Asp Ser Ser Lys Gly Ser Ser Pro Arg Leu Asn Thr Gln Gly Asn
        1715                1720                1725

Thr Ala Leu Ser Ser Ser Leu Glu Pro Ser Tyr Ala Glu Gly Ser
        1730                1735                1740

Gln Met Ser Thr Ser Ile Pro Leu Thr Ser Ser Pro Thr Thr Pro
        1745                1750                1755

Asp Val Glu Phe Ile Gly Gly Ser Thr Phe Trp Thr Lys Glu Val
        1760                1765                1770

Thr Thr Val Met Thr Ser Asp Ile Ser Lys Ser Ser Ala Arg Thr
        1775                1780                1785
```

-continued

```
Glu Ser Ser Ser Ala Thr Leu Met Ser Thr Ala Leu Gly Ser Thr
    1790            1795                1800

Glu Asn Thr Gly Lys Glu Lys Leu Arg Thr Ala Ser Met Asp Leu
    1805            1810                1815

Pro Ser Pro Thr Pro Ser Met Glu Val Thr Pro Trp Ile Ser Leu
    1820            1825                1830

Thr Leu Ser Asn Ala Pro Asn Thr Thr Asp Ser Leu Asp Leu Ser
    1835            1840                1845

His Gly Val His Thr Ser Ser Ala Gly Thr Leu Ala Thr Asp Arg
    1850            1855                1860

Ser Leu Asn Thr Gly Val Thr Arg Ala Ser Arg Leu Glu Asn Gly
    1865            1870                1875

Ser Asp Thr Ser Ser Lys Ser Leu Ser Met Gly Asn Ser Thr His
    1880            1885                1890

Thr Ser Met Thr Tyr Thr Glu Lys Ser Glu Val Ser Ser Ser Ile
    1895            1900                1905

His Pro Arg Pro Glu Thr Ser Ala Pro Gly Ala Glu Thr Thr Leu
    1910            1915                1920

Thr Ser Thr Pro Gly Asn Arg Ala Ile Ser Leu Thr Leu Pro Phe
    1925            1930                1935

Ser Ser Ile Pro Val Glu Glu Val Ile Ser Thr Gly Ile Thr Ser
    1940            1945                1950

Gly Pro Asp Ile Asn Ser Ala Pro Met Thr His Ser Pro Ile Thr
    1955            1960                1965

Pro Pro Thr Ile Val Trp Thr Ser Thr Gly Thr Ile Glu Gln Ser
    1970            1975                1980

Thr Gln Pro Leu His Ala Val Ser Ser Glu Lys Val Ser Val Gln
    1985            1990                1995

Thr Gln Ser Thr Pro Tyr Val Asn Ser Val Ala Val Ser Ala Ser
    2000            2005                2010

Pro Thr His Glu Asn Ser Val Ser Ser Gly Ser Ser Thr Ser Ser
    2015            2020                2025

Pro Tyr Ser Ser Ala Ser Leu Glu Ser Leu Asp Ser Thr Ile Ser
    2030            2035                2040

Arg Arg Asn Ala Ile Thr Ser Trp Leu Trp Asp Leu Thr Thr Ser
    2045            2050                2055

Leu Pro Thr Thr Thr Trp Pro Ser Thr Ser Leu Ser Glu Ala Leu
    2060            2065                2070

Ser Ser Gly His Ser Gly Val Ser Asn Pro Ser Ser Thr Thr Thr
    2075            2080                2085

Glu Phe Pro Leu Phe Ser Ala Ala Ser Thr Ser Ala Ala Lys Gln
    2090            2095                2100

Arg Asn Pro Glu Thr Glu Thr His Gly Pro Gln Asn Thr Ala Ala
    2105            2110                2115

Ser Thr Leu Asn Thr Asp Ala Ser Ser Val Thr Gly Leu Ser Glu
    2120            2125                2130

Thr Pro Val Gly Ala Ser Ile Ser Ser Glu Val Pro Leu Pro Met
    2135            2140                2145

Ala Ile Thr Ser Arg Ser Asp Val Ser Gly Leu Thr Ser Glu Ser
    2150            2155                2160

Thr Ala Asn Pro Ser Leu Gly Thr Ala Ser Ser Ala Gly Thr Lys
    2165            2170                2175
```

```
Leu Thr Arg Thr Ile Ser Leu Pro Thr Ser Glu Ser Leu Val Ser
2180                2185                2190

Phe Arg Met Asn Lys Asp Pro Trp Thr Val Ser Ile Pro Leu Gly
2195                2200                2205

Ser His Pro Thr Thr Asn Thr Glu Thr Ser Ile Pro Val Asn Ser
2210                2215                2220

Ala Gly Pro Pro Gly Leu Ser Thr Val Ala Ser Asp Val Ile Asp
2225                2230                2235

Thr Pro Ser Asp Gly Ala Glu Ser Ile Pro Thr Val Ser Phe Ser
2240                2245                2250

Pro Ser Pro Asp Thr Glu Val Thr Thr Ile Ser His Phe Pro Glu
2255                2260                2265

Lys Thr Thr His Ser Phe Arg Thr Ile Ser Ser Leu Thr His Glu
2270                2275                2280

Leu Thr Ser Arg Val Thr Pro Ile Pro Gly Asp Trp Met Ser Ser
2285                2290                2295

Ala Met Ser Thr Lys Pro Thr Gly Ala Ser Pro Ser Ile Thr Leu
2300                2305                2310

Gly Glu Arg Arg Thr Ile Thr Ser Ala Ala Pro Thr Thr Ser Pro
2315                2320                2325

Ile Val Leu Thr Ala Ser Phe Thr Glu Thr Ser Thr Val Ser Leu
2330                2335                2340

Asp Asn Glu Thr Thr Val Lys Thr Ser Asp Ile Leu Asp Ala Arg
2345                2350                2355

Lys Thr Asn Glu Leu Pro Ser Asp Ser Ser Ser Ser Ser Asp Leu
2360                2365                2370

Ile Asn Thr Ser Ile Ala Ser Ser Thr Met Asp Val Thr Lys Thr
2375                2380                2385

Ala Ser Ile Ser Pro Thr Ser Ile Ser Gly Met Thr Ala Ser Ser
2390                2395                2400

Ser Pro Ser Leu Phe Ser Ser Asp Arg Pro Gln Val Pro Thr Ser
2405                2410                2415

Thr Thr Glu Thr Asn Thr Ala Thr Ser Pro Ser Val Ser Ser Asn
2420                2425                2430

Thr Tyr Ser Leu Asp Gly Gly Ser Asn Val Gly Thr Pro Ser
2435                2440                2445

Thr Leu Pro Pro Phe Thr Ile Thr His Pro Val Glu Thr Ser Ser
2450                2455                2460

Ala Leu Leu Ala Trp Ser Arg Pro Val Arg Thr Phe Ser Thr Met
2465                2470                2475

Val Ser Thr Asp Thr Ala Ser Gly Glu Asn Pro Thr Ser Ser Asn
2480                2485                2490

Ser Val Val Thr Ser Val Pro Ala Pro Gly Thr Trp Thr Ser Val
2495                2500                2505

Gly Ser Thr Thr Asp Leu Pro Ala Met Gly Phe Leu Lys Thr Ser
2510                2515                2520

Pro Ala Gly Glu Ala His Ser Leu Leu Ala Ser Thr Ile Glu Pro
2525                2530                2535

Ala Thr Ala Phe Thr Pro His Leu Ser Ala Ala Val Val Thr Gly
2540                2545                2550

Ser Ser Ala Thr Ser Glu Ala Ser Leu Leu Thr Thr Ser Glu Ser
2555                2560                2565

Lys Ala Ile His Ser Ser Pro Gln Thr Pro Thr Thr Pro Thr Ser
```

```
                2570                2575                2580

Gly Ala Asn Trp Glu Thr Ser Ala Thr Pro Glu Ser Leu Leu Val
            2585                2590                2595

Val Thr Glu Thr Ser Asp Thr Thr Leu Thr Ser Lys Ile Leu Val
        2600                2605                2610

Thr Asp Thr Ile Leu Phe Ser Thr Val Ser Thr Pro Pro Ser Lys
    2615                2620                2625

Phe Pro Ser Thr Gly Thr Leu Ser Gly Ala Ser Phe Pro Thr Leu
2630                2635                2640

Leu Pro Asp Thr Pro Ala Ile Pro Leu Thr Ala Thr Glu Pro Thr
    2645                2650                2655

Ser Ser Leu Ala Thr Ser Phe Asp Ser Thr Pro Leu Val Thr Ile
    2660                2665                2670

Ala Ser Asp Ser Leu Gly Thr Val Pro Glu Thr Thr Leu Thr Met
    2675                2680                2685

Ser Glu Thr Ser Asn Gly Asp Ala Leu Val Leu Lys Thr Val Ser
    2690                2695                2700

Asn Pro Asp Arg Ser Ile Pro Gly Ile Thr Ile Gln Gly Val Thr
    2705                2710                2715

Glu Ser Pro Leu His Pro Ser Ser Thr Ser Pro Ser Lys Ile Val
    2720                2725                2730

Ala Pro Arg Asn Thr Thr Tyr Glu Gly Ser Ile Thr Val Ala Leu
    2735                2740                2745

Ser Thr Leu Pro Ala Gly Thr Gly Ser Leu Val Phe Ser Gln
    2750                2755                2760

Ser Ser Glu Asn Ser Glu Thr Thr Ala Leu Val Asp Ser Ser Ala
    2765                2770                2775

Gly Leu Glu Arg Ala Ser Val Met Pro Leu Thr Thr Gly Ser Gln
    2780                2785                2790

Gly Met Ala Ser Ser Gly Gly Ile Arg Ser Gly Ser Thr His Ser
    2795                2800                2805

Thr Gly Thr Lys Thr Phe Ser Ser Leu Pro Leu Thr Met Asn Pro
    2810                2815                2820

Gly Glu Val Thr Ala Met Ser Glu Ile Thr Thr Asn Arg Leu Thr
    2825                2830                2835

Ala Thr Gln Ser Thr Ala Pro Lys Gly Ile Pro Val Lys Pro Thr
    2840                2845                2850

Ser Ala Glu Ser Gly Leu Leu Thr Pro Val Ser Ala Ser Ser Ser
    2855                2860                2865

Pro Ser Lys Ala Phe Ala Ser Leu Thr Thr Ala Pro Pro Thr Trp
    2870                2875                2880

Gly Ile Pro Gln Ser Thr Leu Thr Phe Glu Phe Ser Glu Val Pro
    2885                2890                2895

Ser Leu Asp Thr Lys Ser Ala Ser Leu Pro Thr Pro Gly Gln Ser
    2900                2905                2910

Leu Asn Thr Ile Pro Asp Ser Asp Ala Ser Thr Ala Ser Ser Ser
    2915                2920                2925

Leu Ser Lys Ser Pro Glu Lys Asn Pro Arg Ala Arg Met Met Thr
    2930                2935                2940

Ser Thr Lys Ala Ile Ser Ala Ser Ser Phe Gln Ser Thr Gly Phe
    2945                2950                2955

Thr Glu Thr Pro Glu Gly Ser Ala Ser Pro Ser Met Ala Gly His
    2960                2965                2970
```

-continued

Glu Pro Arg Val Pro Thr Ser Gly Thr Gly Asp Pro Arg Tyr Ala
2975                2980                2985

Ser Glu Ser Met Ser Tyr Pro Asp Pro Ser Lys Ala Ser Ser Ala
2990                2995                3000

Met Thr Ser Thr Ser Leu Ala Ser Lys Leu Thr Thr Leu Phe Ser
3005                3010                3015

Thr Gly Gln Ala Ala Arg Ser Gly Ser Ser Ser Pro Ile Ser
3020                3025                3030

Leu Ser Thr Glu Lys Glu Thr Ser Phe Leu Ser Pro Thr Ala Ser
3035                3040                3045

Thr Ser Arg Lys Thr Ser Leu Phe Leu Gly Pro Ser Met Ala Arg
3050                3055                3060

Gln Pro Asn Ile Leu Val His Leu Gln Thr Ser Ala Leu Thr Leu
3065                3070                3075

Ser Pro Thr Ser Thr Leu Asn Met Ser Gln Glu Glu Pro Pro Glu
3080                3085                3090

Leu Thr Ser Ser Gln Thr Ile Ala Glu Glu Glu Gly Thr Thr Ala
3095                3100                3105

Glu Thr Gln Thr Leu Thr Phe Thr Pro Ser Glu Thr Pro Thr Ser
3110                3115                3120

Leu Leu Pro Val Ser Ser Pro Thr Glu Pro Thr Ala Arg Arg Lys
3125                3130                3135

Ser Ser Pro Glu Thr Trp Ala Ser Ser Ile Ser Val Pro Ala Lys
3140                3145                3150

Thr Ser Leu Val Glu Thr Thr Asp Gly Thr Leu Val Thr Thr Ile
3155                3160                3165

Lys Met Ser Ser Gln Ala Ala Gln Gly Asn Ser Thr Trp Pro Ala
3170                3175                3180

Pro Ala Glu Glu Thr Gly Ser Ser Pro Ala Gly Thr Ser Pro Gly
3185                3190                3195

Ser Pro Glu Met Ser Thr Thr Leu Lys Ile Met Ser Ser Lys Glu
3200                3205                3210

Pro Ser Ile Ser Pro Glu Ile Arg Ser Thr Val Arg Asn Ser Pro
3215                3220                3225

Trp Lys Thr Pro Glu Thr Thr Val Pro Met Glu Thr Thr Val Glu
3230                3235                3240

Pro Val Thr Leu Gln Ser Thr Ala Leu Gly Ser Gly Ser Thr Ser
3245                3250                3255

Ile Ser His Leu Pro Thr Gly Thr Thr Ser Pro Thr Lys Ser Pro
3260                3265                3270

Thr Glu Asn Met Leu Ala Thr Glu Arg Val Ser Leu Ser Pro Ser
3275                3280                3285

Pro Pro Glu Ala Trp Thr Asn Leu Tyr Ser Gly Thr Pro Gly Gly
3290                3295                3300

Thr Arg Gln Ser Leu Ala Thr Met Ser Ser Val Ser Leu Glu Ser
3305                3310                3315

Pro Thr Ala Arg Ser Ile Thr Gly Thr Gly Gln Gln Ser Ser Pro
3320                3325                3330

Glu Leu Val Ser Lys Thr Thr Gly Met Glu Phe Ser Met Trp His
3335                3340                3345

Gly Ser Thr Gly Gly Thr Thr Gly Asp Thr His Val Ser Leu Ser
3350                3355                3360

| | | | | | | | | | | | |
|---|---|---|---|---|---|---|---|---|---|---|---|
| Thr | Ser | Ser | Asn | Ile | Leu | Glu | Asp | Pro | Val | Thr | Ser |
| | 3365 | | | | 3370 | | | | 3375 | | |
| Pro | Asn | Ser | Val | Ser | Ser | Leu | Thr | Asp | Lys | Ser | Lys |
| | | | 3380 | | | | | 3385 | | | |
| His | Lys | Thr | Glu | Thr | Trp | Val | Ser | Thr | Thr | Ala | Ile |
| | | 3390 | | | | 3395 | | | | 3400 | |
| Pro | Ser | Thr | Val | Leu | Asn | Asn | Lys | Ile | Met | Ala | Ala |
| | | | 3405 | | | | | 3410 | | | |
| Glu | Gln | Thr | Ser | Arg | Ser | Val | Asp | Glu | Ala | Tyr | Ser |
| | | 3415 | | | | 3420 | | | | 3425 | |
| Ser | Thr | Ser | Ser | Trp | Ser | Asp | Gln | Thr | Ser | Gly | Ser |
| | | | 3430 | | | | | 3435 | | | |
| Asp | Ile | Thr | Leu | Gly | Ala | Ser | Pro | Asp | Val | Thr | Asn |
| | | 3440 | | | | 3445 | | | | 3450 | |
| Thr | Leu | Tyr | Ile | Thr | Ser | Thr | Ala | Gln | Thr | Thr | Ser |
| | | | 3455 | | | | | 3460 | | | |
| Leu | Val | Ser | Leu | Pro | Ser | Gly | Asp | Gln | Gly | Ile | Thr |
| | | 3465 | | | | 3470 | | | | 3475 | |
| Ser | Leu | Thr | Asn | Pro | Ser | Gly | Gly | Lys | Thr | Ser | Ser |
| | | | 3480 | | | | | 3485 | | | |
| Ala | Ser | Ser | Val | Thr | Ser | Pro | Ser | Ile | Gly | Leu | Glu |
| | | 3490 | | | | 3495 | | | | 3500 | |
| Thr | Leu | Arg | Ala | Asn | Val | Ser | Ala | Val | Lys | Ser | Asp |
| | | | 3505 | | | | | 3510 | | | |
| Ile | Ala | Pro | Thr | Ala | Gly | His | Leu | Ser | Gln | Thr | Ser |
| | | 3515 | | | | 3520 | | | | 3525 | |
| Ser | Pro | Ala | Glu | Val | Ser | Ile | Leu | Asp | Val | Thr | Thr |
| | | | 3530 | | | | | 3535 | | | |
| Ala | Pro | Thr | Pro | Gly | Ile | Ser | Thr | Thr | Ile | Thr | Thr |
| | | 3540 | | | | 3545 | | | | 3550 | |
| Met | Gly | Thr | Asn | Ser | Ile | Ser | Thr | Thr | Thr | Pro | Asn |
| | | | 3555 | | | | | 3560 | | | |
| Pro | Glu | Val | Gly | Met | Ser | Thr | Met | Asp | Ser | Thr | Pro |
| | | 3565 | | | | 3570 | | | | 3575 | |
| Ala | Thr | Glu | Arg | Arg | Thr | Thr | Ser | Thr | Glu | His | Pro |
| | | | 3580 | | | | | 3585 | | | |
| Ser | Thr | Trp | Ser | Ser | Thr | Ala | Ala | Ser | Asp | Ser | Trp |
| | | 3590 | | | | 3595 | | | | 3600 | |
| Thr | Val | Thr | Asp | Met | Thr | Ser | Asn | Leu | Lys | Val | Ala |
| | | | 3605 | | | | | 3610 | | | |
| Arg | Ser | Pro | Gly | Thr | Ile | Ser | Thr | Met | His | Thr | Thr |
| | | 3615 | | | | 3620 | | | | 3625 | |
| Ser | Phe | Leu | Ala | Ser | Ser | Thr | Glu | Leu | Asp | Ser | Met |
| | | | 3630 | | | | | 3635 | | | |
| Ser | Thr | Pro | His | Gly | Arg | Ile | Thr | Val | Ile | Gly | Thr |
| | | 3640 | | | | 3645 | | | | 3650 | |
| Ser | Leu | Val | Thr | Pro | Ser | Ser | Asp | Ala | Ser | Ala | Val |
| | | | 3655 | | | | | 3660 | | | |
| Lys | Thr | Glu | Thr | Ser | Thr | Ser | Glu | Arg | Thr | Leu | Ser |
| | | 3665 | | | | 3670 | | | | 3675 | |
| Pro | Ser | Asp | Thr | Thr | Ala | Ser | Thr | Pro | Ile | Ser | Thr |
| | | | 3680 | | | | | 3685 | | | |
| Phe | Ser | Arg | Val | Gln | Arg | Met | Ser | Ile | Ser | Val | Pro |
| | | 3690 | | | | 3695 | | | | 3700 | |
| Asp | Ile | Leu | Ser | Thr | Ser | Trp | Thr | Pro | Ser | Ser | Thr |
| | | | 3705 | | | | | 3710 | | | |
| Glu | Ala | Glu | Asp | Val | Pro | Val | Ser | Met | Val | Ser | Thr |
| | | 3715 | | | | 3720 | | | | 3725 | |
| Asp | His | Ala | Ser | Thr | Lys | Thr | Asp | Pro | Asn | Thr | Pro |
| | | | 3730 | | | | | 3735 | | | |
| Leu | Ser | Thr | Phe | Leu | Phe | Asp | Ser | Leu | Ser | Thr | Leu |
| | | 3740 | | | | 3745 | | | | 3750 | |
| Asp | Trp | Asp | Thr | Gly | Arg | Ser | Leu | Ser | Ser | Ala | Thr |
| Ala | Thr | Thr | Ser | Ala | Pro | Gln | Gly | Ala | Thr | Thr | Pro |
| Gln | Glu | Leu | Thr | Leu | Glu | Thr | Met | | | | |

```
                3755                3760                3765
Ile Ser Pro Ala Thr Ser Gln Leu Pro Phe Ser Ile Gly His Ile
    3770                3775                3780
Thr Ser Ala Val Thr Pro Ala Met Ala Arg Ser Ser Gly Val
    3785                3790                3795
Thr Phe Ser Arg Pro Asp Pro Thr Ser Lys Lys Ala Glu Gln Thr
    3800                3805                3810
Ser Thr Gln Leu Pro Thr Thr Thr Ser Ala His Pro Gly Gln Val
    3815                3820                3825
Pro Arg Ser Ala Ala Thr Thr Leu Asp Val Ile Pro His Thr Ala
    3830                3835                3840
Lys Thr Pro Asp Ala Thr Phe Gln Arg Gln Gly Gln Thr Ala Leu
    3845                3850                3855
Thr Thr Glu Ala Arg Ala Thr Ser Asp Ser Trp Asn Glu Lys Glu
    3860                3865                3870
Lys Ser Thr Pro Ser Ala Pro Trp Ile Thr Glu Met Met Asn Ser
    3875                3880                3885
Val Ser Glu Asp Thr Ile Lys Glu Val Thr Ser Ser Ser Val
    3890                3895                3900
Leu Arg Thr Leu Asn Thr Leu Asp Ile Asn Leu Glu Ser Gly Thr
    3905                3910                3915
Thr Ser Ser Pro Ser Trp Lys Ser Ser Pro Tyr Glu Arg Ile Ala
    3920                3925                3930
Pro Ser Glu Ser Thr Thr Asp Lys Glu Ala Ile His Pro Ser Thr
    3935                3940                3945
Asn Thr Val Glu Thr Thr Gly Trp Val Thr Ser Ser Glu His Ala
    3950                3955                3960
Ser His Ser Thr Ile Pro Ala His Ser Ala Ser Ser Lys Leu Thr
    3965                3970                3975
Ser Pro Val Val Thr Thr Ser Thr Arg Glu Gln Ala Ile Val Ser
    3980                3985                3990
Met Ser Thr Thr Thr Trp Pro Glu Ser Thr Arg Ala Arg Thr Glu
    3995                4000                4005
Pro Asn Ser Phe Leu Thr Ile Glu Leu Arg Asp Val Ser Pro Tyr
    4010                4015                4020
Met Asp Thr Ser Ser Thr Thr Gln Thr Ser Ile Ser Ser Pro
    4025                4030                4035
Gly Ser Thr Ala Ile Thr Lys Gly Pro Arg Thr Glu Ile Thr Ser
    4040                4045                4050
Ser Lys Arg Ile Ser Ser Ser Phe Leu Ala Gln Ser Met Arg Ser
    4055                4060                4065
Ser Asp Ser Pro Ser Glu Ala Ile Thr Arg Leu Ser Asn Phe Pro
    4070                4075                4080
Ala Met Thr Glu Ser Gly Gly Met Ile Leu Ala Met Gln Thr Ser
    4085                4090                4095
Pro Pro Gly Ala Thr Ser Leu Ser Ala Pro Thr Leu Asp Thr Ser
    4100                4105                4110
Ala Thr Ala Ser Trp Thr Gly Thr Pro Leu Ala Thr Thr Gln Arg
    4115                4120                4125
Phe Thr Tyr Ser Glu Lys Thr Thr Leu Phe Ser Lys Gly Pro Glu
    4130                4135                4140
Asp Thr Ser Gln Pro Ser Pro Ser Val Glu Glu Thr Ser Ser
    4145                4150                4155
```

-continued

```
Ser  Ser  Ser  Leu  Val  Pro  Ile  His  Ala  Thr  Thr  Ser  Pro  Ser  Asn
     4160                4165                4170

Ile  Leu  Leu  Thr  Ser  Gln  Gly  His  Ser  Pro  Ser  Ser  Thr  Pro  Pro
     4175                4180                4185

Val  Thr  Ser  Val  Phe  Leu  Ser  Glu  Thr  Ser  Gly  Leu  Gly  Lys  Thr
     4190                4195                4200

Thr  Asp  Met  Ser  Arg  Ile  Ser  Leu  Glu  Pro  Gly  Thr  Ser  Leu  Pro
     4205                4210                4215

Pro  Asn  Leu  Ser  Ser  Thr  Ala  Gly  Glu  Ala  Leu  Ser  Thr  Tyr  Glu
     4220                4225                4230

Ala  Ser  Arg  Asp  Thr  Lys  Ala  Ile  His  His  Ser  Ala  Asp  Thr  Ala
     4235                4240                4245

Val  Thr  Asn  Met  Glu  Ala  Thr  Ser  Ser  Glu  Tyr  Ser  Pro  Ile  Pro
     4250                4255                4260

Gly  His  Thr  Lys  Pro  Ser  Lys  Ala  Thr  Ser  Pro  Leu  Val  Thr  Ser
     4265                4270                4275

His  Ile  Met  Gly  Asp  Ile  Thr  Ser  Ser  Thr  Ser  Val  Phe  Gly  Ser
     4280                4285                4290

Ser  Glu  Thr  Thr  Glu  Ile  Glu  Thr  Val  Ser  Ser  Val  Asn  Gln  Gly
     4295                4300                4305

Leu  Gln  Glu  Arg  Ser  Thr  Ser  Gln  Val  Ala  Ser  Ala  Thr  Glu
     4310                4315                4320

Thr  Ser  Thr  Val  Ile  Thr  His  Val  Ser  Ser  Gly  Asp  Ala  Thr  Thr
     4325                4330                4335

His  Val  Thr  Lys  Thr  Gln  Ala  Thr  Phe  Ser  Ser  Gly  Thr  Ser  Ile
     4340                4345                4350

Ser  Ser  Pro  His  Gln  Phe  Ile  Thr  Ser  Thr  Asn  Thr  Phe  Thr  Asp
     4355                4360                4365

Val  Ser  Thr  Asn  Pro  Ser  Thr  Ser  Leu  Ile  Met  Thr  Glu  Ser  Ser
     4370                4375                4380

Gly  Val  Thr  Ile  Thr  Thr  Gln  Thr  Gly  Pro  Thr  Gly  Ala  Ala  Thr
     4385                4390                4395

Gln  Gly  Pro  Tyr  Leu  Leu  Asp  Thr  Ser  Thr  Met  Pro  Tyr  Leu  Thr
     4400                4405                4410

Glu  Thr  Pro  Leu  Ala  Val  Thr  Pro  Asp  Phe  Met  Gln  Ser  Glu  Lys
     4415                4420                4425

Thr  Thr  Leu  Ile  Ser  Lys  Gly  Pro  Lys  Asp  Val  Ser  Trp  Thr  Ser
     4430                4435                4440

Pro  Pro  Ser  Val  Ala  Glu  Thr  Ser  Tyr  Pro  Ser  Ser  Leu  Thr  Pro
     4445                4450                4455

Phe  Leu  Val  Thr  Thr  Ile  Pro  Pro  Ala  Thr  Ser  Thr  Leu  Gln  Gly
     4460                4465                4470

Gln  His  Thr  Ser  Ser  Pro  Val  Ser  Ala  Thr  Ser  Val  Leu  Thr  Ser
     4475                4480                4485

Gly  Leu  Val  Lys  Thr  Thr  Asp  Met  Leu  Asn  Thr  Ser  Met  Glu  Pro
     4490                4495                4500

Val  Thr  Asn  Ser  Pro  Gln  Asn  Leu  Asn  Asn  Pro  Ser  Asn  Glu  Ile
     4505                4510                4515

Leu  Ala  Thr  Leu  Ala  Ala  Thr  Thr  Asp  Ile  Glu  Thr  Ile  His  Pro
     4520                4525                4530

Ser  Ile  Asn  Lys  Ala  Val  Thr  Asn  Met  Gly  Thr  Ala  Ser  Ser  Ala
     4535                4540                4545
```

His Val Leu His Ser Thr Leu Pro Val Ser Ser Glu Pro Ser Thr
4550                4555                4560

Ala Thr Ser Pro Met Val Pro Ala Ser Ser Met Gly Asp Ala Leu
4565                4570                4575

Ala Ser Ile Ser Ile Pro Gly Ser Glu Thr Thr Asp Ile Glu Gly
4580                4585                4590

Glu Pro Thr Ser Ser Leu Thr Ala Gly Arg Lys Glu Asn Ser Thr
4595                4600                4605

Leu Gln Glu Met Asn Ser Thr Thr Glu Ser Asn Ile Ile Leu Ser
4610                4615                4620

Asn Val Ser Val Gly Ala Ile Thr Glu Ala Thr Lys Met Glu Val
4625                4630                4635

Pro Ser Phe Asp Ala Thr Phe Ile Pro Thr Pro Ala Gln Ser Thr
4640                4645                4650

Lys Phe Pro Asp Ile Phe Ser Val Ala Ser Ser Arg Leu Ser Asn
4655                4660                4665

Ser Pro Pro Met Thr Ile Ser Thr His Met Thr Thr Thr Gln Thr
4670                4675                4680

Gly Ser Ser Gly Ala Thr Ser Lys Ile Pro Leu Ala Leu Asp Thr
4685                4690                4695

Ser Thr Leu Glu Thr Ser Ala Gly Thr Pro Ser Val Val Thr Glu
4700                4705                4710

Gly Phe Ala His Ser Lys Ile Thr Thr Ala Met Asn Asn Asp Val
4715                4720                4725

Lys Asp Val Ser Gln Thr Asn Pro Pro Phe Gln Asp Glu Ala Ser
4730                4735                4740

Ser Pro Ser Ser Gln Ala Pro Val Leu Val Thr Thr Leu Pro Ser
4745                4750                4755

Ser Val Ala Phe Thr Pro Gln Trp His Ser Thr Ser Ser Pro Val
4760                4765                4770

Ser Met Ser Ser Val Leu Thr Ser Ser Leu Val Lys Thr Ala Gly
4775                4780                4785

Lys Val Asp Thr Ser Leu Glu Thr Val Thr Ser Ser Pro Gln Ser
4790                4795                4800

Met Ser Asn Thr Leu Asp Asp Ile Ser Val Thr Ser Ala Ala Thr
4805                4810                4815

Thr Asp Ile Glu Thr Thr His Pro Ser Ile Asn Thr Val Val Thr
4820                4825                4830

Asn Val Gly Thr Thr Gly Ser Ala Phe Glu Ser His Ser Thr Val
4835                4840                4845

Ser Ala Tyr Pro Glu Pro Ser Lys Val Thr Ser Pro Asn Val Thr
4850                4855                4860

Thr Ser Thr Met Glu Asp Thr Thr Ile Ser Arg Ser Ile Pro Lys
4865                4870                4875

Ser Ser Lys Thr Thr Arg Thr Glu Thr Glu Thr Thr Ser Ser Leu
4880                4885                4890

Thr Pro Lys Leu Arg Glu Thr Ser Ile Ser Gln Glu Ile Thr Ser
4895                4900                4905

Ser Thr Glu Thr Ser Thr Val Pro Tyr Lys Glu Leu Thr Gly Ala
4910                4915                4920

Thr Thr Glu Val Ser Arg Thr Asp Val Thr Ser Ser Ser Ser Thr
4925                4930                4935

Ser Phe Pro Gly Pro Asp Gln Ser Thr Val Ser Leu Asp Ile Ser

```
                4940            4945            4950
Thr Glu Thr Asn Thr Arg Leu Ser Thr Ser Pro Ile Met Thr Glu
    4955            4960            4965
Ser Ala Glu Ile Thr Ile Thr Thr Gln Thr Gly Pro His Gly Ala
    4970            4975            4980
Thr Ser Gln Asp Thr Phe Thr Met Asp Pro Ser Asn Thr Thr Pro
    4985            4990            4995
Gln Ala Gly Ile His Ser Ala Met Thr His Gly Phe Ser Gln Leu
    5000            5005            5010
Asp Val Thr Thr Leu Met Ser Arg Ile Pro Gln Asp Val Ser Trp
    5015            5020            5025
Thr Ser Pro Pro Ser Val Asp Lys Thr Ser Pro Ser Ser Phe
    5030            5035            5040
Leu Ser Ser Pro Ala Met Thr Thr Pro Ser Leu Ile Ser Ser Thr
    5045            5050            5055
Leu Pro Glu Asp Lys Leu Ser Ser Pro Met Thr Ser Leu Leu Thr
    5060            5065            5070
Ser Gly Leu Val Lys Ile Thr Asp Ile Leu Arg Thr Arg Leu Glu
    5075            5080            5085
Pro Val Thr Ser Ser Leu Pro Asn Phe Ser Ser Thr Ser Asp Lys
    5090            5095            5100
Ile Leu Ala Thr Ser Lys Asp Ser Lys Asp Thr Lys Glu Ile Phe
    5105            5110            5115
Pro Ser Ile Asn Thr Glu Glu Thr Asn Val Lys Ala Asn Asn Ser
    5120            5125            5130
Gly His Glu Ser His Ser Pro Ala Leu Ala Asp Ser Glu Thr Pro
    5135            5140            5145
Lys Ala Thr Thr Gln Met Val Ile Thr Thr Thr Val Gly Asp Pro
    5150            5155            5160
Ala Pro Ser Thr Ser Met Pro Val His Gly Ser Ser Glu Thr Thr
    5165            5170            5175
Asn Ile Lys Arg Glu Pro Thr Tyr Phe Leu Thr Pro Arg Leu Arg
    5180            5185            5190
Glu Thr Ser Thr Ser Gln Glu Ser Ser Phe Pro Thr Asp Thr Ser
    5195            5200            5205
Phe Leu Leu Ser Lys Val Pro Thr Gly Thr Ile Thr Glu Val Ser
    5210            5215            5220
Ser Thr Gly Val Asn Ser Ser Ser Lys Ile Ser Thr Pro Asp His
    5225            5230            5235
Asp Lys Ser Thr Val Pro Pro Asp Thr Phe Thr Gly Glu Ile Pro
    5240            5245            5250
Arg Val Phe Thr Ser Ser Ile Lys Thr Lys Ser Ala Glu Met Thr
    5255            5260            5265
Ile Thr Thr Gln Ala Ser Pro Pro Glu Ser Ala Ser His Ser Thr
    5270            5275            5280
Leu Pro Leu Asp Thr Ser Thr Thr Leu Ser Gln Gly Gly Thr His
    5285            5290            5295
Ser Thr Val Thr Gln Gly Phe Pro Tyr Ser Glu Val Thr Thr Leu
    5300            5305            5310
Met Gly Met Gly Pro Gly Asn Val Ser Trp Met Thr Thr Pro Pro
    5315            5320            5325
Val Glu Glu Thr Ser Ser Val Ser Ser Leu Met Ser Ser Pro Ala
    5330            5335            5340
```

```
Met Thr Ser Pro Ser Pro Val Ser Ser Thr Ser Pro Gln Ser Ile
5345                5350                5355

Pro Ser Ser Pro Leu Pro Val Thr Ala Leu Pro Thr Ser Val Leu
5360                5365                5370

Val Thr Thr Thr Asp Val Leu Gly Thr Thr Ser Pro Glu Ser Val
5375                5380                5385

Thr Ser Ser Pro Pro Asn Leu Ser Ser Ile Thr His Glu Arg Pro
5390                5395                5400

Ala Thr Tyr Lys Asp Thr Ala His Thr Glu Ala Ala Met His His
5405                5410                5415

Ser Thr Asn Thr Ala Val Thr Asn Val Gly Thr Ser Gly Ser Gly
5420                5425                5430

His Lys Ser Gln Ser Ser Val Leu Ala Asp Ser Glu Thr Ser Lys
5435                5440                5445

Ala Thr Pro Leu Met Ser Thr Ser Thr Leu Gly Asp Thr Ser
5450                5455                5460

Val Ser Thr Ser Thr Pro Asn Ile Ser Gln Thr Asn Gln Ile Gln
5465                5470                5475

Thr Glu Pro Thr Ala Ser Leu Ser Pro Arg Leu Arg Glu Ser Ser
5480                5485                5490

Thr Ser Glu Lys Thr Ser Ser Thr Thr Glu Thr Asn Thr Ala Phe
5495                5500                5505

Ser Tyr Val Pro Thr Gly Ala Ile Thr Gln Ala Ser Arg Thr Glu
5510                5515                5520

Ile Ser Ser Arg Thr Ser Ile Ser Asp Leu Asp Arg Pro Thr
5525                5530                5535

Ile Ala Pro Asp Ile Ser Thr Gly Met Ile Thr Arg Leu Phe Thr
5540                5545                5550

Ser Pro Ile Met Thr Lys Ser Ala Glu Met Thr Val Thr Thr Gln
5555                5560                5565

Thr Thr Thr Pro Gly Ala Thr Ser Gln Gly Ile Leu Pro Trp Asp
5570                5575                5580

Thr Ser Thr Thr Leu Phe Gln Gly Gly Thr His Ser Thr Val Ser
5585                5590                5595

Gln Gly Phe Pro His Ser Glu Ile Thr Thr Leu Arg Ser Arg Thr
5600                5605                5610

Pro Gly Asp Val Ser Trp Met Thr Thr Pro Pro Val Glu Glu Thr
5615                5620                5625

Ser Ser Gly Phe Ser Leu Met Ser Pro Ser Met Thr Ser Pro Ser
5630                5635                5640

Pro Val Ser Ser Thr Ser Pro Glu Ser Ile Pro Ser Ser Pro Leu
5645                5650                5655

Pro Val Thr Ala Leu Leu Thr Ser Val Leu Val Thr Thr Thr Asn
5660                5665                5670

Val Leu Gly Thr Thr Ser Pro Glu Pro Val Thr Ser Ser Pro Pro
5675                5680                5685

Asn Leu Ser Ser Pro Thr Gln Glu Arg Leu Thr Thr Tyr Lys Asp
5690                5695                5700

Thr Ala His Thr Glu Ala Met His Ala Ser Met His Thr Asn Thr
5705                5710                5715

Ala Val Ala Asn Val Gly Thr Ser Ile Ser Gly His Glu Ser Gln
5720                5725                5730
```

```
Ser  Ser  Val  Pro  Ala  Asp  Ser  His  Thr  Ser  Lys  Ala  Thr  Ser  Pro
5735                     5740                    5745

Met  Gly  Ile  Thr  Phe  Ala  Met  Gly  Asp  Thr  Ser  Val  Ser  Thr  Ser
5750                     5755                    5760

Thr  Pro  Ala  Phe  Phe  Glu  Thr  Arg  Ile  Gln  Thr  Glu  Ser  Thr  Ser
5765                     5770                    5775

Ser  Leu  Ile  Pro  Gly  Leu  Arg  Asp  Thr  Arg  Thr  Ser  Glu  Glu  Ile
5780                     5785                    5790

Asn  Thr  Val  Thr  Glu  Thr  Ser  Thr  Val  Leu  Ser  Glu  Val  Pro  Thr
5795                     5800                    5805

Thr  Thr  Thr  Thr  Glu  Val  Ser  Arg  Thr  Glu  Val  Ile  Thr  Ser  Ser
5810                     5815                    5820

Arg  Thr  Thr  Ile  Ser  Gly  Pro  Asp  His  Ser  Lys  Met  Ser  Pro  Tyr
5825                     5830                    5835

Ile  Ser  Thr  Glu  Thr  Ile  Thr  Arg  Leu  Ser  Thr  Phe  Pro  Phe  Val
5840                     5845                    5850

Thr  Gly  Ser  Thr  Glu  Met  Ala  Ile  Thr  Asn  Gln  Thr  Gly  Pro  Ile
5855                     5860                    5865

Gly  Thr  Ile  Ser  Gln  Ala  Thr  Leu  Thr  Leu  Asp  Thr  Ser  Ser  Thr
5870                     5875                    5880

Ala  Ser  Trp  Glu  Gly  Thr  His  Ser  Pro  Val  Thr  Gln  Arg  Phe  Pro
5885                     5890                    5895

His  Ser  Glu  Glu  Thr  Thr  Thr  Met  Ser  Arg  Ser  Thr  Lys  Gly  Val
5900                     5905                    5910

Ser  Trp  Gln  Ser  Pro  Pro  Ser  Val  Glu  Glu  Thr  Ser  Ser  Pro  Ser
5915                     5920                    5925

Ser  Pro  Val  Pro  Leu  Pro  Ala  Ile  Thr  Ser  His  Ser  Ser  Leu  Tyr
5930                     5935                    5940

Ser  Ala  Val  Ser  Gly  Ser  Ser  Pro  Thr  Ser  Ala  Leu  Pro  Val  Thr
5945                     5950                    5955

Ser  Leu  Leu  Thr  Ser  Gly  Arg  Arg  Lys  Thr  Ile  Asp  Met  Leu  Asp
5960                     5965                    5970

Thr  His  Ser  Glu  Leu  Val  Thr  Ser  Ser  Leu  Pro  Ser  Ala  Ser  Ser
5975                     5980                    5985

Phe  Ser  Gly  Glu  Ile  Leu  Thr  Ser  Glu  Ala  Ser  Thr  Asn  Thr  Glu
5990                     5995                    6000

Thr  Ile  His  Phe  Ser  Glu  Asn  Thr  Ala  Glu  Thr  Asn  Met  Gly  Thr
6005                     6010                    6015

Thr  Asn  Ser  Met  His  Lys  Leu  His  Ser  Ser  Val  Ser  Ile  His  Ser
6020                     6025                    6030

Gln  Pro  Ser  Gly  His  Thr  Pro  Pro  Lys  Val  Thr  Gly  Ser  Met  Met
6035                     6040                    6045

Glu  Asp  Ala  Ile  Val  Ser  Thr  Ser  Thr  Pro  Gly  Ser  Pro  Glu  Thr
6050                     6055                    6060

Lys  Asn  Val  Asp  Arg  Asp  Ser  Thr  Ser  Pro  Leu  Thr  Pro  Glu  Leu
6065                     6070                    6075

Lys  Glu  Asp  Ser  Thr  Ala  Leu  Val  Met  Asn  Ser  Thr  Thr  Glu  Ser
6080                     6085                    6090

Asn  Thr  Val  Phe  Ser  Ser  Val  Ser  Leu  Asp  Ala  Ala  Thr  Glu  Val
6095                     6100                    6105

Ser  Arg  Ala  Glu  Val  Thr  Tyr  Tyr  Asp  Pro  Thr  Phe  Met  Pro  Ala
6110                     6115                    6120

Ser  Ala  Gln  Ser  Thr  Lys  Ser  Pro  Asp  Ile  Ser  Pro  Glu  Ala  Ser
```

-continued

```
                6125                6130                6135
Ser Ser His Ser Asn Ser Pro Pro Leu Thr Ile Ser Thr His Lys
    6140                6145                6150
Thr Ile Ala Thr Gln Thr Gly Pro Ser Gly Val Thr Ser Leu Gly
    6155                6160                6165
Gln Leu Thr Leu Asp Thr Ser Thr Ile Ala Thr Ser Ala Gly Thr
    6170                6175                6180
Pro Ser Ala Arg Thr Gln Asp Phe Val Asp Ser Glu Thr Thr Ser
    6185                6190                6195
Val Met Asn Asn Asp Leu Asn Asp Val Leu Lys Thr Ser Pro Phe
    6200                6205                6210
Ser Ala Glu Glu Ala Asn Ser Leu Ser Ser Gln Ala Pro Leu Leu
    6215                6220                6225
Val Thr Thr Ser Pro Ser Pro Val Thr Ser Thr Leu Gln Glu His
    6230                6235                6240
Ser Thr Ser Ser Leu Val Ser Val Thr Ser Val Pro Thr Pro Thr
    6245                6250                6255
Leu Ala Lys Ile Thr Asp Met Asp Thr Asn Leu Glu Pro Val Thr
    6260                6265                6270
Arg Ser Pro Gln Asn Leu Arg Asn Thr Leu Ala Thr Ser Glu Ala
    6275                6280                6285
Thr Thr Asp Thr His Thr Met His Pro Ser Ile Asn Thr Ala Val
    6290                6295                6300
Ala Asn Val Gly Thr Thr Ser Ser Pro Asn Glu Phe Tyr Phe Thr
    6305                6310                6315
Val Ser Pro Asp Ser Asp Pro Tyr Lys Ala Thr Ser Ala Val Val
    6320                6325                6330
Ile Thr Ser Thr Ser Gly Asp Ser Ile Val Ser Thr Ser Met Pro
    6335                6340                6345
Arg Ser Ser Ala Met Lys Lys Ile Glu Ser Glu Thr Thr Phe Ser
    6350                6355                6360
Leu Ile Phe Arg Leu Arg Glu Thr Ser Thr Ser Gln Lys Ile Gly
    6365                6370                6375
Ser Ser Ser Asp Thr Ser Thr Val Phe Asp Lys Ala Phe Thr Ala
    6380                6385                6390
Ala Thr Thr Glu Val Ser Arg Thr Glu Leu Thr Ser Ser Ser Arg
    6395                6400                6405
Thr Ser Ile Gln Gly Thr Glu Lys Pro Thr Met Ser Pro Asp Thr
    6410                6415                6420
Ser Thr Arg Ser Val Thr Met Leu Ser Thr Phe Ala Gly Leu Thr
    6425                6430                6435
Lys Ser Glu Glu Arg Thr Ile Ala Thr Gln Thr Gly Pro His Arg
    6440                6445                6450
Ala Thr Ser Gln Gly Thr Leu Thr Trp Asp Thr Ser Ile Thr Thr
    6455                6460                6465
Ser Gln Ala Gly Thr His Ser Ala Met Thr His Gly Phe Ser Gln
    6470                6475                6480
Leu Asp Leu Ser Thr Leu Thr Ser Arg Val Pro Glu Tyr Ile Ser
    6485                6490                6495
Gly Thr Ser Pro Pro Ser Val Glu Lys Thr Ser Ser Ser Ser Ser
    6500                6505                6510
Leu Leu Ser Leu Pro Ala Ile Thr Ser Pro Ser Pro Val Pro Thr
    6515                6520                6525
```

-continued

```
Thr Leu Pro Glu Ser Arg Pro Ser Ser Pro Val His Leu Thr Ser
    6530                6535                6540

Leu Pro Thr Ser Gly Leu Val Lys Thr Thr Asp Met Leu Ala Ser
    6545                6550                6555

Val Ala Ser Leu Pro Pro Asn Leu Gly Ser Thr Ser His Lys Ile
    6560                6565                6570

Pro Thr Thr Ser Glu Asp Ile Lys Asp Thr Glu Lys Met Tyr Pro
    6575                6580                6585

Ser Thr Asn Ile Ala Val Thr Asn Val Gly Thr Thr Thr Ser Glu
    6590                6595                6600

Lys Glu Ser Tyr Ser Ser Val Pro Ala Tyr Ser Glu Pro Pro Lys
    6605                6610                6615

Val Thr Ser Pro Met Val Thr Ser Phe Asn Ile Arg Asp Thr Ile
    6620                6625                6630

Val Ser Thr Ser Met Pro Gly Ser Ser Glu Ile Thr Arg Ile Glu
    6635                6640                6645

Met Glu Ser Thr Phe Ser Leu Ala His Gly Leu Lys Gly Thr Ser
    6650                6655                6660

Thr Ser Gln Asp Pro Ile Val Ser Thr Glu Lys Ser Ala Val Leu
    6665                6670                6675

His Lys Leu Thr Thr Gly Ala Thr Glu Thr Ser Arg Thr Glu Val
    6680                6685                6690

Ala Ser Ser Arg Arg Thr Ser Ile Pro Gly Pro Asp His Ser Thr
    6695                6700                6705

Glu Ser Pro Asp Ile Ser Thr Glu Val Ile Pro Ser Leu Pro Ile
    6710                6715                6720

Ser Leu Gly Ile Thr Glu Ser Ser Asn Met Thr Ile Ile Thr Arg
    6725                6730                6735

Thr Gly Pro Pro Leu Gly Ser Thr Ser Gln Gly Thr Phe Thr Leu
    6740                6745                6750

Asp Thr Pro Thr Thr Ser Ser Arg Ala Gly Thr His Ser Met Ala
    6755                6760                6765

Thr Gln Glu Phe Pro His Ser Glu Met Thr Thr Val Met Asn Lys
    6770                6775                6780

Asp Pro Glu Ile Leu Ser Trp Thr Ile Pro Pro Ser Ile Glu Lys
    6785                6790                6795

Thr Ser Phe Ser Ser Ser Leu Met Pro Ser Pro Ala Met Thr Ser
    6800                6805                6810

Pro Pro Val Ser Ser Thr Leu Pro Lys Thr Ile His Thr Thr Pro
    6815                6820                6825

Ser Pro Met Thr Ser Leu Leu Thr Pro Ser Leu Val Met Thr Thr
    6830                6835                6840

Asp Thr Leu Gly Thr Ser Pro Glu Pro Thr Thr Ser Ser Pro Pro
    6845                6850                6855

Asn Leu Ser Ser Thr Ser His Glu Ile Leu Thr Thr Asp Glu Asp
    6860                6865                6870

Thr Thr Ala Ile Glu Ala Met His Pro Ser Thr Ser Thr Ala Ala
    6875                6880                6885

Thr Asn Val Glu Thr Thr Ser Ser Gly His Gly Ser Gln Ser Ser
    6890                6895                6900

Val Leu Ala Asp Ser Glu Lys Thr Lys Ala Thr Ala Pro Met Asp
    6905                6910                6915
```

```
Thr Thr Ser Thr Met Gly His Thr Thr Val Ser Thr Ser Met Ser
6920            6925                6930

Val Ser Ser Glu Thr Thr Lys Ile Lys Arg Glu Ser Thr Tyr Ser
6935            6940                6945

Leu Thr Pro Gly Leu Arg Glu Thr Ser Ile Ser Gln Asn Ala Ser
6950            6955                6960

Phe Ser Thr Asp Thr Ser Ile Val Leu Ser Glu Val Pro Thr Gly
6965            6970                6975

Thr Thr Ala Glu Val Ser Arg Thr Glu Val Thr Ser Ser Gly Arg
6980            6985                6990

Thr Ser Ile Pro Gly Pro Ser Gln Ser Thr Val Leu Pro Glu Ile
6995            7000                7005

Ser Thr Arg Thr Met Thr Arg Leu Phe Ala Ser Pro Thr Met Thr
7010            7015                7020

Glu Ser Ala Glu Met Thr Ile Pro Thr Gln Thr Gly Pro Ser Gly
7025            7030                7035

Ser Thr Ser Gln Asp Thr Leu Thr Leu Asp Thr Ser Thr Thr Lys
7040            7045                7050

Ser Gln Ala Lys Thr His Ser Thr Leu Thr Gln Arg Phe Pro His
7055            7060                7065

Ser Glu Met Thr Thr Leu Met Ser Arg Gly Pro Gly Asp Met Ser
7070            7075                7080

Trp Gln Ser Ser Pro Ser Leu Glu Asn Pro Ser Ser Leu Pro Ser
7085            7090                7095

Leu Leu Ser Leu Pro Ala Thr Thr Ser Pro Pro Ile Ser Ser
7100            7105                7110

Thr Leu Pro Val Thr Ile Ser Ser Ser Pro Leu Pro Val Thr Ser
7115            7120                7125

Leu Leu Thr Ser Ser Pro Val Thr Thr Thr Asp Met Leu His Thr
7130            7135                7140

Ser Pro Glu Leu Val Thr Ser Ser Pro Pro Lys Leu Ser His Thr
7145            7150                7155

Ser Asp Glu Arg Leu Thr Thr Gly Lys Asp Thr Thr Asn Thr Glu
7160            7165                7170

Ala Val His Pro Ser Thr Asn Thr Ala Ala Ser Asn Val Glu Ile
7175            7180                7185

Pro Ser Ser Gly His Glu Ser Pro Ser Ser Ala Leu Ala Asp Ser
7190            7195                7200

Glu Thr Ser Lys Ala Thr Ser Pro Met Phe Ile Thr Ser Thr Gln
7205            7210                7215

Glu Asp Thr Thr Val Ala Ile Ser Thr Pro His Phe Leu Glu Thr
7220            7225                7230

Ser Arg Ile Gln Lys Glu Ser Ile Ser Ser Leu Ser Pro Lys Leu
7235            7240                7245

Arg Glu Thr Gly Ser Ser Val Glu Thr Ser Ser Ala Ile Glu Thr
7250            7255                7260

Ser Ala Val Leu Ser Glu Val Ser Ile Gly Ala Thr Thr Glu Ile
7265            7270                7275

Ser Arg Thr Glu Val Thr Ser Ser Ser Arg Thr Ser Ile Ser Gly
7280            7285                7290

Ser Ala Glu Ser Thr Met Leu Pro Glu Ile Ser Thr Thr Arg Lys
7295            7300                7305

Ile Ile Lys Phe Pro Thr Ser Pro Ile Leu Ala Glu Ser Ser Glu
```

-continued

```
                    7310            7315              7320

Met Thr Ile Lys Thr Gln Thr Ser Pro Pro Gly Ser Thr Ser Glu
            7325            7330              7335

Ser Thr Phe Thr Leu Asp Thr Ser Thr Pro Ser Leu Val Ile
            7340            7345              7350

Thr His Ser Thr Met Thr Gln Arg Leu Pro His Ser Glu Ile Thr
            7355            7360              7365

Thr Leu Val Ser Arg Gly Ala Gly Asp Val Pro Arg Pro Ser Ser
            7370            7375              7380

Leu Pro Val Glu Glu Thr Ser Pro Pro Ser Ser Gln Leu Ser Leu
            7385            7390              7395

Ser Ala Met Ile Ser Pro Ser Pro Val Ser Ser Thr Leu Pro Ala
            7400            7405              7410

Ser Ser His Ser Ser Ser Ala Ser Val Thr Ser Leu Leu Thr Pro
            7415            7420              7425

Gly Gln Val Lys Thr Thr Glu Val Leu Asp Ala Ser Ala Glu Pro
            7430            7435              7440

Glu Thr Ser Ser Pro Pro Ser Leu Ser Ser Thr Ser Val Glu Ile
            7445            7450              7455

Leu Ala Thr Ser Glu Val Thr Thr Asp Thr Glu Lys Ile His Pro
            7460            7465              7470

Phe Ser Asn Thr Ala Val Thr Lys Val Gly Thr Ser Ser Ser Gly
            7475            7480              7485

His Glu Ser Pro Ser Ser Val Leu Pro Asp Ser Glu Thr Thr Lys
            7490            7495              7500

Ala Thr Ser Ala Met Gly Thr Ile Ser Ile Met Gly Asp Thr Ser
            7505            7510              7515

Val Ser Thr Leu Thr Pro Ala Leu Ser Asn Thr Arg Lys Ile Gln
            7520            7525              7530

Ser Glu Pro Ala Ser Ser Leu Thr Thr Arg Leu Arg Glu Thr Ser
            7535            7540              7545

Thr Ser Glu Glu Thr Ser Leu Ala Thr Glu Ala Asn Thr Val Leu
            7550            7555              7560

Ser Lys Val Ser Thr Gly Ala Thr Thr Glu Val Ser Arg Thr Glu
            7565            7570              7575

Ala Ile Ser Phe Ser Arg Thr Ser Met Ser Gly Pro Glu Gln Ser
            7580            7585              7590

Thr Met Ser Gln Asp Ile Ser Ile Gly Thr Ile Pro Arg Ile Ser
            7595            7600              7605

Ala Ser Ser Val Leu Thr Glu Ser Ala Lys Met Thr Ile Thr Thr
            7610            7615              7620

Gln Thr Gly Pro Ser Glu Ser Thr Leu Glu Ser Thr Leu Asn Leu
            7625            7630              7635

Asn Thr Ala Thr Thr Pro Ser Trp Val Glu Thr His Ser Ile Val
            7640            7645              7650

Ile Gln Gly Phe Pro His Pro Glu Met Thr Thr Ser Met Gly Arg
            7655            7660              7665

Gly Pro Gly Gly Val Ser Trp Pro Ser Pro Pro Phe Val Lys Glu
            7670            7675              7680

Thr Ser Pro Pro Ser Ser Pro Leu Ser Leu Pro Ala Val Thr Ser
            7685            7690              7695

Pro His Pro Val Ser Thr Thr Phe Leu Ala His Ile Pro Pro Ser
            7700            7705              7710
```

-continued

Pro Leu Pro Val Thr Ser Leu Leu Thr Ser Gly Pro Ala Thr Thr
    7715            7720                 7725

Thr Asp Ile Leu Gly Thr Ser Thr Glu Pro Gly Thr Ser Ser Ser
    7730            7735                 7740

Ser Ser Leu Ser Thr Thr Ser His Glu Arg Leu Thr Thr Tyr Lys
    7745            7750                 7755

Asp Thr Ala His Thr Glu Ala Val His Pro Ser Thr Asn Thr Gly
    7760            7765                 7770

Gly Thr Asn Val Ala Thr Thr Ser Ser Gly Tyr Lys Ser Gln Ser
    7775            7780                 7785

Ser Val Leu Ala Asp Ser Ser Pro Met Cys Thr Thr Ser Thr Met
    7790            7795                 7800

Gly Asp Thr Ser Val Leu Thr Ser Thr Pro Ala Phe Leu Glu Thr
    7805            7810                 7815

Arg Arg Ile Gln Thr Glu Leu Ala Ser Ser Leu Thr Pro Gly Leu
    7820            7825                 7830

Arg Glu Ser Ser Gly Ser Glu Gly Thr Ser Ser Gly Thr Lys Met
    7835            7840                 7845

Ser Thr Val Leu Ser Lys Val Pro Thr Gly Ala Thr Thr Glu Ile
    7850            7855                 7860

Ser Lys Glu Asp Val Thr Ser Ile Pro Gly Pro Ala Gln Ser Thr
    7865            7870                 7875

Ile Ser Pro Asp Ile Ser Thr Arg Thr Val Ser Trp Phe Ser Thr
    7880            7885                 7890

Ser Pro Val Met Thr Glu Ser Ala Glu Ile Thr Met Asn Thr His
    7895            7900                 7905

Thr Ser Pro Leu Gly Ala Thr Thr Gln Gly Thr Ser Thr Leu Asp
    7910            7915                 7920

Thr Ser Ser Thr Thr Ser Leu Thr Met Thr His Ser Thr Ile Ser
    7925            7930                 7935

Gln Gly Phe Ser His Ser Gln Met Ser Thr Leu Met Arg Arg Gly
    7940            7945                 7950

Pro Glu Asp Val Ser Trp Met Ser Pro Pro Leu Leu Glu Lys Thr
    7955            7960                 7965

Arg Pro Ser Phe Ser Leu Met Ser Ser Pro Ala Thr Thr Ser Pro
    7970            7975                 7980

Ser Pro Val Ser Ser Thr Leu Pro Glu Ser Ile Ser Ser Ser Pro
    7985            7990                 7995

Leu Pro Val Thr Ser Leu Leu Thr Ser Gly Leu Ala Lys Thr Thr
    8000            8005                 8010

Asp Met Leu His Lys Ser Ser Glu Pro Val Thr Asn Ser Pro Ala
    8015            8020                 8025

Asn Leu Ser Ser Thr Ser Val Glu Ile Leu Ala Thr Ser Glu Val
    8030            8035                 8040

Thr Thr Asp Thr Glu Lys Thr His Pro Ser Ser Asn Arg Thr Val
    8045            8050                 8055

Thr Asp Val Gly Thr Ser Ser Ser Gly His Glu Ser Thr Ser Phe
    8060            8065                 8070

Val Leu Ala Asp Ser Gln Thr Ser Lys Val Thr Ser Pro Met Val
    8075            8080                 8085

Ile Thr Ser Thr Met Glu Asp Thr Ser Val Ser Thr Ser Thr Pro
    8090            8095                 8100

```
Gly Phe Phe Glu Thr Ser Arg Ile Gln Thr Glu Pro Thr Ser Ser
    8105                8110                8115

Leu Thr Leu Gly Leu Arg Lys Thr Ser Ser Glu Gly Thr Ser
    8120                8125                8130

Leu Ala Thr Glu Met Ser Thr Val Leu Ser Gly Val Pro Thr Gly
    8135                8140                8145

Ala Thr Ala Glu Val Ser Arg Thr Glu Val Thr Ser Ser Ser Arg
    8150                8155                8160

Thr Ser Ile Ser Gly Phe Ala Gln Leu Thr Val Ser Pro Glu Thr
    8165                8170                8175

Ser Thr Glu Thr Ile Thr Arg Leu Pro Thr Ser Ser Ile Met Thr
    8180                8185                8190

Glu Ser Ala Glu Met Met Ile Lys Thr Gln Thr Asp Pro Pro Gly
    8195                8200                8205

Ser Thr Pro Glu Ser Thr His Thr Val Asp Ile Ser Thr Thr Pro
    8210                8215                8220

Asn Trp Val Glu Thr His Ser Thr Val Thr Gln Arg Phe Ser His
    8225                8230                8235

Ser Glu Met Thr Thr Leu Val Ser Arg Ser Pro Gly Asp Met Leu
    8240                8245                8250

Trp Pro Ser Gln Ser Ser Val Glu Glu Thr Ser Ser Ala Ser Ser
    8255                8260                8265

Leu Leu Ser Leu Pro Ala Thr Thr Ser Pro Ser Pro Val Ser Ser
    8270                8275                8280

Thr Leu Val Glu Asp Phe Pro Ser Ala Ser Leu Pro Val Thr Ser
    8285                8290                8295

Leu Leu Asn Pro Gly Leu Val Ile Thr Thr Asp Arg Met Gly Ile
    8300                8305                8310

Ser Arg Glu Pro Gly Thr Ser Ser Thr Ser Asn Leu Ser Ser Thr
    8315                8320                8325

Ser His Glu Arg Leu Thr Thr Leu Glu Asp Thr Val Asp Thr Glu
    8330                8335                8340

Asp Met Gln Pro Ser Thr His Thr Ala Val Thr Asn Val Arg Thr
    8345                8350                8355

Ser Ile Ser Gly His Glu Ser Gln Ser Ser Val Leu Ser Asp Ser
    8360                8365                8370

Glu Thr Pro Lys Ala Thr Ser Pro Met Gly Thr Thr Tyr Thr Met
    8375                8380                8385

Gly Glu Thr Ser Val Ser Ile Ser Thr Ser Asp Phe Phe Glu Thr
    8390                8395                8400

Ser Arg Ile Gln Ile Glu Pro Thr Ser Ser Leu Thr Ser Gly Leu
    8405                8410                8415

Arg Glu Thr Ser Ser Ser Glu Arg Ile Ser Ser Ala Thr Glu Gly
    8420                8425                8430

Ser Thr Val Leu Ser Glu Val Pro Ser Gly Ala Thr Thr Glu Val
    8435                8440                8445

Ser Arg Thr Glu Val Ile Ser Ser Arg Gly Thr Ser Met Ser Gly
    8450                8455                8460

Pro Asp Gln Phe Thr Ile Ser Pro Asp Ile Ser Thr Glu Ala Ile
    8465                8470                8475

Thr Arg Leu Ser Thr Ser Pro Ile Met Thr Glu Ser Ala Glu Ser
    8480                8485                8490

Ala Ile Thr Ile Glu Thr Gly Ser Pro Gly Ala Thr Ser Glu Gly
```

```
                     8495                8500                8505

Thr Leu Thr Leu Asp Thr Ser Thr Thr Thr Phe Trp Ser Gly Thr
            8510                8515                8520

His Ser Thr Ala Ser Pro Gly Phe Ser His Ser Glu Met Thr Thr
            8525                8530                8535

Leu Met Ser Arg Thr Pro Gly Asp Val Pro Trp Pro Ser Leu Pro
            8540                8545                8550

Ser Val Glu Glu Ala Ser Ser Val Ser Ser Ser Leu Ser Ser Pro
            8555                8560                8565

Ala Met Thr Ser Thr Ser Phe Phe Ser Thr Leu Pro Glu Ser Ile
            8570                8575                8580

Ser Ser Ser Pro His Pro Val Thr Ala Leu Leu Thr Leu Gly Pro
            8585                8590                8595

Val Lys Thr Thr Asp Met Leu Arg Thr Ser Ser Glu Pro Glu Thr
            8600                8605                8610

Ser Ser Pro Pro Asn Leu Ser Ser Thr Ser Ala Glu Ile Leu Ala
            8615                8620                8625

Thr Ser Glu Val Thr Lys Asp Arg Glu Lys Ile His Pro Ser Ser
            8630                8635                8640

Asn Thr Pro Val Val Asn Val Gly Thr Val Ile Tyr Lys His Leu
            8645                8650                8655

Ser Pro Ser Ser Val Leu Ala Asp Leu Val Thr Thr Lys Pro Thr
            8660                8665                8670

Ser Pro Met Ala Thr Thr Ser Thr Leu Gly Asn Thr Ser Val Ser
            8675                8680                8685

Thr Ser Thr Pro Ala Phe Pro Glu Thr Met Met Thr Gln Pro Thr
            8690                8695                8700

Ser Ser Leu Thr Ser Gly Leu Arg Glu Ile Ser Thr Ser Gln Glu
            8705                8710                8715

Thr Ser Ser Ala Thr Glu Arg Ser Ala Ser Leu Ser Gly Met Pro
            8720                8725                8730

Thr Gly Ala Thr Thr Lys Val Ser Arg Thr Glu Ala Leu Ser Leu
            8735                8740                8745

Gly Arg Thr Ser Thr Pro Gly Pro Ala Gln Ser Thr Ile Ser Pro
            8750                8755                8760

Glu Ile Ser Thr Glu Thr Ile Thr Arg Ile Ser Thr Pro Leu Thr
            8765                8770                8775

Thr Thr Gly Ser Ala Glu Met Thr Ile Thr Pro Lys Thr Gly His
            8780                8785                8790

Ser Gly Ala Ser Ser Gln Gly Thr Phe Thr Leu Asp Thr Ser Ser
            8795                8800                8805

Arg Ala Ser Trp Pro Gly Thr His Ser Ala Ala Thr His Arg Ser
            8810                8815                8820

Pro His Ser Gly Met Thr Thr Pro Met Ser Arg Gly Pro Glu Asp
            8825                8830                8835

Val Ser Trp Pro Ser Arg Pro Ser Val Glu Lys Thr Ser Pro Pro
            8840                8845                8850

Ser Ser Leu Val Ser Leu Ser Ala Val Thr Ser Pro Ser Pro Leu
            8855                8860                8865

Tyr Ser Thr Pro Ser Glu Ser Ser His Ser Ser Pro Leu Arg Val
            8870                8875                8880

Thr Ser Leu Phe Thr Pro Val Met Met Lys Thr Thr Asp Met Leu
            8885                8890                8895
```

```
Asp Thr Ser Leu Glu Pro Val Thr Thr Ser Pro Pro Ser Met Asn
    8900            8905            8910

Ile Thr Ser Asp Glu Ser Leu Ala Thr Ser Lys Ala Thr Met Glu
    8915            8920            8925

Thr Glu Ala Ile Gln Leu Ser Glu Asn Thr Ala Val Thr Gln Met
    8930            8935            8940

Gly Thr Ile Ser Ala Arg Gln Glu Phe Tyr Ser Ser Tyr Pro Gly
    8945            8950            8955

Leu Pro Glu Pro Ser Lys Val Thr Ser Pro Val Val Thr Ser Ser
    8960            8965            8970

Thr Ile Lys Asp Ile Val Ser Thr Thr Ile Pro Ala Ser Ser Glu
    8975            8980            8985

Ile Thr Arg Ile Glu Met Glu Ser Thr Ser Thr Leu Thr Pro Thr
    8990            8995            9000

Pro Arg Glu Thr Ser Thr Ser Gln Glu Ile His Ser Ala Thr Lys
    9005            9010            9015

Pro Ser Thr Val Pro Tyr Lys Ala Leu Thr Ser Ala Thr Ile Glu
    9020            9025            9030

Asp Ser Met Thr Gln Val Met Ser Ser Ser Arg Gly Pro Ser Pro
    9035            9040            9045

Asp Gln Ser Thr Met Ser Gln Asp Ile Ser Thr Glu Val Ile Thr
    9050            9055            9060

Arg Leu Ser Thr Ser Pro Ile Lys Thr Glu Ser Thr Glu Met Thr
    9065            9070            9075

Ile Thr Thr Gln Thr Gly Ser Pro Gly Ala Thr Ser Arg Gly Thr
    9080            9085            9090

Leu Thr Leu Asp Thr Ser Thr Thr Phe Met Ser Gly Thr His Ser
    9095            9100            9105

Thr Ala Ser Gln Gly Phe Ser His Ser Gln Met Thr Ala Leu Met
    9110            9115            9120

Ser Arg Thr Pro Gly Asp Val Pro Trp Leu Ser His Pro Ser Val
    9125            9130            9135

Glu Glu Ala Ser Ser Ala Ser Phe Ser Leu Ser Ser Pro Val Met
    9140            9145            9150

Thr Ser Ser Ser Pro Val Ser Ser Thr Leu Pro Asp Ser Ile His
    9155            9160            9165

Ser Ser Ser Leu Pro Val Thr Ser Leu Leu Thr Ser Gly Leu Val
    9170            9175            9180

Lys Thr Thr Glu Leu Leu Gly Thr Ser Ser Glu Pro Glu Thr Ser
    9185            9190            9195

Ser Pro Pro Asn Leu Ser Ser Thr Ser Ala Glu Ile Leu Ala Ile
    9200            9205            9210

Thr Glu Val Thr Thr Asp Thr Glu Lys Leu Glu Met Thr Asn Val
    9215            9220            9225

Val Thr Ser Gly Tyr Thr His Glu Ser Pro Ser Ser Val Leu Ala
    9230            9235            9240

Asp Ser Val Thr Thr Lys Ala Thr Ser Ser Met Gly Ile Thr Tyr
    9245            9250            9255

Pro Thr Gly Asp Thr Asn Val Leu Thr Ser Thr Pro Ala Phe Ser
    9260            9265            9270

Asp Thr Ser Arg Ile Gln Thr Lys Ser Lys Leu Ser Leu Thr Pro
    9275            9280            9285
```

```
Gly Leu Met Glu Thr Ser Ile Ser Glu Glu Thr Ser Ser Ala Thr
    9290                9295                9300

Glu Lys Ser Thr Val Leu Ser Ser Val Pro Thr Gly Ala Thr Thr
    9305                9310                9315

Glu Val Ser Arg Thr Glu Ala Ile Ser Ser Ser Arg Thr Ser Ile
    9320                9325                9330

Pro Gly Pro Ala Gln Ser Thr Met Ser Ser Asp Thr Ser Met Glu
    9335                9340                9345

Thr Ile Thr Arg Ile Ser Thr Pro Leu Thr Arg Lys Glu Ser Thr
    9350                9355                9360

Asp Met Ala Ile Thr Pro Lys Thr Gly Pro Ser Gly Ala Thr Ser
    9365                9370                9375

Gln Gly Thr Phe Thr Leu Asp Ser Ser Ser Thr Ala Ser Trp Pro
    9380                9385                9390

Gly Thr His Ser Ala Thr Thr Gln Arg Phe Pro Gln Ser Val Val
    9395                9400                9405

Thr Thr Pro Met Ser Arg Gly Pro Glu Asp Val Ser Trp Pro Ser
    9410                9415                9420

Pro Leu Ser Val Glu Lys Asn Ser Pro Pro Ser Ser Leu Val Ser
    9425                9430                9435

Ser Ser Ser Val Thr Ser Pro Ser Pro Leu Tyr Ser Thr Pro Ser
    9440                9445                9450

Gly Ser Ser His Ser Ser Pro Val Pro Val Thr Ser Leu Phe Thr
    9455                9460                9465

Ser Ile Met Met Lys Ala Thr Asp Met Leu Asp Ala Ser Leu Glu
    9470                9475                9480

Pro Glu Thr Thr Ser Ala Pro Asn Met Asn Ile Thr Ser Asp Glu
    9485                9490                9495

Ser Leu Ala Ala Ser Lys Ala Thr Thr Glu Thr Glu Ala Ile His
    9500                9505                9510

Val Phe Glu Asn Thr Ala Ala Ser His Val Glu Thr Thr Ser Ala
    9515                9520                9525

Thr Glu Glu Leu Tyr Ser Ser Ser Pro Gly Phe Ser Glu Pro Thr
    9530                9535                9540

Lys Val Ile Ser Pro Val Val Thr Ser Ser Ser Ile Arg Asp Asn
    9545                9550                9555

Met Val Ser Thr Thr Met Pro Gly Ser Ser Gly Ile Thr Arg Ile
    9560                9565                9570

Glu Ile Glu Ser Met Ser Ser Leu Thr Pro Gly Leu Arg Glu Thr
    9575                9580                9585

Arg Thr Ser Gln Asp Ile Thr Ser Ser Thr Glu Thr Ser Thr Val
    9590                9595                9600

Leu Tyr Lys Met Pro Ser Gly Ala Thr Pro Glu Val Ser Arg Thr
    9605                9610                9615

Glu Val Met Pro Ser Ser Arg Thr Ser Ile Pro Gly Pro Ala Gln
    9620                9625                9630

Ser Thr Met Ser Leu Asp Ile Ser Asp Glu Val Val Thr Arg Leu
    9635                9640                9645

Ser Thr Ser Pro Ile Met Thr Glu Ser Ala Glu Ile Thr Ile Thr
    9650                9655                9660

Thr Gln Thr Gly Tyr Ser Leu Ala Thr Ser Gln Val Thr Leu Pro
    9665                9670                9675

Leu Gly Thr Ser Met Thr Phe Leu Ser Gly Thr His Ser Thr Met
```

```
                    9680                9685                9690

Ser Gln Gly Leu Ser His Ser Glu Met Thr Asn Leu Met Ser Arg
    9695                9700                9705

Gly Pro Glu Ser Leu Ser Trp Thr Ser Pro Arg Phe Val Glu Thr
    9710                9715                9720

Thr Arg Ser Ser Ser Ser Leu Thr Ser Leu Pro Leu Thr Thr Ser
    9725                9730                9735

Leu Ser Pro Val Ser Ser Thr Leu Leu Asp Ser Ser Pro Ser Ser
    9740                9745                9750

Pro Leu Pro Val Thr Ser Leu Ile Leu Pro Gly Leu Val Lys Thr
    9755                9760                9765

Thr Glu Val Leu Asp Thr Ser Ser Glu Pro Lys Thr Ser Ser Ser
    9770                9775                9780

Pro Asn Leu Ser Ser Thr Ser Val Glu Ile Pro Ala Thr Ser Glu
    9785                9790                9795

Ile Met Thr Asp Thr Glu Lys Ile His Pro Ser Ser Asn Thr Ala
    9800                9805                9810

Val Ala Lys Val Arg Thr Ser Ser Ser Val His Glu Ser His Ser
    9815                9820                9825

Ser Val Leu Ala Asp Ser Glu Thr Thr Ile Thr Ile Pro Ser Met
    9830                9835                9840

Gly Ile Thr Ser Ala Val Asp Asp Thr Thr Val Phe Thr Ser Asn
    9845                9850                9855

Pro Ala Phe Ser Glu Thr Arg Arg Ile Pro Thr Glu Pro Thr Phe
    9860                9865                9870

Ser Leu Thr Pro Gly Phe Arg Glu Thr Ser Thr Ser Glu Glu Thr
    9875                9880                9885

Thr Ser Ile Thr Glu Thr Ser Ala Val Leu Tyr Gly Val Pro Thr
    9890                9895                9900

Ser Ala Thr Thr Glu Val Ser Met Thr Glu Ile Met Ser Ser Asn
    9905                9910                9915

Arg Ile His Ile Pro Asp Ser Asp Gln Ser Thr Met Ser Pro Asp
    9920                9925                9930

Ile Ile Thr Glu Val Ile Thr Arg Leu Ser Ser Ser Ser Met Met
    9935                9940                9945

Ser Glu Ser Thr Gln Met Thr Ile Thr Thr Gln Lys Ser Ser Pro
    9950                9955                9960

Gly Ala Thr Ala Gln Ser Thr Leu Thr Leu Ala Thr Thr Thr Ala
    9965                9970                9975

Pro Leu Ala Arg Thr His Ser Thr Val Pro Pro Arg Phe Leu His
    9980                9985                9990

Ser Glu Met Thr Thr Leu Met Ser Arg Ser Pro Glu Asn Pro Ser
    9995               10000               10005

Trp Lys Ser Ser Leu Phe Val Glu Lys Thr Ser Ser Ser Ser Ser
   10010               10015               10020

Leu Leu Ser Leu Pro Val Thr Thr Ser Pro Ser Val Ser Ser Thr
   10025               10030               10035

Leu Pro Gln Ser Ile Pro Ser Ser Ser Phe Ser Val Thr Ser Leu
   10040               10045               10050

Leu Thr Pro Gly Met Val Lys Thr Thr Asp Thr Ser Thr Glu Pro
   10055               10060               10065

Gly Thr Ser Leu Ser Pro Asn Leu Ser Gly Thr Ser Val Glu Ile
   10070               10075               10080
```

-continued

```
Leu Ala  Ala Ser Glu Val Thr  Thr Asp Thr Glu Lys  Ile His Pro
    10085            10090                10095

Ser Ser  Ser Met Ala Val Thr  Asn Val Gly Thr Thr  Ser Ser Gly
    10100            10105                10110

His Glu  Leu Tyr Ser Ser Val  Ser Ile His Ser Glu  Pro Ser Lys
    10115            10120                10125

Ala Thr  Tyr Pro Val Gly Thr  Pro Ser Ser Met Ala  Glu Thr Ser
    10130            10135                10140

Ile Ser  Thr Ser Met Pro Ala  Asn Phe Glu Thr Thr  Gly Phe Glu
    10145            10150                10155

Ala Glu  Pro Phe Ser His Leu  Thr Ser Gly Phe Arg  Lys Thr Asn
    10160            10165                10170

Met Ser  Leu Asp Thr Ser Ser  Val Thr Pro Thr Asn  Thr Pro Ser
    10175            10180                10185

Ser Pro  Gly Ser Thr His Leu  Leu Gln Ser Ser Lys  Thr Asp Phe
    10190            10195                10200

Thr Ser  Ser Ala Lys Thr Ser  Ser Pro Asp Trp Pro  Pro Ala Ser
    10205            10210                10215

Gln Tyr  Thr Glu Ile Pro Val  Asp Ile Ile Thr Pro  Phe Asn Ala
    10220            10225                10230

Ser Pro  Ser Ile Thr Glu Ser  Thr Gly Ile Thr Ser  Phe Pro Glu
    10235            10240                10245

Ser Arg  Phe Thr Met Ser Val  Thr Glu Ser Thr His  His Leu Ser
    10250            10255                10260

Thr Asp  Leu Leu Pro Ser Ala  Glu Thr Ile Ser Thr  Gly Thr Val
    10265            10270                10275

Met Pro  Ser Leu Ser Glu Ala  Met Thr Ser Phe Ala  Thr Thr Gly
    10280            10285                10290

Val Pro  Arg Ala Ile Ser Gly  Ser Gly Ser Pro Phe  Ser Arg Thr
    10295            10300                10305

Glu Ser  Gly Pro Gly Asp Ala  Thr Leu Ser Thr Ile  Ala Glu Ser
    10310            10315                10320

Leu Pro  Ser Ser Thr Pro Val  Pro Phe Ser Ser Ser  Thr Phe Thr
    10325            10330                10335

Thr Thr  Asp Ser Ser Thr Ile  Pro Ala Leu His Glu  Ile Thr Ser
    10340            10345                10350

Ser Ser  Ala Thr Pro Tyr Arg  Val Asp Thr Ser Leu  Gly Thr Glu
    10355            10360                10365

Ser Ser  Thr Thr Glu Gly Arg  Leu Val Met Val Ser  Thr Leu Asp
    10370            10375                10380

Thr Ser  Ser Gln Pro Gly Arg  Thr Ser Ser Ser Pro  Ile Leu Asp
    10385            10390                10395

Thr Arg  Met Thr Glu Ser Val  Glu Leu Gly Thr Val  Thr Ser Ala
    10400            10405                10410

Tyr Gln  Val Pro Ser Leu Ser  Thr Arg Leu Thr Arg  Thr Asp Gly
    10415            10420                10425

Ile Met  Glu His Ile Thr Lys  Ile Pro Asn Glu Ala  Ala His Arg
    10430            10435                10440

Gly Thr  Ile Arg Pro Val Lys  Gly Pro Gln Thr Ser  Thr Ser Pro
    10445            10450                10455

Ala Ser  Pro Lys Gly Leu His  Thr Gly Gly Thr Lys  Arg Met Glu
    10460            10465                10470
```

```
Thr Thr Thr Thr Ala Leu Lys  Thr Thr Thr Thr Ala  Leu Lys Thr
    10475            10480                10485

Thr Ser Arg Ala Thr Leu Thr  Thr Ser Val Tyr Thr  Pro Thr Leu
    10490            10495                10500

Gly Thr Leu Thr Pro Leu Asn  Ala Ser Met Gln Met  Ala Ser Thr
    10505            10510                10515

Ile Pro Thr Glu Met Met Ile  Thr Thr Pro Tyr Val  Phe Pro Asp
    10520            10525                10530

Val Pro Glu Thr Thr Ser Ser  Leu Ala Thr Ser Leu  Gly Ala Glu
    10535            10540                10545

Thr Ser Thr Ala Leu Pro Arg  Thr Thr Pro Ser Val  Phe Asn Arg
    10550            10555                10560

Glu Ser Glu Thr Thr Ala Ser  Leu Val Ser Arg Ser  Gly Ala Glu
    10565            10570                10575

Arg Ser Pro Val Ile Gln Thr  Leu Asp Val Ser Ser  Ser Glu Pro
    10580            10585                10590

Asp Thr Thr Ala Ser Trp Val  Ile His Pro Ala Glu  Thr Ile Pro
    10595            10600                10605

Thr Val Ser Lys Thr Thr Pro  Asn Phe Phe His Ser  Glu Leu Asp
    10610            10615                10620

Thr Val Ser Ser Thr Ala Thr  Ser His Gly Ala Asp  Val Ser Ser
    10625            10630                10635

Ala Ile Pro Thr Asn Ile Ser  Pro Ser Glu Leu Asp  Ala Leu Thr
    10640            10645                10650

Pro Leu Val Thr Ile Ser Gly  Thr Asp Thr Ser Thr  Thr Phe Pro
    10655            10660                10665

Thr Leu Thr Lys Ser Pro His  Glu Thr Glu Thr Arg  Thr Thr Trp
    10670            10675                10680

Leu Thr His Pro Ala Glu Thr  Ser Ser Thr Ile Pro  Arg Thr Ile
    10685            10690                10695

Pro Asn Phe Ser His His Glu  Ser Asp Ala Thr Pro  Ser Ile Ala
    10700            10705                10710

Thr Ser Pro Gly Ala Glu Thr  Ser Ser Ala Ile Pro  Ile Met Thr
    10715            10720                10725

Val Ser Pro Gly Ala Glu Asp  Leu Val Thr Ser Gln  Val Thr Ser
    10730            10735                10740

Ser Gly Thr Asp Arg Asn Met  Thr Ile Pro Thr Leu  Thr Leu Ser
    10745            10750                10755

Pro Gly Glu Pro Lys Thr Ile  Ala Ser Leu Val Thr  His Pro Glu
    10760            10765                10770

Ala Gln Thr Ser Ser Ala Ile  Pro Thr Ser Thr Ile  Ser Pro Ala
    10775            10780                10785

Val Ser Arg Leu Val Thr Ser  Met Val Thr Ser Leu  Ala Ala Lys
    10790            10795                10800

Thr Ser Thr Thr Asn Arg Ala  Leu Thr Asn Ser Pro  Gly Glu Pro
    10805            10810                10815

Ala Thr Thr Val Ser Leu Val  Thr His Pro Ala Gln  Thr Ser Pro
    10820            10825                10830

Thr Val Pro Trp Thr Thr Ser  Ile Phe Phe His Ser  Lys Ser Asp
    10835            10840                10845

Thr Thr Pro Ser Met Thr Thr  Ser His Gly Ala Glu  Ser Ser Ser
    10850            10855                10860

Ala Val Pro Thr Pro Thr Val  Ser Thr Glu Val Pro  Gly Val Val
```

```
                10865               10870               10875

Thr Pro Leu Val Thr Ser Ser Arg Ala Val Ile Ser Thr Thr Ile
        10880               10885               10890

Pro Ile Leu Thr Leu Ser Pro Gly Glu Pro Glu Thr Thr Pro Ser
        10895               10900               10905

Met Ala Thr Ser His Gly Glu Glu Ala Ser Ser Ala Ile Pro Thr
        10910               10915               10920

Pro Thr Val Ser Pro Gly Val Pro Gly Val Val Thr Ser Leu Val
        10925               10930               10935

Thr Ser Ser Arg Ala Val Thr Ser Thr Thr Ile Pro Ile Leu Thr
        10940               10945               10950

Phe Ser Leu Gly Glu Pro Glu Thr Thr Pro Ser Met Ala Thr Ser
        10955               10960               10965

His Gly Thr Glu Ala Gly Ser Ala Val Pro Thr Val Leu Pro Glu
        10970               10975               10980

Val Pro Gly Met Val Thr Ser Leu Val Ala Ser Ser Arg Ala Val
        10985               10990               10995

Thr Ser Thr Thr Leu Pro Thr Leu Thr Leu Ser Pro Gly Glu Pro
        11000               11005               11010

Glu Thr Thr Pro Ser Met Ala Thr Ser His Gly Ala Glu Ala Ser
        11015               11020               11025

Ser Thr Val Pro Thr Val Ser Pro Glu Val Pro Gly Val Val Thr
        11030               11035               11040

Ser Leu Val Thr Ser Ser Ser Gly Val Asn Ser Thr Ser Ile Pro
        11045               11050               11055

Thr Leu Ile Leu Ser Pro Gly Glu Leu Glu Thr Thr Pro Ser Met
        11060               11065               11070

Ala Thr Ser His Gly Ala Glu Ala Ser Ser Ala Val Pro Thr Pro
        11075               11080               11085

Thr Val Ser Pro Gly Val Ser Gly Val Val Thr Pro Leu Val Thr
        11090               11095               11100

Ser Ser Arg Ala Val Thr Ser Thr Thr Ile Pro Ile Leu Thr Leu
        11105               11110               11115

Ser Ser Ser Glu Pro Glu Thr Thr Pro Ser Met Ala Thr Ser His
        11120               11125               11130

Gly Val Glu Ala Ser Ser Ala Val Leu Thr Val Ser Pro Glu Val
        11135               11140               11145

Pro Gly Met Val Thr Ser Leu Val Thr Ser Ser Arg Ala Val Thr
        11150               11155               11160

Ser Thr Thr Ile Pro Thr Leu Thr Ile Ser Ser Asp Glu Pro Glu
        11165               11170               11175

Thr Thr Thr Ser Leu Val Thr His Ser Glu Ala Lys Met Ile Ser
        11180               11185               11190

Ala Ile Pro Thr Leu Ala Val Ser Pro Thr Val Gln Gly Leu Val
        11195               11200               11205

Thr Ser Leu Val Thr Ser Ser Gly Ser Glu Thr Ser Ala Phe Ser
        11210               11215               11220

Asn Leu Thr Val Ala Ser Ser Gln Pro Glu Thr Ile Asp Ser Trp
        11225               11230               11235

Val Ala His Pro Gly Thr Glu Ala Ser Ser Val Val Pro Thr Leu
        11240               11245               11250

Thr Val Ser Thr Gly Glu Pro Phe Thr Asn Ile Ser Leu Val Thr
        11255               11260               11265
```

```
His Pro  Ala Glu Ser Ser Ser     Thr Leu Pro Arg Thr     Thr Ser Arg
    11270           11275                 11280

Phe Ser  His Ser Glu Leu Asp     Thr Met Pro Ser Thr     Val Thr Ser
    11285           11290                 11295

Pro Glu  Ala Glu Ser Ser Ser     Ala Ile Ser Thr Thr     Ile Ser Pro
    11300           11305                 11310

Gly Ile  Pro Gly Val Leu Thr     Ser Leu Val Thr Ser     Ser Gly Arg
    11315           11320                 11325

Asp Ile  Ser Ala Thr Phe Pro     Thr Val Pro Glu Ser     Pro His Glu
    11330           11335                 11340

Ser Glu  Ala Thr Ala Ser Trp     Val Thr His Pro Ala     Val Thr Ser
    11345           11350                 11355

Thr Thr  Val Pro Arg Thr Thr     Pro Asn Tyr Ser His     Ser Glu Pro
    11360           11365                 11370

Asp Thr  Thr Pro Ser Ile Ala     Thr Ser Pro Gly Ala     Glu Ala Thr
    11375           11380                 11385

Ser Asp  Phe Pro Thr Ile Thr     Val Ser Pro Asp Val     Pro Asp Met
    11390           11395                 11400

Val Thr  Ser Gln Val Thr Ser     Ser Gly Thr Asp Thr     Ser Ile Thr
    11405           11410                 11415

Ile Pro  Thr Leu Thr Leu Ser     Ser Gly Glu Pro Glu     Thr Thr Thr
    11420           11425                 11430

Ser Phe  Ile Thr Tyr Ser Glu     Thr His Thr Ser Ser     Ala Ile Pro
    11435           11440                 11445

Thr Leu  Pro Val Ser Pro Gly     Ala Ser Lys Met Leu     Thr Ser Leu
    11450           11455                 11460

Val Ile  Ser Ser Gly Thr Asp     Ser Thr Thr Thr Phe     Pro Thr Leu
    11465           11470                 11475

Thr Glu  Thr Pro Tyr Glu Pro     Glu Thr Thr Ala Ile     Gln Leu Ile
    11480           11485                 11490

His Pro  Ala Glu Thr Asn Thr     Met Val Pro Arg Thr     Thr Pro Lys
    11495           11500                 11505

Phe Ser  His Ser Lys Ser Asp     Thr Thr Leu Pro Val     Ala Ile Thr
    11510           11515                 11520

Ser Pro  Gly Pro Glu Ala Ser     Ser Ala Val Ser Thr     Thr Thr Ile
    11525           11530                 11535

Ser Pro  Asp Met Ser Asp Leu     Val Thr Ser Leu Val     Pro Ser Ser
    11540           11545                 11550

Gly Thr  Asp Thr Ser Thr Thr     Phe Pro Thr Leu Ser     Glu Thr Pro
    11555           11560                 11565

Tyr Glu  Pro Glu Thr Thr Ala     Thr Trp Leu Thr His     Pro Ala Glu
    11570           11575                 11580

Thr Ser  Thr Thr Val Ser Gly     Thr Ile Pro Asn Phe     Ser His Arg
    11585           11590                 11595

Gly Ser  Asp Thr Ala Pro Ser     Met Val Thr Ser Pro     Gly Val Asp
    11600           11605                 11610

Thr Arg  Ser Gly Val Pro Thr     Thr Thr Ile Pro Pro     Ser Ile Pro
    11615           11620                 11625

Gly Val  Val Thr Ser Gln Val     Thr Ser Ser Ala Thr     Asp Thr Ser
    11630           11635                 11640

Thr Ala  Ile Pro Thr Leu Thr     Pro Ser Pro Gly Glu     Pro Glu Thr
    11645           11650                 11655
```

-continued

```
Thr Ala Ser Ser Ala Thr His Pro Gly Thr Gln Thr Gly Phe Thr
    11660              11665              11670

Val Pro Ile Arg Thr Val Pro Ser Ser Glu Pro Asp Thr Met Ala
    11675              11680              11685

Ser Trp Val Thr His Pro Pro Gln Thr Ser Thr Pro Val Ser Arg
    11690              11695              11700

Thr Thr Ser Ser Phe Ser His Ser Ser Pro Asp Ala Thr Pro Val
    11705              11710              11715

Met Ala Thr Ser Pro Arg Thr Glu Ala Ser Ser Ala Val Leu Thr
    11720              11725              11730

Thr Ile Ser Pro Gly Ala Pro Glu Met Val Thr Ser Gln Ile Thr
    11735              11740              11745

Ser Ser Gly Ala Ala Thr Ser Thr Thr Val Pro Thr Leu Thr His
    11750              11755              11760

Ser Pro Gly Met Pro Glu Thr Thr Ala Leu Leu Ser Thr His Pro
    11765              11770              11775

Arg Thr Glu Thr Ser Lys Thr Phe Pro Ala Ser Thr Val Phe Pro
    11780              11785              11790

Gln Val Ser Glu Thr Thr Ala Ser Leu Thr Ile Arg Pro Gly Ala
    11795              11800              11805

Glu Thr Ser Thr Ala Leu Pro Thr Gln Thr Thr Ser Ser Leu Phe
    11810              11815              11820

Thr Leu Leu Val Thr Gly Thr Ser Arg Val Asp Leu Ser Pro Thr
    11825              11830              11835

Ala Ser Pro Gly Val Ser Ala Lys Thr Ala Pro Leu Ser Thr His
    11840              11845              11850

Pro Gly Thr Glu Thr Ser Thr Met Ile Pro Thr Ser Thr Leu Ser
    11855              11860              11865

Leu Gly Leu Leu Glu Thr Thr Gly Leu Leu Ala Thr Ser Ser Ser
    11870              11875              11880

Ala Glu Thr Ser Thr Ser Thr Leu Thr Leu Thr Val Ser Pro Ala
    11885              11890              11895

Val Ser Gly Leu Ser Ser Ala Ser Ile Thr Thr Asp Lys Pro Gln
    11900              11905              11910

Thr Val Thr Ser Trp Asn Thr Glu Thr Ser Pro Ser Val Thr Ser
    11915              11920              11925

Val Gly Pro Pro Glu Phe Ser Arg Thr Val Thr Gly Thr Thr Met
    11930              11935              11940

Thr Leu Ile Pro Ser Glu Met Pro Thr Pro Pro Lys Thr Ser His
    11945              11950              11955

Gly Glu Gly Val Ser Pro Thr Thr Ile Leu Arg Thr Thr Met Val
    11960              11965              11970

Glu Ala Thr Asn Leu Ala Thr Thr Gly Ser Ser Pro Thr Val Ala
    11975              11980              11985

Lys Thr Thr Thr Thr Phe Asn Thr Leu Ala Gly Ser Leu Phe Thr
    11990              11995              12000

Pro Leu Thr Thr Pro Gly Met Ser Thr Leu Ala Ser Glu Ser Val
    12005              12010              12015

Thr Ser Arg Thr Ser Tyr Asn His Arg Ser Trp Ile Ser Thr Thr
    12020              12025              12030

Ser Ser Tyr Asn Arg Arg Tyr Trp Thr Pro Ala Thr Ser Thr Pro
    12035              12040              12045

Val Thr Ser Thr Phe Ser Pro Gly Ile Ser Thr Ser Ser Ile Pro
```

```
                12050                   12055                   12060
Ser  Ser  Thr  Ala  Ala  Thr  Val  Pro  Phe  Met  Val  Pro  Phe  Thr  Leu
     12065                   12070                   12075

Asn  Phe  Thr  Ile  Thr  Asn  Leu  Gln  Tyr  Glu  Glu  Asp  Met  Arg  His
     12080                   12085                   12090

Pro  Gly  Ser  Arg  Lys  Phe  Asn  Ala  Thr  Glu  Arg  Glu  Leu  Gln  Gly
     12095                   12100                   12105

Leu  Leu  Lys  Pro  Leu  Phe  Arg  Asn  Ser  Ser  Leu  Glu  Tyr  Leu  Tyr
     12110                   12115                   12120

Ser  Gly  Cys  Arg  Leu  Ala  Ser  Leu  Arg  Pro  Glu  Lys  Asp  Ser  Ser
     12125                   12130                   12135

Ala  Thr  Ala  Val  Asp  Ala  Ile  Cys  Thr  His  Arg  Pro  Asp  Pro  Glu
     12140                   12145                   12150

Asp  Leu  Gly  Leu  Asp  Arg  Glu  Arg  Leu  Tyr  Trp  Glu  Leu  Ser  Asn
     12155                   12160                   12165

Leu  Thr  Asn  Gly  Ile  Gln  Glu  Leu  Gly  Pro  Tyr  Thr  Leu  Asp  Arg
     12170                   12175                   12180

Asn  Ser  Leu  Tyr  Val  Asn  Gly  Phe  Thr  His  Arg  Ser  Ser  Met  Pro
     12185                   12190                   12195

Thr  Thr  Ser  Thr  Pro  Gly  Thr  Ser  Thr  Val  Asp  Val  Gly  Thr  Ser
     12200                   12205                   12210

Gly  Thr  Pro  Ser  Ser  Ser  Pro  Ser  Pro  Thr  Thr  Ala  Gly  Pro  Leu
     12215                   12220                   12225

Leu  Met  Pro  Phe  Thr  Leu  Asn  Phe  Thr  Ile  Thr  Asn  Leu  Gln  Tyr
     12230                   12235                   12240

Glu  Glu  Asp  Met  Arg  Arg  Thr  Gly  Ser  Arg  Lys  Phe  Asn  Thr  Met
     12245                   12250                   12255

Glu  Ser  Val  Leu  Gln  Gly  Leu  Leu  Lys  Pro  Leu  Phe  Lys  Asn  Thr
     12260                   12265                   12270

Ser  Val  Gly  Pro  Leu  Tyr  Ser  Gly  Cys  Arg  Leu  Thr  Leu  Leu  Arg
     12275                   12280                   12285

Pro  Glu  Lys  Asp  Gly  Ala  Ala  Thr  Gly  Val  Asp  Ala  Ile  Cys  Thr
     12290                   12295                   12300

His  Arg  Leu  Asp  Pro  Lys  Ser  Pro  Gly  Leu  Asn  Arg  Glu  Gln  Leu
     12305                   12310                   12315

Tyr  Trp  Glu  Leu  Ser  Lys  Leu  Thr  Asn  Asp  Ile  Glu  Glu  Leu  Gly
     12320                   12325                   12330

Pro  Tyr  Thr  Leu  Asp  Arg  Asn  Ser  Leu  Tyr  Val  Asn  Gly  Phe  Thr
     12335                   12340                   12345

His  Gln  Ser  Ser  Val  Ser  Thr  Thr  Ser  Thr  Pro  Gly  Thr  Ser  Thr
     12350                   12355                   12360

Val  Asp  Leu  Arg  Thr  Ser  Gly  Thr  Pro  Ser  Ser  Leu  Ser  Ser  Pro
     12365                   12370                   12375

Thr  Ile  Met  Ala  Ala  Gly  Pro  Leu  Leu  Val  Pro  Phe  Thr  Leu  Asn
     12380                   12385                   12390

Phe  Thr  Ile  Thr  Asn  Leu  Gln  Tyr  Gly  Glu  Asp  Met  Gly  His  Pro
     12395                   12400                   12405

Gly  Ser  Arg  Lys  Phe  Asn  Thr  Thr  Glu  Arg  Val  Leu  Gln  Gly  Leu
     12410                   12415                   12420

Leu  Gly  Pro  Ile  Phe  Lys  Asn  Thr  Ser  Val  Gly  Pro  Leu  Tyr  Ser
     12425                   12430                   12435

Gly  Cys  Arg  Leu  Thr  Ser  Leu  Arg  Ser  Glu  Lys  Asp  Gly  Ala  Ala
     12440                   12445                   12450
```

```
Thr Gly Val Asp Ala Ile Cys  Ile His His Leu Asp  Pro Lys Ser
    12455           12460            12465

Pro Gly Leu Asn Arg Glu Arg  Leu Tyr Trp Glu Leu  Ser Gln Leu
    12470           12475            12480

Thr Asn Gly Ile Lys Glu Leu  Gly Pro Tyr Thr Leu  Asp Arg Asn
    12485           12490            12495

Ser Leu Tyr Val Asn Gly Phe  Thr His Arg Thr Ser  Val Pro Thr
    12500           12505            12510

Ser Ser Thr Pro Gly Thr Ser  Thr Val Asp Leu Gly  Thr Ser Gly
    12515           12520            12525

Thr Pro Phe Ser Leu Pro Ser  Pro Ala Thr Ala Gly  Pro Leu Leu
    12530           12535            12540

Val Leu Phe Thr Leu Asn Phe  Thr Ile Thr Asn Leu  Lys Tyr Glu
    12545           12550            12555

Glu Asp Met His Arg Pro Gly  Ser Arg Lys Phe Asn  Thr Thr Glu
    12560           12565            12570

Arg Val Leu Gln Thr Leu Leu  Gly Pro Met Phe Lys  Asn Thr Ser
    12575           12580            12585

Val Gly Leu Leu Tyr Ser Gly  Cys Arg Leu Thr Leu  Leu Arg Ser
    12590           12595            12600

Glu Lys Asp Gly Ala Ala Thr  Gly Val Asp Ala Ile  Cys Thr His
    12605           12610            12615

Arg Leu Asp Pro Lys Ser Pro  Gly Val Asp Arg Glu  Gln Leu Tyr
    12620           12625            12630

Trp Glu Leu Ser Gln Leu Thr  Asn Gly Ile Lys Glu  Leu Gly Pro
    12635           12640            12645

Tyr Thr Leu Asp Arg Asn Ser  Leu Tyr Val Asn Gly  Phe Thr His
    12650           12655            12660

Trp Ile Pro Val Pro Thr Ser  Ser Thr Pro Gly Thr  Ser Thr Val
    12665           12670            12675

Asp Leu Gly Ser Gly Thr Pro  Ser Ser Leu Pro Ser  Pro Thr Thr
    12680           12685            12690

Ala Gly Pro Leu Leu Val Pro  Phe Thr Leu Asn Phe  Thr Ile Thr
    12695           12700            12705

Asn Leu Lys Tyr Glu Glu Asp  Met His Cys Pro Gly  Ser Arg Lys
    12710           12715            12720

Phe Asn Thr Thr Glu Arg Val  Leu Gln Ser Leu Leu  Gly Pro Met
    12725           12730            12735

Phe Lys Asn Thr Ser Val Gly  Pro Leu Tyr Ser Gly  Cys Arg Leu
    12740           12745            12750

Thr Leu Leu Arg Ser Glu Lys  Asp Gly Ala Ala Thr  Gly Val Asp
    12755           12760            12765

Ala Ile Cys Thr His Arg Leu  Asp Pro Lys Ser Pro  Gly Val Asp
    12770           12775            12780

Arg Glu Gln Leu Tyr Trp Glu  Leu Ser Gln Leu Thr  Asn Gly Ile
    12785           12790            12795

Lys Glu Leu Gly Pro Tyr Thr  Leu Asp Arg Asn Ser  Leu Tyr Val
    12800           12805            12810

Asn Gly Phe Thr His Gln Thr  Ser Ala Pro Asn Thr  Ser Thr Pro
    12815           12820            12825

Gly Thr Ser Thr Val Asp Leu  Gly Thr Ser Gly Thr  Pro Ser Ser
    12830           12835            12840
```

```
Leu Pro Ser Pro Thr Ser Ala    Gly Pro Leu Leu Val    Pro Phe Thr
12845               12850                 12855

Leu Asn Phe Thr Ile Thr Asn    Leu Gln Tyr Glu Glu    Asp Met His
12860               12865                 12870

His Pro Gly Ser Arg Lys Phe    Asn Thr Thr Glu Arg    Val Leu Gln
12875               12880                 12885

Gly Leu Leu Gly Pro Met Phe    Lys Asn Thr Ser Val    Gly Leu Leu
12890               12895                 12900

Tyr Ser Gly Cys Arg Leu Thr    Leu Leu Arg Pro Glu    Lys Asn Gly
12905               12910                 12915

Ala Ala Thr Gly Met Asp Ala    Ile Cys Ser His Arg    Leu Asp Pro
12920               12925                 12930

Lys Ser Pro Gly Leu Asn Arg    Glu Gln Leu Tyr Trp    Glu Leu Ser
12935               12940                 12945

Gln Leu Thr His Gly Ile Lys    Glu Leu Gly Pro Tyr    Thr Leu Asp
12950               12955                 12960

Arg Asn Ser Leu Tyr Val Asn    Gly Phe Thr His Arg    Ser Ser Val
12965               12970                 12975

Ala Pro Thr Ser Thr Pro Gly    Thr Ser Thr Val Asp    Leu Gly Thr
12980               12985                 12990

Ser Gly Thr Pro Ser Ser Leu    Pro Ser Pro Thr Thr    Ala Val Pro
12995               13000                 13005

Leu Leu Val Pro Phe Thr Leu    Asn Phe Thr Ile Thr    Asn Leu Gln
13010               13015                 13020

Tyr Gly Glu Asp Met Arg His    Pro Gly Ser Arg Lys    Phe Asn Thr
13025               13030                 13035

Thr Glu Arg Val Leu Gln Gly    Leu Leu Gly Pro Leu    Phe Lys Asn
13040               13045                 13050

Ser Ser Val Gly Pro Leu Tyr    Ser Gly Cys Arg Leu    Ile Ser Leu
13055               13060                 13065

Arg Ser Glu Lys Asp Gly Ala    Ala Thr Gly Val Asp    Ala Ile Cys
13070               13075                 13080

Thr His His Leu Asn Pro Gln    Ser Pro Gly Leu Asp    Arg Glu Gln
13085               13090                 13095

Leu Tyr Trp Gln Leu Ser Gln    Met Thr Asn Gly Ile    Lys Glu Leu
13100               13105                 13110

Gly Pro Tyr Thr Leu Asp Arg    Asn Ser Leu Tyr Val    Asn Gly Phe
13115               13120                 13125

Thr His Arg Ser Ser Gly Leu    Thr Thr Ser Thr Pro    Trp Thr Ser
13130               13135                 13140

Thr Val Asp Leu Gly Thr Ser    Gly Thr Pro Ser Pro    Val Pro Ser
13145               13150                 13155

Pro Thr Thr Thr Gly Pro Leu    Leu Val Pro Phe Thr    Leu Asn Phe
13160               13165                 13170

Thr Ile Thr Asn Leu Gln Tyr    Glu Glu Asn Met Gly    His Pro Gly
13175               13180                 13185

Ser Arg Lys Phe Asn Ile Thr    Glu Ser Val Leu Gln    Gly Leu Leu
13190               13195                 13200

Lys Pro Leu Phe Lys Ser Thr    Ser Val Gly Pro Leu    Tyr Ser Gly
13205               13210                 13215

Cys Arg Leu Thr Leu Leu Arg    Pro Glu Lys Asp Gly    Val Ala Thr
13220               13225                 13230

Arg Val Asp Ala Ile Cys Thr    His Arg Pro Asp Pro    Lys Ile Pro
```

-continued

```
              13235               13240               13245

Gly Leu  Asp Arg Gln Gln Leu  Tyr Trp Glu Leu Ser  Gln Leu Thr
         13250                13255                13260

His Ser  Ile Thr Glu Leu Gly  Pro Tyr Thr Leu Asp  Arg Asp Ser
         13265                13270                13275

Leu Tyr  Val Asn Gly Phe Thr  Gln Arg Ser Ser Val  Pro Thr Thr
         13280                13285                13290

Ser Thr  Pro Gly Thr Phe Thr  Val Gln Pro Glu Thr  Ser Glu Thr
         13295                13300                13305

Pro Ser  Ser Leu Pro Gly Pro  Thr Ala Thr Gly Pro  Val Leu Leu
         13310                13315                13320

Pro Phe  Thr Leu Asn Phe Thr  Ile Thr Asn Leu Gln  Tyr Glu Glu
         13325                13330                13335

Asp Met  Arg Arg Pro Gly Ser  Arg Lys Phe Asn Thr  Thr Glu Arg
         13340                13345                13350

Val Leu  Gln Gly Leu Leu Met  Pro Leu Phe Lys Asn  Thr Ser Val
         13355                13360                13365

Ser Ser  Leu Tyr Ser Gly Cys  Arg Leu Thr Leu Leu  Arg Pro Glu
         13370                13375                13380

Lys Asp  Gly Ala Ala Thr Arg  Val Asp Ala Val Cys  Thr His Arg
         13385                13390                13395

Pro Asp  Pro Lys Ser Pro Gly  Leu Asp Arg Glu Arg  Leu Tyr Trp
         13400                13405                13410

Lys Leu  Ser Gln Leu Thr His  Gly Ile Thr Glu Leu  Gly Pro Tyr
         13415                13420                13425

Thr Leu  Asp Arg His Ser Leu  Tyr Val Asn Gly Phe  Thr His Gln
         13430                13435                13440

Ser Ser  Met Thr Thr Thr Arg  Thr Pro Asp Thr Ser  Thr Met His
         13445                13450                13455

Leu Ala  Thr Ser Arg Thr Pro  Ala Ser Leu Ser Gly  Pro Met Thr
         13460                13465                13470

Ala Ser  Pro Leu Leu Val Leu  Phe Thr Ile Asn Phe  Thr Ile Thr
         13475                13480                13485

Asn Leu  Arg Tyr Glu Glu Asn  Met His His Pro Gly  Ser Arg Lys
         13490                13495                13500

Phe Asn  Thr Thr Glu Arg Val  Leu Gln Gly Leu Leu  Arg Pro Val
         13505                13510                13515

Phe Lys  Asn Thr Ser Val Gly  Pro Leu Tyr Ser Gly  Cys Arg Leu
         13520                13525                13530

Thr Leu  Leu Arg Pro Lys Lys  Asp Gly Ala Ala Thr  Lys Val Asp
         13535                13540                13545

Ala Ile  Cys Thr Tyr Arg Pro  Asp Pro Lys Ser Pro  Gly Leu Asp
         13550                13555                13560

Arg Glu  Gln Leu Tyr Trp Glu  Leu Ser Gln Leu Thr  His Ser Ile
         13565                13570                13575

Thr Glu  Leu Gly Pro Tyr Thr  Leu Asp Arg Asp Ser  Leu Tyr Val
         13580                13585                13590

Asn Gly  Phe Thr Gln Arg Ser  Ser Val Pro Thr Thr  Ser Ile Pro
         13595                13600                13605

Gly Thr  Pro Thr Val Asp Leu  Gly Thr Ser Gly Thr  Pro Val Ser
         13610                13615                13620

Lys Pro  Gly Pro Ser Ala Ala  Ser Pro Leu Leu Val  Leu Phe Thr
         13625                13630                13635
```

-continued

```
Leu Asn Phe Thr Ile Thr Asn Leu Arg Tyr Glu Glu Asn Met Gln
    13640           13645               13650
His Pro Gly Ser Arg Lys Phe Asn Thr Thr Glu Arg Val Leu Gln
    13655           13660               13665
Gly Leu Leu Arg Ser Leu Phe Lys Ser Thr Ser Val Gly Pro Leu
    13670           13675               13680
Tyr Ser Gly Cys Arg Leu Thr Leu Leu Arg Pro Glu Lys Asp Gly
    13685           13690               13695
Thr Ala Thr Gly Val Asp Ala Ile Cys Thr His His Pro Asp Pro
    13700           13705               13710
Lys Ser Pro Arg Leu Asp Arg Glu Gln Leu Tyr Trp Glu Leu Ser
    13715           13720               13725
Gln Leu Thr His Asn Ile Thr Glu Leu Gly Pro Tyr Ala Leu Asp
    13730           13735               13740
Asn Asp Ser Leu Phe Val Asn Gly Phe Thr His Arg Ser Ser Val
    13745           13750               13755
Ser Thr Thr Ser Thr Pro Gly Thr Pro Thr Val Tyr Leu Gly Ala
    13760           13765               13770
Ser Lys Thr Pro Ala Ser Ile Phe Gly Pro Ser Ala Ala Ser His
    13775           13780               13785
Leu Leu Ile Leu Phe Thr Leu Asn Phe Thr Ile Thr Asn Leu Arg
    13790           13795               13800
Tyr Glu Glu Asn Met Trp Pro Gly Ser Arg Lys Phe Asn Thr Thr
    13805           13810               13815
Glu Arg Val Leu Gln Gly Leu Leu Arg Pro Leu Phe Lys Asn Thr
    13820           13825               13830
Ser Val Gly Pro Leu Tyr Ser Gly Cys Arg Leu Thr Leu Leu Arg
    13835           13840               13845
Pro Glu Lys Asp Gly Glu Ala Thr Gly Val Asp Ala Ile Cys Thr
    13850           13855               13860
His Arg Pro Asp Pro Thr Gly Pro Gly Leu Asp Arg Glu Gln Leu
    13865           13870               13875
Tyr Leu Glu Leu Ser Gln Leu Thr His Ser Ile Thr Glu Leu Gly
    13880           13885               13890
Pro Tyr Thr Leu Asp Arg Asp Ser Leu Tyr Val Asn Gly Phe Thr
    13895           13900               13905
His Arg Ser Ser Val Pro Thr Thr Ser Thr Gly Val Val Ser Glu
    13910           13915               13920
Glu Pro Phe Thr Leu Asn Phe Thr Ile Asn Asn Leu Arg Tyr Met
    13925           13930               13935
Ala Asp Met Gly Gln Pro Gly Ser Leu Lys Phe Asn Ile Thr Asp
    13940           13945               13950
Asn Val Met Gln His Leu Leu Ser Pro Leu Phe Gln Arg Ser Ser
    13955           13960               13965
Leu Gly Ala Arg Tyr Thr Gly Cys Arg Val Ile Ala Leu Arg Ser
    13970           13975               13980
Val Lys Asn Gly Ala Glu Thr Arg Val Asp Leu Leu Cys Thr Tyr
    13985           13990               13995
Leu Gln Pro Leu Ser Gly Pro Gly Leu Pro Ile Lys Gln Val Phe
    14000           14005               14010
His Glu Leu Ser Gln Gln Thr His Gly Ile Thr Arg Leu Gly Pro
    14015           14020               14025
```

-continued

| | | | | | | | | | | | |
|---|---|---|---|---|---|---|---|---|---|---|---|
| Tyr | Ser 14030 | Leu | Asp | Lys | Asp 14035 | Ser | Leu | Tyr | Leu 14040 | Asn Gly | Tyr Asn Glu |
| Pro | Gly 14045 | Pro | Asp | Glu | Pro 14050 | Pro | Thr | Thr | Pro 14055 | Lys Pro | Ala Thr Thr |
| Phe | Leu 14060 | Pro | Pro | Leu | Ser 14065 | Glu | Ala | Thr | Thr 14070 | Ala Met | Gly Tyr His |
| Leu | Lys 14075 | Thr | Leu | Thr | Leu 14080 | Asn | Phe | Thr | Ile 14085 | Ser Asn | Leu Gln Tyr |
| Ser | Pro 14090 | Asp | Met | Gly | Lys 14095 | Gly | Ser | Ala | Thr 14100 | Phe Asn | Ser Thr Glu |
| Gly | Val 14105 | Leu | Gln | His | Leu 14110 | Leu | Arg | Pro | Leu 14115 | Phe Gln | Lys Ser Ser |
| Met | Gly 14120 | Pro | Phe | Tyr | Leu 14125 | Gly | Cys | Gln | Leu 14130 | Ile Ser | Leu Arg Pro |
| Glu | Lys 14135 | Asp | Gly | Ala | Ala 14140 | Thr | Gly | Val | Asp 14145 | Thr Thr | Cys Thr Tyr |
| His | Pro 14150 | Asp | Pro | Val | Gly 14155 | Pro | Gly | Leu | Asp 14160 | Ile Gln | Gln Leu Tyr |
| Trp | Glu 14165 | Leu | Ser | Gln | Leu 14170 | Thr | His | Gly | Val 14175 | Thr Gln | Leu Gly Phe |
| Tyr | Val 14180 | Leu | Asp | Arg | Asp 14185 | Ser | Leu | Phe | Ile 14190 | Asn Gly | Tyr Ala Pro |
| Gln | Asn 14195 | Leu | Ser | Ile | Arg 14200 | Gly | Glu | Tyr | Gln 14205 | Ile Asn | Phe His Ile |
| Val | Asn 14210 | Trp | Asn | Leu | Ser 14215 | Asn | Pro | Asp | Pro 14220 | Thr Ser | Ser Glu Tyr |
| Ile | Thr 14225 | Leu | Leu | Arg | Asp 14230 | Ile | Gln | Asp | Lys 14235 | Val Thr | Thr Leu Tyr |
| Lys | Gly 14240 | Ser | Gln | Leu | His 14245 | Asp | Thr | Phe | Arg 14250 | Phe Cys | Leu Val Thr |
| Asn | Leu 14255 | Thr | Met | Asp | Ser 14260 | Val | Leu | Val | Thr 14265 | Val Lys | Ala Leu Phe |
| Ser | Ser 14270 | Asn | Leu | Asp | Pro 14275 | Ser | Leu | Val | Glu 14280 | Gln Val | Phe Leu Asp |
| Lys | Thr 14285 | Leu | Asn | Ala | Ser 14290 | Phe | His | Trp | Leu 14295 | Gly Ser | Thr Tyr Gln |
| Leu | Val 14300 | Asp | Ile | His | Val 14305 | Thr | Glu | Met | Glu 14310 | Ser Ser | Val Tyr Gln |
| Pro | Thr 14315 | Ser | Ser | Ser | Thr 14320 | Gln | His | Phe | Tyr 14325 | Leu Asn | Phe Thr |
| Ile | Thr 14330 | Asn | Leu | Pro | Tyr 14335 | Ser | Gln | Asp | Lys 14340 | Ala Gln | Pro Gly Thr |
| Thr | Asn 14345 | Tyr | Gln | Arg | Asn 14350 | Lys | Arg | Asn | Ile 14355 | Glu Asp | Ala Leu Asn |
| Gln | Leu 14360 | Phe | Arg | Asn | Ser 14365 | Ser | Ile | Lys | Ser 14370 | Tyr Phe | Ser Asp Cys |
| Gln | Val 14375 | Ser | Thr | Phe | Arg 14380 | Ser | Val | Pro | Asn 14385 | Arg His | His Thr Gly |
| Val | Asp 14390 | Ser | Leu | Cys | Asn 14395 | Phe | Ser | Pro | Leu 14400 | Ala Arg | Arg Val Asp |
| Arg | Val 14405 | Ala | Ile | Tyr | Glu 14410 | Glu | Phe | Leu | Arg 14415 | Met Thr | Arg Asn Gly |
| Thr | Gln | Leu | Gln | Asn | Phe | Thr | Leu | Asp | Arg | Ser Ser | Val Leu Val |

```
                14420               14425               14430

Asp Gly  Tyr Ser Pro Asn Arg  Asn Glu Pro Leu Thr  Gly Asn Ser
        14435                14440                14445

Asp Leu  Pro Phe Trp Ala Val  Ile Leu Ile Gly Leu  Ala Gly Leu
        14450                14455                14460

Leu Gly  Val Ile Thr Cys Leu  Ile Cys Gly Val Leu  Val Thr Thr
        14465                14470                14475

Arg Arg  Arg Lys Lys Glu Gly  Glu Tyr Asn Val Gln  Gln Gln Cys
        14480                14485                14490

Pro Gly  Tyr Tyr Gln Ser His  Leu Asp Leu Glu Asp  Leu Gln
        14495                14500                14505

<210> SEQ ID NO 2
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gln Ser Tyr Ile Thr Asp Ser Trp Gly Gln Gly Thr Leu Val Thr
            100                 105                 110

Val Ser Ser
        115

<210> SEQ ID NO 3
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Gln Leu Thr Gln Ser Pro Ser Ala Val Ser Ala Ser Val Gly
1               5                   10                  15

Asp Arg Val Thr Ile Thr Cys Arg Ala Ser Gln Asp Val Ser Lys Trp
                20                  25                  30

Leu Ala Trp Tyr Gln Gln Lys Pro Gly Lys Ala Pro Arg Leu Leu Ile
            35                  40                  45

Ser Ala Ala Ser Gly Leu Gln Ser Trp Val Pro Ser Arg Phe Ser Gly
        50                  55                  60

Ser Gly Ser Gly Thr Glu Phe Thr Leu Ser Ile Ser Ser Leu Gln Pro
65                  70                  75                  80

Glu Asp Phe Ala Thr Tyr Tyr Cys Gln Gln Ala Asn Ser Phe Pro Trp
```

-continued

```
                  85                  90                  95
Thr Phe Gly Gln Gly Thr Lys Val Glu Ile Lys Arg
                 100                 105

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Ser Phe Ser Gly Tyr Tyr
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Asn His Ser Gly Ser Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Arg Gln Ser Tyr Ile Thr Asp Ser
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Asp Val Ser Lys Trp
1               5

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ala Ser
1

<210> SEQ ID NO 9
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 9

Gln Gln Ala Asn Ser Phe Pro Trp Thr
1               5

<210> SEQ ID NO 10
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Ile Ile Met Ser Val Asp Thr Ser Lys Arg Gln Phe Ser Leu
65                  70                  75                  80

Lys Leu Arg Ser Ala Thr Ala Ala Asp Thr Ala Val Tyr Tyr Cys Ala
                85                  90                  95

Arg Trp Ser Pro Phe Ser Tyr Lys Gln Met Tyr Asp Tyr Trp Gly Gln
            100                 105                 110

Gly Thr Leu Val Thr Val Ser Ser
        115                 120

<210> SEQ ID NO 11
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asn Phe Met Leu Thr Gln Pro His Ser Val Ser Glu Ser Pro Gly Lys
1               5                   10                  15

Thr Val Thr Ile Ser Cys Thr Arg Ser Arg Gly Ser Ile Ala Ser Ala
            20                  25                  30

Tyr Val Gln Trp Tyr Gln Gln Arg Pro Gly Ser Ala Pro Ile Thr Val
        35                  40                  45

Ile Tyr Glu Asp Tyr Glu Arg Pro Ser Glu Ile Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Asp
                85                  90                  95

Asn Asp His Val Ile Phe Gly Gly Gly Thr Lys Val Thr Val Leu Gly
            100                 105                 110

<210> SEQ ID NO 12
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Ser Phe Ser Gly Tyr Tyr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Asn His Ser Gly Ser Thr
1               5

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Arg Trp Ser Pro Phe Ser Tyr Lys Gln Met Tyr Asp Tyr
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Ser Ile Ala Ser Ala Tyr
1               5

<210> SEQ ID NO 16
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Asp Tyr
1

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17
```

```
Gln Ser Tyr Asp Asp Asn Asp His Val Ile
1               5                  10
```

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Met Glu Thr Asp Thr Leu Leu Leu Trp Val Leu Leu Leu Trp Val Pro
1               5                   10                  15

Gly Ser Thr Gly
            20
```

<210> SEQ ID NO 19
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Asp Ile Gln Leu Thr Gln Ser Pro Ser Ala Val Ser Ala Ser Val Gly
1               5                   10                  15

Asp Arg Val Thr Ile Thr Cys Arg Ala Ser Gln Asp Val Ser Lys Trp
            20                  25                  30

Leu Ala Trp Tyr Gln Gln Lys Pro Gly Lys Ala Pro Arg Leu Leu Ile
        35                  40                  45

Ser Ala Ala Ser Gly Leu Gln Ser Trp Val Pro Ser Arg Phe Ser Gly
    50                  55                  60

Ser Gly Ser Gly Thr Glu Phe Thr Leu Ser Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys Arg Ser Arg Gly Gly
            100                 105                 110

Gly Gly Ser Gly Gly Gly Gly Ser Gly Gly Gly Ser Leu Glu Met
        115                 120                 125

Ala Gln Val Gln Leu Gln Gln Trp Gly Ala Gly Leu Leu Lys Pro Ser
    130                 135                 140

Glu Thr Leu Ser Leu Thr Cys Ala Val Tyr Gly Gly Ser Phe Ser Gly
145                 150                 155                 160

Tyr Tyr Trp Ser Trp Ile Arg Gln Pro Pro Gly Lys Gly Leu Glu Trp
                165                 170                 175

Ile Gly Glu Ile Asn His Ser Gly Ser Thr Asn Tyr Asn Pro Ser Leu
            180                 185                 190

Lys Ser Arg Val Thr Ile Ser Val Asp Thr Ser Lys Asn Gln Phe Ser
        195                 200                 205

Leu Lys Leu Ser Ser Val Thr Ala Ala Asp Thr Ala Val Tyr Tyr Cys
    210                 215                 220

Ala Arg Gln Ser Tyr Ile Thr Asp Ser Trp Gly Gln Gly Thr Leu Val
225                 230                 235                 240

Thr Val Ser Ser
```

<210> SEQ ID NO 20
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asn Phe Met Leu Thr Gln Pro His Ser Val Ser Glu Ser Pro Gly Lys
1               5                   10                  15

Thr Val Thr Ile Ser Cys Thr Arg Ser Arg Gly Ser Ile Ala Ser Ala
            20                  25                  30

Tyr Val Gln Trp Tyr Gln Arg Pro Gly Ser Ala Pro Ile Thr Val
        35                  40                  45

Ile Tyr Glu Asp Tyr Glu Arg Pro Ser Glu Ile Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Asp
                85                  90                  95

Asn Asp His Val Ile Phe Gly Gly Gly Thr Lys Val Thr Val Leu Gly
            100                 105                 110

Ser Arg Gly Gly Gly Gly Ser Gly Gly Gly Ser Gly Gly Gly Gly
        115                 120                 125

Ser Leu Glu Met Ala Gln Val Gln Leu Gln Gln Trp Gly Ala Gly Leu
130                 135                 140

Leu Lys Pro Ser Glu Thr Leu Ser Leu Thr Cys Ala Val Tyr Gly Gly
145                 150                 155                 160

Ser Phe Ser Gly Tyr Tyr Trp Ser Trp Ile Arg Gln Pro Pro Gly Lys
                165                 170                 175

Gly Leu Glu Trp Ile Gly Glu Ile Asn His Ser Gly Ser Thr Asn Tyr
            180                 185                 190

Asn Pro Ser Leu Lys Ser Arg Ile Ile Met Ser Val Asp Thr Ser Lys
        195                 200                 205

Arg Gln Phe Ser Leu Lys Leu Arg Ser Ala Thr Ala Ala Asp Thr Ala
    210                 215                 220

Val Tyr Tyr Cys Ala Arg Trp Ser Pro Phe Ser Tyr Lys Gln Met Tyr
225                 230                 235                 240

Asp Tyr Trp Gly Gln Gly Thr Leu Val Thr Val Ser Ser
                245                 250

<210> SEQ ID NO 21
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val

```
                    50                  55                  60
Lys Gly Arg Phe Thr Ile Thr Thr Asp Lys Ser Thr Ser Thr Ala Tyr
 65                  70                  75                  80

Met Glu Leu Ser Ser Leu Arg Ser Glu Asp Thr Ala Thr Tyr Tyr Cys
                     85                  90                  95

Ala Arg Tyr Tyr Asp Asp His Tyr Cys Leu Asp Tyr Trp Gly Gln Gly
                100                 105                 110

Thr Thr Val Thr Val Ser Ser Gly Glu Gly Thr Ser Thr Gly Ser Gly
                115                 120                 125

Gly Ser Gly Gly Ser Gly Gly Ala Asp Asp Ile Val Leu Thr Gln Ser
130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
                180                 185                 190

Gly Val Pro Ala Arg Phe Ser Gly Ser Gly Ser Gly Thr Asp Tyr Ser
                195                 200                 205

Leu Thr Ile Asn Ser Leu Glu Ala Glu Asp Ala Ala Thr Tyr Tyr Cys
                210                 215                 220

Gln Gln Trp Ser Ser Asn Pro Leu Thr Phe Gly Gly Gly Thr Lys Val
225                 230                 235                 240

Glu Ile Lys

<210> SEQ ID NO 22
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Glu Thr Asp Thr Leu Leu Leu Trp Val Leu Leu Leu Trp Val Pro
 1               5                  10                  15

Gly Ser Thr Gly Asp Ile Gln Leu Thr Gln Ser Pro Ser Ala Val Ser
                 20                  25                  30

Ala Ser Val Gly Asp Arg Val Thr Ile Thr Cys Arg Ala Ser Gln Asp
             35                  40                  45

Val Ser Lys Trp Leu Ala Trp Tyr Gln Gln Lys Pro Gly Lys Ala Pro
 50                  55                  60

Arg Leu Leu Ile Ser Ala Ala Ser Gly Leu Gln Ser Trp Val Pro Ser
 65                  70                  75                  80

Arg Phe Ser Gly Ser Gly Ser Gly Thr Glu Phe Thr Leu Ser Ile Ser
                 85                  90                  95

Ser Leu Gln Pro Glu Asp Phe Ala Thr Tyr Tyr Cys Gln Gln Ala Asn
                100                 105                 110

Ser Phe Pro Trp Thr Phe Gly Gln Gly Thr Lys Val Glu Ile Lys Arg
            115                 120                 125

Ser Arg Gly Gly Gly Gly Ser Gly Gly Gly Gly Ser Gly Gly Gly Gly
            130                 135                 140

Ser Leu Glu Met Ala Gln Val Gln Leu Gln Gln Trp Gly Ala Gly Leu
145                 150                 155                 160

Leu Lys Pro Ser Glu Thr Leu Ser Leu Thr Cys Ala Val Tyr Gly Gly
```

165                 170                 175
Ser Phe Ser Gly Tyr Tyr Trp Ser Trp Ile Arg Gln Pro Pro Gly Lys
            180                 185                 190

Gly Leu Glu Trp Ile Gly Glu Ile Asn His Ser Gly Ser Thr Asn Tyr
            195                 200                 205

Asn Pro Ser Leu Lys Ser Arg Val Thr Ile Ser Val Asp Thr Ser Lys
            210                 215                 220

Asn Gln Phe Ser Leu Lys Leu Ser Ser Val Thr Ala Ala Asp Thr Ala
225                 230                 235                 240

Val Tyr Tyr Cys Ala Arg Gln Ser Tyr Ile Thr Asp Ser Trp Gly Gln
                245                 250                 255

Gly Thr Leu Val Thr Val Ser Ser Ser Gly Gly Gly Ser Asp
            260                 265                 270

Val Gln Leu Val Gln Ser Gly Ala Glu Val Lys Lys Pro Gly Ala Ser
            275                 280                 285

Val Lys Val Ser Cys Lys Ala Ser Gly Tyr Thr Phe Thr Arg Tyr Thr
            290                 295                 300

Met His Trp Val Arg Gln Ala Pro Gly Gln Gly Leu Glu Trp Ile Gly
305                 310                 315                 320

Tyr Ile Asn Pro Ser Arg Gly Tyr Thr Asn Tyr Ala Asp Ser Val Lys
                325                 330                 335

Gly Arg Phe Thr Ile Thr Thr Asp Lys Ser Thr Ser Thr Ala Tyr Met
            340                 345                 350

Glu Leu Ser Ser Leu Arg Ser Glu Asp Thr Ala Thr Tyr Tyr Cys Ala
            355                 360                 365

Arg Tyr Tyr Asp Asp His Tyr Cys Leu Asp Tyr Trp Gly Gln Gly Thr
            370                 375                 380

Thr Val Thr Val Ser Ser Gly Glu Gly Thr Ser Thr Gly Ser Gly Gly
385                 390                 395                 400

Ser Gly Gly Ser Gly Gly Ala Asp Asp Ile Val Leu Thr Gln Ser Pro
                405                 410                 415

Ala Thr Leu Ser Leu Ser Pro Gly Glu Arg Ala Thr Leu Ser Cys Arg
            420                 425                 430

Ala Ser Gln Ser Val Ser Tyr Met Asn Trp Tyr Gln Gln Lys Pro Gly
            435                 440                 445

Lys Ala Pro Lys Arg Trp Ile Tyr Asp Thr Ser Lys Val Ala Ser Gly
450                 455                 460

Val Pro Ala Arg Phe Ser Gly Ser Gly Ser Gly Thr Asp Tyr Ser Leu
465                 470                 475                 480

Thr Ile Asn Ser Leu Glu Ala Glu Asp Ala Ala Thr Tyr Tyr Cys Gln
                485                 490                 495

Gln Trp Ser Ser Asn Pro Leu Thr Phe Gly Gly Gly Thr Lys Val Glu
            500                 505                 510

Ile Lys His His His His His His
            515                 520

<210> SEQ ID NO 23
<211> LENGTH: 529
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

-continued

```
Met Glu Thr Asp Thr Leu Leu Leu Trp Val Leu Leu Leu Trp Val Pro
 1               5                  10                  15

Gly Ser Thr Gly Asn Phe Met Leu Thr Gln Pro His Ser Val Ser Glu
             20                  25                  30

Ser Pro Gly Lys Thr Val Thr Ile Ser Cys Thr Arg Ser Arg Gly Ser
             35                  40                  45

Ile Ala Ser Ala Tyr Val Gln Trp Tyr Gln Arg Pro Gly Ser Ala
 50                  55                  60

Pro Ile Thr Val Ile Tyr Glu Asp Tyr Glu Arg Pro Ser Glu Ile Pro
 65                  70                  75                  80

Asp Arg Phe Ser Gly Ser Ile Asp Ser Ser Asn Ser Ala Ser Leu
                 85                  90                  95

Thr Ile Ser Gly Leu Lys Thr Glu Asp Glu Ala Asp Tyr Tyr Cys Gln
                100                 105                 110

Ser Tyr Asp Asp Asn Asp His Val Ile Phe Gly Gly Gly Thr Lys Val
                115                 120                 125

Thr Val Leu Gly Ser Arg Gly Gly Gly Ser Gly Gly Gly Ser
        130                 135                 140

Gly Gly Gly Ser Leu Glu Met Ala Gln Val Gln Leu Gln Gln Trp
145                 150                 155                 160

Gly Ala Gly Leu Leu Lys Pro Ser Glu Thr Leu Ser Leu Thr Cys Ala
                165                 170                 175

Val Tyr Gly Gly Ser Phe Ser Gly Tyr Tyr Trp Ser Trp Ile Arg Gln
                180                 185                 190

Pro Pro Gly Lys Gly Leu Glu Trp Ile Gly Glu Ile Asn His Ser Gly
                195                 200                 205

Ser Thr Asn Tyr Asn Pro Ser Leu Lys Ser Arg Ile Ile Met Ser Val
        210                 215                 220

Asp Thr Ser Lys Arg Gln Phe Ser Leu Lys Leu Arg Ser Ala Thr Ala
225                 230                 235                 240

Ala Asp Thr Ala Val Tyr Tyr Cys Ala Arg Trp Ser Pro Phe Ser Tyr
                245                 250                 255

Lys Gln Met Tyr Asp Tyr Trp Gly Gln Gly Thr Leu Val Thr Val Ser
                260                 265                 270

Ser Thr Ser Gly Gly Gly Gly Ser Asp Val Gln Leu Val Gln Ser Gly
        275                 280                 285

Ala Glu Val Lys Lys Pro Gly Ala Ser Val Lys Val Ser Cys Lys Ala
        290                 295                 300

Ser Gly Tyr Thr Phe Thr Arg Tyr Thr Met His Trp Val Arg Gln Ala
305                 310                 315                 320

Pro Gly Gln Gly Leu Glu Trp Ile Gly Tyr Ile Asn Pro Ser Arg Gly
                325                 330                 335

Tyr Thr Asn Tyr Ala Asp Ser Val Lys Gly Arg Phe Thr Ile Thr Thr
                340                 345                 350

Asp Lys Ser Thr Ser Thr Ala Tyr Met Glu Leu Ser Ser Leu Arg Ser
        355                 360                 365

Glu Asp Thr Ala Thr Tyr Tyr Cys Ala Arg Tyr Tyr Asp Asp His Tyr
        370                 375                 380

Cys Leu Asp Tyr Trp Gly Gln Gly Thr Thr Val Thr Val Ser Ser Gly
385                 390                 395                 400

Glu Gly Thr Ser Thr Gly Ser Gly Gly Ser Gly Gly Ser Gly Gly Ala
                405                 410                 415

Asp Asp Ile Val Leu Thr Gln Ser Pro Ala Thr Leu Ser Leu Ser Pro
```

```
                420             425             430
Gly Glu Arg Ala Thr Leu Ser Cys Arg Ala Ser Gln Ser Val Ser Tyr
            435                 440                 445

Met Asn Trp Tyr Gln Gln Lys Pro Gly Lys Ala Pro Lys Arg Trp Ile
    450                 455                 460

Tyr Asp Thr Ser Lys Val Ala Ser Gly Val Pro Ala Arg Phe Ser Gly
465                 470                 475                 480

Ser Gly Ser Gly Thr Asp Tyr Ser Leu Thr Ile Asn Ser Leu Glu Ala
                485                 490                 495

Glu Asp Ala Ala Thr Tyr Tyr Cys Gln Gln Trp Ser Ser Asn Pro Leu
                500                 505                 510

Thr Phe Gly Gly Gly Thr Lys Val Glu Ile Lys His His His His His
            515                 520                 525

His

<210> SEQ ID NO 24
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Trp Glu Leu Ser Gln Leu Thr His Gly Val Thr Gln Leu Gly Phe Tyr
1               5                   10                  15

Val Leu Asp Arg Asp Ser Leu Phe Ile Asn Gly Tyr Ala Pro Gln Asn
            20                  25                  30

Leu Ser Ile Arg Gly Glu Tyr Gln Ile Asn Phe His Ile Val Asn Gln
        35                  40                  45

Asn Leu Ser Asn Pro Asp Pro Thr Ser Ser Glu Tyr Ile Thr Leu Leu
    50                  55                  60

Arg Asp Ile Gln Asp Lys Val Thr Thr Leu Tyr Lys Gly Ser Gln Leu
65                  70                  75                  80

His Asp Thr Phe Arg Phe Cys Leu Val Thr Asn Leu Thr Met Asp Ser
                85                  90                  95

Val Leu Val Thr Val Lys Ala Leu Phe Ser Ser Asn Leu Asp Pro Ser
            100                 105                 110

Leu Val Glu Gln Val Phe Leu Asp Lys Thr Leu Asn Ala Ser Phe His
        115                 120                 125

Gln Leu Gly Ser Thr Tyr Gln Leu Val Asp Ile His Val Thr Glu Met
    130                 135                 140

Glu Ser Ser Val Tyr Gln Pro Thr Ser Ser Ser Thr Gln His Phe
145                 150                 155                 160

Tyr Leu Asn Phe Thr Ile Thr Asn Leu Pro Tyr Ser Gln Asp Lys Ala
                165                 170                 175

Gln Pro Gly Thr Thr Asn Tyr Gln Arg Asn Lys Arg Asn Ile Glu Asp
            180                 185                 190

Ala Leu Asn Gln Leu Phe Arg Asn Ser Ser Ile Lys Ser Tyr Phe Ser
        195                 200                 205

Asp Cys Gln Val Ser Thr Phe Arg Ser Val Pro Asn Arg His His Thr
    210                 215                 220

Gly Val Asp Ser Leu Cys Asn Phe Ser Pro Leu Ala Arg Arg Val Asp
225                 230                 235                 240

Arg Val Ala Ile Tyr Glu Glu Phe Leu Arg Met Thr Arg Asn Gly Thr
```

```
                      245                 250                 255

Gln Leu Gln Asn Phe Thr Leu Asp Arg Ser Ser Val Leu Val Asp Gly
            260                 265                 270

Tyr Ser Pro Asn Arg Asn Glu Pro Leu Thr Gly Asn Ser Asp Leu Pro
        275                 280                 285

Phe Trp Ala Val Ile Leu Ile Gly Leu Ala Gly Leu Leu Gly Leu Ile
290                 295                 300

Thr Cys Leu Ile Cys Gly Val Leu Val Thr Thr Arg Arg Lys Lys
305                 310                 315                 320

Glu Gly Glu Tyr Asn Val Gln Gln Gln Cys Pro Gly Tyr Tyr Gln Ser
            325                 330                 335

His Leu Asp Leu Glu Asp Leu Gln
            340

<210> SEQ ID NO 25
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Asn Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro Phe Trp Ala Val Ile Leu
    50                  55                  60

Ile Gly Leu Ala Gly Leu Leu Gly Leu Ile Thr Cys Leu Ile Cys Gly
65                  70                  75                  80

Val Leu Val Thr Thr Arg Arg Lys Lys Glu Gly Glu Tyr Asn Val
                85                  90                  95

Gln Gln Gln Cys Pro Gly Tyr Tyr Gln Ser His Leu Asp Leu Glu Asp
            100                 105                 110

Leu Gln

<210> SEQ ID NO 26
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asn Phe Ser Pro Leu Ala Arg Arg Val Asp Arg Val Ala Ile Tyr Glu
1               5                   10                  15

Glu Phe Leu Arg Met Asp Leu Pro Phe Trp Ala Val Ile Leu Ile Gly
            20                  25                  30

Leu Ala Gly Leu Leu Gly Leu Ile Thr Cys Leu Ile Cys Gly Val Leu
        35                  40                  45

Val Thr Thr Arg Arg Lys Lys Glu Gly Glu Tyr Asn Val Gln Gln
    50                  55                  60

Gln Cys Pro Gly Tyr Tyr Gln Ser His Leu Asp Leu Glu Asp Leu Gln
65                  70                  75                  80
```

```
<210> SEQ ID NO 27
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Asn Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro Phe Trp Ala Val Ile Leu
    50                  55                  60

Ile Gly Leu Ala Gly Leu Leu Gly Leu Ile Thr Cys Leu Ile Cys Gly
65                  70                  75                  80

Asp Leu Glu Asp Leu Gln
                85

<210> SEQ ID NO 28
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
```

```
                225                 230                 235                 240
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 30
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Gly Ser Pro Val
            35                  40                  45

Lys Ala Gly Val Glu Thr Thr Lys Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 31
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Ala Phe Thr
                20                  25                  30

Leu Asp Arg Ser Ser Val Leu Val Asp Gly Tyr Ser Pro Asn Arg Asn
            35                  40                  45

Glu Pro Leu Thr Gly Asn Ser Asp Leu Pro Phe Trp Ala Val Ile Leu
        50                  55                  60

Ile Gly Leu Ala Gly Leu Leu Gly Leu Ile Thr Cys Leu Ile Cys Gly
65                  70                  75                  80

Val Leu Val Thr Thr Arg Arg Arg Lys Lys Glu Gly Glu Tyr Asn Val
```

```
                    85                  90                  95
Gln Gln Gln Cys Pro Gly Tyr Tyr Gln Ser His Leu Asp Leu Glu Asp
                100                 105                 110

Leu Gln

<210> SEQ ID NO 32
<211> LENGTH: 14447
<212> TYPE: PRT
<213> ORGANISM: Homo sapiens

<400> SEQUENCE: 32

Asp Lys Thr Leu Ala Ser Pro Thr Ser Val Val Gly Arg Thr Thr
1               5                   10                  15

Gln Ser Leu Gly Val Met Ser Ser Ala Leu Pro Glu Ser Thr Ser Arg
                20                  25                  30

Gly Met Thr His Ser Glu Gln Arg Thr Ser Pro Ser Leu Ser Pro Gln
            35                  40                  45

Val Asn Gly Thr Pro Ser Arg Asn Tyr Pro Ala Thr Ser Met Val Ser
    50                  55                  60

Gly Leu Ser Ser Pro Arg Thr Arg Thr Ser Ser Thr Glu Gly Asn Phe
65                  70                  75                  80

Thr Lys Glu Ala Ser Thr Tyr Thr Leu Thr Val Glu Thr Thr Ser Gly
                85                  90                  95

Pro Val Thr Glu Lys Tyr Thr Val Pro Thr Glu Thr Ser Thr Thr Glu
                100                 105                 110

Gly Asp Ser Thr Glu Thr Pro Trp Asp Thr Arg Tyr Ile Pro Val Lys
            115                 120                 125

Ile Thr Ser Pro Met Lys Thr Phe Ala Asp Ser Thr Ala Ser Lys Glu
    130                 135                 140

Asn Ala Pro Val Ser Met Thr Pro Ala Glu Thr Thr Val Thr Asp Ser
145                 150                 155                 160

His Thr Pro Gly Arg Thr Asn Pro Ser Phe Gly Thr Leu Tyr Ser Ser
                165                 170                 175

Phe Leu Asp Leu Ser Pro Lys Gly Thr Pro Asn Ser Arg Gly Glu Thr
                180                 185                 190

Ser Leu Glu Leu Ile Leu Ser Thr Thr Gly Tyr Pro Phe Ser Ser Pro
            195                 200                 205

Glu Pro Gly Ser Ala Gly His Ser Arg Ile Ser Thr Ser Ala Pro Leu
    210                 215                 220

Ser Ser Ser Ala Ser Val Leu Asp Asn Lys Ile Ser Glu Thr Ser Ile
225                 230                 235                 240

Phe Ser Gly Gln Ser Leu Thr Ser Pro Leu Ser Pro Gly Val Pro Glu
                245                 250                 255

Ala Arg Ala Ser Thr Met Pro Asn Ser Ala Ile Pro Phe Ser Met Thr
                260                 265                 270

Leu Ser Asn Ala Glu Thr Ser Ala Glu Arg Val Arg Ser Thr Ile Ser
            275                 280                 285

Ser Leu Gly Thr Pro Ser Ile Ser Thr Lys Gln Thr Ala Glu Thr Ile
    290                 295                 300

Leu Thr Phe His Ala Phe Ala Glu Thr Met Asp Ile Pro Ser Thr His
305                 310                 315                 320

Ile Ala Lys Thr Leu Ala Ser Glu Trp Leu Gly Ser Pro Gly Thr Leu
                325                 330                 335

Gly Gly Thr Ser Thr Ser Ala Leu Thr Thr Thr Ser Pro Ser Thr Thr
```

```
                340             345             350
Leu Val Ser Glu Glu Thr Asn Thr His His Ser Thr Ser Gly Lys Glu
        355                 360             365
Thr Glu Gly Thr Leu Asn Thr Ser Met Thr Pro Leu Glu Thr Ser Ala
    370                 375             380
Pro Gly Glu Glu Ser Glu Met Thr Ala Thr Leu Val Pro Thr Leu Gly
385                 390             395                 400
Phe Thr Thr Leu Asp Ser Lys Ile Arg Ser Pro Ser Gln Val Ser Ser
                405             410             415
Ser His Pro Thr Arg Glu Leu Arg Thr Thr Gly Ser Thr Ser Gly Arg
            420             425             430
Gln Ser Ser Ser Thr Ala Ala His Gly Ser Ser Asp Ile Leu Arg Ala
        435             440             445
Thr Thr Ser Ser Thr Ser Lys Ala Ser Ser Trp Thr Ser Glu Ser Thr
        450             455             460
Ala Gln Gln Phe Ser Glu Pro Gln His Thr Gln Trp Val Glu Thr Ser
465             470              475                 480
Pro Ser Met Lys Thr Glu Arg Pro Pro Ala Ser Thr Ser Val Ala Ala
                485             490             495
Pro Ile Thr Thr Ser Val Pro Ser Val Val Ser Gly Phe Thr Thr Leu
                500             505             510
Lys Thr Ser Ser Thr Lys Gly Ile Trp Leu Glu Glu Thr Ser Ala Asp
            515             520             525
Thr Leu Ile Gly Glu Ser Thr Ala Gly Pro Thr Thr His Gln Phe Ala
        530             535             540
Val Pro Thr Gly Ile Ser Met Thr Gly Gly Ser Ser Thr Arg Gly Ser
545             550             555                 560
Gln Gly Thr Thr His Leu Leu Thr Arg Ala Thr Ala Ser Ser Glu Thr
                565             570             575
Ser Ala Asp Leu Thr Leu Ala Thr Asn Gly Val Pro Val Ser Val Ser
            580             585             590
Pro Ala Val Ser Lys Thr Ala Ala Gly Ser Ser Pro Pro Gly Gly Thr
        595             600             605
Lys Pro Ser Tyr Thr Met Val Ser Ser Val Ile Pro Glu Thr Ser Ser
        610             615             620
Leu Gln Ser Ser Ala Phe Arg Glu Gly Thr Ser Leu Gly Leu Thr Pro
625             630             635                 640
Leu Asn Thr Arg His Pro Phe Ser Ser Pro Glu Pro Asp Ser Ala Gly
                645             650             655
His Thr Lys Ile Ser Thr Ser Ile Pro Leu Leu Ser Ser Ala Ser Val
            660             665             670
Leu Glu Asp Lys Val Ser Ala Thr Ser Thr Phe Ser His His Lys Ala
        675             680             685
Thr Ser Ser Ile Thr Thr Gly Thr Pro Glu Ile Ser Thr Lys Thr Lys
        690             695             700
Pro Ser Ser Ala Val Leu Ser Ser Met Thr Leu Ser Asn Ala Ala Thr
705             710             715                 720
Ser Pro Glu Arg Val Arg Asn Ala Thr Ser Pro Leu Thr His Pro Ser
                725             730             735
Pro Ser Gly Glu Glu Thr Ala Gly Ser Val Leu Thr Leu Ser Thr Ser
            740             745             750
Ala Glu Thr Thr Asp Ser Pro Asn Ile His Pro Thr Gly Thr Leu Thr
        755             760             765
```

-continued

```
Ser Glu Ser Ser Glu Ser Pro Ser Thr Leu Ser Leu Pro Ser Val Ser
    770                 775                 780

Gly Val Lys Thr Thr Phe Ser Ser Thr Pro Ser Thr His Leu Phe
785                 790                 795                 800

Thr Ser Gly Glu Glu Thr Glu Glu Thr Ser Asn Pro Val Ser Gln
                805                 810                 815

Pro Glu Thr Ser Val Ser Arg Val Arg Thr Thr Leu Ala Ser Thr Ser
                820                 825                 830

Val Pro Thr Pro Val Phe Pro Thr Met Asp Thr Trp Pro Thr Arg Ser
            835                 840                 845

Ala Gln Phe Ser Ser Ser His Leu Val Ser Glu Leu Arg Ala Thr Ser
    850                 855                 860

Ser Thr Ser Val Thr Asn Ser Thr Gly Ser Ala Leu Pro Lys Ile Ser
865                 870                 875                 880

His Leu Thr Gly Thr Ala Thr Met Ser Gln Thr Asn Arg Asp Thr Phe
                885                 890                 895

Asn Asp Ser Ala Ala Pro Gln Ser Thr Thr Trp Pro Glu Thr Ser Pro
                900                 905                 910

Arg Phe Lys Thr Gly Leu Pro Ser Ala Thr Thr Val Ser Thr Ser
    915                 920                 925

Ala Thr Ser Leu Ser Ala Thr Val Met Val Ser Lys Phe Thr Ser Pro
930                 935                 940

Ala Thr Ser Ser Met Glu Ala Thr Ser Ile Arg Glu Pro Ser Thr Thr
945                 950                 955                 960

Ile Leu Thr Thr Glu Thr Thr Asn Gly Pro Gly Ser Met Ala Val Ala
                965                 970                 975

Ser Thr Asn Ile Pro Ile Gly Lys Gly Tyr Ile Thr Glu Gly Arg Leu
                980                 985                 990

Asp Thr Ser His Leu Pro Ile Gly Thr Thr Ala Ser Ser Glu Thr Ser
                995                 1000                1005

Met Asp Phe Thr Met Ala Lys Glu Ser Val Ser Met Ser Val Ser
    1010                1015                1020

Pro Ser Gln Ser Met Asp Ala Ala Gly Ser Ser Thr Pro Gly Arg
    1025                1030                1035

Thr Ser Gln Phe Val Asp Thr Phe Ser Asp Asp Val Tyr His Leu
    1040                1045                1050

Thr Ser Arg Glu Ile Thr Ile Pro Arg Asp Gly Thr Ser Ser Ala
    1055                1060                1065

Leu Thr Pro Gln Met Thr Ala Thr His Pro Pro Ser Pro Asp Pro
    1070                1075                1080

Gly Ser Ala Arg Ser Thr Trp Leu Gly Ile Leu Ser Ser Ser Pro
    1085                1090                1095

Ser Ser Pro Thr Pro Lys Val Thr Met Ser Ser Thr Phe Ser Thr
    1100                1105                1110

Gln Arg Val Thr Thr Ser Met Ile Met Asp Thr Val Glu Thr Ser
    1115                1120                1125

Arg Trp Asn Met Pro Asn Leu Pro Ser Thr Thr Ser Leu Thr Pro
    1130                1135                1140

Ser Asn Ile Pro Thr Ser Gly Ala Ile Gly Lys Ser Thr Leu Val
    1145                1150                1155

Pro Leu Asp Thr Pro Ser Pro Ala Thr Ser Leu Glu Ala Ser Glu
    1160                1165                1170
```

```
Gly Gly Leu Pro Thr Leu Ser Thr Tyr Pro Glu Ser Thr Asn Thr
1175                 1180                1185

Pro Ser Ile His Leu Gly Ala His Ala Ser Ser Glu Ser Pro Ser
1190                 1195                1200

Thr Ile Lys Leu Thr Met Ala Ser Val Val Lys Pro Gly Ser Tyr
1205                 1210                1215

Thr Pro Leu Thr Phe Pro Ser Ile Glu Thr His Ile His Val Ser
1220                 1225                1230

Thr Ala Arg Met Ala Tyr Ser Ser Gly Ser Ser Pro Glu Met Thr
1235                 1240                1245

Ala Pro Gly Glu Thr Asn Thr Gly Ser Thr Trp Asp Pro Thr Thr
1250                 1255                1260

Tyr Ile Thr Thr Thr Asp Pro Lys Asp Thr Ser Ser Ala Gln Val
1265                 1270                1275

Ser Thr Pro His Ser Val Arg Thr Leu Arg Thr Thr Glu Asn His
1280                 1285                1290

Pro Lys Thr Glu Ser Ala Thr Pro Ala Ala Tyr Ser Gly Ser Pro
1295                 1300                1305

Lys Ile Ser Ser Ser Pro Asn Leu Thr Ser Pro Ala Thr Lys Ala
1310                 1315                1320

Trp Thr Ile Thr Asp Thr Thr Glu His Ser Thr Gln Leu His Tyr
1325                 1330                1335

Thr Lys Leu Ala Glu Lys Ser Ser Gly Phe Glu Thr Gln Ser Ala
1340                 1345                1350

Pro Gly Pro Val Ser Val Val Ile Pro Thr Ser Pro Thr Ile Gly
1355                 1360                1365

Ser Ser Thr Leu Glu Leu Thr Ser Asp Val Pro Gly Glu Pro Leu
1370                 1375                1380

Val Leu Ala Pro Ser Glu Gln Thr Thr Ile Thr Leu Pro Met Ala
1385                 1390                1395

Thr Trp Leu Ser Thr Ser Leu Thr Glu Glu Met Ala Ser Thr Asp
1400                 1405                1410

Leu Asp Ile Ser Ser Pro Ser Ser Pro Met Ser Thr Phe Ala Ile
1415                 1420                1425

Phe Pro Pro Met Ser Thr Pro Ser His Glu Leu Ser Lys Ser Glu
1430                 1435                1440

Ala Asp Thr Ser Ala Ile Arg Asn Thr Asp Ser Thr Thr Leu Asp
1445                 1450                1455

Gln His Leu Gly Ile Arg Ser Leu Gly Arg Thr Gly Asp Leu Thr
1460                 1465                1470

Thr Val Pro Ile Thr Pro Leu Thr Thr Thr Trp Thr Ser Val Ile
1475                 1480                1485

Glu His Ser Thr Gln Ala Gln Asp Thr Leu Ser Ala Thr Met Ser
1490                 1495                1500

Pro Thr His Val Thr Gln Ser Leu Lys Asp Gln Thr Ser Ile Pro
1505                 1510                1515

Ala Ser Ala Ser Pro Ser His Leu Thr Glu Val Tyr Pro Glu Leu
1520                 1525                1530

Gly Thr Gln Gly Arg Ser Ser Ser Glu Ala Thr Thr Phe Trp Lys
1535                 1540                1545

Pro Ser Thr Asp Thr Leu Ser Arg Glu Ile Glu Thr Gly Pro Thr
1550                 1555                1560

Asn Ile Gln Ser Thr Pro Pro Met Asp Asn Thr Thr Thr Gly Ser
```

```
                1565                1570                1575

Ser  Ser  Ser  Gly  Val  Thr  Leu  Gly  Ile  Ala  His  Leu  Pro  Ile  Gly
          1580                1585                1590

Thr  Ser  Ser  Pro  Ala  Glu  Thr  Ser  Thr  Asn  Met  Ala  Leu  Glu  Arg
     1595                1600                1605

Arg  Ser  Ser  Thr  Ala  Thr  Val  Ser  Met  Ala  Gly  Thr  Met  Gly  Leu
     1610                1615                1620

Leu  Val  Thr  Ser  Ala  Pro  Gly  Arg  Ser  Ile  Ser  Gln  Ser  Leu  Gly
     1625                1630                1635

Arg  Val  Ser  Ser  Val  Leu  Ser  Glu  Ser  Thr  Thr  Glu  Gly  Val  Thr
     1640                1645                1650

Asp  Ser  Ser  Lys  Gly  Ser  Ser  Pro  Arg  Leu  Asn  Thr  Gln  Gly  Asn
     1655                1660                1665

Thr  Ala  Leu  Ser  Ser  Ser  Leu  Glu  Pro  Ser  Tyr  Ala  Glu  Gly  Ser
     1670                1675                1680

Gln  Met  Ser  Thr  Ser  Ile  Pro  Leu  Thr  Ser  Ser  Pro  Thr  Thr  Pro
     1685                1690                1695

Asp  Val  Glu  Phe  Ile  Gly  Gly  Ser  Thr  Phe  Trp  Thr  Lys  Glu  Val
     1700                1705                1710

Thr  Thr  Val  Met  Thr  Ser  Asp  Ile  Ser  Lys  Ser  Ser  Ala  Arg  Thr
     1715                1720                1725

Glu  Ser  Ser  Ser  Ala  Thr  Leu  Met  Ser  Thr  Ala  Leu  Gly  Ser  Thr
     1730                1735                1740

Glu  Asn  Thr  Gly  Lys  Glu  Lys  Leu  Arg  Thr  Ala  Ser  Met  Asp  Leu
     1745                1750                1755

Pro  Ser  Pro  Thr  Pro  Ser  Met  Glu  Val  Thr  Pro  Trp  Ile  Ser  Leu
     1760                1765                1770

Thr  Leu  Ser  Asn  Ala  Pro  Asn  Thr  Thr  Asp  Ser  Leu  Asp  Leu  Ser
     1775                1780                1785

His  Gly  Val  His  Thr  Ser  Ser  Ala  Gly  Thr  Leu  Ala  Thr  Asp  Arg
     1790                1795                1800

Ser  Leu  Asn  Thr  Gly  Val  Thr  Arg  Ala  Ser  Arg  Leu  Glu  Asn  Gly
     1805                1810                1815

Ser  Asp  Thr  Ser  Ser  Lys  Ser  Leu  Ser  Met  Gly  Asn  Ser  Thr  His
     1820                1825                1830

Thr  Ser  Met  Thr  Tyr  Thr  Glu  Lys  Ser  Glu  Val  Ser  Ser  Ser  Ile
     1835                1840                1845

His  Pro  Arg  Pro  Glu  Thr  Ser  Ala  Pro  Gly  Ala  Glu  Thr  Thr  Leu
     1850                1855                1860

Thr  Ser  Thr  Pro  Gly  Asn  Arg  Ala  Ile  Ser  Leu  Thr  Leu  Pro  Phe
     1865                1870                1875

Ser  Ser  Ile  Pro  Val  Glu  Glu  Val  Ile  Ser  Thr  Gly  Ile  Thr  Ser
     1880                1885                1890

Gly  Pro  Asp  Ile  Asn  Ser  Ala  Pro  Met  Thr  His  Ser  Pro  Ile  Thr
     1895                1900                1905

Pro  Pro  Thr  Ile  Val  Trp  Thr  Ser  Thr  Gly  Thr  Ile  Glu  Gln  Ser
     1910                1915                1920

Thr  Gln  Pro  Leu  His  Ala  Val  Ser  Ser  Glu  Lys  Val  Ser  Val  Gln
     1925                1930                1935

Thr  Gln  Ser  Thr  Pro  Tyr  Val  Asn  Ser  Val  Ala  Val  Ser  Ala  Ser
     1940                1945                1950

Pro  Thr  His  Glu  Asn  Ser  Val  Ser  Ser  Gly  Ser  Ser  Thr  Ser  Ser
     1955                1960                1965
```

-continued

```
Pro Tyr Ser Ser Ala Ser Leu Glu Ser Leu Asp Ser Thr Ile Ser
    1970              1975              1980

Arg Arg Asn Ala Ile Thr Ser Trp Leu Trp Asp Leu Thr Thr Ser
    1985              1990              1995

Leu Pro Thr Thr Thr Trp Pro Ser Thr Ser Leu Ser Glu Ala Leu
    2000              2005              2010

Ser Ser Gly His Ser Gly Val Ser Asn Pro Ser Ser Thr Thr Thr
    2015              2020              2025

Glu Phe Pro Leu Phe Ser Ala Ala Ser Thr Ser Ala Ala Lys Gln
    2030              2035              2040

Arg Asn Pro Glu Thr Glu Thr His Gly Pro Gln Asn Thr Ala Ala
    2045              2050              2055

Ser Thr Leu Asn Thr Asp Ala Ser Ser Val Thr Gly Leu Ser Glu
    2060              2065              2070

Thr Pro Val Gly Ala Ser Ile Ser Ser Glu Val Pro Leu Pro Met
    2075              2080              2085

Ala Ile Thr Ser Arg Ser Asp Val Ser Gly Leu Thr Ser Glu Ser
    2090              2095              2100

Thr Ala Asn Pro Ser Leu Gly Thr Ala Ser Ser Ala Gly Thr Lys
    2105              2110              2115

Leu Thr Arg Thr Ile Ser Leu Pro Thr Ser Glu Ser Leu Val Ser
    2120              2125              2130

Phe Arg Met Asn Lys Asp Pro Trp Thr Val Ser Ile Pro Leu Gly
    2135              2140              2145

Ser His Pro Thr Thr Asn Thr Glu Thr Ser Ile Pro Val Asn Ser
    2150              2155              2160

Ala Gly Pro Pro Gly Leu Ser Thr Val Ala Ser Asp Val Ile Asp
    2165              2170              2175

Thr Pro Ser Asp Gly Ala Glu Ser Ile Pro Thr Val Ser Phe Ser
    2180              2185              2190

Pro Ser Pro Asp Thr Glu Val Thr Thr Ile Ser His Phe Pro Glu
    2195              2200              2205

Lys Thr Thr His Ser Phe Arg Thr Ile Ser Ser Leu Thr His Glu
    2210              2215              2220

Leu Thr Ser Arg Val Thr Pro Ile Pro Gly Asp Trp Met Ser Ser
    2225              2230              2235

Ala Met Ser Thr Lys Pro Thr Gly Ala Ser Pro Ser Ile Thr Leu
    2240              2245              2250

Gly Glu Arg Arg Thr Ile Thr Ser Ala Ala Pro Thr Thr Ser Pro
    2255              2260              2265

Ile Val Leu Thr Ala Ser Phe Thr Glu Thr Ser Thr Val Ser Leu
    2270              2275              2280

Asp Asn Glu Thr Thr Val Lys Thr Ser Asp Ile Leu Asp Ala Arg
    2285              2290              2295

Lys Thr Asn Glu Leu Pro Ser Asp Ser Ser Ser Ser Ser Asp Leu
    2300              2305              2310

Ile Asn Thr Ser Ile Ala Ser Ser Thr Met Asp Val Thr Lys Thr
    2315              2320              2325

Ala Ser Ile Ser Pro Thr Ser Ile Ser Gly Met Thr Ala Ser Ser
    2330              2335              2340

Ser Pro Ser Leu Phe Ser Ser Asp Arg Pro Gln Val Pro Thr Ser
    2345              2350              2355
```

-continued

```
Thr Thr Glu Thr Asn Thr Ala Thr Ser Pro Ser Val Ser Ser Asn
    2360             2365             2370

Thr Tyr Ser Leu Asp Gly Gly Ser Asn Val Gly Gly Thr Pro Ser
    2375             2380             2385

Thr Leu Pro Pro Phe Thr Ile Thr His Pro Val Glu Thr Ser Ser
    2390             2395             2400

Ala Leu Leu Ala Trp Ser Arg Pro Val Arg Thr Phe Ser Thr Met
    2405             2410             2415

Val Ser Thr Asp Thr Ala Ser Gly Glu Asn Pro Thr Ser Ser Asn
    2420             2425             2430

Ser Val Val Thr Ser Val Pro Ala Pro Gly Thr Trp Thr Ser Val
    2435             2440             2445

Gly Ser Thr Thr Asp Leu Pro Ala Met Gly Phe Leu Lys Thr Ser
    2450             2455             2460

Pro Ala Gly Glu Ala His Ser Leu Leu Ala Ser Thr Ile Glu Pro
    2465             2470             2475

Ala Thr Ala Phe Thr Pro His Leu Ser Ala Ala Val Val Thr Gly
    2480             2485             2490

Ser Ser Ala Thr Ser Glu Ala Ser Leu Leu Thr Thr Ser Glu Ser
    2495             2500             2505

Lys Ala Ile His Ser Ser Pro Gln Thr Pro Thr Pro Thr Pro Ser
    2510             2515             2520

Gly Ala Asn Trp Glu Thr Ser Ala Thr Pro Glu Ser Leu Leu Val
    2525             2530             2535

Val Thr Glu Thr Ser Asp Thr Thr Leu Thr Ser Lys Ile Leu Val
    2540             2545             2550

Thr Asp Thr Ile Leu Phe Ser Thr Val Ser Thr Pro Pro Ser Lys
    2555             2560             2565

Phe Pro Ser Thr Gly Thr Leu Ser Gly Ala Ser Phe Pro Thr Leu
    2570             2575             2580

Leu Pro Asp Thr Pro Ala Ile Pro Leu Thr Ala Thr Glu Pro Thr
    2585             2590             2595

Ser Ser Leu Ala Thr Ser Phe Asp Ser Thr Pro Leu Val Thr Ile
    2600             2605             2610

Ala Ser Asp Ser Leu Gly Thr Val Pro Glu Thr Thr Leu Thr Met
    2615             2620             2625

Ser Glu Thr Ser Asn Gly Asp Ala Leu Val Leu Lys Thr Val Ser
    2630             2635             2640

Asn Pro Asp Arg Ser Ile Pro Gly Ile Thr Ile Gln Gly Val Thr
    2645             2650             2655

Glu Ser Pro Leu His Pro Ser Ser Thr Ser Pro Ser Lys Ile Val
    2660             2665             2670

Ala Pro Arg Asn Thr Thr Tyr Glu Gly Ser Ile Thr Val Ala Leu
    2675             2680             2685

Ser Thr Leu Pro Ala Gly Thr Thr Gly Ser Leu Val Phe Ser Gln
    2690             2695             2700

Ser Ser Glu Asn Ser Glu Thr Thr Ala Leu Val Asp Ser Ser Ala
    2705             2710             2715

Gly Leu Glu Arg Ala Ser Val Met Pro Leu Thr Thr Gly Ser Gln
    2720             2725             2730

Gly Met Ala Ser Ser Gly Gly Ile Arg Ser Gly Ser Thr His Ser
    2735             2740             2745

Thr Gly Thr Lys Thr Phe Ser Ser Leu Pro Leu Thr Met Asn Pro
```

```
              2750                2755                2760

Gly Glu Val Thr Ala Met Ser Glu Ile Thr Thr Asn Arg Leu Thr
    2765                2770                2775

Ala Thr Gln Ser Thr Ala Pro Lys Gly Ile Pro Val Lys Pro Thr
    2780                2785                2790

Ser Ala Glu Ser Gly Leu Leu Thr Pro Val Ser Ala Ser Ser Ser
    2795                2800                2805

Pro Ser Lys Ala Phe Ala Ser Leu Thr Thr Ala Pro Pro Thr Trp
    2810                2815                2820

Gly Ile Pro Gln Ser Thr Leu Thr Phe Glu Phe Ser Glu Val Pro
    2825                2830                2835

Ser Leu Asp Thr Lys Ser Ala Ser Leu Pro Thr Pro Gly Gln Ser
    2840                2845                2850

Leu Asn Thr Ile Pro Asp Ser Asp Ala Ser Thr Ala Ser Ser Ser
    2855                2860                2865

Leu Ser Lys Ser Pro Glu Lys Asn Pro Arg Ala Arg Met Met Thr
    2870                2875                2880

Ser Thr Lys Ala Ile Ser Ala Ser Ser Phe Gln Ser Thr Gly Phe
    2885                2890                2895

Thr Glu Thr Pro Glu Gly Ser Ala Ser Pro Ser Met Ala Gly His
    2900                2905                2910

Glu Pro Arg Val Pro Thr Ser Gly Thr Gly Asp Pro Arg Tyr Ala
    2915                2920                2925

Ser Glu Ser Met Ser Tyr Pro Asp Pro Ser Lys Ala Ser Ser Ala
    2930                2935                2940

Met Thr Ser Thr Ser Leu Ala Ser Lys Leu Thr Thr Leu Phe Ser
    2945                2950                2955

Thr Gly Gln Ala Ala Arg Ser Gly Ser Ser Ser Ser Pro Ile Ser
    2960                2965                2970

Leu Ser Thr Glu Lys Glu Thr Ser Phe Leu Ser Pro Thr Ala Ser
    2975                2980                2985

Thr Ser Arg Lys Thr Ser Leu Phe Leu Gly Pro Ser Met Ala Arg
    2990                2995                3000

Gln Pro Asn Ile Leu Val His Leu Gln Thr Ser Ala Leu Thr Leu
    3005                3010                3015

Ser Pro Thr Ser Thr Leu Asn Met Ser Gln Glu Glu Pro Pro Glu
    3020                3025                3030

Leu Thr Ser Ser Gln Thr Ile Ala Glu Glu Glu Gly Thr Thr Ala
    3035                3040                3045

Glu Thr Gln Thr Leu Thr Phe Thr Pro Ser Glu Thr Pro Thr Ser
    3050                3055                3060

Leu Leu Pro Val Ser Ser Pro Thr Glu Pro Thr Ala Arg Arg Lys
    3065                3070                3075

Ser Ser Pro Glu Thr Trp Ala Ser Ser Ile Ser Val Pro Ala Lys
    3080                3085                3090

Thr Ser Leu Val Glu Thr Thr Asp Gly Thr Leu Val Thr Thr Ile
    3095                3100                3105

Lys Met Ser Ser Gln Ala Ala Gln Gly Asn Ser Thr Trp Pro Ala
    3110                3115                3120

Pro Ala Glu Glu Thr Gly Ser Ser Pro Ala Gly Thr Ser Pro Gly
    3125                3130                3135

Ser Pro Glu Met Ser Thr Thr Leu Lys Ile Met Ser Ser Lys Glu
    3140                3145                3150
```

```
Pro Ser Ile Ser Pro Glu Ile Arg Ser Thr Val Arg Asn Ser Pro
    3155            3160                3165

Trp Lys Thr Pro Glu Thr Thr Val Pro Met Glu Thr Thr Val Glu
    3170            3175                3180

Pro Val Thr Leu Gln Ser Thr Ala Leu Gly Ser Gly Ser Thr Ser
    3185            3190                3195

Ile Ser His Leu Pro Thr Gly Thr Thr Ser Pro Thr Lys Ser Pro
    3200            3205                3210

Thr Glu Asn Met Leu Ala Thr Glu Arg Val Ser Leu Ser Pro Ser
    3215            3220                3225

Pro Pro Glu Ala Trp Thr Asn Leu Tyr Ser Gly Thr Pro Gly Gly
    3230            3235                3240

Thr Arg Gln Ser Leu Ala Thr Met Ser Ser Val Ser Leu Glu Ser
    3245            3250                3255

Pro Thr Ala Arg Ser Ile Thr Gly Thr Gly Gln Gln Ser Ser Pro
    3260            3265                3270

Glu Leu Val Ser Lys Thr Thr Gly Met Glu Phe Ser Met Trp His
    3275            3280                3285

Gly Ser Thr Gly Gly Thr Thr Gly Asp Thr His Val Ser Leu Ser
    3290            3295                3300

Thr Ser Ser Asn Ile Leu Glu Asp Pro Val Thr Ser Pro Asn Ser
    3305            3310                3315

Val Ser Ser Leu Thr Asp Lys Ser Lys His Lys Thr Glu Thr Trp
    3320            3325                3330

Val Ser Thr Thr Ala Ile Pro Ser Thr Val Leu Asn Asn Lys Ile
    3335            3340                3345

Met Ala Ala Glu Gln Gln Thr Ser Arg Ser Val Asp Glu Ala Tyr
    3350            3355                3360

Ser Ser Thr Ser Ser Trp Ser Asp Gln Thr Ser Gly Ser Asp Ile
    3365            3370                3375

Thr Leu Gly Ala Ser Pro Asp Val Thr Asn Thr Leu Tyr Ile Thr
    3380            3385                3390

Ser Thr Ala Gln Thr Thr Ser Leu Val Ser Leu Pro Ser Gly Asp
    3395            3400                3405

Gln Gly Ile Thr Ser Leu Thr Asn Pro Ser Gly Gly Lys Thr Ser
    3410            3415                3420

Ser Ala Ser Ser Val Thr Ser Pro Ser Ile Gly Leu Glu Thr Leu
    3425            3430                3435

Arg Ala Asn Val Ser Ala Val Lys Ser Asp Ile Ala Pro Thr Ala
    3440            3445                3450

Gly His Leu Ser Gln Thr Ser Ser Pro Ala Glu Val Ser Ile Leu
    3455            3460                3465

Asp Val Thr Thr Ala Pro Thr Pro Gly Ile Ser Thr Thr Ile Thr
    3470            3475                3480

Thr Met Gly Thr Asn Ser Ile Ser Thr Thr Thr Pro Asn Pro Glu
    3485            3490                3495

Val Gly Met Ser Thr Met Asp Ser Thr Pro Ala Thr Glu Arg Arg
    3500            3505                3510

Thr Thr Ser Thr Glu His Pro Ser Thr Trp Ser Ser Thr Ala Ala
    3515            3520                3525

Ser Asp Ser Trp Thr Val Thr Asp Met Thr Ser Asn Leu Lys Val
    3530            3535                3540
```

```
Ala Arg Ser Pro Gly Thr Ile Ser Thr Met His Thr Thr Ser Phe
    3545                3550                3555

Leu Ala Ser Ser Thr Glu Leu Asp Ser Met Ser Thr Pro His Gly
    3560                3565                3570

Arg Ile Thr Val Ile Gly Thr Ser Leu Val Thr Pro Ser Ser Asp
    3575                3580                3585

Ala Ser Ala Val Lys Thr Glu Thr Ser Thr Ser Glu Arg Thr Leu
    3590                3595                3600

Ser Pro Ser Asp Thr Thr Ala Ser Thr Pro Ile Ser Thr Phe Ser
    3605                3610                3615

Arg Val Gln Arg Met Ser Ile Ser Val Pro Asp Ile Leu Ser Thr
    3620                3625                3630

Ser Trp Thr Pro Ser Ser Thr Glu Ala Glu Asp Val Pro Val Ser
    3635                3640                3645

Met Val Ser Thr Asp His Ala Ser Thr Lys Thr Asp Pro Asn Thr
    3650                3655                3660

Pro Leu Ser Thr Phe Leu Phe Asp Ser Leu Ser Thr Leu Asp Trp
    3665                3670                3675

Asp Thr Gly Arg Ser Leu Ser Ser Ala Thr Ala Thr Thr Ser Ala
    3680                3685                3690

Pro Gln Gly Ala Thr Thr Pro Gln Glu Leu Thr Leu Glu Thr Met
    3695                3700                3705

Ile Ser Pro Ala Thr Ser Gln Leu Pro Phe Ser Ile Gly His Ile
    3710                3715                3720

Thr Ser Ala Val Thr Pro Ala Ala Met Ala Arg Ser Ser Gly Val
    3725                3730                3735

Thr Phe Ser Arg Pro Asp Pro Thr Ser Lys Lys Ala Glu Gln Thr
    3740                3745                3750

Ser Thr Gln Leu Pro Thr Thr Thr Ser Ala His Pro Gly Gln Val
    3755                3760                3765

Pro Arg Ser Ala Ala Thr Thr Leu Asp Val Ile Pro His Thr Ala
    3770                3775                3780

Lys Thr Pro Asp Ala Thr Phe Gln Arg Gln Gly Gln Thr Ala Leu
    3785                3790                3795

Thr Thr Glu Ala Arg Ala Thr Ser Asp Ser Trp Asn Glu Lys Glu
    3800                3805                3810

Lys Ser Thr Pro Ser Ala Pro Trp Ile Thr Glu Met Met Asn Ser
    3815                3820                3825

Val Ser Glu Asp Thr Ile Lys Glu Val Thr Ser Ser Ser Ser Val
    3830                3835                3840

Leu Arg Thr Leu Asn Thr Leu Asp Ile Asn Leu Glu Ser Gly Thr
    3845                3850                3855

Thr Ser Ser Pro Ser Trp Lys Ser Ser Pro Tyr Glu Arg Ile Ala
    3860                3865                3870

Pro Ser Glu Ser Thr Thr Asp Lys Glu Ala Ile His Pro Ser Thr
    3875                3880                3885

Asn Thr Val Glu Thr Thr Gly Trp Val Thr Ser Ser Glu His Ala
    3890                3895                3900

Ser His Ser Thr Ile Pro Ala His Ser Ala Ser Ser Lys Leu Thr
    3905                3910                3915

Ser Pro Val Val Thr Thr Ser Thr Arg Glu Gln Ala Ile Val Ser
    3920                3925                3930

Met Ser Thr Thr Thr Trp Pro Glu Ser Thr Arg Ala Arg Thr Glu
```

```
                  3935              3940              3945

Pro Asn Ser Phe Leu Thr Ile Glu Leu Arg Asp Val Ser Pro Tyr
    3950              3955              3960

Met Asp Thr Ser Ser Thr Thr Gln Thr Ser Ile Ile Ser Ser Pro
    3965              3970              3975

Gly Ser Thr Ala Ile Thr Lys Gly Pro Arg Thr Glu Ile Thr Ser
    3980              3985              3990

Ser Lys Arg Ile Ser Ser Ser Phe Leu Ala Gln Ser Met Arg Ser
    3995              4000              4005

Ser Asp Ser Pro Ser Glu Ala Ile Thr Arg Leu Ser Asn Phe Pro
    4010              4015              4020

Ala Met Thr Glu Ser Gly Gly Met Ile Leu Ala Met Gln Thr Ser
    4025              4030              4035

Pro Pro Gly Ala Thr Ser Leu Ser Ala Pro Thr Leu Asp Thr Ser
    4040              4045              4050

Ala Thr Ala Ser Trp Thr Gly Thr Pro Leu Ala Thr Thr Gln Arg
    4055              4060              4065

Phe Thr Tyr Ser Glu Lys Thr Thr Leu Phe Ser Lys Gly Pro Glu
    4070              4075              4080

Asp Thr Ser Gln Pro Ser Pro Pro Ser Val Glu Glu Thr Ser Ser
    4085              4090              4095

Ser Ser Ser Leu Val Pro Ile His Ala Thr Thr Ser Pro Ser Asn
    4100              4105              4110

Ile Leu Leu Thr Ser Gln Gly His Ser Pro Ser Ser Thr Pro Pro
    4115              4120              4125

Val Thr Ser Val Phe Leu Ser Glu Thr Ser Gly Leu Gly Lys Thr
    4130              4135              4140

Thr Asp Met Ser Arg Ile Ser Leu Glu Pro Gly Thr Ser Leu Pro
    4145              4150              4155

Pro Asn Leu Ser Ser Thr Ala Gly Glu Ala Leu Ser Thr Tyr Glu
    4160              4165              4170

Ala Ser Arg Asp Thr Lys Ala Ile His His Ser Ala Asp Thr Ala
    4175              4180              4185

Val Thr Asn Met Glu Ala Thr Ser Ser Glu Tyr Ser Pro Ile Pro
    4190              4195              4200

Gly His Thr Lys Pro Ser Lys Ala Thr Ser Pro Leu Val Thr Ser
    4205              4210              4215

His Ile Met Gly Asp Ile Thr Ser Ser Thr Ser Val Phe Gly Ser
    4220              4225              4230

Ser Glu Thr Thr Glu Ile Glu Thr Val Ser Ser Val Asn Gln Gly
    4235              4240              4245

Leu Gln Glu Arg Ser Thr Ser Gln Val Ala Ser Ser Ala Thr Glu
    4250              4255              4260

Thr Ser Thr Val Ile Thr His Val Ser Ser Gly Asp Ala Thr Thr
    4265              4270              4275

His Val Thr Lys Thr Gln Ala Thr Phe Ser Ser Gly Thr Ser Ile
    4280              4285              4290

Ser Ser Pro His Gln Phe Ile Thr Ser Thr Asn Thr Phe Thr Asp
    4295              4300              4305

Val Ser Thr Asn Pro Ser Thr Ser Leu Ile Met Thr Glu Ser Ser
    4310              4315              4320

Gly Val Thr Ile Thr Thr Gln Thr Gly Pro Thr Gly Ala Ala Thr
    4325              4330              4335
```

-continued

Gln Gly Pro Tyr Leu Leu Asp Thr Ser Thr Met Pro Tyr Leu Thr
4340            4345            4350

Glu Thr Pro Leu Ala Val Thr Pro Asp Phe Met Gln Ser Glu Lys
4355            4360            4365

Thr Thr Leu Ile Ser Lys Gly Pro Lys Asp Val Ser Trp Thr Ser
4370            4375            4380

Pro Pro Ser Val Ala Glu Thr Ser Tyr Pro Ser Ser Leu Thr Pro
4385            4390            4395

Phe Leu Val Thr Thr Ile Pro Pro Ala Thr Ser Thr Leu Gln Gly
4400            4405            4410

Gln His Thr Ser Ser Pro Val Ser Ala Thr Ser Val Leu Thr Ser
4415            4420            4425

Gly Leu Val Lys Thr Thr Asp Met Leu Asn Thr Ser Met Glu Pro
4430            4435            4440

Val Thr Asn Ser Pro Gln Asn Leu Asn Asn Pro Ser Asn Glu Ile
4445            4450            4455

Leu Ala Thr Leu Ala Ala Thr Thr Asp Ile Glu Thr Ile His Pro
4460            4465            4470

Ser Ile Asn Lys Ala Val Thr Asn Met Gly Thr Ala Ser Ser Ala
4475            4480            4485

His Val Leu His Ser Thr Leu Pro Val Ser Ser Glu Pro Ser Thr
4490            4495            4500

Ala Thr Ser Pro Met Val Pro Ala Ser Ser Met Gly Asp Ala Leu
4505            4510            4515

Ala Ser Ile Ser Ile Pro Gly Ser Glu Thr Thr Asp Ile Glu Gly
4520            4525            4530

Glu Pro Thr Ser Ser Leu Thr Ala Gly Arg Lys Glu Asn Ser Thr
4535            4540            4545

Leu Gln Glu Met Asn Ser Thr Thr Glu Ser Asn Ile Ile Leu Ser
4550            4555            4560

Asn Val Ser Val Gly Ala Ile Thr Glu Ala Thr Lys Met Glu Val
4565            4570            4575

Pro Ser Phe Asp Ala Thr Phe Ile Pro Thr Pro Ala Gln Ser Thr
4580            4585            4590

Lys Phe Pro Asp Ile Phe Ser Val Ala Ser Ser Arg Leu Ser Asn
4595            4600            4605

Ser Pro Pro Met Thr Ile Ser Thr His Met Thr Thr Gln Thr
4610            4615            4620

Gly Ser Ser Gly Ala Thr Ser Lys Ile Pro Leu Ala Leu Asp Thr
4625            4630            4635

Ser Thr Leu Glu Thr Ser Ala Gly Thr Pro Ser Val Val Thr Glu
4640            4645            4650

Gly Phe Ala His Ser Lys Ile Thr Thr Ala Met Asn Asn Asp Val
4655            4660            4665

Lys Asp Val Ser Gln Thr Asn Pro Pro Phe Gln Asp Glu Ala Ser
4670            4675            4680

Ser Pro Ser Ser Gln Ala Pro Val Leu Val Thr Thr Leu Pro Ser
4685            4690            4695

Ser Val Ala Phe Thr Pro Gln Trp His Ser Thr Ser Ser Pro Val
4700            4705            4710

Ser Met Ser Ser Val Leu Thr Ser Ser Leu Val Lys Thr Ala Gly
4715            4720            4725

```
Lys Val Asp Thr Ser Leu Glu Thr Val Thr Ser Ser Pro Gln Ser
    4730                4735            4740

Met Ser Asn Thr Leu Asp Asp Ile Ser Val Thr Ser Ala Ala Thr
    4745                4750            4755

Thr Asp Ile Glu Thr Thr His Pro Ser Ile Asn Thr Val Val Thr
    4760                4765            4770

Asn Val Gly Thr Thr Gly Ser Ala Phe Glu Ser His Ser Thr Val
    4775                4780            4785

Ser Ala Tyr Pro Glu Pro Ser Lys Val Thr Ser Pro Asn Val Thr
    4790                4795            4800

Thr Ser Thr Met Glu Asp Thr Thr Ile Ser Arg Ser Ile Pro Lys
    4805                4810            4815

Ser Ser Lys Thr Thr Arg Thr Glu Thr Glu Thr Ser Ser Leu
    4820                4825            4830

Thr Pro Lys Leu Arg Glu Thr Ser Ile Ser Gln Glu Ile Thr Ser
    4835                4840            4845

Ser Thr Glu Thr Ser Thr Val Pro Tyr Lys Glu Leu Thr Gly Ala
    4850                4855            4860

Thr Thr Glu Val Ser Arg Thr Asp Val Thr Ser Ser Ser Ser Thr
    4865                4870            4875

Ser Phe Pro Gly Pro Asp Gln Ser Thr Val Ser Leu Asp Ile Ser
    4880                4885            4890

Thr Glu Thr Asn Thr Arg Leu Ser Thr Ser Pro Ile Met Thr Glu
    4895                4900            4905

Ser Ala Glu Ile Thr Ile Thr Thr Gln Thr Gly Pro His Gly Ala
    4910                4915            4920

Thr Ser Gln Asp Thr Phe Thr Met Asp Pro Ser Asn Thr Thr Pro
    4925                4930            4935

Gln Ala Gly Ile His Ser Ala Met Thr His Gly Phe Ser Gln Leu
    4940                4945            4950

Asp Val Thr Thr Leu Met Ser Arg Ile Pro Gln Asp Val Ser Trp
    4955                4960            4965

Thr Ser Pro Pro Ser Val Asp Lys Thr Ser Ser Pro Ser Ser Phe
    4970                4975            4980

Leu Ser Ser Pro Ala Met Thr Thr Pro Ser Leu Ile Ser Ser Thr
    4985                4990            4995

Leu Pro Glu Asp Lys Leu Ser Ser Pro Met Thr Ser Leu Leu Thr
    5000                5005            5010

Ser Gly Leu Val Lys Ile Thr Asp Ile Leu Arg Thr Arg Leu Glu
    5015                5020            5025

Pro Val Thr Ser Ser Leu Pro Asn Phe Ser Ser Thr Ser Asp Lys
    5030                5035            5040

Ile Leu Ala Thr Ser Lys Asp Ser Lys Asp Thr Lys Glu Ile Phe
    5045                5050            5055

Pro Ser Ile Asn Thr Glu Glu Thr Asn Val Lys Ala Asn Asn Ser
    5060                5065            5070

Gly His Glu Ser His Ser Pro Ala Leu Ala Asp Ser Glu Thr Pro
    5075                5080            5085

Lys Ala Thr Thr Gln Met Val Ile Thr Thr Thr Val Gly Asp Pro
    5090                5095            5100

Ala Pro Ser Thr Ser Met Pro Val His Gly Ser Ser Glu Thr Thr
    5105                5110            5115

Asn Ile Lys Arg Glu Pro Thr Tyr Phe Leu Thr Pro Arg Leu Arg
```

```
              5120                5125                5130

Glu Thr Ser Thr Ser Gln Glu Ser Ser Phe Pro Thr Asp Thr Ser
         5135                5140                5145

Phe Leu Leu Ser Lys Val Pro Thr Gly Thr Ile Thr Glu Val Ser
         5150                5155                5160

Ser Thr Gly Val Asn Ser Ser Lys Ile Ser Thr Pro Asp His
         5165                5170                5175

Asp Lys Ser Thr Val Pro Asp Thr Phe Thr Gly Glu Ile Pro
         5180                5185                5190

Arg Val Phe Thr Ser Ser Ile Lys Thr Lys Ser Ala Glu Met Thr
         5195                5200                5205

Ile Thr Thr Gln Ala Ser Pro Pro Glu Ser Ala Ser His Ser Thr
         5210                5215                5220

Leu Pro Leu Asp Thr Ser Thr Thr Leu Ser Gln Gly Gly Thr His
         5225                5230                5235

Ser Thr Val Thr Gln Gly Phe Pro Tyr Ser Glu Val Thr Thr Leu
         5240                5245                5250

Met Gly Met Gly Pro Gly Asn Val Ser Trp Met Thr Thr Pro Pro
         5255                5260                5265

Val Glu Glu Thr Ser Ser Val Ser Ser Leu Met Ser Ser Pro Ala
         5270                5275                5280

Met Thr Ser Pro Ser Pro Val Ser Ser Thr Ser Pro Gln Ser Ile
         5285                5290                5295

Pro Ser Ser Pro Leu Pro Val Thr Ala Leu Pro Thr Ser Val Leu
         5300                5305                5310

Val Thr Thr Thr Asp Val Leu Gly Thr Thr Ser Pro Glu Ser Val
         5315                5320                5325

Thr Ser Ser Pro Pro Asn Leu Ser Ser Ile Thr His Glu Arg Pro
         5330                5335                5340

Ala Thr Tyr Lys Asp Thr Ala His Thr Glu Ala Ala Met His His
         5345                5350                5355

Ser Thr Asn Thr Ala Val Thr Asn Val Gly Thr Ser Gly Ser Gly
         5360                5365                5370

His Lys Ser Gln Ser Ser Val Leu Ala Asp Ser Glu Thr Ser Lys
         5375                5380                5385

Ala Thr Pro Leu Met Ser Thr Thr Ser Thr Leu Gly Asp Thr Ser
         5390                5395                5400

Val Ser Thr Ser Thr Pro Asn Ile Ser Gln Thr Asn Gln Ile Gln
         5405                5410                5415

Thr Glu Pro Thr Ala Ser Leu Ser Pro Arg Leu Arg Glu Ser Ser
         5420                5425                5430

Thr Ser Glu Lys Thr Ser Ser Thr Thr Glu Thr Asn Thr Ala Phe
         5435                5440                5445

Ser Tyr Val Pro Thr Gly Ala Ile Thr Gln Ala Ser Arg Thr Glu
         5450                5455                5460

Ile Ser Ser Ser Arg Thr Ser Ile Ser Asp Leu Asp Arg Pro Thr
         5465                5470                5475

Ile Ala Pro Asp Ile Ser Thr Gly Met Ile Thr Arg Leu Phe Thr
         5480                5485                5490

Ser Pro Ile Met Thr Lys Ser Ala Glu Met Thr Val Thr Thr Gln
         5495                5500                5505

Thr Thr Thr Pro Gly Ala Thr Ser Gln Gly Ile Leu Pro Trp Asp
         5510                5515                5520
```

```
Thr Ser Thr Thr Leu Phe Gln Gly Gly Thr His Ser Thr Val Ser
    5525            5530            5535
Gln Gly Phe Pro His Ser Glu Ile Thr Thr Leu Arg Ser Arg Thr
    5540            5545            5550
Pro Gly Asp Val Ser Trp Met Thr Thr Pro Pro Val Glu Glu Thr
    5555            5560            5565
Ser Ser Gly Phe Ser Leu Met Ser Pro Ser Met Thr Ser Pro Ser
    5570            5575            5580
Pro Val Ser Ser Thr Ser Pro Glu Ser Ile Pro Ser Ser Pro Leu
    5585            5590            5595
Pro Val Thr Ala Leu Leu Thr Ser Val Leu Val Thr Thr Thr Asn
    5600            5605            5610
Val Leu Gly Thr Thr Ser Pro Glu Pro Val Thr Ser Ser Pro Pro
    5615            5620            5625
Asn Leu Ser Ser Pro Thr Gln Glu Arg Leu Thr Thr Tyr Lys Asp
    5630            5635            5640
Thr Ala His Thr Glu Ala Met His Ala Ser Met His Thr Asn Thr
    5645            5650            5655
Ala Val Ala Asn Val Gly Thr Ser Ile Ser Gly His Glu Ser Gln
    5660            5665            5670
Ser Ser Val Pro Ala Asp Ser His Thr Ser Lys Ala Thr Ser Pro
    5675            5680            5685
Met Gly Ile Thr Phe Ala Met Gly Asp Thr Ser Val Ser Thr Ser
    5690            5695            5700
Thr Pro Ala Phe Phe Glu Thr Arg Ile Gln Thr Glu Ser Thr Ser
    5705            5710            5715
Ser Leu Ile Pro Gly Leu Arg Asp Thr Arg Thr Ser Glu Glu Ile
    5720            5725            5730
Asn Thr Val Thr Glu Thr Ser Thr Val Leu Ser Glu Val Pro Thr
    5735            5740            5745
Thr Thr Thr Thr Glu Val Ser Arg Thr Glu Val Ile Thr Ser Ser
    5750            5755            5760
Arg Thr Thr Ile Ser Gly Pro Asp His Ser Lys Met Ser Pro Tyr
    5765            5770            5775
Ile Ser Thr Glu Thr Ile Thr Arg Leu Ser Thr Phe Pro Phe Val
    5780            5785            5790
Thr Gly Ser Thr Glu Met Ala Ile Thr Asn Gln Thr Gly Pro Ile
    5795            5800            5805
Gly Thr Ile Ser Gln Ala Thr Leu Thr Leu Asp Thr Ser Ser Thr
    5810            5815            5820
Ala Ser Trp Glu Gly Thr His Ser Pro Val Thr Gln Arg Phe Pro
    5825            5830            5835
His Ser Glu Glu Thr Thr Thr Met Ser Arg Ser Thr Lys Gly Val
    5840            5845            5850
Ser Trp Gln Ser Pro Pro Ser Val Glu Glu Thr Ser Ser Pro Ser
    5855            5860            5865
Ser Pro Val Pro Leu Pro Ala Ile Thr Ser His Ser Ser Leu Tyr
    5870            5875            5880
Ser Ala Val Ser Gly Ser Ser Pro Thr Ser Ala Leu Pro Val Thr
    5885            5890            5895
Ser Leu Leu Thr Ser Gly Arg Arg Lys Thr Ile Asp Met Leu Asp
    5900            5905            5910
```

```
Thr His Ser Glu Leu Val Thr Ser Ser Leu Pro Ser Ala Ser Ser
    5915                5920                5925

Phe Ser Gly Glu Ile Leu Thr Ser Glu Ala Ser Thr Asn Thr Glu
    5930                5935                5940

Thr Ile His Phe Ser Glu Asn Thr Ala Glu Thr Asn Met Gly Thr
    5945                5950                5955

Thr Asn Ser Met His Lys Leu His Ser Ser Val Ser Ile His Ser
    5960                5965                5970

Gln Pro Ser Gly His Thr Pro Pro Lys Val Thr Gly Ser Met Met
    5975                5980                5985

Glu Asp Ala Ile Val Ser Ser Thr Pro Gly Ser Pro Glu Thr
    5990                5995                6000

Lys Asn Val Asp Arg Asp Ser Thr Ser Pro Leu Thr Pro Glu Leu
    6005                6010                6015

Lys Glu Asp Ser Thr Ala Leu Val Met Asn Ser Thr Thr Glu Ser
    6020                6025                6030

Asn Thr Val Phe Ser Ser Val Ser Leu Asp Ala Ala Thr Glu Val
    6035                6040                6045

Ser Arg Ala Glu Val Thr Tyr Tyr Asp Pro Thr Phe Met Pro Ala
    6050                6055                6060

Ser Ala Gln Ser Thr Lys Ser Pro Asp Ile Ser Pro Glu Ala Ser
    6065                6070                6075

Ser Ser His Ser Asn Ser Pro Leu Thr Ile Ser Thr His Lys
    6080                6085                6090

Thr Ile Ala Thr Gln Thr Gly Pro Ser Gly Val Thr Ser Leu Gly
    6095                6100                6105

Gln Leu Thr Leu Asp Thr Ser Thr Ile Ala Thr Ser Ala Gly Thr
    6110                6115                6120

Pro Ser Ala Arg Thr Gln Asp Phe Val Asp Ser Glu Thr Thr Ser
    6125                6130                6135

Val Met Asn Asn Asp Leu Asn Asp Val Leu Lys Thr Ser Pro Phe
    6140                6145                6150

Ser Ala Glu Glu Ala Asn Ser Leu Ser Ser Gln Ala Pro Leu Leu
    6155                6160                6165

Val Thr Thr Ser Pro Ser Pro Val Thr Ser Thr Leu Gln Glu His
    6170                6175                6180

Ser Thr Ser Ser Leu Val Ser Val Thr Ser Val Pro Thr Pro Thr
    6185                6190                6195

Leu Ala Lys Ile Thr Asp Met Asp Thr Asn Leu Glu Pro Val Thr
    6200                6205                6210

Arg Ser Pro Gln Asn Leu Arg Asn Thr Leu Ala Thr Ser Glu Ala
    6215                6220                6225

Thr Thr Asp Thr His Thr Met His Pro Ser Ile Asn Thr Ala Val
    6230                6235                6240

Ala Asn Val Gly Thr Thr Ser Ser Pro Asn Glu Phe Tyr Phe Thr
    6245                6250                6255

Val Ser Pro Asp Ser Asp Pro Tyr Lys Ala Thr Ser Ala Val Val
    6260                6265                6270

Ile Thr Ser Thr Ser Gly Asp Ser Ile Val Ser Thr Ser Met Pro
    6275                6280                6285

Arg Ser Ser Ala Met Lys Lys Ile Glu Ser Glu Thr Thr Phe Ser
    6290                6295                6300

Leu Ile Phe Arg Leu Arg Glu Thr Ser Thr Ser Gln Lys Ile Gly
```

-continued

```
            6305                6310                6315

Ser  Ser  Ser  Asp  Thr  Ser  Val  Phe  Asp  Lys  Ala  Phe  Thr  Ala
            6320                6325                6330

Ala  Thr  Thr  Glu  Val  Ser  Arg  Thr  Glu  Leu  Thr  Ser  Ser  Ser  Arg
            6335                6340                6345

Thr  Ser  Ile  Gln  Gly  Thr  Glu  Lys  Pro  Thr  Met  Ser  Pro  Asp  Thr
            6350                6355                6360

Ser  Thr  Arg  Ser  Val  Thr  Met  Leu  Ser  Thr  Phe  Ala  Gly  Leu  Thr
            6365                6370                6375

Lys  Ser  Glu  Glu  Arg  Thr  Ile  Ala  Thr  Gln  Thr  Gly  Pro  His  Arg
            6380                6385                6390

Ala  Thr  Ser  Gln  Gly  Thr  Leu  Thr  Trp  Asp  Thr  Ser  Ile  Thr  Thr
            6395                6400                6405

Ser  Gln  Ala  Gly  Thr  His  Ser  Ala  Met  Thr  His  Gly  Phe  Ser  Gln
            6410                6415                6420

Leu  Asp  Leu  Ser  Thr  Leu  Thr  Ser  Arg  Val  Pro  Glu  Tyr  Ile  Ser
            6425                6430                6435

Gly  Thr  Ser  Pro  Pro  Ser  Val  Glu  Lys  Thr  Ser  Ser  Ser  Ser  Ser
            6440                6445                6450

Leu  Leu  Ser  Leu  Pro  Ala  Ile  Thr  Ser  Pro  Ser  Pro  Val  Pro  Thr
            6455                6460                6465

Thr  Leu  Pro  Glu  Ser  Arg  Pro  Ser  Ser  Pro  Val  His  Leu  Thr  Ser
            6470                6475                6480

Leu  Pro  Thr  Ser  Gly  Leu  Val  Lys  Thr  Thr  Asp  Met  Leu  Ala  Ser
            6485                6490                6495

Val  Ala  Ser  Leu  Pro  Pro  Asn  Leu  Gly  Ser  Thr  Ser  His  Lys  Ile
            6500                6505                6510

Pro  Thr  Thr  Ser  Glu  Asp  Ile  Lys  Asp  Thr  Glu  Lys  Met  Tyr  Pro
            6515                6520                6525

Ser  Thr  Asn  Ile  Ala  Val  Thr  Asn  Val  Gly  Thr  Thr  Thr  Ser  Glu
            6530                6535                6540

Lys  Glu  Ser  Tyr  Ser  Ser  Val  Pro  Ala  Tyr  Ser  Glu  Pro  Pro  Lys
            6545                6550                6555

Val  Thr  Ser  Pro  Met  Val  Thr  Ser  Phe  Asn  Ile  Arg  Asp  Thr  Ile
            6560                6565                6570

Val  Ser  Thr  Ser  Met  Pro  Gly  Ser  Ser  Glu  Ile  Thr  Arg  Ile  Glu
            6575                6580                6585

Met  Glu  Ser  Thr  Phe  Ser  Leu  Ala  His  Gly  Leu  Lys  Gly  Thr  Ser
            6590                6595                6600

Thr  Ser  Gln  Asp  Pro  Ile  Val  Ser  Thr  Glu  Lys  Ser  Ala  Val  Leu
            6605                6610                6615

His  Lys  Leu  Thr  Thr  Gly  Ala  Thr  Glu  Thr  Ser  Arg  Thr  Glu  Val
            6620                6625                6630

Ala  Ser  Ser  Arg  Arg  Thr  Ser  Ile  Pro  Gly  Pro  Asp  His  Ser  Thr
            6635                6640                6645

Glu  Ser  Pro  Asp  Ile  Ser  Thr  Glu  Val  Ile  Pro  Ser  Leu  Pro  Ile
            6650                6655                6660

Ser  Leu  Gly  Ile  Thr  Glu  Ser  Ser  Asn  Met  Thr  Ile  Ile  Thr  Arg
            6665                6670                6675

Thr  Gly  Pro  Pro  Leu  Gly  Ser  Thr  Ser  Gln  Gly  Thr  Phe  Thr  Leu
            6680                6685                6690

Asp  Thr  Pro  Thr  Thr  Ser  Ser  Arg  Ala  Gly  Thr  His  Ser  Met  Ala
            6695                6700                6705
```

Thr Gln Glu Phe Pro His Ser Glu Met Thr Thr Val Met Asn Lys
6710                6715                6720

Asp Pro Glu Ile Leu Ser Trp Thr Ile Pro Pro Ser Ile Glu Lys
6725                6730                6735

Thr Ser Phe Ser Ser Ser Leu Met Pro Ser Pro Ala Met Thr Ser
6740                6745                6750

Pro Pro Val Ser Ser Thr Leu Pro Lys Thr Ile His Thr Thr Pro
6755                6760                6765

Ser Pro Met Thr Ser Leu Leu Thr Pro Ser Leu Val Met Thr Thr
6770                6775                6780

Asp Thr Leu Gly Thr Ser Pro Glu Pro Thr Thr Ser Ser Pro Pro
6785                6790                6795

Asn Leu Ser Ser Thr Ser His Glu Ile Leu Thr Thr Asp Glu Asp
6800                6805                6810

Thr Thr Ala Ile Glu Ala Met His Pro Ser Thr Ser Thr Ala Ala
6815                6820                6825

Thr Asn Val Glu Thr Thr Ser Ser Gly His Gly Ser Gln Ser Ser
6830                6835                6840

Val Leu Ala Asp Ser Glu Lys Thr Lys Ala Thr Ala Pro Met Asp
6845                6850                6855

Thr Thr Ser Thr Met Gly His His Thr Thr Val Ser Thr Ser Met Ser
6860                6865                6870

Val Ser Ser Glu Thr Thr Lys Ile Lys Arg Glu Ser Thr Tyr Ser
6875                6880                6885

Leu Thr Pro Gly Leu Arg Glu Thr Ser Ile Ser Gln Asn Ala Ser
6890                6895                6900

Phe Ser Thr Asp Thr Ser Ile Val Leu Ser Glu Val Pro Thr Gly
6905                6910                6915

Thr Thr Ala Glu Val Ser Arg Thr Glu Val Thr Ser Ser Gly Arg
6920                6925                6930

Thr Ser Ile Pro Gly Pro Ser Gln Ser Thr Val Leu Pro Glu Ile
6935                6940                6945

Ser Thr Arg Thr Met Thr Arg Leu Phe Ala Ser Pro Thr Met Thr
6950                6955                6960

Glu Ser Ala Glu Met Thr Ile Pro Thr Gln Thr Gly Pro Ser Gly
6965                6970                6975

Ser Thr Ser Gln Asp Thr Leu Thr Leu Asp Thr Ser Thr Thr Lys
6980                6985                6990

Ser Gln Ala Lys Thr His Ser Thr Leu Thr Gln Arg Phe Pro His
6995                7000                7005

Ser Glu Met Thr Thr Leu Met Ser Arg Gly Pro Gly Asp Met Ser
7010                7015                7020

Trp Gln Ser Ser Pro Ser Leu Glu Asn Pro Ser Ser Leu Pro Ser
7025                7030                7035

Leu Leu Ser Leu Pro Ala Thr Thr Ser Pro Pro Ile Ser Ser
7040                7045                7050

Thr Leu Pro Val Thr Ile Ser Ser Ser Pro Leu Pro Val Thr Ser
7055                7060                7065

Leu Leu Thr Ser Ser Pro Val Thr Thr Thr Asp Met Leu His Thr
7070                7075                7080

Ser Pro Glu Leu Val Thr Ser Ser Pro Pro Lys Leu Ser His Thr
7085                7090                7095

-continued

| | | | | | | | | | | | |
|---|---|---|---|---|---|---|---|---|---|---|---|
| Ser | Asp | Glu | Arg | Leu | Thr | Thr | Gly | Lys | Asp | Thr | Thr |
| | 7100 | | | | | 7105 | | | | | 7110 |
| Asn | Thr | Glu | | | | | | | | | |
| Ala | Val | His | Pro | Ser | Thr | Asn | Thr | Ala | Ala | Ser | Asn |
| | 7115 | | | | | 7120 | | | | | 7125 |
| Val | Glu | Ile | | | | | | | | | |
| Pro | Ser | Ser | Gly | His | Glu | Ser | Pro | Ser | Ser | Ala | Leu |
| | 7130 | | | | | 7135 | | | | | 7140 |
| Ala | Asp | Ser | | | | | | | | | |
| Glu | Thr | Ser | Lys | Ala | Thr | Ser | Pro | Met | Phe | Ile | Thr |
| | 7145 | | | | | 7150 | | | | | 7155 |
| Ser | Thr | Gln | | | | | | | | | |
| Glu | Asp | Thr | Thr | Val | Ala | Ile | Ser | Thr | Pro | His | Phe |
| | 7160 | | | | | 7165 | | | | | 7170 |
| Leu | Glu | Thr | | | | | | | | | |
| Ser | Arg | Ile | Gln | Lys | Glu | Ser | Ile | Ser | Ser | Leu | Ser |
| | 7175 | | | | | 7180 | | | | | 7185 |
| Pro | Lys | Leu | | | | | | | | | |
| Arg | Glu | Thr | Gly | Ser | Ser | Val | Glu | Thr | Ser | Ser | Ala |
| | 7190 | | | | | 7195 | | | | | 7200 |
| Ile | Glu | Thr | | | | | | | | | |
| Ser | Ala | Val | Leu | Ser | Glu | Val | Ser | Ile | Gly | Ala | Thr |
| | 7205 | | | | | 7210 | | | | | 7215 |
| Thr | Glu | Ile | | | | | | | | | |
| Ser | Arg | Thr | Glu | Val | Thr | Ser | Ser | Ser | Arg | Thr | Ser |
| | 7220 | | | | | 7225 | | | | | 7230 |
| Ile | Ser | Gly | | | | | | | | | |
| Ser | Ala | Glu | Ser | Thr | Met | Leu | Pro | Glu | Ile | Ser | Thr |
| | 7235 | | | | | 7240 | | | | | 7245 |
| Thr | Arg | Lys | | | | | | | | | |
| Ile | Ile | Lys | Phe | Pro | Thr | Ser | Pro | Ile | Leu | Ala | Glu |
| | 7250 | | | | | 7255 | | | | | 7260 |
| Ser | Ser | Glu | | | | | | | | | |
| Met | Thr | Ile | Lys | Thr | Gln | Thr | Ser | Pro | Pro | Gly | Ser |
| | 7265 | | | | | 7270 | | | | | 7275 |
| Thr | Ser | Glu | | | | | | | | | |
| Ser | Thr | Phe | Thr | Leu | Asp | Ser | Thr | Thr | Pro | Ser | Leu |
| | 7280 | | | | | 7285 | | | | | 7290 |
| Val | Ile | | | | | | | | | | |
| Thr | His | Ser | Thr | Met | Thr | Gln | Arg | Leu | Pro | His | Ser |
| | 7295 | | | | | 7300 | | | | | 7305 |
| Glu | Ile | Thr | | | | | | | | | |
| Thr | Leu | Val | Ser | Arg | Gly | Ala | Gly | Asp | Val | Pro | Arg |
| | 7310 | | | | | 7315 | | | | | 7320 |
| Pro | Ser | Ser | | | | | | | | | |
| Leu | Pro | Val | Glu | Glu | Thr | Ser | Pro | Pro | Ser | Ser | Gln |
| | 7325 | | | | | 7330 | | | | | 7335 |
| Leu | Ser | Leu | | | | | | | | | |
| Ser | Ala | Met | Ile | Ser | Pro | Ser | Pro | Val | Ser | Ser | Thr |
| | 7340 | | | | | 7345 | | | | | 7350 |
| Leu | Pro | Ala | | | | | | | | | |
| Ser | Ser | His | Ser | Ser | Ser | Ala | Ser | Val | Thr | Ser | Leu |
| | 7355 | | | | | 7360 | | | | | 7365 |
| Leu | Thr | Pro | | | | | | | | | |
| Gly | Gln | Val | Lys | Thr | Thr | Glu | Val | Leu | Asp | Ala | Ser |
| | 7370 | | | | | 7375 | | | | | 7380 |
| Ala | Glu | Pro | | | | | | | | | |
| Glu | Thr | Ser | Ser | Pro | Pro | Ser | Leu | Ser | Ser | Thr | Ser |
| | 7385 | | | | | 7390 | | | | | 7395 |
| Val | Glu | Ile | | | | | | | | | |
| Leu | Ala | Thr | Ser | Glu | Val | Thr | Thr | Asp | Thr | Glu | Lys |
| | 7400 | | | | | 7405 | | | | | 7410 |
| Ile | His | Pro | | | | | | | | | |
| Phe | Ser | Asn | Thr | Ala | Val | Thr | Lys | Val | Gly | Thr | Ser |
| | 7415 | | | | | 7420 | | | | | 7425 |
| Ser | Ser | Gly | | | | | | | | | |
| His | Glu | Ser | Pro | Ser | Ser | Val | Leu | Pro | Asp | Ser | Glu |
| | 7430 | | | | | 7435 | | | | | 7440 |
| Thr | Thr | Lys | | | | | | | | | |
| Ala | Thr | Ser | Ala | Met | Gly | Thr | Ile | Ser | Ile | Met | Gly |
| | 7445 | | | | | 7450 | | | | | 7455 |
| Asp | Thr | Ser | | | | | | | | | |
| Val | Ser | Thr | Leu | Thr | Pro | Ala | Leu | Ser | Asn | Thr | Arg |
| | 7460 | | | | | 7465 | | | | | 7470 |
| Lys | Ile | Gln | | | | | | | | | |
| Ser | Glu | Pro | Ala | Ser | Ser | Leu | Thr | Thr | Arg | Leu | Arg |
| | 7475 | | | | | 7480 | | | | | 7485 |
| Glu | Thr | Ser | | | | | | | | | |
| Thr | Ser | Glu | Glu | Thr | Ser | Leu | Ala | Thr | Glu | Ala | Asn |
| Thr | Val | Leu | | | | | | | | | |

|   |   |   |   |   |   |   |   |   |   |
|---|---|---|---|---|---|---|---|---|---|
| 7490 | | | | 7495 | | | 7500 | | |

Ser Lys Val Ser Thr Gly Ala Thr Thr Glu Val Ser Arg Thr Glu
7505                7510                    7515

Ala Ile Ser Phe Ser Arg Thr Ser Met Ser Gly Pro Glu Gln Ser
7520                7525                    7530

Thr Met Ser Gln Asp Ile Ser Ile Gly Thr Ile Pro Arg Ile Ser
7535                7540                    7545

Ala Ser Ser Val Leu Thr Glu Ser Ala Lys Met Thr Ile Thr Thr
7550                7555                    7560

Gln Thr Gly Pro Ser Glu Ser Thr Leu Glu Ser Thr Leu Asn Leu
7565                7570                    7575

Asn Thr Ala Thr Thr Pro Ser Trp Val Glu Thr His Ser Ile Val
7580                7585                    7590

Ile Gln Gly Phe Pro His Pro Glu Met Thr Thr Ser Met Gly Arg
7595                7600                    7605

Gly Pro Gly Gly Val Ser Trp Pro Ser Pro Pro Phe Val Lys Glu
7610                7615                    7620

Thr Ser Pro Pro Ser Ser Pro Leu Ser Leu Pro Ala Val Thr Ser
7625                7630                    7635

Pro His Pro Val Ser Thr Thr Phe Leu Ala His Ile Pro Pro Ser
7640                7645                    7650

Pro Leu Pro Val Thr Ser Leu Leu Thr Ser Gly Pro Ala Thr Thr
7655                7660                    7665

Thr Asp Ile Leu Gly Thr Ser Thr Glu Pro Gly Thr Ser Ser Ser
7670                7675                    7680

Ser Ser Leu Ser Thr Thr Ser His Glu Arg Leu Thr Thr Tyr Lys
7685                7690                    7695

Asp Thr Ala His Thr Glu Ala Val His Pro Ser Thr Asn Thr Gly
7700                7705                    7710

Gly Thr Asn Val Ala Thr Thr Ser Ser Gly Tyr Lys Ser Gln Ser
7715                7720                    7725

Ser Val Leu Ala Asp Ser Ser Pro Met Cys Thr Thr Ser Thr Met
7730                7735                    7740

Gly Asp Thr Ser Val Leu Thr Ser Thr Pro Ala Phe Leu Glu Thr
7745                7750                    7755

Arg Arg Ile Gln Thr Glu Leu Ala Ser Ser Leu Thr Pro Gly Leu
7760                7765                    7770

Arg Glu Ser Ser Gly Ser Glu Gly Thr Ser Ser Gly Thr Lys Met
7775                7780                    7785

Ser Thr Val Leu Ser Lys Val Pro Thr Gly Ala Thr Thr Glu Ile
7790                7795                    7800

Ser Lys Glu Asp Val Thr Ser Ile Pro Gly Pro Ala Gln Ser Thr
7805                7810                    7815

Ile Ser Pro Asp Ile Ser Thr Arg Thr Val Ser Trp Phe Ser Thr
7820                7825                    7830

Ser Pro Val Met Thr Glu Ser Ala Glu Ile Thr Met Asn Thr His
7835                7840                    7845

Thr Ser Pro Leu Gly Ala Thr Thr Gln Gly Thr Ser Thr Leu Asp
7850                7855                    7860

Thr Ser Ser Thr Thr Ser Leu Thr Met Thr His Ser Thr Ile Ser
7865                7870                    7875

Gln Gly Phe Ser His Ser Gln Met Ser Thr Leu Met Arg Arg Gly
7880                7885                    7890

-continued

Pro Glu Asp Val Ser Trp Met Ser Pro Leu Leu Glu Lys Thr
7895                7900            7905

Arg Pro Ser Phe Ser Leu Met Ser Ser Pro Ala Thr Thr Ser Pro
7910                7915            7920

Ser Pro Val Ser Ser Thr Leu Pro Glu Ser Ile Ser Ser Ser Pro
7925                7930            7935

Leu Pro Val Thr Ser Leu Leu Thr Ser Gly Leu Ala Lys Thr Thr
7940                7945            7950

Asp Met Leu His Lys Ser Ser Glu Pro Val Thr Asn Ser Pro Ala
7955                7960            7965

Asn Leu Ser Ser Thr Ser Val Glu Ile Leu Ala Thr Ser Glu Val
7970                7975            7980

Thr Thr Asp Thr Glu Lys Thr His Pro Ser Ser Asn Arg Thr Val
7985                7990            7995

Thr Asp Val Gly Thr Ser Ser Gly His Glu Ser Thr Ser Phe
8000                8005            8010

Val Leu Ala Asp Ser Gln Thr Ser Lys Val Thr Ser Pro Met Val
8015                8020            8025

Ile Thr Ser Thr Met Glu Asp Thr Ser Val Ser Thr Ser Thr Pro
8030                8035            8040

Gly Phe Phe Glu Thr Ser Arg Ile Gln Thr Glu Pro Thr Ser Ser
8045                8050            8055

Leu Thr Leu Gly Leu Arg Lys Thr Ser Ser Glu Gly Thr Ser
8060                8065            8070

Leu Ala Thr Glu Met Ser Thr Val Leu Ser Gly Val Pro Thr Gly
8075                8080            8085

Ala Thr Ala Glu Val Ser Arg Thr Glu Val Thr Ser Ser Ser Arg
8090                8095            8100

Thr Ser Ile Ser Gly Phe Ala Gln Leu Thr Val Ser Pro Glu Thr
8105                8110            8115

Ser Thr Glu Thr Ile Thr Arg Leu Pro Thr Ser Ser Ile Met Thr
8120                8125            8130

Glu Ser Ala Glu Met Met Ile Lys Thr Gln Thr Asp Pro Pro Gly
8135                8140            8145

Ser Thr Pro Glu Ser Thr His Thr Val Asp Ile Ser Thr Thr Pro
8150                8155            8160

Asn Trp Val Glu Thr His Ser Thr Val Thr Gln Arg Phe Ser His
8165                8170            8175

Ser Glu Met Thr Thr Leu Val Ser Arg Ser Pro Gly Asp Met Leu
8180                8185            8190

Trp Pro Ser Gln Ser Ser Val Glu Glu Thr Ser Ser Ala Ser Ser
8195                8200            8205

Leu Leu Ser Leu Pro Ala Thr Thr Ser Pro Ser Pro Val Ser Ser
8210                8215            8220

Thr Leu Val Glu Asp Phe Pro Ser Ala Ser Leu Pro Val Thr Ser
8225                8230            8235

Leu Leu Asn Pro Gly Leu Val Ile Thr Thr Asp Arg Met Gly Ile
8240                8245            8250

Ser Arg Glu Pro Gly Thr Ser Ser Thr Ser Asn Leu Ser Ser Thr
8255                8260            8265

Ser His Glu Arg Leu Thr Thr Leu Glu Asp Thr Val Asp Thr Glu
8270                8275            8280

```
Asp Met Gln Pro Ser Thr His Thr Ala Val Thr Asn Val Arg Thr
    8285                8290                8295

Ser Ile Ser Gly His Glu Ser Gln Ser Ser Val Leu Ser Asp Ser
    8300                8305                8310

Glu Thr Pro Lys Ala Thr Ser Pro Met Gly Thr Thr Tyr Thr Met
    8315                8320                8325

Gly Glu Thr Ser Val Ser Ile Ser Thr Ser Asp Phe Phe Glu Thr
    8330                8335                8340

Ser Arg Ile Gln Ile Glu Pro Thr Ser Ser Leu Thr Ser Gly Leu
    8345                8350                8355

Arg Glu Thr Ser Ser Ser Glu Arg Ile Ser Ser Ala Thr Glu Gly
    8360                8365                8370

Ser Thr Val Leu Ser Glu Val Pro Ser Gly Ala Thr Thr Glu Val
    8375                8380                8385

Ser Arg Thr Glu Val Ile Ser Ser Arg Gly Thr Ser Met Ser Gly
    8390                8395                8400

Pro Asp Gln Phe Thr Ile Ser Pro Asp Ile Ser Thr Glu Ala Ile
    8405                8410                8415

Thr Arg Leu Ser Thr Ser Pro Ile Met Thr Glu Ser Ala Glu Ser
    8420                8425                8430

Ala Ile Thr Ile Glu Thr Gly Ser Pro Gly Ala Thr Ser Glu Gly
    8435                8440                8445

Thr Leu Thr Leu Asp Thr Ser Thr Thr Thr Phe Trp Ser Gly Thr
    8450                8455                8460

His Ser Thr Ala Ser Pro Gly Phe Ser His Ser Glu Met Thr Thr
    8465                8470                8475

Leu Met Ser Arg Thr Pro Gly Asp Val Pro Trp Pro Ser Leu Pro
    8480                8485                8490

Ser Val Glu Glu Ala Ser Ser Val Ser Ser Ser Leu Ser Ser Pro
    8495                8500                8505

Ala Met Thr Ser Thr Ser Phe Phe Ser Thr Leu Pro Glu Ser Ile
    8510                8515                8520

Ser Ser Ser Pro His Pro Val Thr Ala Leu Leu Thr Leu Gly Pro
    8525                8530                8535

Val Lys Thr Thr Asp Met Leu Arg Thr Ser Ser Glu Pro Glu Thr
    8540                8545                8550

Ser Ser Pro Pro Asn Leu Ser Ser Thr Ser Ala Glu Ile Leu Ala
    8555                8560                8565

Thr Ser Glu Val Thr Lys Asp Arg Glu Lys Ile His Pro Ser Ser
    8570                8575                8580

Asn Thr Pro Val Val Asn Val Gly Thr Val Ile Tyr Lys His Leu
    8585                8590                8595

Ser Pro Ser Ser Val Leu Ala Asp Leu Val Thr Thr Lys Pro Thr
    8600                8605                8610

Ser Pro Met Ala Thr Thr Ser Thr Leu Gly Asn Thr Ser Val Ser
    8615                8620                8625

Thr Ser Thr Pro Ala Phe Pro Glu Thr Met Met Thr Gln Pro Thr
    8630                8635                8640

Ser Ser Leu Thr Ser Gly Leu Arg Glu Ile Ser Thr Ser Gln Glu
    8645                8650                8655

Thr Ser Ser Ala Thr Glu Arg Ser Ala Ser Leu Ser Gly Met Pro
    8660                8665                8670

Thr Gly Ala Thr Thr Lys Val Ser Arg Thr Glu Ala Leu Ser Leu
```

-continued

```
              8675                8680                8685

Gly Arg Thr Ser Thr Pro Gly Pro Ala Gln Ser Thr Ile Ser Pro
    8690                8695                8700

Glu Ile Ser Thr Glu Thr Ile Thr Arg Ile Ser Thr Pro Leu Thr
    8705                8710                8715

Thr Thr Gly Ser Ala Glu Met Thr Ile Thr Pro Lys Thr Gly His
    8720                8725                8730

Ser Gly Ala Ser Ser Gln Gly Thr Phe Thr Leu Asp Thr Ser Ser
    8735                8740                8745

Arg Ala Ser Trp Pro Gly Thr His Ser Ala Ala Thr His Arg Ser
    8750                8755                8760

Pro His Ser Gly Met Thr Thr Pro Met Ser Arg Gly Pro Glu Asp
    8765                8770                8775

Val Ser Trp Pro Ser Arg Pro Ser Val Glu Lys Thr Ser Pro Pro
    8780                8785                8790

Ser Ser Leu Val Ser Leu Ser Ala Val Thr Ser Pro Ser Pro Leu
    8795                8800                8805

Tyr Ser Thr Pro Ser Glu Ser Ser His Ser Ser Pro Leu Arg Val
    8810                8815                8820

Thr Ser Leu Phe Thr Pro Val Met Met Lys Thr Thr Asp Met Leu
    8825                8830                8835

Asp Thr Ser Leu Glu Pro Val Thr Thr Ser Pro Pro Ser Met Asn
    8840                8845                8850

Ile Thr Ser Asp Glu Ser Leu Ala Thr Ser Lys Ala Thr Met Glu
    8855                8860                8865

Thr Glu Ala Ile Gln Leu Ser Glu Asn Thr Ala Val Thr Gln Met
    8870                8875                8880

Gly Thr Ile Ser Ala Arg Gln Glu Phe Tyr Ser Ser Tyr Pro Gly
    8885                8890                8895

Leu Pro Glu Pro Ser Lys Val Thr Ser Pro Val Val Thr Ser Ser
    8900                8905                8910

Thr Ile Lys Asp Ile Val Ser Thr Thr Ile Pro Ala Ser Ser Glu
    8915                8920                8925

Ile Thr Arg Ile Glu Met Glu Ser Thr Ser Thr Leu Thr Pro Thr
    8930                8935                8940

Pro Arg Glu Thr Ser Thr Ser Gln Glu Ile His Ser Ala Thr Lys
    8945                8950                8955

Pro Ser Thr Val Pro Tyr Lys Ala Leu Thr Ser Ala Thr Ile Glu
    8960                8965                8970

Asp Ser Met Thr Gln Val Met Ser Ser Ser Arg Gly Pro Ser Pro
    8975                8980                8985

Asp Gln Ser Thr Met Ser Gln Asp Ile Ser Thr Glu Val Ile Thr
    8990                8995                9000

Arg Leu Ser Thr Ser Pro Ile Lys Thr Glu Ser Thr Glu Met Thr
    9005                9010                9015

Ile Thr Thr Gln Thr Gly Ser Pro Gly Ala Thr Ser Arg Gly Thr
    9020                9025                9030

Leu Thr Leu Asp Thr Ser Thr Thr Phe Met Ser Gly Thr His Ser
    9035                9040                9045

Thr Ala Ser Gln Gly Phe Ser His Ser Gln Met Thr Ala Leu Met
    9050                9055                9060

Ser Arg Thr Pro Gly Asp Val Pro Trp Leu Ser His Pro Ser Val
    9065                9070                9075
```

-continued

```
Glu Glu Ala Ser Ser Ala Ser Phe Ser Leu Ser Ser Pro Val Met
    9080            9085            9090
Thr Ser Ser Ser Pro Val Ser Ser Thr Leu Pro Asp Ser Ile His
    9095            9100            9105
Ser Ser Ser Leu Pro Val Thr Ser Leu Leu Thr Ser Gly Leu Val
    9110            9115            9120
Lys Thr Thr Glu Leu Leu Gly Thr Ser Ser Glu Pro Glu Thr Ser
    9125            9130            9135
Ser Pro Pro Asn Leu Ser Ser Thr Ser Ala Glu Ile Leu Ala Ile
    9140            9145            9150
Thr Glu Val Thr Thr Asp Thr Glu Lys Leu Glu Met Thr Asn Val
    9155            9160            9165
Val Thr Ser Gly Tyr Thr His Glu Ser Pro Ser Ser Val Leu Ala
    9170            9175            9180
Asp Ser Val Thr Thr Lys Ala Thr Ser Ser Met Gly Ile Thr Tyr
    9185            9190            9195
Pro Thr Gly Asp Thr Asn Val Leu Thr Ser Thr Pro Ala Phe Ser
    9200            9205            9210
Asp Thr Ser Arg Ile Gln Thr Lys Ser Lys Leu Ser Leu Thr Pro
    9215            9220            9225
Gly Leu Met Glu Thr Ser Ile Ser Glu Glu Thr Ser Ser Ala Thr
    9230            9235            9240
Glu Lys Ser Thr Val Leu Ser Ser Val Pro Thr Gly Ala Thr Thr
    9245            9250            9255
Glu Val Ser Arg Thr Glu Ala Ile Ser Ser Ser Arg Thr Ser Ile
    9260            9265            9270
Pro Gly Pro Ala Gln Ser Thr Met Ser Ser Asp Thr Ser Met Glu
    9275            9280            9285
Thr Ile Thr Arg Ile Ser Thr Pro Leu Thr Arg Lys Glu Ser Thr
    9290            9295            9300
Asp Met Ala Ile Thr Pro Lys Thr Gly Pro Ser Gly Ala Thr Ser
    9305            9310            9315
Gln Gly Thr Phe Thr Leu Asp Ser Ser Ser Thr Ala Ser Trp Pro
    9320            9325            9330
Gly Thr His Ser Ala Thr Thr Gln Arg Phe Pro Gln Ser Val Val
    9335            9340            9345
Thr Thr Pro Met Ser Arg Gly Pro Glu Asp Val Ser Trp Pro Ser
    9350            9355            9360
Pro Leu Ser Val Glu Lys Asn Ser Pro Pro Ser Ser Leu Val Ser
    9365            9370            9375
Ser Ser Ser Val Thr Ser Pro Ser Pro Leu Tyr Ser Thr Pro Ser
    9380            9385            9390
Gly Ser Ser His Ser Ser Pro Val Pro Val Thr Ser Leu Phe Thr
    9395            9400            9405
Ser Ile Met Met Lys Ala Thr Asp Met Leu Asp Ala Ser Leu Glu
    9410            9415            9420
Pro Glu Thr Thr Ser Ala Pro Asn Met Asn Ile Thr Ser Asp Glu
    9425            9430            9435
Ser Leu Ala Ala Ser Lys Ala Thr Thr Glu Thr Glu Ala Ile His
    9440            9445            9450
Val Phe Glu Asn Thr Ala Ala Ser His Val Glu Thr Thr Ser Ala
    9455            9460            9465
```

-continued

```
Thr Glu Glu Leu Tyr Ser Ser Ser Pro Gly Phe Ser Glu Pro Thr
    9470            9475                9480
Lys Val Ile Ser Pro Val Val Thr Ser Ser Ile Arg Asp Asn
    9485            9490                9495
Met Val Ser Thr Thr Met Pro Gly Ser Ser Gly Ile Thr Arg Ile
    9500            9505                9510
Glu Ile Glu Ser Met Ser Ser Leu Thr Pro Gly Leu Arg Glu Thr
    9515            9520                9525
Arg Thr Ser Gln Asp Ile Thr Ser Ser Thr Glu Thr Ser Thr Val
    9530            9535                9540
Leu Tyr Lys Met Pro Ser Gly Ala Thr Pro Glu Val Ser Arg Thr
    9545            9550                9555
Glu Val Met Pro Ser Ser Arg Thr Ser Ile Pro Gly Pro Ala Gln
    9560            9565                9570
Ser Thr Met Ser Leu Asp Ile Ser Asp Glu Val Val Thr Arg Leu
    9575            9580                9585
Ser Thr Ser Pro Ile Met Thr Glu Ser Ala Glu Ile Thr Ile Thr
    9590            9595                9600
Thr Gln Thr Gly Tyr Ser Leu Ala Thr Ser Gln Val Thr Leu Pro
    9605            9610                9615
Leu Gly Thr Ser Met Thr Phe Leu Ser Gly Thr His Ser Thr Met
    9620            9625                9630
Ser Gln Gly Leu Ser His Ser Glu Met Thr Asn Leu Met Ser Arg
    9635            9640                9645
Gly Pro Glu Ser Leu Ser Trp Thr Ser Pro Arg Phe Val Glu Thr
    9650            9655                9660
Thr Arg Ser Ser Ser Ser Leu Thr Ser Leu Pro Leu Thr Thr Ser
    9665            9670                9675
Leu Ser Pro Val Ser Ser Thr Leu Leu Asp Ser Ser Pro Ser Ser
    9680            9685                9690
Pro Leu Pro Val Thr Ser Leu Ile Leu Pro Gly Leu Val Lys Thr
    9695            9700                9705
Thr Glu Val Leu Asp Thr Ser Ser Glu Pro Lys Thr Ser Ser Ser
    9710            9715                9720
Pro Asn Leu Ser Ser Thr Ser Val Glu Ile Pro Ala Thr Ser Glu
    9725            9730                9735
Ile Met Thr Asp Thr Glu Lys Ile His Pro Ser Ser Asn Thr Ala
    9740            9745                9750
Val Ala Lys Val Arg Thr Ser Ser Ser Val His Glu Ser His Ser
    9755            9760                9765
Ser Val Leu Ala Asp Ser Glu Thr Thr Ile Thr Ile Pro Ser Met
    9770            9775                9780
Gly Ile Thr Ser Ala Val Asp Asp Thr Thr Val Phe Thr Ser Asn
    9785            9790                9795
Pro Ala Phe Ser Glu Thr Arg Arg Ile Pro Thr Glu Pro Thr Phe
    9800            9805                9810
Ser Leu Thr Pro Gly Phe Arg Glu Thr Ser Thr Glu Glu Thr
    9815            9820                9825
Thr Ser Ile Thr Glu Thr Ser Ala Val Leu Tyr Gly Val Pro Thr
    9830            9835                9840
Ser Ala Thr Thr Glu Val Ser Met Thr Glu Ile Met Ser Ser Asn
    9845            9850                9855
Arg Ile His Ile Pro Asp Ser Asp Gln Ser Thr Met Ser Pro Asp
```

```
                    9860              9865              9870

Ile  Ile  Thr  Glu  Val  Ile  Thr  Arg  Leu  Ser  Ser  Ser  Ser  Met  Met
         9875              9880              9885

Ser  Glu  Ser  Thr  Gln  Met  Thr  Ile  Thr  Thr  Gln  Lys  Ser  Ser  Pro
         9890              9895              9900

Gly  Ala  Thr  Ala  Gln  Ser  Thr  Leu  Thr  Leu  Ala  Thr  Thr  Thr  Ala
         9905              9910              9915

Pro  Leu  Ala  Arg  Thr  His  Ser  Thr  Val  Pro  Pro  Arg  Phe  Leu  His
         9920              9925              9930

Ser  Glu  Met  Thr  Thr  Leu  Met  Ser  Arg  Ser  Pro  Glu  Asn  Pro  Ser
         9935              9940              9945

Trp  Lys  Ser  Ser  Leu  Phe  Val  Glu  Lys  Thr  Ser  Ser  Ser  Ser  Ser
         9950              9955              9960

Leu  Leu  Ser  Leu  Pro  Val  Thr  Thr  Ser  Pro  Ser  Val  Ser  Ser  Thr
         9965              9970              9975

Leu  Pro  Gln  Ser  Ile  Pro  Ser  Ser  Ser  Phe  Ser  Val  Thr  Ser  Leu
         9980              9985              9990

Leu  Thr  Pro  Gly  Met  Val  Lys  Thr  Thr  Asp  Thr  Ser  Thr  Glu  Pro
         9995              10000             10005

Gly  Thr  Ser  Leu  Ser  Pro  Asn  Leu  Ser  Gly  Thr  Ser  Val  Glu  Ile
         10010             10015             10020

Leu  Ala  Ala  Ser  Glu  Val  Thr  Thr  Asp  Thr  Glu  Lys  Ile  His  Pro
         10025             10030             10035

Ser  Ser  Ser  Met  Ala  Val  Thr  Asn  Val  Gly  Thr  Thr  Ser  Ser  Gly
         10040             10045             10050

His  Glu  Leu  Tyr  Ser  Ser  Val  Ser  Ile  His  Ser  Glu  Pro  Ser  Lys
         10055             10060             10065

Ala  Thr  Tyr  Pro  Val  Gly  Thr  Pro  Ser  Ser  Met  Ala  Glu  Thr  Ser
         10070             10075             10080

Ile  Ser  Thr  Ser  Met  Pro  Ala  Asn  Phe  Glu  Thr  Thr  Gly  Phe  Glu
         10085             10090             10095

Ala  Glu  Pro  Phe  Ser  His  Leu  Thr  Ser  Gly  Phe  Arg  Lys  Thr  Asn
         10100             10105             10110

Met  Ser  Leu  Asp  Thr  Ser  Ser  Val  Thr  Pro  Thr  Asn  Thr  Pro  Ser
         10115             10120             10125

Ser  Pro  Gly  Ser  Thr  His  Leu  Leu  Gln  Ser  Ser  Lys  Thr  Asp  Phe
         10130             10135             10140

Thr  Ser  Ser  Ala  Lys  Thr  Ser  Ser  Pro  Asp  Trp  Pro  Pro  Ala  Ser
         10145             10150             10155

Gln  Tyr  Thr  Glu  Ile  Pro  Val  Asp  Ile  Ile  Thr  Pro  Phe  Asn  Ala
         10160             10165             10170

Ser  Pro  Ser  Ile  Thr  Glu  Ser  Thr  Gly  Ile  Thr  Ser  Phe  Pro  Glu
         10175             10180             10185

Ser  Arg  Phe  Thr  Met  Ser  Val  Thr  Glu  Ser  Thr  His  His  Leu  Ser
         10190             10195             10200

Thr  Asp  Leu  Leu  Pro  Ser  Ala  Glu  Thr  Ile  Ser  Thr  Gly  Thr  Val
         10205             10210             10215

Met  Pro  Ser  Leu  Ser  Glu  Ala  Met  Thr  Ser  Phe  Ala  Thr  Thr  Gly
         10220             10225             10230

Val  Pro  Arg  Ala  Ile  Ser  Gly  Ser  Gly  Ser  Pro  Phe  Ser  Arg  Thr
         10235             10240             10245

Glu  Ser  Gly  Pro  Gly  Asp  Ala  Thr  Leu  Ser  Thr  Ile  Ala  Glu  Ser
         10250             10255             10260
```

```
Leu Pro Ser Ser Thr Pro Val Pro Phe Ser Ser Ser Thr Phe Thr
    10265           10270               10275

Thr Thr Asp Ser Ser Thr Ile Pro Ala Leu His Glu Ile Thr Ser
    10280           10285               10290

Ser Ser Ala Thr Pro Tyr Arg Val Asp Thr Ser Leu Gly Thr Glu
    10295           10300               10305

Ser Ser Thr Thr Glu Gly Arg Leu Val Met Val Ser Thr Leu Asp
    10310           10315               10320

Thr Ser Ser Gln Pro Gly Arg Thr Ser Ser Ser Pro Ile Leu Asp
    10325           10330               10335

Thr Arg Met Thr Glu Ser Val Glu Leu Gly Thr Val Thr Ser Ala
    10340           10345               10350

Tyr Gln Val Pro Ser Leu Ser Thr Arg Leu Thr Arg Thr Asp Gly
    10355           10360               10365

Ile Met Glu His Ile Thr Lys Ile Pro Asn Glu Ala Ala His Arg
    10370           10375               10380

Gly Thr Ile Arg Pro Val Lys Gly Pro Gln Thr Ser Thr Ser Pro
    10385           10390               10395

Ala Ser Pro Lys Gly Leu His Thr Gly Gly Thr Lys Arg Met Glu
    10400           10405               10410

Thr Thr Thr Thr Ala Leu Lys Thr Thr Thr Thr Ala Leu Lys Thr
    10415           10420               10425

Thr Ser Arg Ala Thr Leu Thr Thr Ser Val Tyr Thr Pro Thr Leu
    10430           10435               10440

Gly Thr Leu Thr Pro Leu Asn Ala Ser Met Gln Met Ala Ser Thr
    10445           10450               10455

Ile Pro Thr Glu Met Met Ile Thr Thr Pro Tyr Val Phe Pro Asp
    10460           10465               10470

Val Pro Glu Thr Thr Ser Ser Leu Ala Thr Ser Leu Gly Ala Glu
    10475           10480               10485

Thr Ser Thr Ala Leu Pro Arg Thr Thr Pro Ser Val Phe Asn Arg
    10490           10495               10500

Glu Ser Glu Thr Thr Ala Ser Leu Val Ser Arg Ser Gly Ala Glu
    10505           10510               10515

Arg Ser Pro Val Ile Gln Thr Leu Asp Val Ser Ser Ser Glu Pro
    10520           10525               10530

Asp Thr Thr Ala Ser Trp Val Ile His Pro Ala Glu Thr Ile Pro
    10535           10540               10545

Thr Val Ser Lys Thr Thr Pro Asn Phe Phe His Ser Glu Leu Asp
    10550           10555               10560

Thr Val Ser Ser Thr Ala Thr Ser His Gly Ala Asp Val Ser Ser
    10565           10570               10575

Ala Ile Pro Thr Asn Ile Ser Pro Ser Glu Leu Asp Ala Leu Thr
    10580           10585               10590

Pro Leu Val Thr Ile Ser Gly Thr Asp Thr Ser Thr Thr Phe Pro
    10595           10600               10605

Thr Leu Thr Lys Ser Pro His Glu Thr Glu Thr Arg Thr Thr Trp
    10610           10615               10620

Leu Thr His Pro Ala Glu Thr Ser Ser Thr Ile Pro Arg Thr Ile
    10625           10630               10635

Pro Asn Phe Ser His His Glu Ser Asp Ala Thr Pro Ser Ile Ala
    10640           10645               10650
```

-continued

| | | | | | | | | | | |
|---|---|---|---|---|---|---|---|---|---|---|
| Thr | Ser | Pro | Gly | Ala | Glu | Thr | Ser | Ser | Ala | Ile | Pro | Ile | Met | Thr |
| | 10655 | | | | 10660 | | | | 10665 | | | | | |
| Val | Ser | Pro | Gly | Ala | Glu | Asp | Leu | Val | Thr | Ser | Gln | Val | Thr | Ser |
| | 10670 | | | | 10675 | | | | 10680 | | | | | |
| Ser | Gly | Thr | Asp | Arg | Asn | Met | Thr | Ile | Pro | Thr | Leu | Thr | Leu | Ser |
| | 10685 | | | | 10690 | | | | 10695 | | | | | |
| Pro | Gly | Glu | Pro | Lys | Thr | Ile | Ala | Ser | Leu | Val | Thr | His | Pro | Glu |
| | 10700 | | | | 10705 | | | | 10710 | | | | | |
| Ala | Gln | Thr | Ser | Ser | Ala | Ile | Pro | Thr | Ser | Thr | Ile | Ser | Pro | Ala |
| | 10715 | | | | 10720 | | | | 10725 | | | | | |
| Val | Ser | Arg | Leu | Val | Thr | Ser | Met | Val | Thr | Ser | Leu | Ala | Ala | Lys |
| | 10730 | | | | 10735 | | | | 10740 | | | | | |
| Thr | Ser | Thr | Thr | Asn | Arg | Ala | Leu | Thr | Asn | Ser | Pro | Gly | Glu | Pro |
| | 10745 | | | | 10750 | | | | 10755 | | | | | |
| Ala | Thr | Thr | Val | Ser | Leu | Val | Thr | His | Pro | Ala | Gln | Thr | Ser | Pro |
| | 10760 | | | | 10765 | | | | 10770 | | | | | |
| Thr | Val | Pro | Trp | Thr | Thr | Ser | Ile | Phe | Phe | His | Ser | Lys | Ser | Asp |
| | 10775 | | | | 10780 | | | | 10785 | | | | | |
| Thr | Thr | Pro | Ser | Met | Thr | Thr | Ser | His | Gly | Ala | Glu | Ser | Ser | Ser |
| | 10790 | | | | 10795 | | | | 10800 | | | | | |
| Ala | Val | Pro | Thr | Pro | Thr | Val | Ser | Thr | Glu | Val | Pro | Gly | Val | Val |
| | 10805 | | | | 10810 | | | | 10815 | | | | | |
| Thr | Pro | Leu | Val | Thr | Ser | Ser | Arg | Ala | Val | Ile | Ser | Thr | Thr | Ile |
| | 10820 | | | | 10825 | | | | 10830 | | | | | |
| Pro | Ile | Leu | Thr | Leu | Ser | Pro | Gly | Glu | Pro | Glu | Thr | Thr | Pro | Ser |
| | 10835 | | | | 10840 | | | | 10845 | | | | | |
| Met | Ala | Thr | Ser | His | Gly | Glu | Glu | Ala | Ser | Ser | Ala | Ile | Pro | Thr |
| | 10850 | | | | 10855 | | | | 10860 | | | | | |
| Pro | Thr | Val | Ser | Pro | Gly | Val | Pro | Gly | Val | Val | Thr | Ser | Leu | Val |
| | 10865 | | | | 10870 | | | | 10875 | | | | | |
| Thr | Ser | Ser | Arg | Ala | Val | Thr | Ser | Thr | Thr | Ile | Pro | Ile | Leu | Thr |
| | 10880 | | | | 10885 | | | | 10890 | | | | | |
| Phe | Ser | Leu | Gly | Glu | Pro | Glu | Thr | Thr | Pro | Ser | Met | Ala | Thr | Ser |
| | 10895 | | | | 10900 | | | | 10905 | | | | | |
| His | Gly | Thr | Glu | Ala | Gly | Ser | Ala | Val | Pro | Thr | Val | Leu | Pro | Glu |
| | 10910 | | | | 10915 | | | | 10920 | | | | | |
| Val | Pro | Gly | Met | Val | Thr | Ser | Leu | Val | Ala | Ser | Ser | Arg | Ala | Val |
| | 10925 | | | | 10930 | | | | 10935 | | | | | |
| Thr | Ser | Thr | Thr | Leu | Pro | Thr | Leu | Thr | Leu | Ser | Pro | Gly | Glu | Pro |
| | 10940 | | | | 10945 | | | | 10950 | | | | | |
| Glu | Thr | Thr | Pro | Ser | Met | Ala | Thr | Ser | His | Gly | Ala | Glu | Ala | Ser |
| | 10955 | | | | 10960 | | | | 10965 | | | | | |
| Ser | Thr | Val | Pro | Thr | Val | Ser | Pro | Glu | Val | Pro | Gly | Val | Val | Thr |
| | 10970 | | | | 10975 | | | | 10980 | | | | | |
| Ser | Leu | Val | Thr | Ser | Ser | Ser | Gly | Val | Asn | Ser | Thr | Ser | Ile | Pro |
| | 10985 | | | | 10990 | | | | 10995 | | | | | |
| Thr | Leu | Ile | Leu | Ser | Pro | Gly | Glu | Leu | Glu | Thr | Thr | Pro | Ser | Met |
| | 11000 | | | | 11005 | | | | 11010 | | | | | |
| Ala | Thr | Ser | His | Gly | Ala | Glu | Ala | Ser | Ser | Ala | Val | Pro | Thr | Pro |
| | 11015 | | | | 11020 | | | | 11025 | | | | | |
| Thr | Val | Ser | Pro | Gly | Val | Ser | Gly | Val | Val | Thr | Pro | Leu | Val | Thr |
| | 11030 | | | | 11035 | | | | 11040 | | | | | |
| Ser | Ser | Arg | Ala | Val | Thr | Ser | Thr | Thr | Ile | Pro | Ile | Leu | Thr | Leu |

-continued

|  | 11045 |  |  |  | 11050 |  |  |  | 11055 |  |  |
|---|---|---|---|---|---|---|---|---|---|---|---|
| Ser | Ser | Ser | Glu | Pro | Glu | Thr | Thr | Pro | Ser | Met | Ala | Thr | Ser | His |
|  | 11060 |  |  |  | 11065 |  |  |  | 11070 |  |  |
| Gly | Val | Glu | Ala | Ser | Ser | Ala | Val | Leu | Thr | Val | Ser | Pro | Glu | Val |
|  | 11075 |  |  |  | 11080 |  |  |  | 11085 |  |  |
| Pro | Gly | Met | Val | Thr | Ser | Leu | Val | Thr | Ser | Ser | Arg | Ala | Val | Thr |
|  | 11090 |  |  |  | 11095 |  |  |  | 11100 |  |  |
| Ser | Thr | Thr | Ile | Pro | Thr | Leu | Thr | Ile | Ser | Ser | Asp | Glu | Pro | Glu |
|  | 11105 |  |  |  | 11110 |  |  |  | 11115 |  |  |
| Thr | Thr | Thr | Ser | Leu | Val | Thr | His | Ser | Glu | Ala | Lys | Met | Ile | Ser |
|  | 11120 |  |  |  | 11125 |  |  |  | 11130 |  |  |
| Ala | Ile | Pro | Thr | Leu | Ala | Val | Ser | Pro | Thr | Val | Gln | Gly | Leu | Val |
|  | 11135 |  |  |  | 11140 |  |  |  | 11145 |  |  |
| Thr | Ser | Leu | Val | Thr | Ser | Ser | Gly | Ser | Glu | Thr | Ser | Ala | Phe | Ser |
|  | 11150 |  |  |  | 11155 |  |  |  | 11160 |  |  |
| Asn | Leu | Thr | Val | Ala | Ser | Ser | Gln | Pro | Glu | Thr | Ile | Asp | Ser | Trp |
|  | 11165 |  |  |  | 11170 |  |  |  | 11175 |  |  |
| Val | Ala | His | Pro | Gly | Thr | Glu | Ala | Ser | Ser | Val | Val | Pro | Thr | Leu |
|  | 11180 |  |  |  | 11185 |  |  |  | 11190 |  |  |
| Thr | Val | Ser | Thr | Gly | Glu | Pro | Phe | Thr | Asn | Ile | Ser | Leu | Val | Thr |
|  | 11195 |  |  |  | 11200 |  |  |  | 11205 |  |  |
| His | Pro | Ala | Glu | Ser | Ser | Ser | Thr | Leu | Pro | Arg | Thr | Thr | Ser | Arg |
|  | 11210 |  |  |  | 11215 |  |  |  | 11220 |  |  |
| Phe | Ser | His | Ser | Glu | Leu | Asp | Thr | Met | Pro | Ser | Thr | Val | Thr | Ser |
|  | 11225 |  |  |  | 11230 |  |  |  | 11235 |  |  |
| Pro | Glu | Ala | Glu | Ser | Ser | Ser | Ala | Ile | Ser | Thr | Thr | Ile | Ser | Pro |
|  | 11240 |  |  |  | 11245 |  |  |  | 11250 |  |  |
| Gly | Ile | Pro | Gly | Val | Leu | Thr | Ser | Leu | Val | Thr | Ser | Ser | Gly | Arg |
|  | 11255 |  |  |  | 11260 |  |  |  | 11265 |  |  |
| Asp | Ile | Ser | Ala | Thr | Phe | Pro | Thr | Val | Pro | Glu | Ser | Pro | His | Glu |
|  | 11270 |  |  |  | 11275 |  |  |  | 11280 |  |  |
| Ser | Glu | Ala | Thr | Ala | Ser | Trp | Val | Thr | His | Pro | Ala | Val | Thr | Ser |
|  | 11285 |  |  |  | 11290 |  |  |  | 11295 |  |  |
| Thr | Thr | Val | Pro | Arg | Thr | Thr | Pro | Asn | Tyr | Ser | His | Ser | Glu | Pro |
|  | 11300 |  |  |  | 11305 |  |  |  | 11310 |  |  |
| Asp | Thr | Thr | Pro | Ser | Ile | Ala | Thr | Ser | Pro | Gly | Ala | Glu | Ala | Thr |
|  | 11315 |  |  |  | 11320 |  |  |  | 11325 |  |  |
| Ser | Asp | Phe | Pro | Thr | Ile | Thr | Val | Ser | Pro | Asp | Val | Pro | Asp | Met |
|  | 11330 |  |  |  | 11335 |  |  |  | 11340 |  |  |
| Val | Thr | Ser | Gln | Val | Thr | Ser | Ser | Gly | Thr | Asp | Thr | Ser | Ile | Thr |
|  | 11345 |  |  |  | 11350 |  |  |  | 11355 |  |  |
| Ile | Pro | Thr | Leu | Thr | Leu | Ser | Ser | Gly | Glu | Pro | Glu | Thr | Thr | Thr |
|  | 11360 |  |  |  | 11365 |  |  |  | 11370 |  |  |
| Ser | Phe | Ile | Thr | Tyr | Ser | Glu | Thr | His | Thr | Ser | Ser | Ala | Ile | Pro |
|  | 11375 |  |  |  | 11380 |  |  |  | 11385 |  |  |
| Thr | Leu | Pro | Val | Ser | Pro | Gly | Ala | Ser | Lys | Met | Leu | Thr | Ser | Leu |
|  | 11390 |  |  |  | 11395 |  |  |  | 11400 |  |  |
| Val | Ile | Ser | Ser | Gly | Thr | Asp | Ser | Thr | Thr | Thr | Phe | Pro | Thr | Leu |
|  | 11405 |  |  |  | 11410 |  |  |  | 11415 |  |  |
| Thr | Glu | Thr | Pro | Tyr | Glu | Pro | Glu | Thr | Thr | Ala | Ile | Gln | Leu | Ile |
|  | 11420 |  |  |  | 11425 |  |  |  | 11430 |  |  |
| His | Pro | Ala | Glu | Thr | Asn | Thr | Met | Val | Pro | Arg | Thr | Thr | Pro | Lys |
|  | 11435 |  |  |  | 11440 |  |  |  | 11445 |  |  |

-continued

```
Phe Ser His Ser Lys Ser Asp     Thr Thr Leu Pro Val     Ala Ile Thr
    11450           11455                   11460

Ser Pro Gly Pro Glu Ala Ser     Ser Ala Val Ser Thr     Thr Thr Ile
    11465           11470                   11475

Ser Pro Asp Met Ser Asp Leu     Val Thr Ser Leu Val     Pro Ser Ser
    11480           11485                   11490

Gly Thr Asp Thr Ser Thr Thr     Phe Pro Thr Leu Ser     Glu Thr Pro
    11495           11500                   11505

Tyr Glu Pro Glu Thr Thr Ala     Thr Trp Leu Thr His     Pro Ala Glu
    11510           11515                   11520

Thr Ser Thr Thr Val Ser Gly     Thr Ile Pro Asn Phe     Ser His Arg
    11525           11530                   11535

Gly Ser Asp Thr Ala Pro Ser     Met Val Thr Ser Pro     Gly Val Asp
    11540           11545                   11550

Thr Arg Ser Gly Val Pro Thr     Thr Thr Ile Pro Pro     Ser Ile Pro
    11555           11560                   11565

Gly Val Val Thr Ser Gln Val     Thr Ser Ser Ala Thr     Asp Thr Ser
    11570           11575                   11580

Thr Ala Ile Pro Thr Leu Thr     Pro Ser Pro Gly Glu     Pro Glu Thr
    11585           11590                   11595

Thr Ala Ser Ser Ala Thr His     Pro Gly Thr Gln Thr     Gly Phe Thr
    11600           11605                   11610

Val Pro Ile Arg Thr Val Pro     Ser Ser Glu Pro Asp     Thr Met Ala
    11615           11620                   11625

Ser Trp Val Thr His Pro Pro     Gln Thr Ser Thr Pro     Val Ser Arg
    11630           11635                   11640

Thr Thr Ser Ser Phe Ser His     Ser Ser Pro Asp Ala     Thr Pro Val
    11645           11650                   11655

Met Ala Thr Ser Pro Arg Thr     Glu Ala Ser Ser Ala     Val Leu Thr
    11660           11665                   11670

Thr Ile Ser Pro Gly Ala Pro     Glu Met Val Thr Ser     Gln Ile Thr
    11675           11680                   11685

Ser Ser Gly Ala Ala Thr Ser     Thr Thr Val Pro Thr     Leu Thr His
    11690           11695                   11700

Ser Pro Gly Met Pro Glu Thr     Thr Ala Leu Leu Ser     Thr His Pro
    11705           11710                   11715

Arg Thr Glu Thr Ser Lys Thr     Phe Pro Ala Ser Thr     Val Phe Pro
    11720           11725                   11730

Gln Val Ser Glu Thr Thr Ala     Ser Leu Thr Ile Arg     Pro Gly Ala
    11735           11740                   11745

Glu Thr Ser Thr Ala Leu Pro     Thr Gln Thr Thr Ser     Ser Leu Phe
    11750           11755                   11760

Thr Leu Leu Val Thr Gly Thr     Ser Arg Val Asp Leu     Ser Pro Thr
    11765           11770                   11775

Ala Ser Pro Gly Val Ser Ala     Lys Thr Ala Pro Leu     Ser Thr His
    11780           11785                   11790

Pro Gly Thr Glu Thr Ser Thr     Met Ile Pro Thr Ser     Thr Leu Ser
    11795           11800                   11805

Leu Gly Leu Leu Glu Thr Thr     Gly Leu Leu Ala Thr     Ser Ser Ser
    11810           11815                   11820

Ala Glu Thr Ser Thr Ser Thr     Leu Thr Leu Thr Val     Ser Pro Ala
    11825           11830                   11835
```

```
Val Ser  Gly Leu Ser Ser Ala  Ser Ile Thr Thr Asp  Lys Pro Gln
    11840            11845             11850

Thr Val  Thr Ser Trp Asn Thr  Glu Thr Ser Pro Ser  Val Thr Ser
    11855            11860             11865

Val Gly  Pro Pro Glu Phe Ser  Arg Thr Val Thr Gly  Thr Thr Met
    11870            11875             11880

Thr Leu  Ile Pro Ser Glu Met  Pro Thr Pro Pro Lys  Thr Ser His
    11885            11890             11895

Gly Glu  Gly Val Ser Pro Thr  Thr Ile Leu Arg Thr  Thr Met Val
    11900            11905             11910

Glu Ala  Thr Asn Leu Ala Thr  Thr Gly Ser Ser Pro  Thr Val Ala
    11915            11920             11925

Lys Thr  Thr Thr Thr Phe Asn  Thr Leu Ala Gly Ser  Leu Phe Thr
    11930            11935             11940

Pro Leu  Thr Thr Pro Gly Met  Ser Thr Leu Ala Ser  Glu Ser Val
    11945            11950             11955

Thr Ser  Arg Thr Ser Tyr Asn  His Arg Ser Trp Ile  Ser Thr Thr
    11960            11965             11970

Ser Ser  Tyr Asn Arg Arg Tyr  Trp Thr Pro Ala Thr  Ser Thr Pro
    11975            11980             11985

Val Thr  Ser Thr Phe Ser Pro  Gly Ile Ser Thr Ser  Ser Ile Pro
    11990            11995             12000

Ser Ser  Thr Ala Ala Thr Val  Pro Phe Met Val Pro  Phe Thr Leu
    12005            12010             12015

Asn Phe  Thr Ile Thr Asn Leu  Gln Tyr Glu Glu Asp  Met Arg His
    12020            12025             12030

Pro Gly  Ser Arg Lys Phe Asn  Ala Thr Glu Arg Glu  Leu Gln Gly
    12035            12040             12045

Leu Leu  Lys Pro Leu Phe Arg  Asn Ser Ser Leu Glu  Tyr Leu Tyr
    12050            12055             12060

Ser Gly  Cys Arg Leu Ala Ser  Leu Arg Pro Glu Lys  Asp Ser Ser
    12065            12070             12075

Ala Thr  Ala Val Asp Ala Ile  Cys Thr His Arg Pro  Asp Pro Glu
    12080            12085             12090

Asp Leu  Gly Leu Asp Arg Glu  Arg Leu Tyr Trp Glu  Leu Ser Asn
    12095            12100             12105

Leu Thr  Asn Gly Ile Gln Glu  Leu Gly Pro Tyr Thr  Leu Asp Arg
    12110            12115             12120

Asn Ser  Leu Tyr Val Asn Gly  Phe Thr His Arg Ser  Ser Met Pro
    12125            12130             12135

Thr Thr  Ser Thr Pro Gly Thr  Ser Thr Val Asp Val  Gly Thr Ser
    12140            12145             12150

Gly Thr  Pro Ser Ser Ser Pro  Ser Pro Thr Thr Ala  Gly Pro Leu
    12155            12160             12165

Leu Met  Pro Phe Thr Leu Asn  Phe Thr Ile Thr Asn  Leu Gln Tyr
    12170            12175             12180

Glu Glu  Asp Met Arg Arg Thr  Gly Ser Arg Lys Phe  Asn Thr Met
    12185            12190             12195

Glu Ser  Val Leu Gln Gly Leu  Leu Lys Pro Leu Phe  Lys Asn Thr
    12200            12205             12210

Ser Val  Gly Pro Leu Tyr Ser  Gly Cys Arg Leu Thr  Leu Leu Arg
    12215            12220             12225

Pro Glu  Lys Asp Gly Ala Ala  Thr Gly Val Asp Ala  Ile Cys Thr
```

```
            12230               12235               12240

His Arg Leu Asp Pro Lys Ser     Pro Gly Leu Asn Arg     Glu Gln Leu
            12245               12250               12255

Tyr Trp Glu Leu Ser Lys Leu     Thr Asn Asp Ile Glu     Glu Leu Gly
            12260               12265               12270

Pro Tyr Thr Leu Asp Arg Asn     Ser Leu Tyr Val Asn     Gly Phe Thr
            12275               12280               12285

His Gln Ser Ser Val Ser Thr     Thr Ser Thr Pro Gly     Thr Ser Thr
            12290               12295               12300

Val Asp Leu Arg Thr Ser Gly     Thr Pro Ser Ser Leu     Ser Ser Pro
            12305               12310               12315

Thr Ile Met Ala Ala Gly Pro     Leu Leu Val Pro Phe     Thr Leu Asn
            12320               12325               12330

Phe Thr Ile Thr Asn Leu Gln     Tyr Gly Glu Asp Met     Gly His Pro
            12335               12340               12345

Gly Ser Arg Lys Phe Asn Thr     Thr Glu Arg Val Leu     Gln Gly Leu
            12350               12355               12360

Leu Gly Pro Ile Phe Lys Asn     Thr Ser Val Gly Pro     Leu Tyr Ser
            12365               12370               12375

Gly Cys Arg Leu Thr Ser Leu     Arg Ser Glu Lys Asp     Gly Ala Ala
            12380               12385               12390

Thr Gly Val Asp Ala Ile Cys     Ile His His Leu Asp     Pro Lys Ser
            12395               12400               12405

Pro Gly Leu Asn Arg Glu Arg     Leu Tyr Trp Glu Leu     Ser Gln Leu
            12410               12415               12420

Thr Asn Gly Ile Lys Glu Leu     Gly Pro Tyr Thr Leu     Asp Arg Asn
            12425               12430               12435

Ser Leu Tyr Val Asn Gly Phe     Thr His Arg Thr Ser     Val Pro Thr
            12440               12445               12450

Ser Ser Thr Pro Gly Thr Ser     Thr Val Asp Leu Gly     Thr Ser Gly
            12455               12460               12465

Thr Pro Phe Ser Leu Pro Ser     Pro Ala Thr Ala Gly     Pro Leu Leu
            12470               12475               12480

Val Leu Phe Thr Leu Asn Phe     Thr Ile Thr Asn Leu     Lys Tyr Glu
            12485               12490               12495

Glu Asp Met His Arg Pro Gly     Ser Arg Lys Phe Asn     Thr Thr Glu
            12500               12505               12510

Arg Val Leu Gln Thr Leu Leu     Gly Pro Met Phe Lys     Asn Thr Ser
            12515               12520               12525

Val Gly Leu Leu Tyr Ser Gly     Cys Arg Leu Thr Leu     Leu Arg Ser
            12530               12535               12540

Glu Lys Asp Gly Ala Ala Thr     Gly Val Asp Ala Ile     Cys Thr His
            12545               12550               12555

Arg Leu Asp Pro Lys Ser Pro     Gly Val Asp Arg Glu     Gln Leu Tyr
            12560               12565               12570

Trp Glu Leu Ser Gln Leu Thr     Asn Gly Ile Lys Glu     Leu Gly Pro
            12575               12580               12585

Tyr Thr Leu Asp Arg Asn Ser     Leu Tyr Val Asn Gly     Phe Thr His
            12590               12595               12600

Trp Ile Pro Val Pro Thr Ser     Ser Thr Pro Gly Thr     Ser Thr Val
            12605               12610               12615

Asp Leu Gly Ser Gly Thr Pro     Ser Ser Leu Pro Ser     Pro Thr Thr
            12620               12625               12630
```

```
Ala Gly Pro Leu Leu Val Pro   Phe Thr Leu Asn Phe    Thr Ile Thr
    12635           12640                 12645

Asn Leu Lys Tyr Glu Glu Asp   Met His Cys Pro Gly    Ser Arg Lys
    12650           12655                 12660

Phe Asn Thr Thr Glu Arg Val   Leu Gln Ser Leu Leu    Gly Pro Met
    12665           12670                 12675

Phe Lys Asn Thr Ser Val Gly   Pro Leu Tyr Ser Gly    Cys Arg Leu
    12680           12685                 12690

Thr Leu Leu Arg Ser Glu Lys   Asp Gly Ala Ala Thr    Gly Val Asp
    12695           12700                 12705

Ala Ile Cys Thr His Arg Leu   Asp Pro Lys Ser Pro    Gly Val Asp
    12710           12715                 12720

Arg Glu Gln Leu Tyr Trp Glu   Leu Ser Gln Leu Thr    Asn Gly Ile
    12725           12730                 12735

Lys Glu Leu Gly Pro Tyr Thr   Leu Asp Arg Asn Ser    Leu Tyr Val
    12740           12745                 12750

Asn Gly Phe Thr His Gln Thr   Ser Ala Pro Asn Thr    Ser Thr Pro
    12755           12760                 12765

Gly Thr Ser Thr Val Asp Leu   Gly Thr Ser Gly Thr    Pro Ser Ser
    12770           12775                 12780

Leu Pro Ser Pro Thr Ser Ala   Gly Pro Leu Leu Val    Pro Phe Thr
    12785           12790                 12795

Leu Asn Phe Thr Ile Thr Asn   Leu Gln Tyr Glu Glu    Asp Met His
    12800           12805                 12810

His Pro Gly Ser Arg Lys Phe   Asn Thr Thr Glu Arg    Val Leu Gln
    12815           12820                 12825

Gly Leu Leu Gly Pro Met Phe   Lys Asn Thr Ser Val    Gly Leu Leu
    12830           12835                 12840

Tyr Ser Gly Cys Arg Leu Thr   Leu Leu Arg Pro Glu    Lys Asn Gly
    12845           12850                 12855

Ala Ala Thr Gly Met Asp Ala   Ile Cys Ser His Arg    Leu Asp Pro
    12860           12865                 12870

Lys Ser Pro Gly Leu Asn Arg   Glu Gln Leu Tyr Trp    Glu Leu Ser
    12875           12880                 12885

Gln Leu Thr His Gly Ile Lys   Glu Leu Gly Pro Tyr    Thr Leu Asp
    12890           12895                 12900

Arg Asn Ser Leu Tyr Val Asn   Gly Phe Thr His Arg    Ser Ser Val
    12905           12910                 12915

Ala Pro Thr Ser Thr Pro Gly   Thr Ser Thr Val Asp    Leu Gly Thr
    12920           12925                 12930

Ser Gly Thr Pro Ser Ser Leu   Pro Ser Pro Thr Thr    Ala Val Pro
    12935           12940                 12945

Leu Leu Val Pro Phe Thr Leu   Asn Phe Thr Ile Thr    Asn Leu Gln
    12950           12955                 12960

Tyr Gly Glu Asp Met Arg His   Pro Gly Ser Arg Lys    Phe Asn Thr
    12965           12970                 12975

Thr Glu Arg Val Leu Gln Gly   Leu Leu Gly Pro Leu    Phe Lys Asn
    12980           12985                 12990

Ser Ser Val Gly Pro Leu Tyr   Ser Gly Cys Arg Leu    Ile Ser Leu
    12995           13000                 13005

Arg Ser Glu Lys Asp Gly Ala   Ala Thr Gly Val Asp    Ala Ile Cys
    13010           13015                 13020
```

| | | | | | | | | | | |
|---|---|---|---|---|---|---|---|---|---|---|
|Thr|His 13025|His|Leu|Asn|Pro 13030|Gln|Ser|Pro|Gly 13035|Leu|Asp|Arg|Glu|Gln|
|Leu|Tyr 13040|Trp|Gln|Leu|Ser 13045|Gln|Met|Thr|Asn 13050|Gly|Ile|Lys|Glu|Leu|
|Gly|Pro 13055|Tyr|Thr|Leu|Asp 13060|Arg|Asn|Ser|Leu 13065|Tyr|Val|Asn|Gly|Phe|
|Thr|His 13070|Arg|Ser|Ser|Gly 13075|Leu|Thr|Thr|Ser 13080|Thr|Pro|Trp|Thr|Ser|
|Thr|Val 13085|Asp|Leu|Gly|Thr 13090|Ser|Gly|Thr|Pro 13095|Ser|Pro|Val|Pro|Ser|
|Pro|Thr 13100|Thr|Thr|Gly|Pro 13105|Leu|Leu|Val|Pro 13110|Phe|Thr|Leu|Asn|Phe|
|Thr|Ile 13115|Thr|Asn|Leu|Gln 13120|Tyr|Glu|Glu|Asn 13125|Met|Gly|His|Pro|Gly|
|Ser|Arg 13130|Lys|Phe|Asn|Ile 13135|Thr|Glu|Ser|Val 13140|Leu|Gln|Gly|Leu|Leu|
|Lys|Pro 13145|Leu|Phe|Lys|Ser 13150|Thr|Ser|Val|Gly 13155|Pro|Leu|Tyr|Ser|Gly|
|Cys|Arg 13160|Leu|Thr|Leu|Leu 13165|Arg|Pro|Glu|Lys 13170|Asp|Gly|Val|Ala|Thr|
|Arg|Val 13175|Asp|Ala|Ile|Cys 13180|Thr|His|Arg|Pro 13185|Asp|Pro|Lys|Ile|Pro|
|Gly|Leu 13190|Asp|Arg|Gln|Gln 13195|Leu|Tyr|Trp|Glu 13200|Leu|Ser|Gln|Leu|Thr|
|His|Ser 13205|Ile|Thr|Glu|Leu 13210|Gly|Pro|Tyr|Thr 13215|Leu|Asp|Arg|Asp|Ser|
|Leu|Tyr 13220|Val|Asn|Gly|Phe 13225|Thr|Gln|Arg|Ser 13230|Ser|Val|Pro|Thr|Thr|
|Ser|Thr 13235|Pro|Gly|Thr|Phe 13240|Thr|Val|Gln|Pro 13245|Glu|Thr|Ser|Glu|Thr|
|Pro|Ser 13250|Ser|Leu|Pro|Gly 13255|Pro|Thr|Ala|Thr 13260|Gly|Pro|Val|Leu|Leu|
|Pro|Phe 13265|Thr|Leu|Asn|Phe 13270|Thr|Ile|Thr|Asn 13275|Leu|Gln|Tyr|Glu|Glu|
|Asp|Met 13280|Arg|Arg|Pro|Gly 13285|Ser|Arg|Lys|Phe 13290|Asn|Thr|Thr|Glu|Arg|
|Val|Leu 13295|Gln|Gly|Leu|Leu 13300|Met|Pro|Leu|Phe 13305|Lys|Asn|Thr|Ser|Val|
|Ser|Ser 13310|Leu|Tyr|Ser|Gly 13315|Cys|Arg|Leu|Thr 13320|Leu|Leu|Arg|Pro|Glu|
|Lys|Asp 13325|Gly|Ala|Ala|Thr 13330|Arg|Val|Asp|Ala 13335|Val|Cys|Thr|His|Arg|
|Pro|Asp 13340|Pro|Lys|Ser|Pro 13345|Gly|Leu|Asp|Arg 13350|Glu|Arg|Leu|Tyr|Trp|
|Lys|Leu 13355|Ser|Gln|Leu|Thr 13360|His|Gly|Ile|Thr 13365|Glu|Leu|Gly|Pro|Tyr|
|Thr|Leu 13370|Asp|Arg|His|Ser 13375|Leu|Tyr|Val|Asn 13380|Gly|Phe|Thr|His|Gln|
|Ser|Ser 13385|Met|Thr|Thr|Thr 13390|Arg|Thr|Pro|Asp 13395|Thr|Ser|Thr|Met|His|
|Leu|Ala 13400|Thr|Ser|Arg|Thr 13405|Pro|Ala|Ser|Leu 13410|Ser|Gly|Pro|Met|Thr|
|Ala|Ser|Pro|Leu|Leu|Val|Leu|Phe|Thr|Ile|Asn|Phe|Thr|Ile|Thr|

-continued

```
            13415               13420               13425

Asn Leu Arg Tyr Glu Glu Asn Met His His Pro Gly Ser Arg Lys
        13430               13435               13440

Phe Asn Thr Thr Glu Arg Val Leu Gln Gly Leu Leu Arg Pro Val
        13445               13450               13455

Phe Lys Asn Thr Ser Val Gly Pro Leu Tyr Ser Gly Cys Arg Leu
        13460               13465               13470

Thr Leu Leu Arg Pro Lys Lys Asp Gly Ala Ala Thr Lys Val Asp
        13475               13480               13485

Ala Ile Cys Thr Tyr Arg Pro Asp Pro Lys Ser Pro Gly Leu Asp
        13490               13495               13500

Arg Glu Gln Leu Tyr Trp Glu Leu Ser Gln Leu Thr His Ser Ile
        13505               13510               13515

Thr Glu Leu Gly Pro Tyr Thr Leu Asp Arg Asp Ser Leu Tyr Val
        13520               13525               13530

Asn Gly Phe Thr Gln Arg Ser Ser Val Pro Thr Thr Ser Ile Pro
        13535               13540               13545

Gly Thr Pro Thr Val Asp Leu Gly Thr Ser Gly Thr Pro Val Ser
        13550               13555               13560

Lys Pro Gly Pro Ser Ala Ala Ser Pro Leu Leu Val Leu Phe Thr
        13565               13570               13575

Leu Asn Phe Thr Ile Thr Asn Leu Arg Tyr Glu Glu Asn Met Gln
        13580               13585               13590

His Pro Gly Ser Arg Lys Phe Asn Thr Thr Glu Arg Val Leu Gln
        13595               13600               13605

Gly Leu Leu Arg Ser Leu Phe Lys Ser Thr Ser Val Gly Pro Leu
        13610               13615               13620

Tyr Ser Gly Cys Arg Leu Thr Leu Leu Arg Pro Glu Lys Asp Gly
        13625               13630               13635

Thr Ala Thr Gly Val Asp Ala Ile Cys Thr His His Pro Asp Pro
        13640               13645               13650

Lys Ser Pro Arg Leu Asp Arg Glu Gln Leu Tyr Trp Glu Leu Ser
        13655               13660               13665

Gln Leu Thr His Asn Ile Thr Glu Leu Gly Pro Tyr Ala Leu Asp
        13670               13675               13680

Asn Asp Ser Leu Phe Val Asn Gly Phe Thr His Arg Ser Ser Val
        13685               13690               13695

Ser Thr Thr Ser Thr Pro Gly Thr Pro Thr Val Tyr Leu Gly Ala
        13700               13705               13710

Ser Lys Thr Pro Ala Ser Ile Phe Gly Pro Ser Ala Ala Ser His
        13715               13720               13725

Leu Leu Ile Leu Phe Thr Leu Asn Phe Thr Ile Thr Asn Leu Arg
        13730               13735               13740

Tyr Glu Glu Asn Met Trp Pro Gly Ser Arg Lys Phe Asn Thr Thr
        13745               13750               13755

Glu Arg Val Leu Gln Gly Leu Leu Arg Pro Leu Phe Lys Asn Thr
        13760               13765               13770

Ser Val Gly Pro Leu Tyr Ser Gly Cys Arg Leu Thr Leu Leu Arg
        13775               13780               13785

Pro Glu Lys Asp Gly Glu Ala Thr Gly Val Asp Ala Ile Cys Thr
        13790               13795               13800

His Arg Pro Asp Pro Thr Gly Pro Gly Leu Asp Arg Glu Gln Leu
        13805               13810               13815
```

```
Tyr Leu Glu Leu Ser Gln Leu     Thr His Ser Ile Thr     Glu Leu Gly
    13820           13825                   13830

Pro Tyr Thr Leu Asp Arg Asp     Ser Leu Tyr Val Asn     Gly Phe Thr
    13835           13840                   13845

His Arg Ser Ser Val Pro Thr     Thr Ser Thr Gly Val     Val Ser Glu
    13850           13855                   13860

Glu Pro Phe Thr Leu Asn Phe     Thr Ile Asn Asn Leu     Arg Tyr Met
    13865           13870                   13875

Ala Asp Met Gly Gln Pro Gly     Ser Leu Lys Phe Asn     Ile Thr Asp
    13880           13885                   13890

Asn Val Met Gln His Leu Leu     Ser Pro Leu Phe Gln     Arg Ser Ser
    13895           13900                   13905

Leu Gly Ala Arg Tyr Thr Gly     Cys Arg Val Ile Ala     Leu Arg Ser
    13910           13915                   13920

Val Lys Asn Gly Ala Glu Thr     Arg Val Asp Leu Leu     Cys Thr Tyr
    13925           13930                   13935

Leu Gln Pro Leu Ser Gly Pro     Gly Leu Pro Ile Lys     Gln Val Phe
    13940           13945                   13950

His Glu Leu Ser Gln Gln Thr     His Gly Ile Thr Arg     Leu Gly Pro
    13955           13960                   13965

Tyr Ser Leu Asp Lys Asp Ser     Leu Tyr Leu Asn Gly     Tyr Asn Glu
    13970           13975                   13980

Pro Gly Pro Asp Glu Pro Pro     Thr Thr Pro Lys Pro     Ala Thr Thr
    13985           13990                   13995

Phe Leu Pro Pro Leu Ser Glu     Ala Thr Thr Ala Met     Gly Tyr His
    14000           14005                   14010

Leu Lys Thr Leu Thr Leu Asn     Phe Thr Ile Ser Asn     Leu Gln Tyr
    14015           14020                   14025

Ser Pro Asp Met Gly Lys Gly     Ser Ala Thr Phe Asn     Ser Thr Glu
    14030           14035                   14040

Gly Val Leu Gln His Leu Leu     Arg Pro Leu Phe Gln     Lys Ser Ser
    14045           14050                   14055

Met Gly Pro Phe Tyr Leu Gly     Cys Gln Leu Ile Ser     Leu Arg Pro
    14060           14065                   14070

Glu Lys Asp Gly Ala Ala Thr     Gly Val Asp Thr Thr     Cys Thr Tyr
    14075           14080                   14085

His Pro Asp Pro Val Gly Pro     Gly Leu Asp Ile Gln     Gln Leu Tyr
    14090           14095                   14100

Trp Glu Leu Ser Gln Leu Thr     His Gly Val Thr Gln     Leu Gly Phe
    14105           14110                   14115

Tyr Val Leu Asp Arg Asp Ser     Leu Phe Ile Asn Gly     Tyr Ala Pro
    14120           14125                   14130

Gln Asn Leu Ser Ile Arg Gly     Glu Tyr Gln Ile Asn     Phe His Ile
    14135           14140                   14145

Val Asn Trp Asn Leu Ser Asn     Pro Asp Pro Thr Ser     Ser Glu Tyr
    14150           14155                   14160

Ile Thr Leu Leu Arg Asp Ile     Gln Asp Lys Val Thr     Thr Leu Tyr
    14165           14170                   14175

Lys Gly Ser Gln Leu His Asp     Thr Phe Arg Phe Cys     Leu Val Thr
    14180           14185                   14190

Asn Leu Thr Met Asp Ser Val     Leu Val Thr Val Lys     Ala Leu Phe
    14195           14200                   14205
```

```
Ser Ser Asn Leu Asp Pro Ser     Leu Val Glu Gln Val     Phe Leu Asp
    14210           14215               14220
Lys Thr Leu Asn Ala Ser Phe     His Trp Leu Gly Ser     Thr Tyr Gln
    14225           14230               14235
Leu Val Asp Ile His Val Thr     Glu Met Glu Ser Ser     Val Tyr Gln
    14240           14245               14250
Pro Thr Ser Ser Ser Ser Thr     Gln His Phe Tyr Leu     Asn Phe Thr
    14255           14260               14265
Ile Thr Asn Leu Pro Tyr Ser     Gln Asp Lys Ala Gln     Pro Gly Thr
    14270           14275               14280
Thr Asn Tyr Gln Arg Asn Lys     Arg Asn Ile Glu Asp     Ala Leu Asn
    14285           14290               14295
Gln Leu Phe Arg Asn Ser Ser     Ile Lys Ser Tyr Phe     Ser Asp Cys
    14300           14305               14310
Gln Val Ser Thr Phe Arg Ser     Val Pro Asn Arg His     His Thr Gly
    14315           14320               14325
Val Asp Ser Leu Cys Asn Phe     Ser Pro Leu Ala Arg     Arg Val Asp
    14330           14335               14340
Arg Val Ala Ile Tyr Glu Glu     Phe Leu Arg Met Thr     Arg Asn Gly
    14345           14350               14355
Thr Gln Leu Gln Asn Phe Thr     Leu Asp Arg Ser Ser     Val Leu Val
    14360           14365               14370
Asp Gly Tyr Ser Pro Asn Arg     Asn Glu Pro Leu Thr     Gly Asn Ser
    14375           14380               14385
Asp Leu Pro Phe Trp Ala Val     Ile Leu Ile Gly Leu     Ala Gly Leu
    14390           14395               14400
Leu Gly Val Ile Thr Cys Leu     Ile Cys Gly Val Leu     Val Thr Thr
    14405           14410               14415
Arg Arg Arg Lys Lys Glu Gly     Glu Tyr Asn Val Gln     Gln Gln Cys
    14420           14425               14430
Pro Gly Tyr Tyr Gln Ser His     Leu Asp Leu Glu Asp     Leu Gln
    14435           14440               14445

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 33

His His His His His His
1               5
```

ANTIBODIES TO MUCIN-16 (MUC16), ENCODING POLYNUCLEOTIDES AND METHODS OF TREATING MUC16-POSITIVE CANCER

CROSS-REFERENCE TO RELATED PATENT APPLICATIONS

This application is a U.S. National Stage Application under 35 U.S.C. § 371 of PCT Patent Application No. PCT/US2019/061503, filed on Nov. 14, 2019, which claims the benefit of and priority to U.S. Provisional Appl. No. 62/768,730, filed Nov. 16, 2018, the disclosure of each of which is incorporated by reference herein in its entirety.

STATEMENT OF GOVERNMENT SUPPORT

This invention was made with government support under CA190174 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 23, 2019, is named 115872-0494_SL.txt and is 299,423 bytes in size.

BACKGROUND OF THE INVENTION

Mucins are important biomolecules for cellular homeostasis and protection of epithelial surfaces. Changes in expression of mucins in cancers, such as ovarian cancer, are useful as a biomarker for diagnosis, prognosis and treatment (Singh A P, et al., Lancet Oncol 2008; 9(11): 1076-85). MUC16 is a mucin that is over expressed on most ovarian carcinoma cells and is an established surrogate serum marker (CA-125) for the detection and progression of ovarian cancers (Badgwell D, et al., Dis Markers 23(5-6):397410 (2007); Bast R C, Jr, et al., Int J Gynecol Cancer 15 Suppl 3:274-81 (2005); Fritsche H A, et al., Clin Chem 44(7): 1379-80 (1998); and Krivak T C et al., Gynecol Oncol 115(1):81-5 (2009)).

MUC16 is a highly glycosylated mucin composed of a large extracellular domain (CA-125), which is cleaved and released, and a retained domain (MUC-CD) (FIG. 1). MUC-CD comprises a non-repeating extracellular domain (MUC16 ectodomain) proximal to a cleavage site, a transmembrane domain, and a cytoplasmic tail with potential phosphorylation sites. Distal to the cleavage site, the released extracellular domain (CA-125) contains 16-20 tandem repeats of 156 amino acids, each with many potential glycosylation sites (O'Brien T J, et al., Tumor Biol 22(6): 348-66 (2001)). Since the MUC16 antigen is otherwise expressed only at low levels in normal tissues of the uterus, endometrium, fallopian tubes, ovaries, and serosa of the abdominal and thoracic cavities, MUC16 is a potentially attractive target for immune-based therapies, including the targeting and treatment of cancer.

A significant portion of the extracellular domain of MUC16 is cleaved and secreted (i.e., CA-125), which limits the utility of this portion of MUC16 to be used as a target antigen on ovarian carcinomas. Many reported MUC16 monoclonal antibodies bind to epitopes present on the large secreted CA-125 fraction of the glycoprotein, and not to the retained MUC16 ectodomain (Bellone S Am J Obstet Gynecol 200(1):75 el-10 (2009), Berek J S. Expert Opin Biol Ther. 4(7): 1159-65 (2004); O'Brien T J, et al., Int J Biol Markers 13(4): 188-95 (1998)). Thus, the generation of new antibodies to the region of MUC16 that is not shed are needed for diagnostic and therapeutic purposes.

SUMMARY OF THE INVENTION

Provided herein are compositions, methods, and uses of anti-Mucin 16 (MUC16) constructs that comprise antibody moieties that immunospecifically bind to Mucin 16 (MUC16), and modulate expression and/or activity of MUC16 for managing or treating MUC16-mediated disorders, such as cancer.

Provided herein, in certain embodiments, are anti-mucin 16 (MUC16) constructs comprising an antibody moiety that immunospecifically recognizes a mucin 16 (MUC16) polypeptide, wherein the antibody moiety comprises (a)(i) a variable heavy (VH) chain comprising a heavy chain complementarity determining region (HC-CDR) 1, an HC-CDR2, and an HC-CDR3 of the heavy chain variable domain of SEQ ID NO: 2; and (ii) a variable light (VL) chain comprising a light chain complementarity determining region (LC-CDR) 1, an LC-CDR2, and an LC-CDR3 of the light chain variable domain of SEQ ID NO: 3; or (b)(i) a variable heavy (VH) chain comprising a heavy chain complementarity determining region (HC-CDR) 1, an HC-CDR2, and an HC-CDR3 of the heavy chain variable domain of SEQ ID NO: 10; and (ii) a variable light (VL) chain comprising a light chain complementarity determining region (LC-CDR) 1, an LC-CDR2, and an LC-CDR3 of the light chain variable domain of SEQ ID NO: 11. In some embodiments, the antibody moiety immunospecifically recognizes a human MUC16. In some embodiments, the MUC16 is glycosylated. In some embodiments, the MUC16 is N-glycosylated at Asn1800 or Asn1806.

In some embodiments, the antibody moiety of the anti-mucin 16 (MUC16) constructs provided herein comprises (a)(i) a variable heavy (VH) chain comprising a heavy chain complementarity determining region (HC-CDR) 1 comprising the amino acid sequence of SEQ ID NO: 4; a HC-CDR2 comprising the amino acid sequence of SEQ ID NO: 5; and a HC-CDR3 comprising the amino acid sequence of SEQ ID NO: 6; and (ii) a variable light (VL) chain comprising: a light chain complementarity determining region (LC-CDR) 1 comprising the amino acid sequence of SEQ ID NO: 7; a LC-CDR2 comprising the amino acid sequence of SEQ ID NO: 8; and a LC-CDR3 comprising the amino acid sequence of SEQ ID NO: 9; or (b)(i) a variable heavy (VH) chain comprising a HC-CDR1 comprising the amino acid sequence of SEQ ID NO: 12; a HC-CDR2 comprising the amino acid sequence of SEQ ID NO: 13; and a HC-CDR3 comprising the amino acid sequence of SEQ ID NO: 14; and (ii) a variable light (VL) chain comprising: a LC-CDR1 comprising the amino acid sequence of SEQ ID NO: 15; a LC-CDR2 comprising the amino acid sequence of SEQ ID NO: 16; and a LC-CDR3 comprising the amino acid sequence of SEQ ID NO: 17.

In some embodiments, the antibody moiety of the anti-mucin 16 (MUC16) constructs provided herein immunospecifically binds to the ectodomain of MUC16. In some embodiments, the antibody moiety is a full-length antibody, a Fab, a Fab', a F(ab')2, an Fv, or a single chain Fv (scFv). In some embodiments, the VH chain and the VL chain are human VH chain and VL chain. In some embodiments, the antibody moiety is a monoclonal antibody. In some embodiments, the antibody moiety immunospecifically binds to a MUC16 c114 polypeptide comprising the amino acid sequence of SEQ ID NO: 25.

In some embodiments, the anti-MUC16 constructs provided herein inhibit in vitro invasion of a tumor cell that expresses MUC16 in a Matrigel invasion assay. In some embodiments, the tumor cell is an ovarian tumor cell.

In some embodiments, the antibody moiety of the anti-mucin 16 (MUC16) constructs provided herein comprises a VH comprising the amino acid sequence of SEQ ID NO: 2. In some embodiments, the antibody moiety comprises a VL comprising the amino acid sequence of SEQ ID NO: 3. In some embodiments, the antibody moiety comprises a VH comprising the amino acid sequence of SEQ ID NO: 10. In some embodiments, the antibody moiety comprises a VL comprising the amino acid sequence of SEQ ID NO: 11. In some embodiments, the antibody moiety comprises a VH comprising the amino acid sequence of SEQ ID NO: 2 and a VL comprising the amino acid sequence of SEQ ID NO: 3. In some embodiments, the antibody moiety comprises a VH comprising the amino acid sequence of SEQ ID NO: 10 and a VL comprising the amino acid sequence of SEQ ID NO: 11. In some embodiments, the antibody moiety comprises human-derived heavy and light chain constant regions. In some embodiments, the heavy chain constant region has an isotype selected from the group consisting of gamma 1, gamma 2, gamma 3, and gamma 4. In some embodiments, the light chain constant region has an isotype selected from the group consisting of kappa and lambda. In some embodiments, the antibody moiety is an immunoglobulin comprising two identical heavy chains and two identical light chains. In some embodiments, the immunoglobulin is an IgG.

In some embodiments, the anti-MUC16 construct provided herein is monospecific. In some embodiments, the anti-MUC16 construct provided herein is multispecific. In some embodiments, the anti-MUC16 construct provided herein is bispecific. In some embodiments, the anti-MUC16 construct provided herein is a tandem scFv, a diabody (Db), a single chain diabody (scDb), a dual-affinity retargeting (DART) antibody, a F(ab')2, a dual variable domain (DVD) antibody, a knob-into-hole (KiH) antibody, a dock and lock (DNL) antibody, a chemically cross-linked antibody, a heteromultimeric antibody, or a heteroconjugate antibody. In some embodiments, the anti-MUC16 construct provided herein is a tandem scFv comprising two scFvs linked by a peptide linker. In some embodiments, the antibody moiety that immunospecifically recognizes MUC16 is a first antibody moiety, and wherein the anti-MUC16 construct further comprises a second antibody moiety that immunospecifically recognizes a second antigen. In some embodiments, the second antigen is an antigen on the surface of a T cell. In some embodiments, the second antigen is a CD3. In some embodiments, the second antigen is selected from the group consisting of CD3γ, CD3δ, CD3ε, and CD3ζ. In some embodiments, the second antigen is CD3ε.

In some embodiments, the anti-MUC16 construct provided herein is a chimeric antigen receptor (CAR). In some embodiments, the CAR comprises a co-stimulatory domain. In some embodiments, the CAR comprises a CD3 zeta (ζ) chain cytoplasmic signaling domain.

In some embodiments, the anti-MUC16 construct provided herein is further conjugated to a peptide agent, a detection agent, an imaging agent, a therapeutic agent, or a cytotoxic agent.

Also provided herein, in certain embodiments, are polypeptides comprising an amino acid sequence of one or more of SEQ ID NOs: 2-17 or an amino acid of an anti-MUC16 construct provided herein.

Also provided herein, in certain embodiments, are polynucleotides comprising a nucleic acid sequence encoding one or more polypeptides comprising an amino acid sequence of one or more of SEQ ID NOs: 2-17 or an amino acid of an anti-MUC16 construct provided herein. Provided herein, in certain embodiments, are vectors comprising the polynucleotide provided herein operably linked to a promoter.

Also provided herein, in certain embodiments, are cells comprising the anti-MUC16 construct provided herein, a polypeptide provided herein, a polynucleotide provided herein, or a vector provided herein. In some embodiments, the cell is a mammalian cell. In some embodiments, the cell is an immune cell. In some embodiments, the cell is a lymphocyte. In some embodiments, the cell is a T cell or a B cell.

Also provided herein, in certain embodiments, are pharmaceutical compositions comprising: a therapeutically effective amount of the anti-MUC16 construct provided herein, a polypeptide provided herein, polynucleotide provided herein, or a vector provided herein; and a pharmaceutically acceptable carrier.

Also provided herein, in certain embodiments, are methods of treating a MUC16-associated disease or disorder in a patient in need thereof, comprising administering to said patient a pharmaceutical composition comprising a therapeutically effective amount of the anti-MUC16 construct provided herein, a polypeptide provided herein, polynucleotide provided herein, or a vector provided herein. In some embodiments, the MUC16-associated disease or disorder is a cancer. In some embodiments, the cancer is a cancer of the ovary, lung, pancreas, breast, uterine, fallopian tube, or primary peritoneum. In some embodiments, the cancer is a metastatic cancer. In some embodiments, the pharmaceutical composition inhibits metastasis in the patient. In some embodiments, the patient is a human patient.

Also provided herein, in certain embodiments, are methods for producing an effector cell, comprising genetically modifying a cell with one or more nucleic acids encoding the anti-MUC16 construct provided herein.

Also provided herein, in certain embodiments, are methods of comprising introducing one or more nucleic acids encoding the anti-MUC16 construct provided herein into one or more primary cells isolated from a patient and administering cells comprising the one or more nucleic acids to the patient. In some embodiments, the method further comprises expanding the cells prior to administering the cells to the patient. In some embodiments, the primary cells are lymphocytes. In some embodiments, the primary cells are T cells.

In some embodiments, the methods of treatment provided herein further comprises administering a therapeutically effective amount of an additional therapeutic agent to the patient. In some embodiments, the therapeutic agent is an anti-cancer agent. In some embodiments, the therapeutic agent is a chemotherapeutic agent.

Also provided herein, in certain embodiments, are methods of detecting MUC16 in a sample, comprising: (a) contacting the sample with the anti-MUC16 construct provided herein; and (b) detecting the binding, directly or indirectly, between the anti-MUC16 construct and MUC16 that is present in the sample. In some embodiments, the anti-MUC16 construct is conjugated to a detectable label. In some embodiments, the detectable label is a chromogenic, enzymatic, radioisotopic, isotopic, fluorescent, toxic, chemiluminescent, nuclear magnetic resonance contrast agent. In some embodiments, the binding between the anti-MUC16 construct and any MUC16 in the sample is detected directly by detecting the detectable label. In some embodiments, the binding between the anti-MUC16 construct and any MUC16 in the sample is detected indirectly using a secondary antibody.

Also provided herein, in certain embodiments, are methods of diagnosing an individual suspected of having a MUC16-associated disease or disorder, comprising a) administering an effective amount of the anti-MUC16 construct provided herein to the individual; and b) determining the level of the binding, directly or indirectly, between the anti-MUC16 construct and any MUC16 in the individual, wherein a level of the binding above a threshold level indicates that the individual has the MUC16-associated disease or disorder. In some embodiments, the anti-MUC16 construct is conjugated to a detectable label. In some embodiments, the detectable label is a chromogenic, enzymatic, radioisotopic, isotopic, fluorescent, toxic, chemiluminescent, nuclear magnetic resonance contrast agent. In some embodiments, the binding between the anti-MUC16 construct and any MUC16 in the sample is detected directly by detecting the detectable label. In some embodiments, the binding between the anti-MUC16 construct and any MUC16 in the sample is detected indirectly using a secondary antibody.

A method of diagnosing an individual suspected of having a MUC16-associated disease or disorder, comprising a) contacting a sample comprising cells derived from the individual with the anti-MUC16 construct provided herein; and b) determining the number of cells in the sample bound to the anti-MUC16 construct, wherein a value for the number of cells bound to the anti-MUC16 construct above a threshold level indicates that the individual has the MUC16-associated disease or disorder. In some embodiments, the anti-MUC16 construct is conjugated to a detectable label. In some embodiments, the detectable label is a chromogenic, enzymatic, radioisotopic, isotopic, fluorescent, toxic, chemiluminescent, nuclear magnetic resonance contrast agent. In some embodiments, the binding between the anti-MUC16 construct and any MUC16 in the sample is detected directly by detecting the detectable label. In some embodiments, the binding between the anti-MUC16 construct and any MUC16 in the sample is detected indirectly using a secondary antibody.

Also provided herein, in certain embodiments, are methods of generating an anti-MUC16 construct that immunospecifically binds to a human MUC16 polypeptide, comprising selecting a human scFv specific for human MUC16 from a human scFv antibody phage display library. In some embodiments, selecting a human scFv specific for human MUC16 comprises contacting the human scFv antibody phage display library with a cell that expresses a recombinant MUC16 polypeptide. In some embodiments, the recombinant MUC16 polypeptide comprises the sequence of SEQ ID NO: 25.

Also provided herein, in certain embodiments, are uses of anti-MUC16 constructs, anti-MUC16 polypeptides, polynucleotides encoding anti-MUC16 constructs or anti-MUC16 polypeptides, vectors comprising the polynucleotides, or cells comprising any the polypeptides and polynucleotides thereof provided herein for the treatment of a disease or disorder associated with positive MUC16 expression. In some embodiments, the disease or disorder associated with positive MUC16 expression is a cancer.

Also provided herein, in certain embodiments, are uses of the anti-MUC16 constructs, anti-MUC16 polypeptides, polynucleotides encoding anti-MUC16 constructs or anti-MUC16 polypeptides, vectors comprising the polynucleotides, or cells comprising any the polypeptides and polynucleotides thereof provided herein in the manufacture of a medicament for the treatment of a disease or disorder associated with positive MUC16 expression. In some embodiments, the disease or disorder associated with positive MUC16 expression is a cancer.

Also provided herein, in certain embodiments, are uses of anti-MUC16 constructs, anti-MUC16 polypeptides, polynucleotides encoding anti-MUC16 constructs or anti-MUC16 polypeptides, vectors comprising the polynucleotides, or cells comprising any the polypeptides and polynucleotides thereof provided herein for the diagnosis of a disease or disorder associated with positive MUC16 expression. In some embodiments, the disease or disorder associated with positive MUC16 expression is a cancer.

BRIEF DESCRIPTION OF THE DRAWINGS

FIG. 2 shows an amino acid alignment between wildtype MUC16-C114 (SEQ ID NO: 25) and the N30 mutant MUC16-C114 (SEQ ID NO: 31) ectodomains.

DETAILED DESCRIPTION OF THE INVENTION

Figure 1:
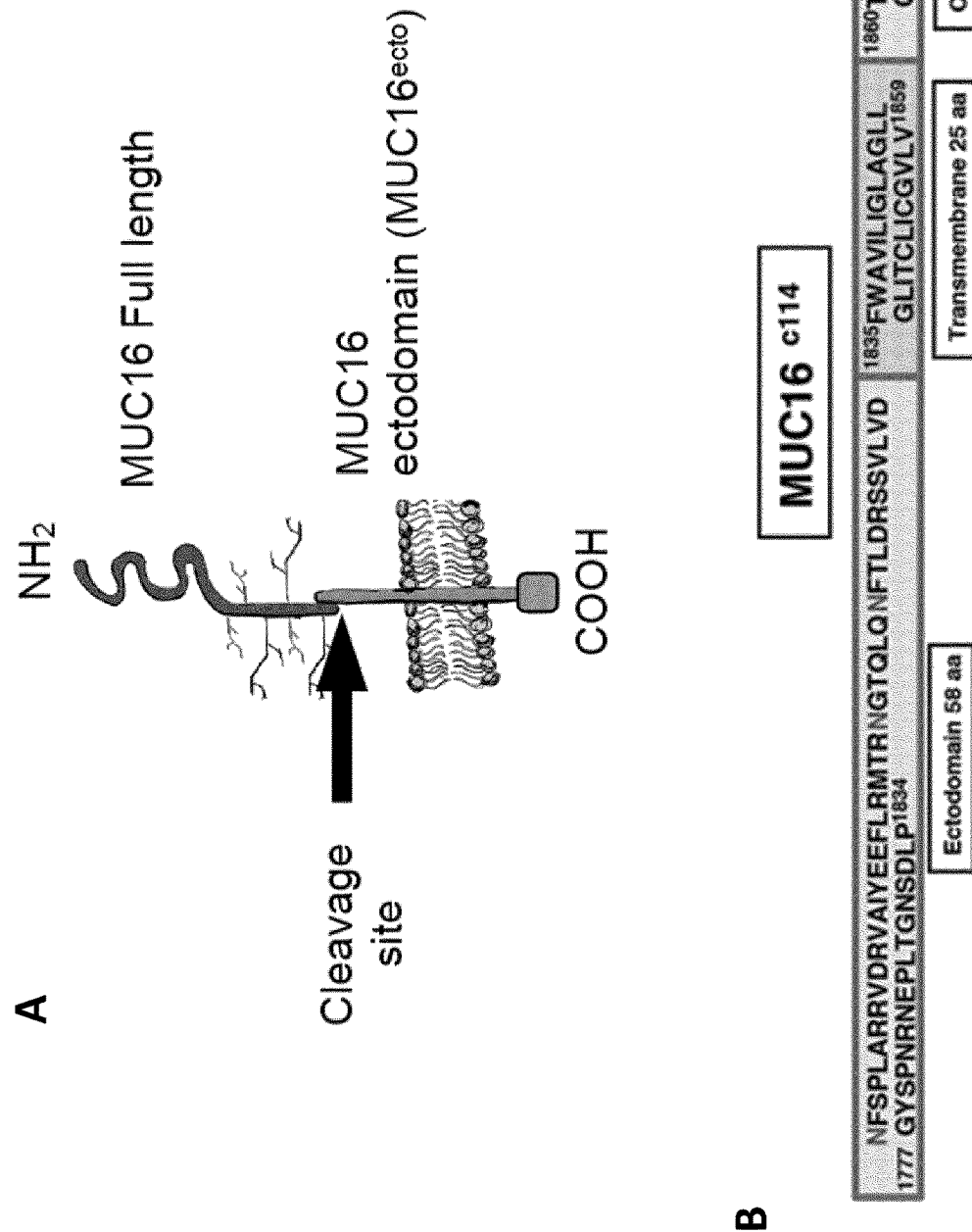
FIG. 1A shows a schematic illustration of the structure of MUC16.
FIG. 1B shows schematic and amino acid sequence of the truncated form of MUC16, called MUC16 c114 (SEQ ID NO: 25), which includes the 58 amino acid ectodomain, the 25 amino acid transmembrane domain, and the 31 amino acid cytoplasmic tail. Numbering in figure is based on original publication identifying Muc16, Yin and Lloyd (2001) *J Biol Chem* 276: 27371-27375.

The present application in one aspect provides anti-MUC16 antibody agents, such as anti-MUC16 constructs that comprise an antibody moiety that specifically recognizes an epitope of MUC16, such as an epitope of the retained extracellular domain of MUC16 (MUC16 ectodomain).

Using phage display technology, scFvs that are specific for the retained extracellular domain of human MUC16 were identified. Flow cytometry assays demonstrated that these antibodies recognize MUC16-expressing cancer cell lines. The present application thus provides anti-MUC16 antibody agents, such as anti-MUC16 constructs that comprise an antibody moiety that immunospecifically binds MUC16. The anti-MUC16 antibody agents include, for example, anti-MUC16 antibodies, e.g., full-length anti-MUC16 antibodies and antigen-binding fragments thereof, anti-MUC16 scFvs, anti-MUC16 antibody fusion proteins (e.g., anti-MUC16 Fc fusion proteins and chimeric antigen receptors (CAR)), multi-specific antibodies, e.g., bispecific antibodies, and anti-MUC16 antibody conjugates (i.e., anti-MUC16 immunoconjugates) thereof.

In another aspect, provided are nucleic acids encoding the anti-MUC16 antibody agents, such as anti-MUC16 antibodies, e.g., full-length anti-MUC16 antibodies and antigen-binding fragments thereof, anti-MUC16 scFvs, anti-MUC16 antibody fusion proteins (e.g., anti-MUC16 Fc fusion proteins and chimeric antigen receptors (CAR)), multi-specific antibodies, e.g., bispecific antibodies, and anti-MUC16 antibody conjugates (i.e., anti-MUC16 immunoconjugates) thereof.

In another aspect, provided are compositions, such as pharmaceutical compositions, comprising an anti-MUC16 antibody agent, such as full-length anti-MUC16 antibodies and antigen-binding fragments thereof, anti-MUC16 scFvs, anti-MUC16 antibody fusion proteins (e.g., anti-MUC16 Fc fusion proteins and chimeric antigen receptors (CAR)), multi-specific antibodies, e.g., bispecific antibodies, and anti-MUC16 antibody conjugates (i.e., anti-MUC16 immunoconjugates) thereof.

Also provided are methods of making and using the anti-MUC16 antibody agents and antibodies, such as for treating cancer, as well as kits and articles of manufacture useful for such methods.

Definitions

Unless defined otherwise, all technical and scientific terms used herein have the meaning commonly understood by a person skilled in the art to which this disclosure belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al., (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

As used herein, the term "MUC 16" or "MUC 16 polypeptide" or "MUC 16 peptide" refers to the MUC 16 tethered mucin protein as described in Yin B W and Lloyd K O, 2001, *J Biol Chem.* 276(29):27371-5. GenBank™ accession number NP 078966.2 (SEQ ID NO: 1) provides an exemplary human MUC 16 nucleic acid sequence. GenBank™ accession number NP 078966.2 (SEQ ID NO: 1) provides an exemplary human MUC16 amino acid sequence. Native MUC 16 comprises an intracellular domain, a transmembrane domain, an ectodomain proximal to the putative cleavage site, and a large, heavily glycosylated region of 12-20 repeats, each 156 amino acids long (FIG. 1A). "Immature" MUC16 refers to SEQ ID NO: 1, which comprises the MUC16 signal sequence (amino acid residues 1-60 of SEQ ID NO: 1). "Mature MUC 16" refers to native MUC 16 as expressed on the cell surface, i.e., where the signal sequence has been removed by cellular processing, for example, SEQ ID NO: 32, where the first 60 amino acid residues of SEQ ID NO: 1 have been removed (i.e., SEQ ID NO: 1 is the "immature" form of MUC16).

The polypeptide represented by the amino acid sequence of SEQ ID NO: 25 is referred to herein as MUC16 C114 and consists of the C-terminal 114 amino acid residues of mature MUC16 (SEQ ID NO: 32 being the sequence of mature MUC16). MUC16 C114 comprises a 58 amino acid ectodomain, a 25 amino acid transmembrane domain and a 31 amino acid cytoplasmic tail (FIG. 1B). MUC16c114 is capable of being N-glycosylated at the asparagine amino acid residues at positions 1, 24, and 30 of SEQ ID NO: 25 (also referred to as amino acid positions Asn1777, Asn1800, and Asn1806 according the original MUC16 publication Yin B W and Lloyd K O, 2001, *J Biol Chem.* 276(29):27371-5).

As used herein, the singular forms "a", "an" and "the" are intended to include the plural forms as well, unless the context clearly indicates otherwise.

As used herein, the terms "about" when used to modify a numeric value or numeric range, indicate that deviations of 5% to 10% above and 5% to 10% below the value or range remain within the intended meaning of the recited value or range.

As used herein, the term "administration" of an agent to a subject includes any route of introducing or delivering the agent to a subject to perform its intended function. Administration can be carried out by any suitable route, including, but not limited to, intravenously, intramuscularly, intraperitoneally, subcutaneously, and other suitable routes as described herein. Administration includes self-administration and the administration by another.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to agents that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as norleucine) or modified peptide backbones, but retain the same basic chemical structure as a naturally occurring amino acid. In some embodiments, amino acids forming a polypeptide are in the D form. In some embodiments, the amino acids forming a polypeptide are in the L form. In some embodiments, a first plurality of amino acids forming a polypeptide are in the D form and a second plurality are in the L form.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter code.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

As used herein, the term "effective amount" or "therapeutically effective amount" refers to a quantity of an agent sufficient to achieve a desired therapeutic effect. In the context of therapeutic applications, the amount of a therapeutic peptide administered to the subject can depend on the type and severity of the infection and on the characteristics of the individual, such as general health, age, sex, body weight and tolerance to drugs. It can also depend on the degree, severity and type of disease. The skilled artisan will be able to determine appropriate dosages depending on these and other factors.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell. The expression level of a gene can be determined by measuring the amount of mRNA or protein in a cell or tissue sample. In one aspect, the expression level of a gene from one sample can be directly compared to the expression level of that gene from a control or reference sample. In another aspect, the expression level of a gene from one sample can be directly compared to the expression level of that gene from the same sample following administration of the compositions disclosed herein. The term "expression" also refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5) presentation of a polypeptide or protein on the cell surface; and (6) secretion or presentation or release of a polypeptide or protein from a cell.

The term "linker" refers to synthetic sequences (e.g., amino acid sequences) that connect or link two sequences, e.g., that link two polypeptide domains. In some embodiments, the linker contains 1, 2, 3, 4, 5, 6, 7, 8, 9, or 10 of amino acid sequences.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')2, and Fab. F(ab')2, and Fab fragments that lack the Fc fragment of intact antibody, clear more rapidly from the circulation, and may have less non-specific tissue binding of an intact antibody (Wahl et al., *J. Nucl. Med.* 24:316-325 (1983)). The antibodies of the invention comprise whole native antibodies, monoclonal antibodies, human antibodies, humanized antibodies, camelised antibodies, multispecific antibodies, bispecific antibodies, chimeric antibodies, Fab, Fab', single chain V region fragments (scFv), single domain antibodies (e.g., nobodies and single domain camelid antibodies), $V_{NAR}$ fragments, Bi-specific T-cell engager antibodies, minibodies, disulfide-linked Fvs (sdFv), and anti-idiotypic (anti-Id) antibodies, intrabodies, fusion polypeptides, unconventional antibodies and antigen-binding fragments of any of the above. In particular, antibodies include immunoglobulin molecules and immunologically active fragments of immunoglobulin molecules, i.e., molecules that contain an antigen-binding site Immunoglobulin molecules can be of any type (e.g., IgG, IgE, IgM, IgD, IgA and IgY), class (e.g., IgG1, IgG2, IgG3, IgG4, IgA1 and IgA2) or subclass.

In certain embodiments, an antibody is a glycoprotein comprising at least two heavy (H) chains and two light (L) chains inter-connected by disulfide bonds. Each heavy chain is comprised of a heavy chain variable region (abbreviated herein as VH) and a heavy chain constant ($C_H$) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. As used herein interchangeably, the terms "antigen-binding portion", "antigen-binding fragment", or "antigen-binding region" of an antibody, refer to the region or portion of an antibody that binds to the antigen and which confers antigen specificity to the antibody; fragments of antigen-binding proteins, for example, antibodies includes one or more fragments of an antibody that retain the ability to specifically bind to an antigen (e.g., an peptide/HLA complex). It has been shown that the antigen-binding function of an antibody can be performed by fragments of a full-length antibody. Examples of antigen-binding portions encompassed within the term "antibody fragments" of an antibody include a Fab fragment, a monovalent fragment consisting of the $V_L$, $V_H$, $C_L$ and CHI domains; a $F(ab)_2$ fragment, a bivalent fragment comprising two Fab fragments linked by a disulfide bridge at the hinge region; a Fd fragment consisting of the $V_H$ and CHI domains; a Fv fragment consisting of the $V_L$ and $V_H$ domains of a single arm of an antibody; a dAb fragment (Ward et al., Nature 341: 544-546 (1989)), which consists of a $V_H$ domain; and an isolated complementarity determining region (CDR).

Antibodies and antibody fragments can be wholly or partially derived from mammals (e.g., humans, non-human primates, goats, guinea pigs, hamsters, horses, mice, rats, rabbits and sheep) or non-mammalian antibody producing animals (e.g., chickens, ducks, geese, snakes, urodele amphibians). The antibodies and antibody fragments can be produced in animals or produced outside of animals, such as from yeast or phage (e.g., as a single antibody or antibody fragment or as part of an antibody library).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., Science 242:423-426 (1988); and Huston et al., Proc. Natl. Acad. Sci. 85: 5879-5883 (1988). These antibody fragments are obtained using conventional techniques known to those of ordinary skill in the art, and the fragments are screened for utility in the same manner as are intact antibodies.

An "isolated antibody" or "isolated antigen-binding protein" is one which has been identified and separated and/or recovered from a component of its natural environment. "Synthetic antibodies" or "recombinant antibodies" are generally generated using recombinant technology or using peptide synthetic techniques known to those of skill in the art.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., about 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain.

Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al., Proc. Nat. Acad. Sci. USA, 85:5879-5883 (1988)). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hybridoma (Larchmt) 27(6):455-51 (2008); Peter et al., J Cachexia Sarcopenia Muscle (2012); Shieh et al., J Imunol 183(4):2277-85 (2009); Giomarelli et al., Thromb Haemost 97(6):955-63 (2007); Fife et al., J Clin Invst 116(8):2252-61 (2006); Brocks et al., Immunotechnology 3(3): 173-84 (1997); Moosmayer et al., Ther Immunol 2(10):31-40 (1995) Agonistic scFvs having stimulatory activity have been described (see, e.g., Peter et al., J Biol Chem 25278(38):36740-7 (2003); Xie et al., Nat Biotech 15(8):768-71 (1997); Ledbetter et al., Crit Rev Immunol 17(5-6):427-55 (1997); Ho et al., Bio Chim Biophys Acta 1638(3):257-66 (2003)).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each ($ab^1$) region comprises two separate amino acid chains, a part of a H chain and a light (L) chain linked by an S—S bond for binding an antigen and where the remaining H chain portions are linked together. A "$F(ab')_2$" fragment can be split into two individual Fab' fragments.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al., Sequences of Proteins of Immunological Interest, Fifth Edition, U.S. Department of Health and Human Services, NIH Publication No. 91-3242(1991)).

As used herein, the term "constant region" or "constant domain" is interchangeable and has its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, an "epitope" is a term in the art and can refer to a localized region of an antigen to which an antibody can immunospecifically bind. An epitope can be, e.g., contiguous amino acids of a polypeptide (linear or contiguous epitope) or an epitope can, e.g., come together from two or more noncontiguous regions of a polypeptide or polypeptides (conformational, non-linear, discontinuous, or non-contiguous epitope).

As used herein, the term "ligand" refers to a molecule that binds to a receptor. In particular, the ligand binds a receptor on another cell, allowing for cell-to-cell recognition and/or interaction.

As used herein, the term "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes (e.g., either monovalent or multivalent). Methods for calculating the affinity of an antibody for an antigen are known in the art, comprising use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay). Nucleic acid molecules useful in the presently disclosed subject matter include any nucleic acid molecule that encodes a polypeptide or a fragment thereof. In certain embodiments, nucleic acid molecules useful in the presently disclosed subject matter include nucleic acid molecules that encode an antibody or an antigen-binding portion thereof. Such nucleic acid molecules need not be 100% identical with an endogenous nucleic acid sequence, but will typically exhibit substantial identity. Polynucleotides having "substantial homology" or "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger, *Methods Enzymol.* 152:399 (1987); Kimmel, A. R., *Methods Enzymol.* 152:507 (1987)).

As used herein, the terms "immunospecifically binds," "immunospecifically recognizes," "specifically binds," and "specifically recognizes" are analogous terms in the context of antibodies and refer to antibodies and antigen-binding fragments thereof that bind to an antigen (e.g., epitope or immune complex) via the antigen-binding sites as understood by one skilled in the art, and does not exclude cross-reactivity of the antibody or antigen-binding fragment with other antigens.

The terms "substantially homologous" or "substantially identical" mean a polypeptide or nucleic acid molecule that exhibits at least 50% or greater homology or identity to a reference amino acid sequence (for example, any one of the amino acid sequences described herein) or nucleic acid sequence (for example, any one of the nucleic acid sequences described herein). For example, such a sequence is at least about 60%, about 65%, about 70%, about 75%, about 80%, about 85%, about 90%, about 95% or about 99% homologous or identical at the amino acid level or nucleic acid to the sequence used for comparison (e.g., a wild-type, or native, sequence). In some embodiments, a substantially homologous or substantially identical polypeptide contains one or more amino acid amino acid substitutions, insertions, or deletions relative to the sequence used for comparison. In some embodiments, a substantially homologous or substantially identical polypeptide contains one or more non-natural amino acids or amino acid analogs, including, D-amino acids and retroinverso amino acids, to replace homologous sequences.

Sequence homology or sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between $e^{-3}$ and $e^{-100}$ indicating a closely related sequence.

As used herein, the term "analog" refers to a structurally related polypeptide or nucleic acid molecule having the function of a reference polypeptide or nucleic acid molecule.

As used herein, the term "a conservative sequence modification" refers to an amino acid modification that does not significantly affect or alter the binding characteristics of the presently disclosed anti-MUC16 antibody agent or an antigen-binding fragment thereof comprising the amino acid sequence. Conservative modifications can include amino acid substitutions, additions and deletions. Modifications can be introduced into the human scFv of the presently disclosed anti-MUC16 antibody or an antigen-binding fragment thereof by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (1) above) using the functional assays described herein. In certain embodiments, no more than one, no more than two, no more than three, no more than four, no more than five residues within a specified sequence or a CDR region are altered.

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "modulate" refers positively or negatively alter. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%), 1%), 0.5%), or 0.1%) of other material, e.g., cellular material, culture medium, other nucleic acid molecules, chemical precursors and/or other chemicals.

As used herein, the term "isolated cell" refers to a cell that is separated from the molecular and/or cellular components that naturally accompany the cell.

An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease (e.g., a neoplasia), or otherwise reduce the pathological consequences of the disease (e.g., a neoplasia). The effective amount is generally determined by the physician on a case-by-case basis and is within the skill of one in the art. Several factors are typically considered when determining an appropriate dosage to achieve an effective amount. These factors include age, sex and weight of the subject, the condition being treated, the severity of the condition and the form and effective concentration of the engineered immune cells administered.

As used herein, the term "neoplasia" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasia can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasia include cancers, such as sarcomas, carcinomas, or plasmacytomas (malignant tumor of the plasma cells).

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, non-human primates, rodents, and the like (e.g., which is to be the recipient of a particular treatment, or from whom cells are harvested).

Anti-MUC16 Antibody Agents

Provided herein are anti-MUC16 antibody agents that immunospecifically bind to MUC16. In some embodiments, the anti-MUC16 antibody agent immunospecifically binds to the retained extracellular domain of MUC16. In some embodiments, the anti-MUC16 antibody agent is an anti-MUC16 construct that comprises an antibody moiety that immunospecifically binds to MUC16. In some embodiments, the anti-MUC16 antibody agent is an anti-MUC16 antibody (e.g., a full-length anti-MUC16 antibody or an antigen binding fragment thereof). In some embodiments, the anti-MUC16 antibody agent binds to an MUC16-expressing cell (e.g., an MUC16-expressing cancer cell).

Anti-MUC16 antibody agents, such as anti-MUC16 antibodies or antigen-binding fragments thereof, can include, e.g., monoclonal antibodies, polyclonal antibodies, recombinantly produced antibodies, monospecific antibodies, multispecific antibodies (including bispecific antibodies (BsAb)), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, single domain antibodies, monovalent antibodies, single chain antibodies or single-chain variable fragments (scFv), camelized antibodies, affybodies, and disulfide-linked Fvs (dsFv), Fc fusion proteins, immunoconjugates, or fragments thereof. Such antibodies and antigen-binding fragments can be made by methods known in the art.

In some embodiments, the anti-MUC16 antibody agent is a full-length antibody (e.g., full-length IgG) or antigen-binding fragment thereof, which specifically binds to MUC16.

In some embodiments, reference to an antibody agent that immunospecifically binds to MUC16 means that the antibody agent binds to MUC16 with an affinity that is at least about 10 times (including for example at least about any of 10, $10^2$, $10^3$, $10^4$, $10^5$, $10^6$, or $10^7$ times) its binding affinity for non-target. In some embodiments, the non-target is an antigen that is not MUC16. Binding affinity can be determined by methods known in the art, such as ELISA, fluorescence activated cell sorting (FACS) analysis, or radioimmunoprecipitation assay (RIA). $K_d$ can be determined by methods known in the art, such as surface plasmon resonance (SPR) assay utilizing, for example, Biacore instruments, or kinetic exclusion assay (KinExA) utilizing, for example, Sapidyne instruments.

Although anti-MUC16 antibody agents containing human sequences (e.g., human heavy and light chain variable domain sequences comprising human CDR sequences) are extensively discussed herein, non-human anti-MUC16 antibody agents are also contemplated. In some embodiments, non-human anti-MUC16 antibody agents comprise human CDR sequences from an anti-MUC16 antibody agent as described herein and non-human framework sequences. Non-human framework sequences include, in some embodiments, any sequence that can be used for generating synthetic heavy and/or light chain variable domains using one or more human CDR sequences as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. In some embodiments, a non-human anti-MUC16 antibody agent includes an anti-MUC16 antibody agent generated by grafting one or more human CDR sequences as described herein onto a non-human framework sequence (e.g., a mouse or chicken framework sequence).

The complete amino acid sequence of an exemplary human MUC16 comprises or consists of the amino acid sequence of SEQ ID NO: 1. In some embodiments, the anti-MUC16 antibody agent described herein specifically recognizes an epitope within human MUC16. In some embodiments, the anti-MUC16 antibody agent described herein specifically recognizes an epitope within the retained extracellular domain of human MUC16. In some embodiments, the anti-MUC16 antibody agent described herein immunospecifically binds to that MUC16 ectodomain (FIG. 1). In some embodiments, the anti-MUC16 antibody agent described herein immunospecifically binds to a cell expressing human MUC16. In some embodiments, the anti-MUC16 antibody agent described herein immunospecifically binds to a cell expressing a recombinant MUC16 polypeptide. In some embodiments, the MUC16 polypeptide is MUC16-c344 having the amino acid sequence set forth in SEQ ID NO:24. In some embodiments, the MUC16 polypeptide is MUC16-c114 having the amino acid sequence set forth in SEQ ID NO:25.

In some embodiments, the anti-MUC16 antibody agent cross-reacts with MUC16 polypeptide from a species other than human. In some embodiments, the anti-MUC16 antibody agent is completely specific for human MUC16 and does not exhibit species or other types of non-human cross-reactivity.

In some embodiments, the anti-MUC16 antibody agent specifically recognizes MUC16 expressed on the cell surface of a cancer cell (such as solid tumor). In some embodiments, the anti-MUC16 antibody agent specifically recognizes MUC16 expressed on the cell surface of one or more of ovarian cancer cells, breast cancer cells, prostate cancer cells, colon cancer cells, lung cancer cells, brain cancer cells, pancreatic cancer cells, kidney cancer cells, fallopian tube cancer cells, uterine (e.g., endometrial) cancer cells, primary peritoneum cancer cells or cancer cells of any other tissue that expresses MUC16. In some embodiments, the anti-MUC16 antibody agent specifically recognizes MUC16 expressed on the cell surface of a cancer cell line, e.g. ovarian cancer cell lines, such as OVCAR3, OVCA-432, OVCA-433 and CAOV3.

In some embodiments, the anti-MUC16 antibody agent cross-reacts with at least one allelic variant of the MUC16 protein, or fragments thereof. In some embodiments, the allelic variant has up to about 30, such as about any of 1, 2, 3, 4, 5, 6, 7, 8, 9, 10, 15, 20, 25, or 30, amino acid substitutions, such as a conservative amino acid substitution, when compared to the naturally occurring MUC16, or fragments thereof. In some embodiments, the anti-MUC16 antibody agent does not cross-react with any allelic variant of the MUC16 protein, or fragments thereof.

In some embodiments, the anti-MUC16 antibody agent cross-reacts with at least one interspecies variant of the MUC16 protein. In some embodiments, for example, the MUC16 protein, or fragments thereof. is human MUC16 and the interspecies variant of the MUC16 protein, or fragments thereof, is a mouse or rat variant thereof. In some embodiments, the anti-MUC16 antibody agent does not cross-react with any interspecies variant of the MUC16 protein.

In some embodiments, according to any of the anti-MUC16 antibody agents described herein, the anti-MUC16 antibody agent comprises an anti-MUC16 antibody moiety that specifically binds to MUC16. In some embodiments, the anti-MUC16 antibody moiety comprises an antibody heavy chain constant region and an antibody light chain constant region.

In some embodiments, the anti-MUC16 antibody moiety comprises an IgG1 heavy chain constant region. In some embodiments, the anti-MUC16 antibody moiety comprises an IgG2 heavy chain constant region. In some embodiments, the anti-MUC16 antibody moiety comprises an IgG3 heavy chain constant region.

In some embodiments, the anti-MUC16 antibody moiety comprises an IgG1 heavy chain constant region. In some embodiments, the heavy chain constant region comprises or consists of the amino acid sequence of SEQ ID NO: 28.

In some embodiments, the anti-MUC16 antibody moiety comprises an IgG4 heavy chain constant region. In some embodiments, the IgG4 heavy chain constant region comprises or consists of the amino acid sequence of SEQ ID NO: 29.

In some embodiments, the anti-MUC16 antibody moiety comprises a lambda light chain constant region. In some embodiments, the light chain constant region comprises or consists of the amino acid sequence of SEQ ID NO: 30.

In some embodiments, the anti-MUC16 antibody moiety comprises a kappa light chain constant region.

In some embodiments, the anti-MUC16 antibody moiety comprises an antibody heavy chain variable domain and an antibody light chain variable domain.

In some embodiments, the anti-MUC16 antibody moiety comprises a heavy chain variable domain comprising one, two or three HC-CDRs of SEQ ID NO: 2. In some embodiments, the anti-MUC16 antibody moiety comprises a heavy chain variable domain comprising HC-CDR1, HC-CDR2 and HC-CDR3 of the heavy chain variable domain of SEQ ID NO: 2. In some embodiments, the anti-MUC16 antibody moiety comprises a heavy chain variable domain comprising a HC-CDR1, HC-CDR2 and HC-CDR3 set forth in SEQ ID NOS: 4, 5, and 6, respectively. In some embodiments, the anti-MUC16 antibody moiety comprises a heavy chain variable domain comprising SEQ ID NO: 2. In some embodiments, the anti-MUC16 antibody moiety comprises a heavy chain variable domain set forth in SEQ ID NO: 2.

In some embodiments, the anti-MUC16 antibody moiety comprises a light chain variable domain comprising one, two or three LC-CDRs of SEQ ID NO: 3. In some embodiments, the anti-MUC16 antibody moiety comprises a light chain variable domain comprising LC-CDR1, LC-CDR2 and LC-CDR3 of the light chain variable domain of SEQ ID NO: 3. In some embodiments, the anti-MUC16 antibody moiety comprises a light chain variable domain comprising a LC-CDR1, LC-CDR2 and LC-CDR3 set forth in SEQ ID NOS: 7, 8, and 9, respectively. In some embodiments, the anti-MUC16 antibody moiety comprises a light chain variable domain comprising SEQ ID NO: 3. In some embodiments, the anti-MUC16 antibody moiety comprises a light chain variable domain set forth in SEQ ID NO: 3.

In some embodiments, the anti-MUC16 antibody moiety comprises a heavy chain variable domain comprising HC-CDR1, HC-CDR2 and HC-CDR3 of the heavy chain variable domain of SEQ ID NO: 2, and a light chain variable domain comprising LC-CDR1, LC-CDR2 and LC-CDR3 of the light chain variable domain of SEQ ID NO: 3. In some embodiments, the anti-MUC16 antibody moiety comprises a heavy chain variable domain comprising set forth in SEQ ID NOS: 4, 5, and 6, respectively, and a light chain variable domain comprising LC-CDR1, LC-CDR2 and LC-CDR3 set forth in SEQ ID NOS: 7, 8, and 9, respectively. In some embodiments, the anti-MUC16 antibody moiety comprises a heavy chain variable domain comprising SEQ ID NO: 2, and a light chain variable domain comprising SEQ ID NO: 3. In some embodiments, the anti-MUC16 antibody moiety comprises a heavy chain variable domain set forth in SEQ ID NO: 2, and a light chain variable domain set forth in SEQ ID NO: 3.

In some embodiments, the antibody heavy chain variable domain comprises the amino acid sequence of SEQ ID NO: 2, or a variant thereof comprising up to about 5 (such as about any of 1, 2, 3, 4, or 5) amino acid substitutions or having at least about 95% (for example at least about any of 96%, 97%, 98%, or 99%) sequence identity to SEQ ID NO: 2. In some embodiments, the light chain variable domain comprises the amino acid sequence of SEQ ID NO: 3, or a variant thereof comprising up to about 5 (such as about any of 1, 2, 3, 4, or 5) amino acid substitutions or having at least about 95% (for example at least about any of 96%, 97%, 98%, or 99%) sequence identity to SEQ ID NO: 3.

In some embodiments, the anti-MUC16 antibody moiety comprises a heavy chain variable domain comprising one, two or three HC-CDRs of SEQ ID NO: 10. In some embodiments, the anti-MUC16 antibody moiety comprises a heavy chain variable domain comprising HC-CDR1, HC-CDR2 and HC-CDR3 of the heavy chain variable domain of SEQ ID NO: 10. In some embodiments, the anti-MUC16 antibody moiety comprises a heavy chain variable domain comprising a HC-CDR1, HC-CDR2 and HC-CDR3 set forth in SEQ ID NOS: 12, 13, and 14, respectively. In some embodiments, the anti-MUC16 antibody moiety comprises a heavy chain variable domain comprising SEQ ID NO: 10. In some embodiments, the anti-MUC16 antibody moiety comprises a heavy chain variable domain set forth in SEQ ID NO: 10.

In some embodiments, the anti-MUC16 antibody moiety comprises a light chain variable domain comprising one, two or three LC-CDRs of SEQ ID NO: 11. In some embodiments, the anti-MUC16 antibody moiety comprises a light chain variable domain comprising LC-CDR1, LC-CDR2 and LC-CDR3 of the light chain variable domain of SEQ ID NO: 11. In some embodiments, the anti-MUC16 antibody moiety comprises a light chain variable domain comprising a LC-CDR1, LC-CDR2 and LC-CDR3 set forth in SEQ ID NOS: 15, 16, and 17, respectively. In some embodiments, the anti-MUC16 antibody moiety comprises a light chain variable domain comprising SEQ ID NO: 11. In some embodiments, the anti-MUC16 antibody moiety comprises a light chain variable domain set forth in SEQ ID NO: 11.

In some embodiments, the anti-MUC16 antibody moiety comprises a heavy chain variable domain comprising HC-CDR1, HC-CDR2 and HC-CDR3 of the heavy chain variable domain of SEQ ID NO: 10, and a light chain variable domain comprising LC-CDR1, LC-CDR2 and LC-CDR3 of the light chain variable domain of SEQ ID NO: 11. In some embodiments, the anti-MUC16 antibody moiety comprises a heavy chain variable domain comprising set forth in SEQ ID NOS: 12, 13, and 14, respectively, and a light chain variable domain comprising LC-CDR1, LC-CDR2 and LC-CDR3 set forth in SEQ ID NOS: 15, 16, and 17, respectively. In some embodiments, the anti-MUC16 antibody moiety comprises a heavy chain variable domain comprising SEQ ID NO: 10, and a light chain variable domain comprising SEQ ID NO: 11. In some embodiments, the anti-MUC16 antibody moiety comprises a heavy chain variable domain set forth in SEQ ID NO: 10, and a light chain variable domain set forth in SEQ ID NO: 11.

In some embodiments, the antibody heavy chain variable domain comprises the amino acid sequence of SEQ ID NO: 10, or a variant thereof comprising up to about 5 (such as about any of 1, 2, 3, 4, or 5) amino acid substitutions or having at least about 95% (for example at least about any of 96%, 97%, 98%, or 99%) sequence identity to SEQ ID NO: 10. In some embodiments, the light chain variable domain comprises the amino acid sequence of SEQ ID NO: 11, or a variant thereof comprising up to about 5 (such as about any of 1, 2, 3, 4, or 5) amino acid substitutions or having at least about 95% (for example at least about any of 96%, 97%, 98%, or 99%) sequence identity to SEQ ID NO: 11.

Exemplary antibody sequences are shown in the Tables below. The exemplary CDR sequences in Table 2 are predicted using the IgBLAST algorithm. See, for example, Ye J. et al., Nucleic Acids Research 41:W34-W40 (2013), the disclosure of which is incorporated herein by reference in its entirety. Those skilled in the art will recognize that many algorithms are known for prediction of CDR positions in antibody heavy chain and light chain variable regions, and antibody agents comprising CDRs from antibodies described herein, but based on prediction algorithms other than IgBLAST, are within the scope of this invention.

The exemplary antibody heavy chain and light chain variable region sequences are delimited according to the INTERNATIONAL IMMUNOGENETICS INFORMATION SYSTEM® (IMGT). See, for example, Lefranc, M.-P. et al., Nucleic Acids Res., 43:D413-422 (2015), the disclosure of which is incorporated herein by reference in its entirety. Those skilled in the art will recognize that antibody agents comprising $V_H$ or $V_L$ sequences from antibodies described herein, but based on algorithms other than IMGT, are within the scope of this invention.

TABLE 2

Exemplary anti-MUC16 antibody CDR sequences.

| Clone ID | HC-CDR1 | HC-CDR2 | HC-CDR3 |
|---|---|---|---|
| 8 | GGSFSGYY (SEQ ID NO: 4) | INHSGST (SEQ ID NO: 5) | ARQSYITDS (SEQ ID NO: 6) |
| 12 | GGSFSGYY (SEQ ID NO: 12) | INHSGST (SEQ ID NO: 13) | ARWSPFSYKQMYDY (SEQ ID NO: 14) |

| Clone ID | LC-CDR1 | LC-CDR2 | LC-CDR3 |
|---|---|---|---|
| 8 | QDVSKW (SEQ ID NO: 7) | AAS (SEQ ID NO: 8) | QQANSFPWT (SEQ ID NO: 9) |
| 12 | RGSIASAY (SEQ ID NO: 15) | EDY (SEQ ID NO: 16) | QSYDDNDHVI (SEQ ID NO: 17) |

TABLE 3

Exemplary anti-MUC16 antibody VH and VL domain sequences.

| Clone ID | Description | Sequence |
|---|---|---|
| 8 | VH domain | QVQLQQWGAGLLKPSETLSLTCAVYGGSFS GYYWSWIRQPPGKGLEWIGEINHSGSTNYN PSLKSRVTISVDTSKNQFSLKLSSVTAADTAV YYCARQSYITDSWGQGTLVTVSS (SEQ ID NO: 2) |
| 8 | VL domain | DIQLTQSPSAVSASVGDRVTITCRASQDVSKW LAWYQQKPGKAPRLLISAASGLQSWVPSRFSG SGSGTEFTLSISSLQPEDFATYYCQQANSFPWT FGQGTKVEIKR (SEQ ID NO: 3) |
| 12 | VH domain | QVQLQQWGAGLLKPSETLSLTCAVYGGSFSG YYWSWIRQPPGKGLEWIGEINHSGSTNYNPSL KSRIIMSVDTSKRQFSLKLRSATAADTAVYYC ARWSPFSYKQMYDYWGQGTLVTVSS (SEQ ID NO: 10) |
| 12 | VL domain | NFMLTQPHSVSESPGKTVTISCTRSRGSIASAY VQWYQQRPGSAPITVIYEDYERPSEIPDRFSGS IDSSSNSASLTISGLKTEDEADYYCQSYDDNDH VIFGGGTKVTVLG (SEQ ID NO: 11) |

Full-Length Anti-MUC16 Antibody

The anti-MUC16 antibody agent in some embodiments is a full-length anti-MUC16 antibody. In some embodiments, the full-length anti-MUC16 antibody is an IgA, IgD, IgE, IgG, or IgM. In some embodiments, the full-length anti-MUC16 antibody comprises IgG constant domains, such as constant domains of any of IgG1, IgG2, IgG3, and IgG4 including variants thereof. In some embodiments, the full-length anti-MUC16 antibody comprises a lambda light chain constant region. In some embodiments, the full-length anti-MUC16 antibody comprises a kappa light chain constant region. In some embodiments, the full-length anti-MUC16 antibody is a full-length human anti-MUC16 antibody. In some embodiments, the full-length anti-MUC16 antibody comprises an Fc sequence of a mouse immunoglobulin. In some embodiments, the full-length anti-MUC16 antibody comprises an Fc sequence that has been altered or otherwise changed so that it has enhanced antibody dependent cellular cytotoxicity (ADCC) or complement dependent cytotoxicity (CDC) effector function.

Thus, for example, in some embodiments, there is provided a full-length anti-MUC16 antibody comprising IgG1 or IgG4 constant domains, wherein the anti-MUC16 antibody specifically binds to MUC16 on a tumor cell. In some embodiments, the IgG1 is human IgG1. In some embodiments, the IgG1 is human IgG4. In some embodiments, the anti-MUC16 heavy chain constant region comprises or consists of the amino acid sequence of SEQ ID NO: 28 or 29. In some embodiments, the anti-MUC16 light chain constant region comprises or consists of the amino acid sequence of SEQ ID NO: 30. In some embodiments, the anti-MUC16 heavy chain constant region comprises or consists of the amino acid sequence of SEQ ID NO: 28 or 29 and the anti-MUC16 light chain constant region comprises or consists of the amino acid sequence of SEQ ID NO: 30. In some embodiments, binding of the anti-MUC16 antibody to an MUC16-expressing cell (e.g., an MUC16-expressing cancer cell) inhibits tumor growth or metastasis of a tumor or induces regression of a tumor. In some embodiments, binding of the anti-MUC16 antibody to an MUC16-expressing cell (e.g., an MUC16-expressing cancer cell) inhibits Matrigel invasion in vitro of the MUC16-expressing cells.

In some embodiments, there is provided a full-length anti-MUC16 antibody comprising IgG1 or IgG4 constant domains, wherein the anti-MUC16 antibody comprises a) a heavy chain variable domain comprising an HC-CDR1 comprising the amino acid sequence of SEQ ID NO: 4, an HC-CDR2 comprising the amino acid sequence of SEQ ID NO: 5, and an HC-CDR3 comprising the amino acid sequence of SEQ ID NO: 6; and b) a light chain variable domain comprising an LC-CDR1 comprising the amino acid sequence of SEQ ID NO: 7, an LC-CDR2 comprising the amino acid sequence of SEQ ID NO: 8, and an LC-CDR3 comprising the amino acid sequence of SEQ ID NO: 9. In some embodiments, the IgG1 is human IgG1. In some embodiments, the IgG4 is human IgG4. In some embodiments, the anti-MUC16 heavy chain constant region comprises or consists of the amino acid sequence of SEQ ID NO: 28 or 29. In some embodiments, the anti-MUC16 light chain constant region comprises or consists of the amino acid sequence of SEQ ID NO: 30.

In some embodiments, there is provided a full-length anti-MUC16 antibody comprising IgG1 or IgG4 constant domains, wherein the anti-MUC16 antibody comprises a) a heavy chain variable domain comprising an HC-CDR1 comprising the amino acid sequence of SEQ ID NO: 12, an HC-CDR2 comprising the amino acid sequence of SEQ ID NO: 13, and an HC-CDR3 comprising the amino acid sequence of SEQ ID NO: 14; and b) a light chain variable domain comprising an LC-CDR1 comprising the amino acid sequence of SEQ ID NO: 15, an LC-CDR2 comprising the amino acid sequence of SEQ ID NO: 16, and an LC-CDR3 comprising the amino acid sequence of SEQ ID NO: 17. In some embodiments, the IgG1 is human IgG1. In some embodiments, the IgG4 is human IgG4. In some embodiments, the anti-MUC16 heavy chain constant region comprises or consists of the amino acid sequence of SEQ ID NO: 28 or 29. In some embodiments, the anti-MUC16 light chain constant region comprises or consists of the amino acid sequence of SEQ ID NO: 30.

Chimeric Anti-MUC16 Constructs

In some embodiments, the anti-MUC16 antibody agent is an anti-MUC16 chimeric antigen receptor (CAR) or variant thereof that specifically binds to MUC16. In some embodiments, the anti-MUC16 antibody agent is an anti-MUC16 CAR. CARs are well known in the art, and the anti-MUC16 antibody agent can be a CAR according to any CAR known in the art, such as described in Sadelain et al., *Nature* 545: 423-431 (2017), the disclosure of which is explicitly incorporated herein for use in the present invention and for possible inclusion in one or more claims herein. In some embodiments, the anti-MUC16 CAR comprises an anti-MUC16 antibody moiety according to any of the anti-MUC16 antibody moieties described herein. For example, in some embodiments, there is provided an anti-MUC16 CAR comprising an anti-MUC16 antibody moiety. In some embodiments, the anti-MUC16 antibody moiety of an anti-MUC16 CAR comprises a) an antibody heavy chain variable domain comprising an HC-CDR1 comprising the amino acid sequence of SEQ ID NO: 4, an HC-CDR2 comprising the amino acid sequence of SEQ ID NO: 5, and an HC-CDR3 comprising the amino acid sequence of SEQ ID NO: 6; and b) a light chain variable domain comprising an LC-CDR1 comprising the amino acid sequence of SEQ ID NO: 7, an LC-CDR2 comprising the amino acid sequence of SEQ ID NO: 8, and an LC-CDR3 comprising the amino acid sequence of SEQ ID NO: 9. In some embodiments, the heavy chain variable domain comprises the amino acid sequence of SEQ ID NO: 2, or a variant thereof having at least about 95% (for example at least about any of 96%, 97%, 98%, or 99%) sequence identity, and the light chain variable domain comprises the amino acid sequence of SEQ ID NO: 3, or a variant thereof having at least about 95% sequence identity.

In some embodiments, the anti-MUC16 antibody moiety of an anti-MUC16 CAR comprises a) a heavy chain variable domain comprising an HC-CDR1 comprising the amino acid sequence of SEQ ID NO: 12, an HC-CDR2 comprising the amino acid sequence of SEQ ID NO: 13, and an HC-CDR3 comprising the amino acid sequence of SEQ ID NO: 14; and b) a light chain variable domain comprising an LC-CDR1 comprising the amino acid sequence of SEQ ID NO: 15, an LC-CDR2 comprising the amino acid sequence of SEQ ID NO: 16, and an LC-CDR3 comprising the amino acid sequence of SEQ ID NO: 17. In some embodiments, the heavy chain variable domain comprises the amino acid sequence of SEQ ID NO: 10, or a variant thereof having at least about 95% (for example at least about any of 96%, 97%, 98%, or 99%) sequence identity, and the light chain variable domain comprises the amino acid sequence of SEQ ID NO: 11, or a variant thereof having at least about 95% sequence identity.

In some embodiments, the anti-MUC16 antibody agent is an anti-MUC16 chimeric receptor comprising T cell receptor (TCR) transmembrane domains. For example, in some embodiments, the anti-MUC16 antibody agent is an antibody-T cell receptor (abTCR) as described in PCT Patent Application Publication No. WO2017070608, the disclosure of which is explicitly incorporated herein for use in the present invention and for possible inclusion in one or more claims herein. In some embodiments, the anti-MUC16 abTCR comprises an anti-MUC16 antibody moiety according to any of the anti-MUC16 antibody moieties described herein. For example, in some embodiments, there is provided an anti-MUC16 abTCR comprising an anti-MUC16 antibody moiety.

In some embodiments, the anti-MUC16 antibody moiety of an anti-MUC16 abTCR comprises a) an antibody heavy chain variable domain comprising an HC-CDR1 comprising the amino acid sequence of SEQ ID NO: 4, an HC-CDR2 comprising the amino acid sequence of SEQ ID NO: 5, and an HC-CDR3 comprising the amino acid sequence of SEQ ID NO: 6; and b) a light chain variable domain comprising an LC-CDR1 comprising the amino acid sequence of SEQ ID NO: 7, an LC-CDR2 comprising the amino acid sequence of SEQ ID NO: 8, and an LC-CDR3 comprising the amino acid sequence of SEQ ID NO: 9. In some embodiments, the heavy chain variable domain of an anti-MUC16 abTCR comprises the amino acid sequence of SEQ ID NO: 2, or a variant thereof having at least about 95% (for example at least about any of 96%, 97%, 98%, or 99%) sequence identity, and the light chain variable domain comprises the amino acid sequence of SEQ ID NO: 3, or a variant thereof having at least about 95% sequence identity.

In some embodiments, the anti-MUC16 antibody moiety of an anti-MUC16 abTCR comprises a) a heavy chain variable domain comprising an HC-CDR1 comprising the amino acid sequence of SEQ ID NO: 12, an HC-CDR2 comprising the amino acid sequence of SEQ ID NO: 13, and an HC-CDR3 comprising the amino acid sequence of SEQ ID NO: 14; and b) a light chain variable domain comprising an LC-CDR1 comprising the amino acid sequence of SEQ ID NO: 15, an LC-CDR2 comprising the amino acid sequence of SEQ ID NO: 16, and an LC-CDR3 comprising the amino acid sequence of SEQ ID NO: 17. In some embodiments, the heavy chain variable domain of an anti-MUC16 abTCR comprises the amino acid sequence of SEQ ID NO: 10, or a variant thereof having at least about 95% (for example at least about any of 96%, 97%, 98%, or 99%) sequence identity, and the light chain variable domain comprises the amino acid sequence of SEQ ID NO: 11, or a variant thereof having at least about 95% sequence identity.

In some embodiments, the anti-MUC16 antibody agent is a chimeric co-stimulatory receptor comprising an anti-MUC16 antibody moiety that specifically binds to MUC16 and a co-stimulatory signaling domain. In some embodiments, the anti-MUC16 chimeric co-stimulatory receptor is capable of stimulating an immune cell on the surface of which it is functionally expressed upon binding MUC16. In some embodiments, the anti-MUC16 chimeric co-stimulatory receptor lacks a functional primary immune cell signaling sequence. In some embodiments, the anti-MUC16 chimeric co-stimulatory receptor lacks any primary immune cell signaling sequence. In some embodiments, the anti-MUC16 chimeric co-stimulatory receptor comprises a single polypeptide chain comprising the anti-MUC16 antibody moiety, a transmembrane domain, and the co-stimulatory signaling domain. In some embodiments, the anti-MUC16 chimeric co-stimulatory receptor comprises a first polypeptide chain and a second polypeptide chain, wherein the first and second polypeptide chains together form the anti-MUC16 antibody moiety, a transmembrane module, and co-stimulatory signaling module comprising the co-stimulatory signaling domain. In some embodiments, the first and second polypeptide chains are separate polypeptide chains, and the anti-MUC16 chimeric co-stimulatory receptor is a multimer, such as a dimer. In some embodiments, the first and second polypeptide chains are covalently linked, such as by a peptide linkage, or by another chemical linkage, such as a disulfide linkage. In some embodiments, the first polypeptide chain and the second polypeptide chain are linked by at least one disulfide bond. In some embodiments, the anti-MUC16 antibody moiety is a Fab, a Fab', a (Fab')2, an Fv, or a single chain Fv (scFv).

Examples of co-stimulatory immune cell signaling domains for use in the anti-MUC16 chimeric co-stimulatory receptors of the invention include the cytoplasmic sequences of co-receptors of the T cell receptor (TCR), which can act in concert with a chimeric receptor (e.g., a CAR or abTCR) to initiate signal transduction following chimeric receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of intracellular signaling sequence: those that initiate antigen-dependent primary activation through the TCR (referred to herein as "primary immune cell signaling sequences") and those that act in an antigen-independent manner to provide a secondary or co-stimulatory signal (referred to herein as "co-stimulatory immune cell signaling sequences").

Primary immune cell signaling sequences that act in a stimulatory manner may contain signaling motifs which are known as immunoreceptor tyrosine-based activation motifs or ITAMs. Examples of ITAM-containing primary immune cell signaling sequences include those derived from TCRζ, FcRγ, FcRβ, CD3γ, CD3δ, CD3ε, CD5, CD22, CD79a, CD79b, and CD66d. A "functional" primary immune cell signaling sequence is a sequence that is capable of transducing an immune cell activation signal when operably coupled to an appropriate receptor. "Non-functional" primary immune cell signaling sequences, which may comprise fragments or variants of primary immune cell signaling sequences, are unable to transduce an immune cell activation signal. The anti-MUC16 chimeric co-stimulatory receptors described herein lack a functional primary immune cell signaling sequence, such as a functional signaling sequence comprising an ITAM. In some embodiments, the anti-MUC16 chimeric co-stimulatory receptors lack any primary immune cell signaling sequence.

The co-stimulatory immune cell signaling sequence can be a portion of the intracellular domain of a co-stimulatory molecule including, for example, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like.

In some embodiments, the anti-MUC16 antibody moiety of an anti-MUC16 chimeric co-stimulatory receptor comprises a) an HC-CDR1 comprising the amino acid sequence of SEQ ID NO: 4, an HC-CDR2 comprising the amino acid sequence of SEQ ID NO: 5, and an HC-CDR3 comprising the amino acid sequence of SEQ ID NO: 6; and b) a light chain variable domain comprising an LC-CDR1 comprising the amino acid sequence of SEQ ID NO: 7, an LC-CDR2 comprising the amino acid sequence of SEQ ID NO: 8, and an LC-CDR3 comprising the amino acid sequence of SEQ ID NO: 9. In some embodiments, the heavy chain variable domain comprises the amino acid sequence of SEQ ID NO: 2, or a variant thereof having at least about 95% (for example at least about any of 96%, 97%, 98%, or 99%) sequence identity, and the light chain variable domain comprises the amino acid sequence of SEQ ID NO: 3, or a variant thereof having at least about 95% sequence identity.

In some embodiments, the anti-MUC16 antibody moiety of an anti-MUC16 chimeric co-stimulatory receptor comprises a) a heavy chain variable domain comprising an HC-CDR1 comprising the amino acid sequence of SEQ ID NO: 12, an HC-CDR2 comprising the amino acid sequence of SEQ ID NO: 13, and an HC-CDR3 comprising the amino acid sequence of SEQ ID NO: 14; and b) a light chain variable domain comprising an LC-CDR1 comprising the amino acid sequence of SEQ ID NO: 15, an LC-CDR2 comprising the amino acid sequence of SEQ ID NO: 16, and an LC-CDR3 comprising the amino acid sequence of SEQ ID NO: 17. In some embodiments, the heavy chain variable domain comprises the amino acid sequence of SEQ ID NO: 10, or a variant thereof having at least about 95% (for example at least about any of 96%, 97%, 98%, or 99%) sequence identity, and the light chain variable domain comprises the amino acid sequence of SEQ ID NO: 11, or a variant thereof having at least about 95% sequence identity.

In some embodiments, the anti-MUC16 chimeric co-stimulatory receptor is expressed in an immune cell. In some embodiments, the anti-MUC16 chimeric co-stimulatory receptor is expressed in an immune cell that expresses another chimeric receptor. In some embodiments, the other chimeric receptor is a CAR or an abTCR. In some embodiments, the other chimeric receptor binds to MUC16. In some embodiments, the other chimeric receptor does not bind to MUC16. In some embodiments, the other chimeric receptor binds to an antigen associated with a cancer characterized by high expression of MUC16 and/or high aerobic glycolysis. In some embodiments, the other chimeric receptor binds to an antigen associated with any of the cancers described herein (such as kidney cancer, cervical cancer, prostate cancer, breast cancer, colon cancer, brain cancer, or pancreatic cancer). In some embodiments, the other chimeric receptor binds to an antigen associated with kidney cancer. In some embodiments, the kidney cancer is renal cell carcinoma (RCC). In some embodiments, the RCC is metastatic RCC. In some embodiments, the immune cell is a T cell. In some embodiments, expression of the anti-MUC16 chimeric co-stimulatory receptor in the immune cell is inducible. In some embodiments, the expression of the anti-MUC16 chimeric co-stimulatory receptor in the immune cell is inducible upon signaling through the other chimeric receptor.

Binding Affinity

Binding affinity can be indicated by $K_d$, $K_{off}$, $K_{on}$, or $K_d$. The term "$K_{off}$", as used herein, is intended to refer to the off-rate constant for dissociation of an antibody agent from the antibody agent/antigen complex, as determined from a kinetic selection set up. The term "$K_{on}$", as used herein, is intended to refer to the on-rate constant for association of an antibody agent to the antigen to form the antibody agent/antigen complex. The term equilibrium dissociation constant "$K_d$", as used herein, refers to the dissociation constant of a particular antibody agent-antigen interaction, and describes the concentration of antigen required to occupy one half of all of the antibody-binding domains present in a solution of antibody agent molecules at equilibrium, and is equal to $K_{off}/K_{on}$. The measurement of $K_d$ presupposes that all binding agents are in solution. In the case where the antibody agent is tethered to a cell wall, e.g., in a yeast expression system, the corresponding equilibrium rate constant is expressed as EC50, which gives a good approximation of $K_d$. The affinity constant, $K_a$, is the inverse of the dissociation constant, $K_d$.

The dissociation constant ($K_d$) is used as an indicator showing affinity of antibody moieties to antigens. For example, easy analysis is possible by the Scatchard method using antibody agents marked with a variety of marker agents, as well as by using Biacore (made by Amersham Biosciences), analysis of biomolecular interactions by surface plasmon resonance, according to the user's manual and attached kit. The $K_d$ value that can be derived using these methods is expressed in units of M (Mols). An antibody agent that specifically binds to a target may have a $K_d$ of, for example, $\leq 10^{-7}$ M, $\leq 10^{-8}$ M, $\leq 10^{-9}$ M, $\leq 10^{-20}$ M, $\leq 10^{-11}$ M, $\leq 10^{-12}$ M, or $\leq 10^{-13}$ M.

Binding specificity of the antibody agent can be determined experimentally by methods known in the art. Such methods comprise, but are not limited to, Western blots, ELISA-, RIA-, ECL-, IRMA-, EIA-, BIAcore-tests and peptide scans. In some embodiments, the binding affinity of the anti-MUC16 antibody agent is measured by testing the binding affinity of the anti-MUC16 antibody agent to cells expressing MUC16 on the surface (e.g., HepG2 cells).

In some embodiments, the anti-MUC16 antibody agent specifically binds to a target MUC16 (e.g., nMUC16) with a $K_d$ of about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). Thus in some embodiments, the $K_d$ of the binding between the anti-nMUC16 antibody agent and nMUC16, the $K_d$ of the binding between the anti-sMUC16 antibody agent and sMUC16, or the $K_d$ of the binding between the anti-MUC16 antibody agent and MUC16 (any format), is about $10^{-7}$ M to about $10^{-13}$M, about $1 \times 10^{-7}$M to about $5 \times 10^{-13}$M, about $10^{-7}$ M to about $10^{-12}$M, about $10^{-7}$ M to about $10^{-11}$ M, about $10^{-7}$M to about $10^{-10}$ M, about $10^{-7}$M to about $10^{-9}$M, about $10^{-8}$M to about $10^{-13}$M, about $1 \times 10^{-8}$M to about $5 \times 10^{-13}$M, about $10^{-8}$M to about $10^{-12}$M, about $10^{-8}$M to about $10^{-11}$ M, about $10^{-8}$ M to about $10^{-10}$ M, about $10^{-8}$ M to about $10^{-9}$ M, about $5\times10^{-9}$ M to about $1\times10^{-13}$ M, about $5\times10^{-9}$ M to about $1\times10^{-12}$ M, about $5\times10^{-9}$ M to about $1\times10^{-11}$ M, about $5\times10^{-9}$ M to about $1\times10^{-10}$ M, about $10^{-9}$ M to about $10^{-13}$ M, about $10^{-9}$ M to about $10^{-12}$ M, about $10^{-9}$ M to about $10^{-11}$ M, about $10^{-9}$ M to about $10^{-10}$ M, about $5\times10^{-11}$ M to about $1\times10^{-13}$ M, about $5\times10^{-11}$ M to about $1\times10^{-12}$ M, about $5\times10^{-11}$ M to about $1\times10^{-11}$ M, about $10^{-11}$ M to about $10^{-13}$ M, about $1\times10^{-11}$ M to about $5\times10^{-13}$ M, about $1\times10^{-11}$ M to about $1\times10^{-12}$ M, about $1\times10^{-11}$ M to about $5\times10^{-12}$ M, about $1\times10^{-11}$ M to about $1\times10^{-11}$ M, about $10^{-11}$ M to about $10^{-13}$ M, about $1\times10^{-11}$ M to about $5\times10^{-13}$ M, about $10^{-11}$ M to about $10^{-12}$ M, or about $10^{-12}$ M to about $10^{-13}$ M. In some embodiments, the $K_d$ of the binding between the anti-nMUC16 antibody agent and an nMUC16 is about $10^{-7}$ M to about $10^{-13}$ M.

In some embodiments, the $K_d$ of the binding between the anti-MUC16 antibody agent and a non-target is more than the $K_d$ of the binding between the anti-MUC16 antibody agent and the target, and is herein referred to in some embodiments as the binding affinity of the anti-MUC16 antibody agent to the target (e.g., cell surface-bound MUC16) is higher than that to a non-target. In some embodiments, the non-target is an antigen that is not MUC16. In some embodiments, the $K_d$ of the binding between the anti-MUC16 antibody agent (against nMUC16) and a non-MUC16 target can be at least about 10 times, such as about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between the anti-MUC16 antibody agent and a target MUC16.

In some embodiments, the anti-MUC16 antibody agent binds to a non-target with a $K_d$ of about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the non-target is an antigen that is not MUC16. Thus in some embodiments, the $K_d$ of the binding between the anti-MUC16 antibody agent and a non-MUC16 target is about $10^{-1}$ M to about $10^{-6}$ M, about $1\times10^{-1}$ M to about $5\times10^{-6}$ M, about $10^{-1}$ M to about $10^{-5}$ M, about $1\times10^{-1}$ M to about $5\times10^{-5}$ M, about $10^{-1}$ M to about $10^{-4}$ M, about $1\times10^{-1}$ M to about $5\times10^{-4}$ M, about $10^{-1}$ M to about $10^{-3}$ M, about $1\times10^{-1}$ M to about $5\times10^{-3}$ M, about $10^{-1}$ M to about $10^{-2}$ M, about $10^{-2}$ M to about $10^{-6}$ M, about $1\times10^{-2}$ M to about $5\times10^{-6}$ M, about $10^{-2}$ M to about $10^{-5}$ M, about $1\times10^{-2}$ M to about $5\times10^{-5}$ M, about $10^{-2}$ M to about $10^{-4}$ M, about $1\times10^{-2}$ M to about $5\times10^{-4}$ M, about $10^{-2}$ M to about $10^{-3}$ M, about $10^{-3}$ M to about $10^{-5}$ M, about $1\times10^{-3}$ M to about $5\times10^{-6}$ M, about $10^{-3}$ M to about $10^{-5}$ M, about $1\times10^{-3}$ M to about $5\times10^{-5}$ M, about $10^{-3}$ M to about $10^{-4}$ M, about $10^{-4}$ M to about $10^{-6}$ M, about $1\times10^{-4}$ M to about $5\times10^{-6}$ M, about $10^{-4}$ M to about $10^{-5}$ M, or about $10^{-5}$ M to about $10^{-6}$ M.

In some embodiments, when referring to that the anti-MUC16 antibody agent specifically recognizes a target MUC16 (e.g., cell surface-bound MUC16) at a high binding affinity, and binds to a non-target at a low binding affinity, the anti-MUC16 antibody agent will bind to the target MUC16 (e.g., cell surface-bound MUC16) with a $K_d$ of about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M), and will bind to the non-target with a $K_d$ of about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M).

In some embodiments, when referring to that the anti-MUC16 antibody agent specifically recognizes a cell surface-bound MUC16, the binding affinity of the anti-MUC16 antibody agent is compared to a control anti-MUC16 antibody agent. In some embodiments, the $K_d$ of the binding between the control anti-MUC16 antibody agent and a cell surface-bound MUC16 can be at least about 2 times, such as about 2 times, about 3 times, about 4 times, about 5 times, about 6 times, about 7 times, about 8 times, about 9 times, about 10 times, about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between the anti-nMUC16 antibody agent described herein and a cell surface-bound MUC16.

Functional Activities of Anti-Muc16 Antibody Agents

In certain embodiments, an anti-MUC16 antibody agent or an antigen-binding fragment thereof described herein inhibits Matrigel invasion in vitro of cells recombinantly expressing a MUC16 polypeptide. In some embodiments the MUC16 comprises SEQ ID NO: 25 (MUC16 c114). In certain embodiments, the cells recombinantly expressing glycosylated MUC16 c114 are SKOV3 cells. In certain embodiments, the MUC16 polypeptide is glycosylated. In certain embodiments, the glycosylated form of MUC16 polypeptide is N-glycosylated at amino acid residue Asn30 (corresponding to Asn1806 of mature MUC16 (SEQ ID NO: 1)). In certain embodiments, MUC16 polypeptide is N-glycosylated at amino acid residues Asn24 and Asn30 (corresponding to Asn1800 and Asn1806, respectively, of mature MUC16 (SEQ ID NO: 1)). In certain embodiments, the MUC16 polypeptide is N-glycosylated at amino acid residues Asn1, Asn24, and Asn30 of SEQ ID NO: 25 (also referred to as Asn1777, Asn1800, and Asn1806, respectively, in Yin and Lloyd (2001) *J Biol Chem* 276: 27371-27375). In certain embodiments, the glycosylation comprises N-linked chitobiose. In certain embodiments, the glycosylation consists of an N-linked chitobiose. In certain embodiments, Matrigel invasion is inhibited by at least 1.25, 1.5, 1.75, 2, 3, 4, 5, 6, 7, 8, 9, or 10-fold as compared to Matrigel invasion in vitro of the cells wherein the cells are treated with a control antibody (e.g., an antibody that does not target MUC16). In certain embodiments, Matrigel invasion is inhibited by about 1.25, 1.5, 1.75, 2, 3, 4, 5, 6, 7, 8, 9, or 10-fold as compared to Matrigel invasion in vitro of the cells wherein the cells are treated with a control antibody (e.g., an antibody that does not target MUC16).

Assays to determine the MUC16 anti-MUC16 antibody agent or antigen-binding fragment-mediated inhibition of Matrigel invasion are known to a person skilled in the art. For example, BD BioCoat™ Matrigel™ Invasion Inserts or Chambers (catalog #354480 in 24 well plate) and Control Inserts (catalog #354578 in 24 well plate) can be purchased from BD Biosciences, MA. Matrigel Invasion assay can be performed as per manufacturer's protocol. Briefly, the Matrigel chambers in 24 well plates (stored at −20° C.) and control inserts (stored at 4° C.) are allowed to come to room temperature. Both inserts are rehydrated with 0.5 mL of serum free medium in the insert as well as in the outside well of the 24 well plate, for 2 hours at 37° C. 5% $CO_2$ humidified incubator. Cultured SKOV3 cells are trypsinized and washed with culture medium. A million cells are separated into another centrifuge tube and washed 3 times with serum free medium. These cells are later adjusted to give 5,000 cells in 0.5 mL serum free medium. The medium in the rehydrated inserts are removed and the insert was transferred into a new 24 well plate containing 0.75 mL of 10% Fetal Bovine Serum (FBS) containing culture medium in the well which serves as a chemo attractant. Immediately, 0.5 mL of the cells (5,000 cells) in serum free medium is added to the insert. Proper care is taken to see that there is no air bubble is trapped in the insert and the outside well. The 24 well plate is incubated at 37° C. 5% CO2 humidified incubator for 48 hrs. After incubation, the non-invading cells are removed from the upper surface of the membrane by "scrubbing" by inserting a cotton tipped swab into Matrigel or control insert and gently applied pressure while moving the tip of the swab over the membrane surface. The scrubbing is repeated with a second swab moistened with medium. Then the inserts are stained in a new 24 well plate containing 0.5 mL of 0.5% crystal violet stain in distilled water for 30 minutes. Following staining the inserts are rinsed in 3 beakers of distilled water to remove excess stain. The inserts are air dried for in a new 24 well plate. The invaded cells are hand counted under an inverted microscope at 200× magnification. Several fields of triplicate membranes were counted and recorded in the figure.

In certain embodiments, an anti-MUC16 antibody agent or an antigen-binding fragment thereof described herein is capable of inhibiting or reducing metastasis, inhibiting tumor growth or inducing tumor regression in mouse model studies. For example, tumor cell lines can be introduced into athymic nude mice, and the athymic mice can be administered an anti-MUC16 antibody agent or an antigen-binding fragment thereof described herein one or more times, and tumor progression of the injected tumor cells can be monitored over a period of weeks and/or months. In some cases, administration of an anti-MUC16 antibody agent or an antigen-binding fragment thereof to the athymic nude mice can occur prior to introduction of the tumor cell lines. In a certain embodiment, SKOV3 cells expressing MUC16 c114 are utilized for the mouse xenograft models described herein.

In some embodiments, an anti-MUC16 antibody agent or an antigen-binding fragment thereof described herein inhibits tumor growth or induce tumor regression in a mouse model by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art, as compared to mock-treated mice. In some embodiments, an anti-MUC16 antibody agent or an antigen-binding fragment thereof described herein inhibits tumor growth or induce tumor regression in a mouse model by at least about 25% or 35%), optionally to about 75%, as assessed by methods described herein or known to one of skill in the art, as compared to mock-treated mice. In some embodiments, an anti-MUC16 antibody agent or an antigen-binding fragment thereof described herein inhibit tumor growth or induce tumor regression in a mouse model by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, as compared to mock-treated mice. Mock-treated mice can, for example, be treated with phosphate buffered saline or a control (e.g., anti-IgG antibody).

Determining tumor growth inhibition or tumor regression can be assessed, for example, by monitoring tumor size over a period of time, such as by physical measurement of palpable tumors, or other visual detection methods. For example, tumor cell lines can be generated to recombinantly express a visualization agent, such as green fluorescent protein (GFP) or luciferase, then in vivo visualization of GFP can be carried out by microscopy, and in vivo visualization of luciferase can be carried out by administering luciferase substrate to the xenograft mice and detecting luminescent due to the luciferase enzyme processing the luciferase substrate. The degree or level of detection of GFP or luciferase correlates to the size of the tumor in the xenograft mice.

In certain embodiments, an anti-MUC16 antibody agent or an antigen-binding fragment thereof described herein can increase survival of animals in tumor xenograft models as compared to mock-treated mice. In some embodiments, an anti-MUC16 antibody agent or an antigen-binding fragment thereof described herein increases survival of mice in tumor xenograft models by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, as compared to mock-treated mice. In some embodiments, an anti-MUC16 antibody agent or an antigen-binding fragment thereof described herein increases survival of mice in tumor xenograft models by at least about 25% or 35%, optionally to about 75%), as assessed by methods described herein or known to one of skill in the art, as compared to mock-treated mice in tumor xenograft models. In some embodiments, an anti-MUC16 antibody agent or an antigen-binding fragment thereof described herein increases survival of mice in tumor xenograft models by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, as compared to mock-treated mice in tumor xenograft models. Survival can, for example, be determined by plotting a survival curve of number of surviving mice against time (e.g., days or weeks) after tumor cell line injection. Mock-treated mice can, for example, be treated with phosphate buffered saline or a control (e.g., anti-IgG antibody).

In certain embodiments, an anti-MUC16 antibody agent or an antigen-binding fragment thereof described herein is internalized into a cell expressing a MUC16 polypeptide upon contacting the cell with the anti-MUC16 antibody agent or an antigen-binding fragment thereof. "Internalized" or "internalization," when in reference to a molecule that is internalized by a cell, refers to passage of the molecule that is in contact with the extracellular surface of a cell membrane across the cell membrane to the intracellular surface of the cell membrane and/or into the cell cytoplasm. In certain embodiments, the cells recombinantly expressing glycosylated MUC16 c114 are SKOV3 cells. In certain embodiments, the glycosylated form of MUC16 c114 is N-glycosylated, e.g., at Asn1, Asn24, and Asn30 of SEQ ID NO: 25 (also referred to as Asn1777, Asn1800, and Asn1806, respectively, in Yin and Lloyd (2001) *J Biol Chem* 276: 27371-27375). In certain embodiments, the glycosylation comprises N-linked chitobiose. In certain embodiments, the glycosylation consists of an N-linked chitobiose.

Assays to determine internalization of an anti-MUC16 antibody agent or an antigen-binding fragment thereof described herein to a cell, such as, for example, using radiolabeled antibodies, are known to a person skilled in the art. For example, internalization of 89Zr-labled antibody can be investigated on SKOV3 cells expressing MUC16 c114. Briefly, approximately $1 \times 10^5$ cells are seeded in a 12-well plate and incubated overnight at 37° C. 5% CO2 incubator.

A volume of radiolabeled protein is added to each well and the plates are incubated at 37° C. and 4° C. for 1, 5, 12, and 24 hours. Following each incubation period, the medium is collected and the cells are rinsed with 1 mL of phosphate buffered saline (PBS). Surface-bound activity is collected by washing the cells in 1 mL of 100 mM acetic acid with 100 mM glycine (1:1, pH 3.5) at 4° C. The adherent cells are then lysed with 1 mL of 1 M NaOH. Each wash is collected and counted for activity. The ratio of activity of the final wash to the total activity of all the washes is used to determine the % internalized. In certain embodiments, the assay is performed at 37° C. In certain embodiments, the anti-MUC16 antibody agent or an antigen-binding fragment thereof is internalized in at least 1, 2, 3, 5, 6, 7, 8, 9, or 10 percent of cells incubated with the anti-MUC16 antibody agent or an antigen-binding fragment thereof. In certain embodiments, the anti-MUC16 antibody agent or an antigen-binding fragment thereof is internalized in about 1, 2, 3, 5, 6, 7, 8, 9, or 10 percent of cells incubated with the anti-MUC16 antibody agent or an antigen-binding fragment thereof. In certain embodiments, the anti-MUC16 antibody agent or an antigen-binding fragment thereof is internalized within 1, 2, 3, 4, 8, 12, 16, 20, or 24 hours of contacting the cells with the anti-MUC16 antibody agent or an antigen-binding fragment thereof.

Nucleic Acids

Nucleic acid molecules encoding the anti-MUC16 antibody agents or an antigen-binding fragment thereof (such as anti-MUC16 antibodies, e.g., full-length anti-MUC16 antibodies) are also contemplated. In some embodiments, there is provided a nucleic acid (or a set of nucleic acids) encoding a full-length anti-MUC16 antibody, including any of the full-length anti-MUC16 antibodies described herein, or an antigen-binding fragment thereof. In some embodiments, the nucleic acid (or a set of nucleic acids) encoding the anti-MUC16 antibody agent described herein may further comprises a nucleic acid sequence encoding a peptide tag (such as protein purification tag, e.g., His-tag, HA tag).

Also contemplated here are isolated host cells comprising an anti-MUC16 antibody agent, an isolated nucleic acid encoding the polypeptide components of the anti-MUC16 antibody agent, or a vector comprising a nucleic acid encoding the polypeptide components of the anti-MUC16 antibody agent described herein.

The present application also includes variants to these nucleic acid sequences. For example, the variants include nucleotide sequences that hybridize to the nucleic acid sequences encoding the anti-MUC16 antibody agents (such as anti-MUC16 antibodies, e.g., full-length anti-MUC16 antibodies), antigen-binding fragments thereof, or anti-MUC16 antibody moieties of the present application under at least moderately stringent hybridization conditions.

The present invention also provides vectors in which a nucleic acid of the present invention is inserted.

In brief summary, the expression of an anti-MUC16 antibody agent (e.g., full-length anti-MUC16 antibody) or an antigen-binding fragment thereof by a natural or synthetic nucleic acid encoding the anti-MUC16 antibody agent can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Green and Sambrook (2013, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Ban virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the expression of the anti-MUC16 antibody agent is inducible. In some embodiments, a nucleic acid sequence encoding the anti-MUC16 antibody agent is operably linked to an inducible promoter, including any inducible promoter described herein.

Inducible Promoters

The use of an inducible promoter provides a molecular switch capable of turning on expression of the polynucleotide sequence which it is operatively linked when such expression is desired, or turning off the expression when expression is not desired. Exemplary inducible promoter systems for use in eukaryotic cells include, but are not limited to, hormone-regulated elements (e.g., see Mader, S. and White, J. H. *Proc. Natl. Acad. Sci. USA* 90:5603-5607 (1993)), synthetic ligand-regulated elements (see, e.g., Spencer, D. M. et al 1993) *Science* 262: 1019-1024) and ionizing radiation-regulated elements (e.g., see Manome, Y. et al., *Biochemistry* 32: 10607-10613 (1993); Datta, R. et al., *Proc. Natl. Acad. Sci. USA* 89: 1014-10153 (1992)). Further exemplary inducible promoter systems for use in in vitro or in vivo mammalian systems are reviewed in Gingrich et al., *Annual Rev. Neurosci* 21:377-405 (1998). In some embodiments, the inducible promoter system for use to express the anti-MUC16 antibody agent is the Tet system. In some embodiments, the inducible promoter system for use to express the anti-MUC16 antibody agent is the lac repressor system from *E. coli*.

An exemplary inducible promoter system for use in the present invention is the Tet system. Such systems are based on the Tet system described by Gossen et al., (1993). In an exemplary embodiment, a polynucleotide of interest is under the control of a promoter that comprises one or more Tet operator (TetO) sites. In the inactive state, Tet repressor (TetR) will bind to the TetO sites and repress transcription from the promoter. In the active state, e.g., in the presence of an inducing agent such as tetracycline (Tc), anhydrotetracycline, doxycycline (Dox), or an active analog thereof, the inducing agent causes release of TetR from TetO, thereby allowing transcription to take place. Doxycycline is a member of the tetracycline family of antibiotics having the chemical name of 1-dimethylamino-2,4a,5,7,12-pentahydroxy-11-methyl-4,6-dioxo-1,4a,11,11a,12,12a-hexahydrotetracene-3-carboxamide.

In one embodiment, a TetR is codon-optimized for expression in mammalian cells, e.g., murine or human cells. Most amino acids are encoded by more than one codon due to the degeneracy of the genetic code, allowing for substantial variations in the nucleotide sequence of a given nucleic acid without any alteration in the amino acid sequence encoded by the nucleic acid. However, many organisms display differences in codon usage, also known as "codon bias" (i.e., bias for use of a particular codon(s) for a given amino acid). Codon bias often correlates with the presence of a predominant species of tRNA for a particular codon, which in turn increases efficiency of mRNA translation. Accordingly, a coding sequence derived from a particular organism (e.g., a prokaryote) may be tailored for improved expression in a different organism (e.g., a eukaryote) through codon optimization.

Other specific variations of the Tet system include the following "Tet-Off" and "Tet-On" systems. In the Tet-Off system, transcription is inactive in the presence of Tc or Dox. In that system, a tetracycline-controlled transactivator protein (tTA), which is composed of TetR fused to the strong transactivating domain of VP16 from Herpes simplex virus, regulates expression of a target nucleic acid that is under transcriptional control of a tetracycline-responsive promoter element (TRE). The TRE is made up of TetO sequence concatamers fused to a promoter (commonly the minimal promoter sequence derived from the human cytomegalovirus (hCMV) immediate-early promoter). In the absence of Tc or Dox, tTA binds to the TRE and activates transcription of the target gene. In the presence of Tc or Dox, tTA cannot bind to the TRE, and expression from the target gene remains inactive.

Conversely, in the Tet-On system, transcription is active in the presence of Tc or Dox. The Tet-On system is based on a reverse tetracycline-controlled transactivator, rtTA. Like tTA, rtTA is a fusion protein comprised of the TetR repressor and the VP16 transactivation domain. However, a four amino acid change in the TetR DNA binding moiety alters rtTA's binding characteristics such that it can only recognize the tetO sequences in the TRE of the target transgene in the presence of Dox. Thus, in the Tet-On system, transcription of the TRE-regulated target gene is stimulated by rtTA only in the presence of Dox.

Another inducible promoter system is the lac repressor system from *E. coli* (See Brown et al., Cell 49:603-612 (1987)). The lac repressor system functions by regulating transcription of a polynucleotide of interest operably linked to a promoter comprising the lac operator (lacO). The lac repressor (lacR) binds to LacO, thus preventing transcription of the polynucleotide of interest. Expression of the polynucleotide of interest is induced by a suitable inducing agent, e.g., isopropyl-β-D-thiogalactopyranoside (IPTG).

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, there is provided nucleic acid encoding a full-length anti-MUC16 antibody according to any of the full-length anti-MUC16 antibodies described herein. In some embodiments, the nucleic acid comprises one or more nucleic acid sequences encoding the heavy and light chains of the full-length anti-MUC16 antibody. In some embodiments, each of the one or more nucleic acid sequences are contained in separate vectors. In some embodiments, at least some of the nucleic acid sequences are contained in the same vector. In some embodiments, all of the nucleic acid sequences are contained in the same vector. Vectors may be selected, for example, from the group consisting of mammalian expression vectors and viral vectors (such as those derived from retroviruses, adenoviruses, adeno-associated viruses, herpes viruses, and lentiviruses).

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Green and Sambrook (2013, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method of inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Preparation of Anti-MUC16 Antibody Agents and Anti-MUC16 Antibody Moieties

In some embodiments, the anti-MUC16 antibody agent is a monoclonal antibody or derived from a monoclonal antibody. In some embodiments, the anti-MUC16 antibody agent comprises $V_H$ and $V_L$ domains, or variants thereof, from the monoclonal antibody. In some embodiments, the anti-MUC16 antibody agent further comprises $C_H1$ and $C_L$ domains, or variants thereof, from the monoclonal antibody. Monoclonal antibodies can be prepared, e.g., using known methods in the art, including hybridoma methods, phage display methods, or using recombinant DNA methods. Additionally, exemplary phage display methods are described herein and in the Examples below.

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, Calif. and the American Type Culture Collection, Manassas, $V_H$. Human myeloma and mouse-human heteromyeloma cell lines also have been described for the production of human monoclonal antibodies.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones can be sub cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In some embodiments, according to any of the anti-MUC16 antibody agents described herein, the anti-MUC16 antibody agent comprises sequences from a clone selected from an antibody library (such as a phage library presenting scFv or Fab fragments). The clone may be identified by screening combinatorial libraries for antibody fragments with the desired activity or activities. For example, a variety of methods are known in the art for generating phage display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N.J., 2001) and further described, e.g., in McCafferty et al., *Nature* 348:552-554; Clackson et al., *Nature* 352: 624-628 (1991); Marks et al., *J. Mol. Biol.* 222: 581-597 (1992); Marks and Bradbury, *Methods in Molecular Biology* 248: 161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

The anti-MUC16 antibody agents can be prepared using phage display to screen libraries for anti-MUC16 antibody moieties specific to the target MUC16 (e.g., nMUC16). The library can be a human scFv phage display library having a diversity of at least one×$10^9$ (such as at least about any of $1×10^9$, $2.5×10^9$, $5×10^9$, $7.5×10^9$, $1×10^{10}$, $2.5×10^{10}$, $5×10^{10}$, $7.5×10^{10}$, or $1×10^{11}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al., *Nat. Biotechnol.* 23(3):344-348, 2005). In some embodiments, the heavy chain CDR3 of the semi-synthetic human library has a length from about 5 to about 24 (such as about any of 5, 6, 7, 8, 9, 10, 11, 12, 13, 14, 15, 16, 17, 18, 19, 20, 21, 22, 23, or 24) amino acids. In some embodiments, the library is a fully-synthetic phage display library. In some embodiments, the library is a non-human phage display library.

Phage clones that bind to the target MUC16 (e.g., nMUC16) with high affinity can be selected by iterative binding of phage to the target MUC16, which is bound to a solid support (such as, for example, beads for solution panning or mammalian cells for cell panning), followed by removal of non-bound phage and by elution of specifically bound phage. The bound phage clones are then eluted and used to infect an appropriate host cell, such as *E. coli* XL1-Blue, for expression and purification. In an example of cell panning, HEK293 cells over-expressing MUC16 on cell surface are mixed with the phage library, after which the cells are collected and the bound clones are eluted and used to infect an appropriate host cell for expression and purification (all see Examples). The panning can be performed for multiple (such as about any of 2, 3, 4, 5, 6 or more) rounds with solution panning, cell panning, or a combination of both, to enrich for phage clones binding specifically to the target MUC16. Enriched phage clones can be tested for specific binding to the target MUC16 by any methods known in the art, including for example ELISA and FACS.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). Hybridoma cells as described above or MUC16-specific phage clones of the invention can serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains and/or framework regions in place of the homologous non-human sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody agent of the invention, or can be substituted for the variable domains of one antigen-combining site of an antibody agent of the invention to create a chimeric bivalent antibody agent.

The antibodies can be monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using any method known in the art.

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. In some embodiments, the first heavy-chain constant region (CH1) containing the site necessary for light-chain binding is present in at least one of the fusions. DNAs encoding the immunoglobulin heavy-chain fusions and, if desired, the immunoglobulin light chain, are inserted into separate expression vectors, and are co-transfected into a suitable host organism.

Human and Humanized Antibodies

The anti-MUC16 antibody agents (e.g., full-length anti-MUC16 antibodies) or an antigen-binding fragment thereof can be humanized antibody agents or human antibody agents. Humanized forms of non-human (e.g., murine) antibody moieties are chimeric immunoglobulins, immunoglobulin chains, or fragments thereof (such as Fv, Fab, Fab', F(ab')$_2$, scFv, or other antigen-binding subsequences of antibodies) that typically contain minimal sequence derived from non-human immunoglobulin. Humanized antibody moieties include human immunoglobulins, immunoglobulin chains, or fragments thereof (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibody moieties can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence.

Generally, a humanized antibody agent has one or more amino acid residues introduced into it from a source that is non-human. These non-human amino acid residues are often referred to as "import" residues, which are typically taken from an "import" variable domain. According to some embodiments, humanization can be essentially performed following the method of Winter and co-workers (Jones et al., Nature, 321: 522-525 (1986); Riechmann et al., Nature, 332: 323-327 (1988); Verhoeyen et al., Science, 239: 1534-1536 (1988)), by substituting rodent CDRs or CDR sequences for the corresponding sequences of a human antibody. Accordingly, such "humanized" antibody moieties are antibody moieties (U.S. Pat. No. 4,816,567), wherein substantially less than an intact human variable domain has been substituted by the corresponding sequence from a non-human species. In practice, humanized antibody moieties are typically human antibody moieties in which some CDR residues and possibly some FR residues are substituted by residues from analogous sites in rodent antibodies.

As an alternative to humanization, human antibody moieties can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., PNAS USA, 90:2551 (1993); Jakobovits et al., Nature, 362:255-258 (1993); Bruggemann et al., Year in Immunol., 7:33 (1993); U.S. Pat. Nos. 5,545,806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); Lonberg and Huszar, Intern. Rev. Immunol., 13: 65-93 (1995).

Human antibody agents may also be generated by in vitro activated B cells (see U.S. Pat. Nos. 5,567,610 and 5,229,275) or by using various techniques known in the art, including phage display libraries. Hoogenboom and Winter, J. Mol. Biol., 227:381 (1991); Marks et al., J. Mol. Biol., 222:581 (1991). The techniques of Cole et al. and Boerner et al. are also available for the preparation of human monoclonal antibodies. Cole et al., Monoclonal Antibodies and Cancer Therapy, Alan R. Liss, p. 77 (1985) and Boerner et al., J. Immunol., 147(1): 86-95 (1991).

Anti-MUC16 Antibody Agent Variants

In some embodiments, amino acid sequence variants of the anti-MUC16 antibody agents (e.g., full-length anti-MUC16 antibody) or an antigen-binding fragment thereof provided herein are contemplated. For example, it may be desirable to improve the binding affinity and/or other biological properties of the antibody agent. Amino acid sequence variants of an antibody agent may be prepared by introducing appropriate modifications into the nucleotide sequence encoding the antibody agent, or by peptide synthesis. Such modifications include, for example, deletions from, and/or insertions into and/or substitutions of residues within the amino acid sequences of the antibody agent. Any combination of deletion, insertion, and substitution can be made to arrive at the final construct, provided that the final construct possesses the desired characteristics, e.g., antigen-binding.

In some embodiments, anti-MUC16 antibody agent variants having one or more amino acid substitutions are provided. Sites of interest for substitutional mutagenesis include the HVRs and FRs. Amino acid substitutions may be introduced into an antibody agent of interest and the products screened for a desired activity, e.g., retained/improved antigen binding, decreased immunogenicity, or improved ADCC or CDC.

Conservative substitutions are shown in Table 4 below.

TABLE 4

CONSERVATIVE SUBSTITUTIONS

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties: hydrophobic: Norleucine, Met, Ala, Val, Leu, Ile; neutral hydrophilic: Cys, Ser, Thr, Asn, Gln; acidic: Asp, Glu; basic: His, Lys, Arg; residues that influence chain orientation: Gly, Pro; and aromatic: Trp, Tyr, Phe. Non-conservative substitutions involves exchanging a member of one of these classes for another class.

An exemplary substitutional variant is an affinity matured antibody agent, which may be conveniently generated, e.g., using phage display-based affinity maturation techniques. Briefly, one or more CDR residues are mutated and the variant antibody moieties displayed on phage and screened for a particular biological activity (e.g., binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or specificity determining residues (SDRs), with the resulting variant $V_H$ or $V_L$ being tested for binding affinity. Affinity maturation by constructing and reselecting from secondary libraries has been described, e.g., in Hoogenboom et al., in Methods in Molecular Biology 178:1-37 (O'Brien et al., ed., Human Press, Totowa, N.J., (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody agent variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody agent to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant $V_H$ and $V_L$ sequences provided above, each HVR either is unaltered, or contains no more than one, two or three amino acid substitutions.

A useful method for identification of residues or regions of an antibody agent that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody agent with antigen is affected. Further substitutions may be introduced at the amino acid locations demonstrating functional sensitivity to the initial substitutions. Alternatively, or additionally, a crystal structure of an antigen-antibody agent complex can be determined to identify contact points between the antibody agent and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody agent with an N-terminal methionyl residue. Other insertional variants of the antibody agent molecule include the fusion to the N- or C-terminus of the antibody agent to an enzyme (e.g. for ADEPT) or a polypeptide which increases the serum half-life of the antibody agent.

Fc Region Variants

In some embodiments, one or more amino acid modifications may be introduced into the Fc region of an antibody agent (e.g., a full-length anti-MUC16 antibody or anti-MUC16 Fc fusion protein) provided herein, thereby generating an Fc region variant. In some embodiments, the Fc region variant has enhanced ADCC effector function, often related to binding to Fc receptors (FcRs). In some embodiments, the Fc region variant has decreased ADCC effector function. There are many examples of changes or mutations to Fc sequences that can alter effector function. For example, WO 00/42072 and Shields et al., *J Biol. Chem.* 9(2): 6591-6604 (2001) describe antibody variants with improved or diminished binding to FcRs. The contents of those publications are specifically incorporated herein by reference.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., an anti-MUC16 antibody). The typical ADCC involves activation of NK cells by antibodies. An NK cell expresses CD16 which is an Fc receptor. This receptor recognizes, and binds to, the Fc portion of an antibody bound to the surface of a target cell. The most common Fc receptor on the surface of an NK cell is called CD16 or FcγRIII. Binding of the Fc receptor to the Fc region of an antibody results in NK cell activation, release of cytolytic granules and consequent target cell apoptosis. The contribution of ADCC to tumor cell killing can be measured with a specific test that uses NK-92 cells that have been transfected with a high-affinity FcR. Results are compared to wild-type NK-92 cells that do not express the FcR.

In some embodiments, the invention contemplates an anti-MUC16 antibody agent variant (such as a full-length anti-MUC16 antibody variant) comprising an Fc region that possesses some but not all effector functions, which makes it a desirable candidate for applications in which the half-life of the anti-MUC16 antibody agent in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody agent lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al., *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M et al., *J. Exp. Med.* 166:1351-1361 (1987)). Alternatively, non-radioactive assay methods may be employed (see, for example, ACTT™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Nat'l Acad. Sci. USA* 95:652-656 (1998). C1q binding assays may also be carried out to confirm that the antibody agent is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int=l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody agent variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, there is provided an anti-MUC16 antibody agent (such as a full-length anti-MUC16 antibody) variant comprising a variant Fc region comprising one or more amino acid substitutions which improve ADCC. In some embodiments, the variant Fc region comprises one or more amino acid substitutions which improve ADCC, wherein the substitutions are at positions 298, 333, and/or 334 of the variant Fc region (EU numbering of residues). In some embodiments, the anti-MUC16 antibody agent (e.g., full-length anti-MUC16 antibody) variant comprises the following amino acid substitution in its variant Fc region: S298A, E333A, and K334A.

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

In some embodiments, there is provided an anti-MUC16 antibody agent (such as a full-length anti-MUC16 antibody) variant comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-MUC16 antibody agents (such as full-length anti-MUC16 antibodies) comprising any of the Fc variants described herein, or combinations thereof, are contemplated.

Glycosylation Variants

In some embodiments, an anti-MUC16 antibody agent (such as a full-length anti-MUC16 antibody) or an antigen-binding fragment thereof provided herein is altered to increase or decrease the extent to which the anti-MUC16 antibody agent is glycosylated. Addition or deletion of glycosylation sites to an anti-MUC16 antibody agent may be conveniently accomplished by altering the amino acid sequence of the anti-MUC16 antibody agent or polypeptide portion thereof such that one or more glycosylation sites is created or removed.

Where the anti-MUC16 antibody agent or an antigen-binding fragment thereof comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-MUC16 antibody agent of the invention may be made in order to create anti-MUC16 antibody agent variants with certain improved properties.

The N-glycans attached to the CH2 domain of Fc is heterogeneous. Antibodies or Fc fusion proteins generated in CHO cells are fucosylated by fucosyltransferase activity. See Shoji-Hosaka et al., *J. Biochem.* 140:777-83 (2006). Normally, a small percentage of naturally occurring afucosylated IgGs may be detected in human serum. N-glycosylation of the Fc is important for binding to FcγR; and afucosylation of the N-glycan increases Fc's binding capacity to FcγRIIIa. Increased FcγRIIIa binding can enhance ADCC, which can be advantageous in certain antibody agent therapeutic applications in which cytotoxicity is desirable.

In some embodiments, an enhanced effector function can be detrimental when Fc-mediated cytotoxicity is undesirable. In some embodiments, the Fc fragment or CH2 domain is not glycosylated. In some embodiments, the N-glycosylation site in the CH2 domain is mutated to prevent from glycosylation.

In some embodiments, anti-MUC16 antibody agent (such as a full-length anti-MUC16 antibody) variants are provided comprising an Fc region wherein a carbohydrate structure attached to the Fc region has reduced fucose or lacks fucose, which may improve ADCC function. Specifically, anti-MUC16 antibody agents are contemplated herein that have reduced fucose relative to the amount of fucose on the same anti-MUC16 antibody agent produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In some embodiments, the anti-MUC16 antibody agent is one wherein less than about 50%, 40%, 30%, 20%, 10%, or 5% of the N-linked glycans thereon comprise fucose. For example, the amount of fucose in such an anti-MUC16 antibody agent may be from 1% to 80%, from 1% to 65%, from 5% to 65% or from 20% to 40%. In some embodiments, the anti-MUC16 antibody agent is one wherein none of the N-linked glycans thereon comprise fucose, i.e., wherein the anti-MUC16 antibody agent is completely without fucose, or has no fucose or is afucosylated. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody agent variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al., *J. Mol. Biol.* 336:1239-1249 (2004); Yamane-Ohnuki et al., *Biotech. Bioeng.* 87: 614 (2004). Examples of cell lines capable of producing defucosylated antibodies include Lec13 CHO cells deficient in protein fucosylation (Ripka et al., *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such asa-1,6-fucosyltransferase gene, FUT8, knockout CHO cells (see, e.g., Yamane-Ohnuki et al., *Biotech. Bioeng.* 87: 614 (2004); Kanda, Y. et al., *Biotechnol. Bioeng.*, 94(4):680-688 (2006); and WO2003/085107).

Anti-MUC16 antibody agent (such as a full-length anti-MUC16 antibody) variants are further provided with bisected oligosaccharides, e.g., in which a biantennary oligosaccharide attached to the Fc region of the anti-MUC16 antibody agent is bisected by GlcNAc. Such anti-MUC16 antibody agent (such as a full-length anti-MUC16 antibody) variants may have reduced fucosylation and/or improved ADCC function. Examples of such antibody agent variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering*, 93(5): 851-861 (2006). Anti-MUC16 antibody agent (such as full-length anti-MUC16 antibody) variants with at least one galactose residue in the oligosaccharide attached to the Fc region are also provided. Such anti-MUC16 antibody agent variants may have improved CDC function. Such antibody agent variants are described, e.g., in WO 1997/30087 (Patel et al.); WO 1998/58964 (Raju, S.); and WO 1999/22764 (Raju, S.).

In some embodiments, the anti-MUC16 antibody agent (such as a full-length anti-MUC16 antibody) variants comprising an Fc region are capable of binding to an FcγRIII. In some embodiments, the anti-MUC16 antibody agent (such as a full-length anti-MUC16 antibody) variants comprising an Fc region have ADCC activity in the presence of human effector cells (e.g., T cell) or have increased ADCC activity in the presence of human effector cells compared to the otherwise same anti-MUC16 antibody agent (such as a full-length anti-MUC16 antibody) comprising a human wild-type IgG1Fc region.

Cysteine Engineered Variants

In some embodiments, it may be desirable to create cysteine engineered anti-MUC16 antibody agents (such as a full-length anti-MUC16 antibody) or an antigen-binding fragment thereof in which one or more amino acid residues are substituted with cysteine residues. In some embodiments, the substituted residues occur at accessible sites of the anti-MUC16 antibody agent or an antigen-binding fragment thereof. By substituting those residues with cysteine, reactive thiol groups are thereby positioned at accessible sites of the anti-MUC16 antibody agent and may be used to conjugate the anti-MUC16 antibody agent to other moieties, such as drug moieties or linker-drug moieties, to create an anti-MUC16 immunoconjugate, as described further herein. Cysteine engineered anti-MUC16 antibody agents (such as anti-MUC16 antibodies, e.g., full-length anti-MUC16 antibodies) may be generated as described, e.g., in U.S. Pat. No. 7,521,541.

Derivatives

In some embodiments, an anti-MUC16 antibody agent (such as a full-length anti-MUC16 antibody) or an antigen-binding fragment thereof provided herein may be further modified to contain additional non-proteinaceous moieties that are known in the art and readily available. The moieties suitable for derivatization of the anti-MUC16 antibody agent include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the anti-MUC16 antibody agent may vary, and if more than one polymer are attached, they can be the same or different molecules. In general, the number and/or type of polymers used for derivatization can be determined based on considerations including, but not limited to, the particular properties or functions of the anti-MUC16 antibody agent to be improved, whether the anti-MUC16 antibody agent derivative will be used in a therapy under defined conditions, etc.

In some embodiments, conjugates of an anti-MUC16 antibody agent (such as a full-length anti-MUC16 antibody) or an antigen-binding fragment thereof and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the anti-MUC16 antibody agent-nonproteinaceous moiety are killed.

Antibody Conjugates

In certain embodiments, provided herein are anti-MUC16 antibody agent or antigen-binding fragments thereof conjugates, wherein said anti-MUC16 antibody agent or antigen-binding fragments thereof is conjugated to one or more agents, e.g., an imaging agent or a cytotoxic agent. Also provided herein are bispecific antibody conjugates, wherein said bispecific antibody is conjugated to one or more agent, e.g., an imaging agent or a cytotoxic agent. Also provided herein are antibody heavy chain conjugates, wherein said antibody heavy chain is conjugated to one or more agent, e.g., an imaging agent or a cytotoxic agent. Also provided herein are antibody light chain conjugates, wherein said antibody light chain is conjugated to one or more agent, e.g., an imaging agent or a cytotoxic agent. Also provided herein are fusion protein conjugates, wherein said fusion protein is conjugated to an agent, e.g., an imaging agent or a cytotoxic agent. In certain embodiments, the agent is conjugated covalently or non-covalently.

In certain embodiments, the imaging agent is a detectable label, such as, a chromogenic, enzymatic, radioisotopic, isotopic, fluorescent, toxic, chemiluminescent, nuclear magnetic resonance contrast agent or other label.

Non-limiting examples of suitable chromogenic labels include diaminobenzidine and 4-hydroxyazo-benzene-2-carboxylic acid.

Non-limiting examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Suitable radioisotopes are well known to those skilled in the art and include beta-emitters, gamma-emitters, positron-emitters, and x-ray emitters. Non-limiting examples of suitable radioisotopic labels include $^{3}H$, $^{18}F$, $^{111}In$, $^{125}I$, $^{131}I$, $^{32}P$, $^{33}P$, $^{35}S$, $^{11}C$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{223}Ra$, $^{223}Ra$, $^{89}Zr$, $^{177}Lu$, and $^{109}Pd$. In certain embodiments, $^{111}In$ is a preferred isotope for in vivo imaging as it avoids the problem of dehalogenation of $^{125}I$ or $^{131}I$-labeled anti-MUC16 antibody agents or antigen-binding fragments thereof in the liver. In addition, $^{111}In$ has a more favorable gamma emission energy for imaging (Perkins et al, *Eur. J. Nucl. Med.* 70:296-301 (1985); Carasquillo et ah, *J. Nucl. Med.* 25:281-287 (1987)). For example, $^{111}In$ coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861-870 (1987)).

Non-limiting examples of suitable non-radioactive isotopic labels include 157Gd, $^{55}Mn$, $^{162}Dy$, $^{52}Tr$, and $^{56}Fe$.

Non-limiting examples of suitable fluorescent labels include a $^{152}Eu$ label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label.

Non-limiting examples of chemiluminescent labels include a luminol label, an isoluminol label, an aromatic acridinium ester label, an imidazole label, an acridinium salt label, an oxalate ester label, a luciferin label, a luciferase label, and an aequorin label.

Non-limiting examples of nuclear magnetic resonance contrasting agents include heavy metal nuclei such as Gd, Mn, and iron.

Techniques known to one of ordinary skill in the art for conjugating the above-described labels to said anti-MUC16 antibody agents or antigen-binding fragments thereof, bispecific antibodies, antibody heavy chains, antibody light chains, and fusion proteins are described in, for example, Kennedy et at., Clin. CMm. Acta 70: 1-31 (1976), and Schurs et al, Clin. CMm. Acta 81: 1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Nonlimiting examples of cytotoxic agents include a cytostatic or cytocidal agent, a radioactive metal ion, e.g., alpha-emitters, and toxins, e.g., *pseudomonas* exotoxin, abrin, cholera toxin, ricin A, and diphtheria toxin.

In certain embodiments, the agent is a diagnostic agent. A diagnostic agent is an agent useful in diagnosing or detecting a disease by locating the cells containing the antigen. Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, and fluorescent compounds. In order to load an anti-MUC16 antibody agent or antigen-binding fragment thereof with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, for example, ethylenediaminetetraacetic acid (EDTA), diethylenetriaminepentaacetic acid (DTP A), porphyrins, polyamines, crown ethers, bis-thiosemicarbazones, polyoximes, and like groups known to be useful for this purpose. Chelates are coupled to the antibodies using standard chemistries. The chelate is normally linked to the antibody by a group which enables formation of a bond to the molecule with minimal loss of immunoreactivity and minimal aggregation and/or internal cross-linking other, more unusual, methods and reagents for conjugating chelates to antibodies are disclosed in U.S. Pat. No. 4,824,659 to Hawthorne, entitled "Antibody Conjugates," issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with an anti-MUC16 antibody agent or antigen-binding fragment thereof provided herein.

Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed herein.

Pharmaceutical Compositions

Also provided herein are compositions (such as pharmaceutical compositions, also referred to herein as formulations) comprising an anti-MUC16 antibody agent (such as a full-length anti-MUC16 antibody) or an antigen-binding fragment thereof, nucleic acid encoding the antibody agent, vector comprising the nucleic acid encoding the antibody agent, or host cell comprising the nucleic acid or vector. In some embodiments, there is provided a pharmaceutical composition comprising an anti-MUC16 antibody agent and optionally a pharmaceutically acceptable carrier.

Suitable formulations of the anti-MUC16 antibody agents (such as anti-MUC16 antibodies, e.g., full-length anti-MUC16 antibodies) or an antigen-binding fragment thereof are obtained by mixing an anti-MUC16 antibody agent having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be treated herein. Lipofectins or liposomes can be used to deliver the anti-MUC16 antibody agents of this invention into cells.

The formulation herein may also contain one or more active compounds in addition to the anti-MUC16 antibody agent (such as a full-length anti-MUC16 antibody) or an antigen-binding fragment thereof as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent in addition to the anti-MUC16 antibody agent or an antigen-binding fragment thereof. Such molecules are suitably present in combination in amounts that are effective for the purpose intended. The effective amount of such other agents depends on the amount of anti-MUC16 antibody agent present in the formulation, the type of disease or disorder or treatment, and other factors discussed above. These are generally used in the same dosages and with administration routes as described herein or about from 1 to 99% of the heretofore employed dosages.

The anti-MUC16 antibody agents (such as anti-MUC16 antibodies, e.g., full-length anti-MUC16 antibodies) or an antigen-binding fragment thereof may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Sustained-release preparations may be prepared.

Sustained-release preparations of the anti-MUC16 antibody agents (such as anti-MUC16 antibodies, e.g., full-length anti-MUC16 antibodies) or an antigen-binding fragment thereof can be prepared. Suitable examples of sustained-release preparations include semipermeable matrices of solid hydrophobic polymers containing the antibody agent (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L- glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D (−)-3-hydroxybutyric acid. While polymers such as ethylene-vinyl acetate and lactic acid-glycolic acid enable release of molecules for over 100 days, certain hydro gels release proteins for shorter time periods. When encapsulated antibody agents remain in the body for a long time, they can denature or aggregate as a result of exposure to moisture at 37° C., resulting in a loss of biological activity and possible changes in immunogenicity. Rational strategies can be devised for stabilization of anti-MUC16 antibody agents depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In some embodiments, the anti-MUC16 antibody agent (such as a full-length anti-MUC16 antibody) or an antigen-binding fragment thereof is formulated in a buffer comprising a citrate, NaCl, acetate, succinate, glycine, polysorbate 80 (Tween 80), or any combination of the foregoing. In some embodiments, the anti-MUC16 antibody agent or an antigen-binding fragment thereof is formulated in a buffer comprising about 100 mM to about 150 mM glycine. In some embodiments, the anti-MUC16 antibody agent or an antigen-binding fragment thereof is formulated in a buffer comprising about 50 mM to about 100 mM NaCl. In some embodiments, the anti-MUC16 antibody agent or an antigen-binding fragment thereof is formulated in a buffer comprising about 10 mM to about 50 mM acetate. In some embodiments, the anti-MUC16 antibody agent or an antigen-binding fragment thereof is formulated in a buffer comprising about 10 mM to about 50 mM succinate. In some embodiments, the anti-MUC16 antibody agent or an antigen-binding fragment thereof is formulated in a buffer comprising about 0.005% to about 0.02% polysorbate 80. In some embodiments, the anti-MUC16 antibody agent or an antigen-binding fragment thereof is formulated in a buffer having a pH between about 5.1 and 5.6. In some embodiments, the anti-MUC16 antibody agent or an antigen-binding fragment thereof is formulated in a buffer comprising 10 mM citrate, 100 mM NaCl, 100 mM glycine, and 0.01% polysorbate 80, wherein the formulation is at pH 5.5.

The formulations to be used for in vivo administration must be sterile. This is readily accomplished by, e.g., filtration through sterile filtration membranes.

Methods of Treatment Using Anti-MUC16 Antibody Agents

In certain embodiments, provided herein are methods for treating a cancer in a subject, in particular, a MUC16-positive cancer in a subject, comprising administering to the subject in need thereof a therapeutically effective amount of anti-MUC16 antibody agent or an antigen-binding fragment thereof. In some embodiments, the anti-MUC16 antibody agent or antigen-binding fragment thereof is administered at a therapeutically effective dose, such as a dose described herein. In some embodiments, the anti-MUC16 antibody agent or antigen-binding fragment thereof is administered according to a method as described herein. In some embodiments, the anti-MUC16 antibody agent or antigen-binding fragment thereof is administered in combination with one or more additional pharmaceutically active agents.

For use of an anti-MUC16 antibody agent or antigen-binding fragment thereof in a subject of a particular species, an anti-MUC16 antibody agent or antigen-binding fragment thereof is used that binds to MUC16 of that particular species. For example, to treat a human, an anti-MUC16 antibody agent or antigen-binding fragment thereof is used that binds to human MUC16. In some embodiments, the anti-MUC16 antibody agent or antigen-binding fragment thereof is an immunoglobulin.

In addition, for use of an anti-MUC16 antibody agent or antigen-binding fragment thereof in a subject of a particular species, the anti-MUC16 antibody agent, preferably, the constant region of an anti-MUC16 antibody agent or antigen-binding fragment thereof, is derived from that particular species. For example, to treat a human, an anti-MUC16 antibody agent or antigen-binding fragment thereof can comprise an anti-MUC16 antibody agent or antigen-binding fragment thereof that is an immunoglobulin, wherein the immunoglobulin comprises a human constant region. In some embodiments, the subject is a human.

In some embodiments, the MUC16-positive cancer is ovarian cancer, lung cancer, pancreatic cancer, breast cancer, fallopian tube cancer, uterine (e.g., endometrial) cancer, primary peritoneum cancer or cancer of any other tissue that expresses the MUC16 receptor.

In some embodiments, treatment can be to achieve beneficial or desired clinical results including, but not limited to, alleviation of a symptom, diminishment of extent of a disease, stabilizing (i.e., not worsening) of state of a disease, delay or slowing of disease progression, amelioration or palliation of the disease state, and remission (whether partial or total), whether detectable or undetectable. In a specific embodiment, "treatment" can also be to prolong survival as compared to expected survival if not receiving treatment. In some embodiments, the administration of an anti-MUC16 antibody agent or an antigen-binding fragment thereof described herein, or a pharmaceutical composition described herein to a subject with cancer (e.g., ovarian cancer, lung cancer, pancreatic cancer, breast cancer, fallopian tube cancer, uterine (e.g., endometrial) cancer, or primary peritoneum cancer, or cancer of any other tissue that expresses the MUC16 receptor) achieves at least one, two, three, four or more of the following effects: (i) the reduction or amelioration of the severity of one or more symptoms of cancer; (ii) the reduction in the duration of one or more symptoms associated with cancer; (iii) the prevention in the recurrence of a symptom associated with cancer; (iv) the reduction in hospitalization of a subject; (v) a reduction in hospitalization length; (vi) the increase in the survival of a subject; (vii) the enhancement or improvement of the therapeutic effect of another therapy; (viii) the inhibition of the development or onset of one or more symptoms associated with cancer; (ix) the reduction in the number of symptoms associated with cancer; (x) improvement in quality of life as assessed by methods well known in the art; (x) inhibition of the recurrence of a tumor; (xi) the regression of tumors and/or one or more symptoms associated therewith; (xii) the inhibition of the progression of tumors and/or one or more symptoms associated therewith; (xiii) a reduction in the growth of a tumor; (xiv) a decrease in tumor size (e.g., volume or diameter); (xv) a reduction in the formation of a newly formed tumor; (xvi) prevention, eradication, removal, or control of primary, regional and/or metastatic tumors; (xvii) a decrease in the number or size of metastases; (xviii) a reduction in mortality; (xix) an increase in relapse free survival; (xx) the size of the tumor is maintained and does not increase or increases by less than the increase of a tumor after administration of a standard therapy as measured by conventional methods available to one of skill in the art, such as magnetic resonance imaging (MRI), dynamic contrast-enhanced MRI (DCE-MRI), X-ray, and computed tomography (CT) scan, or a positron emission tomography (PET) scan; and/or (xxi) an increase in the length of remission in patients. Treatment can be to achieve one or more of the foregoing.

Diagnostic Uses

In certain embodiments, anti-MUC16 antibody agents or antigen-binding fragments thereof described herein can be used for diagnostic purposes to detect, diagnose, or monitor a condition described herein (e.g., a condition involving MUC16-positive cancer cells). In certain embodiments, anti-MUC16 antibody agents or antigen-binding fragments thereof for use in diagnostic purposes are labeled.

In certain embodiments, provided herein are methods for the detection of a condition described herein comprising (a) assaying the expression of MUC16 or a fragment thereof in cells or a tissue sample of a subject using one or more anti-MUC16 antibody agents or antigen-binding fragments thereof described herein; and (b) comparing the level of MUC16 or the fragment thereof expression with a control level, for example, levels in normal tissue samples (e.g., from a subject not having a condition described herein, or from the same patient before onset of the condition), whereby an increase or decrease in the assayed level of MUC16 or the fragment thereof expression compared to the control level of MUC16 or the fragment thereof expression is indicative of a condition described herein.

Antibodies described herein can be used to assay the levels of MUC16 or a fragment thereof in a biological sample using classical immunohistological methods as described herein or as known to those of skill in the art (e.g., see Jalkanen et al., *J. Cell. Biol.* 101:976-985 (1985); and Jalkanen et al., *J. Cell. Biol.* 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, 121I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. In some embodiments, the assay labels are conjugated to the anti-MUC16 antibody agents or antigen-binding fragment thereof provided herein for direct detection. In some embodiments, the assay labels are conjugated to a secondary antibody that binds to an anti-MUC16 antibody agents or antigen-binding fragment thereof provided herein. The secondary antibody type is selected according to the class of the primary antibody (e.g., IgG or IgM), the source host, and the kind of label which is preferred. In some embodiments, the secondary antibody is a class or isotype specific antibody (e.g., IgG, IgM, IgA, IgE or IgG). In some embodiments, the secondary antibody is a subclass specific antibody (e.g., IgG1, IgG2, IgG2, IgG4, IgA1, or IgA2). In some embodiments, the secondary antibody binds to one or more classes or subclasses of antibodies. In some embodiments, the secondary antibody binds to the heavy chain of the primary antibody. In some embodiments, the secondary antibody binds to the light chain of the primary antibody. In some embodiments, the secondary antibody binds to a kappa light chain of the primary antibody. In some embodiments, the secondary antibody binds to a lambda light chain of the primary antibody. In some embodiments, the secondary antibody is an anti-Fc or an anti-F(ab) or anti-(Fab')2 fragment antibody. In some embodiments, the secondary antibody is a rabbit, mouse, goat, donkey or chicken antibody.

In certain embodiments, monitoring of a condition described herein (e.g., a MUC16-positive cancer), is carried out by repeating the method for diagnosing for a period of time after initial diagnosis.

Presence of the labeled molecule can be detected in the subject (i.e., in vivo) using methods known in the art for in vivo scanning. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

An anti-MUC16 antibody agent or antigen-binding fragment thereof as described herein, or composition containing, or cells expressing the antibodies, or antigen-binding fragments thereof, described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival and subcutaneous routes. Pulmonary administration can also be employed, e.g., by use of an inhaler or nebulizer, and formulation with an aerosolizing agent for use as a spray. In one embodiment, an anti-MUC16 antibody agent or antigen-binding fragment thereof, or a composition described herein is administered parenterally to a subject. In some embodiments, said parenteral administration is intravenous, intramuscular, or subcutaneous.

The amount of an anti-MUC16 antibody agent or antigen-binding fragment thereof, or composition which will be effective in the treatment and/or prevention of a condition will depend on the nature of the disease, and can be determined by standard clinical techniques.

The precise dose to be employed in a composition will also depend on the route of administration, and the type of cancer, and should be decided according to the judgment of the practitioner and each subject's circumstances. For example, effective doses may also vary depending upon means of administration, target site, physiological state of the patient (including age, body weight and health), whether the patient is human or animal, other medications administered, or whether treatment is prophylactic or therapeutic. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

For an anti-MUC16 antibody agent or an antigen-binding fragment thereof, the dosage may range from about 0.0001 to 100 mg/kg, and more usually 0.01 to 15 mg/kg, of the patient body weight. For example, dosages can be 1 mg/kg body weight, 10 mg/kg body weight, or within the range of 1-10 mg/kg or in other words, 70 mg or 700 mg or within the range of 70-700 mg, respectively, for a 70 kg patient. Generally, human antibodies have a longer half-life within the human body than antibodies from other species due to the immune response to the foreign polypeptides. Thus, lower dosages of human antibodies and less frequent administration is often possible.

In certain embodiments, such as in the administration of engineered cells expressing the antibodies or antigen-binding fragments thereof, or CARs, a subject is administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges. In some embodiments, the dose of total cells and/or dose of individual sub-populations of cells is within a range of between at or about $10^4$ and at or about $10^9$ cells/kilograms (kg) body weight, such as between $10^5$ and $10^6$ cells/kg body weight, for example, at or about $1 \times 10^5$ cells/kg, $1.5 \times 10^5$ cells/kg, $2 \times 10^5$ cells/kg, or $1 \times 10^6$ cells/kg, $2 \times 10^6$ cells/kg, $5 \times 10^6$ cells/kg, or $10 \times 10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^7$ T cells/kg body weight.

An anti-MUC16 antibody agent or antigen-binding fragment thereof can be administered on multiple occasions. Intervals between single dosages can be 1 week, 2 weeks, 3 weeks, 4 weeks, 1 month, 2 months, 3 months, 6 months, 1 year, or 2 years.

Combination Therapies

In some embodiments, the methods provided herein for treating cancer (e.g., ovarian cancer, pancreatic cancer, lung cancer, breast cancer, fallopian tube cancer, uterine (e.g., endometrial) cancer, or primary peritoneum cancer) in a subject, comprising administering to a subject in need thereof a pharmaceutical composition comprising an anti-MUC16 antibody agent or an antigen-binding fragment thereof described herein, further comprise administering to the subject one or more additional therapeutic agents. In some embodiments, the additional therapeutic agent is for treating the cancer in the subject (e.g., ovarian cancer, pancreatic cancer, lung cancer, breast cancer, fallopian tube cancer, uterine (e.g., endometrial) cancer, and primary peritoneum cancer). In some embodiments, the additional therapeutic agent is for treating any side effects of treatment with an anti-MUC16 antibody agent or an antigen-binding fragment thereof described herein.

In some embodiments, the additional agent is an agent used to treat ovarian cancer. In some embodiments, the additional agent is an agent used to treat pancreatic cancer. In some embodiments, the additional agent is an agent used to treat lung cancer. In some embodiments, the additional agent is an agent used to treat breast cancer. In some embodiments, the additional agent is an agent used to treat fallopian tube cancer. In some embodiments, the additional agent is an agent used to treat uterine (e.g., endometrial) cancer. In some embodiments, the additional agent is an agent used to treat primary peritoneum cancer.

An anti-MUC16 antibody agent or antigen-binding fragment thereof described herein can be administered with an additional therapeutic agent concurrently or sequentially (before and/or after). The antibody or antigen binding fragment thereof and the additional therapeutic agent can be administered in the same or different compositions, and by the same or different routes of administration. A first therapy (which is an anti-MUC16 antibody agent or an antigen-binding fragment thereof described herein, or the additional therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second therapy (the anti-MUC16 antibody agent or an antigen-binding fragment thereof described herein, or the additional therapeutic agent) to a subject with cancer (e.g., ovarian cancer, pancreatic cancer, lung cancer, breast cancer, fallopian tube cancer, uterine (e.g., endometrial) cancer, and primary peritoneum cancer). In certain embodiments, an additional therapeutic agent administered to a subject in combination with an anti-MUC16 antibody agent or an antigen-binding fragment thereof described herein is administered in the same composition (pharmaceutical composition). In other embodiments, an additional therapeutic agent administered in combination with an anti-MUC16 antibody agent or an antigen-binding fragment thereof described herein is administered to a subject in a different composition than the anti-MUC16 antibody agent or an antigen-binding fragment thereof described herein (e.g., two or more pharmaceutical compositions are used).

Exemplary Patient Populations

A subject treated in accordance with the methods provided herein can be any mammal, such as a rodent, a cat, a canine, a horse, a cow, a pig, a monkey, a primate, or a human, etc. In some embodiments, the subject is a human. In some embodiments, the subject is a canine. As used herein, the terms "subject" and "patient" are used interchangeably.

In certain embodiments, a subject treated in accordance with the methods provided herein has been diagnosed with a MUC16-positive cancer, including but not limited to, ovary, lung, pancreas, breast, uterine, fallopian tube, or primary peritoneum cancer, or cancer of any other tissue that expresses the MUC16.

Articles of Manufacture and Kits

In some embodiments of the invention, there is provided an article of manufacture containing materials useful for the treatment of a cancer characterized by high MUC16 expression and/or high aerobic glycolysis (e.g., kidney cancer, cervical cancer, or prostate cancer), or for delivering an anti-MUC16 antibody agent (such as a full-length anti-MUC16 antibody) to a cell expressing MUC16 on its surface. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is an anti-MUC16 antibody agent of the invention. The label or package insert indicates that the composition is used for treating the particular condition. The label or package insert will further comprise instructions for administering the anti-MUC16 antibody agent composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating cancer (such as HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma).

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of a cancer characterized by high MUC16 expression and/or high aerobic glycolysis (e.g., kidney cancer, cervical cancer, or prostate cancer), or for delivering an anti-MUC16 antibody agent (such as a full-length anti-MUC16 antibody) to a cell expressing MUC16 on its surface, optionally in combination with the articles of manufacture. Kits of the invention include one or more containers comprising an anti-MUC16 antibody agent composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an anti-MUC16 antibody agent (such as a full-length anti-MUC16 antibody). In some embodiments, the kit comprises a) a composition comprising an anti-MUC16 antibody agent, and b) an effective amount of at least one other agent, wherein the other agent enhances the effect (e.g., treatment effect, detecting effect) of the anti-MUC16 antibody agent. In some embodiments, the kit comprises a) a composition comprising an anti-MUC16 antibody agent, and b) instructions for administering the anti-MUC16 antibody agent composition to an individual for treatment of a cancer characterized by high MUC16 expression and/or high aerobic glycolysis (e.g., kidney cancer, cervical cancer, or prostate cancer). In some embodiments, the kit comprises a) a composition comprising an anti-MUC16 antibody agent, b) an effective amount of at least one other agent, wherein the other agent enhances the effect (e.g., treatment effect, detecting effect) of the anti-MUC16 antibody agent, and c) instructions for administering the anti-MUC16 antibody agent composition and the other agent(s) to an individual for treatment of a cancer characterized by high MUC16 expression and/or high aerobic glycolysis (e.g., kidney cancer, cervical cancer, or prostate cancer). The anti-MUC16 antibody agent and the other agent(s) can be present in separate containers or in a single container. For example, the kit may comprise one distinct composition or two or more compositions wherein one composition comprises an anti-MUC16 antibody agent and another composition comprises another agent.

In some embodiments, the kit comprises a nucleic acid (or set of nucleic acids) encoding an anti-MUC16 antibody agent (such as a full-length anti-MUC16 antibody). In some embodiments, the kit comprises a) a nucleic acid (or set of nucleic acids) encoding an anti-MUC16 antibody agent, and b) a host cell for expressing the nucleic acid (or set of nucleic acids). In some embodiments, the kit comprises a) a nucleic acid (or set of nucleic acids) encoding an anti-MUC16 antibody agent, and b) instructions for i) expressing the anti-MUC16 antibody agent in a host cell, ii) preparing a composition comprising the anti-MUC16 antibody agent, and iii) administering the composition comprising the anti-MUC16 antibody agent to an individual for the treatment of a cancer characterized by high MUC16 expression and/or high aerobic glycolysis (e.g., kidney cancer, cervical cancer, or prostate cancer). In some embodiments, the kit comprises a) a nucleic acid (or set of nucleic acids) encoding an anti-MUC16 antibody agent, b) a host cell for expressing the nucleic acid (or set of nucleic acids), and c) instructions for i) expressing the anti-MUC16 antibody agent in the host cell, ii) preparing a composition comprising the anti-MUC16 antibody agent, and iii) administering the composition comprising the anti-MUC16 antibody agent to an individual for the treatment of a cancer characterized by high MUC16 expression and/or high aerobic glycolysis (e.g., kidney cancer, cervical cancer, or prostate cancer).

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the anti-MUC16 antibody agent compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of an anti-MUC16 antibody agent (such as a full-length anti-MUC16 antibody) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the anti-MUC16 antibody agent and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

The present technology is further illustrated by the following Examples, which should not be construed as limiting in any way. The following Examples demonstrate the preparation, characterization, and use of illustrative anti-MUC16 antibodies of the present technology. The following Examples demonstrate the production of human and bispecific antibodies of the present technology, and characterization of their binding specificities and in vivo biological activities.

Example 1: Selection and Characterization of scFvs Specific for Human MUC16

This example demonstrates the selection and characterization of human scFvs specific for human MUC16 (hMUC16) from a collection of human scFv antibody phage display libraries. In particular, this example demonstrates the selection of human scFvs that specifically bind to ectodomain of hMUC16 (MUC16-C114) in its native format (i.e., cell surface-bound MUC16). The example also demonstrates the further selection of human scFvs that target the crucial N-glycosylation site (N30 in c114 or N1806 in a full-length mature MUC16 protein) on the MUC16 ectodomain to inhibit the glycosylation dependent effects of MUC16 on metastasis and invasion. A structural representation of native MUC16 and the truncated MUC16-C114, along with its amino acid sequence, is shown in FIG. 1. The scFvs were selected based on high selectivity for human MUC16 via panning against cell surface-bound MUC16-C114. These human anti-MUC16 scFvs provide a valuable source of antibody components for the construction of anti-MUC16 antibody agents in various formats, e.g., full-length IgG, bi-specific anti-MUC16 antibodies, multi-specific anti-MUC16 antibodies, and the like.

Figure 3:
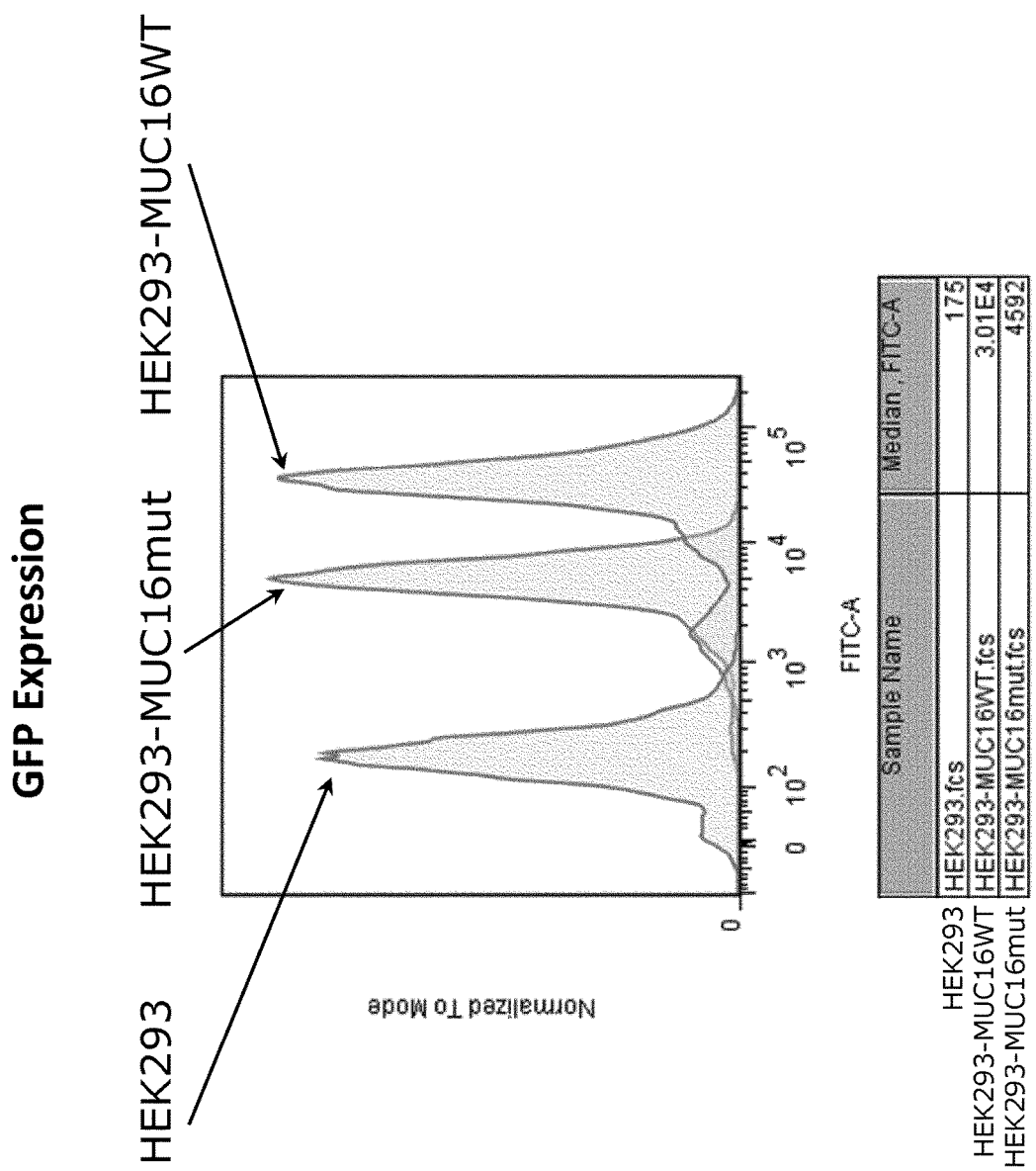
FIG. 3 illustrates fluorescence activated cell sorting (FACS) analysis of GFP expression in HEK293 stable cell lines that express wild-type MUC16-C114 (HEK293-MUC16WT) or N30 mutant MUC16-C114 (HEK293-MUC16mut). Control HEK293 cells are shown for comparison.

Two HEK293 stable cell lines expressing MUC16 proteins were generated for membrane bound expression of MUC16 for use in the selection and characterization of scFvs that specifically target N30 N-glycosylation on the MUC16 ectodomain. One cell line was generated to express a wildtype MUC16-C114-GFP fusion protein (HEK293-MUC16WT), and one cell line was generated to express an N30 mutant MUC16-C114-GFP fusion protein (HEK293-MUC16mut). The alignment between wildtype MUC16-C114 and the N30 mutant MUC16-C114 ectodomains is shown in FIG. 2. As shown in FIG. 2, the N30 mutant MUC16-C114 has an N30A substitution. MUC16 expression of the HEK293-MUC16WT and HEK293-MUC16mut cells was confirmed by measuring GFP expression by fluorescence activated cell sorting (FACS). The parental HEK293 cell line showed no GFP signal. By contrast, the HEK293-MUC16WT and the HEK293-MUC16mut cell lines exhibited GFP expression, though HEK293-MUC16WT had a stronger GFP signal than the HEK293-MUC16mut cell line (FIG. 3). The HEK293-MUC16WT cells showed a GFP signal of 170× mean fluorescence intensity (MFI) increase, while the MUC16mut cells showed a 26× MFI increase.

A collection of human scFv antibody phage display libraries (diversity over $10 \times 10^{10}$) constructed by Eureka Therapeutics (trademarked as E-ALPHA® phage libraries) was used for the selection of human scFvs specific for hMUC16.

The E-ALPHA® scFv phage libraries were screened (panned) against hMUC16 by co-incubation with negative control parental HEK293 cells and MUC16-C114-GFP fusion protein expressing HEK293 cells (HEK293-MUC16WT). After extended washing with PBS, HEK293-MUC16WT cells with bound scFv antibody phage were spun down. The bound clones were then eluted and used for 2-3 additional rounds of panning to enrich for scFv phage clones that bound MUC16 specifically. The bound clones were then eluted and used to infect E. coli XL1-Blue cells. The phage clones expressed in bacteria were then purified.

540 phage clones identified from the cell panning were then tested by FACS analysis for binding to HEK293-MUC16WT cells. Briefly, 0.2 million cells (in PBS+5% FBS+0.05% $NaN_3$) were incubated for 2 h at 4° C. with 50 µl of ~$1.0 \times 10^{11}$ pfu/mL page in PBS. FACS was carried out using primary antibody mouse anti-M13 mAb (Thermo #MA1-12900) and secondary antibody PE anti-mouse IgG (Vectors Lab #EI-2007). 53 unique clones were identified and 40 clones demonstrated specific binding for HEK293-MUC16 WT cells.

Figure 4:
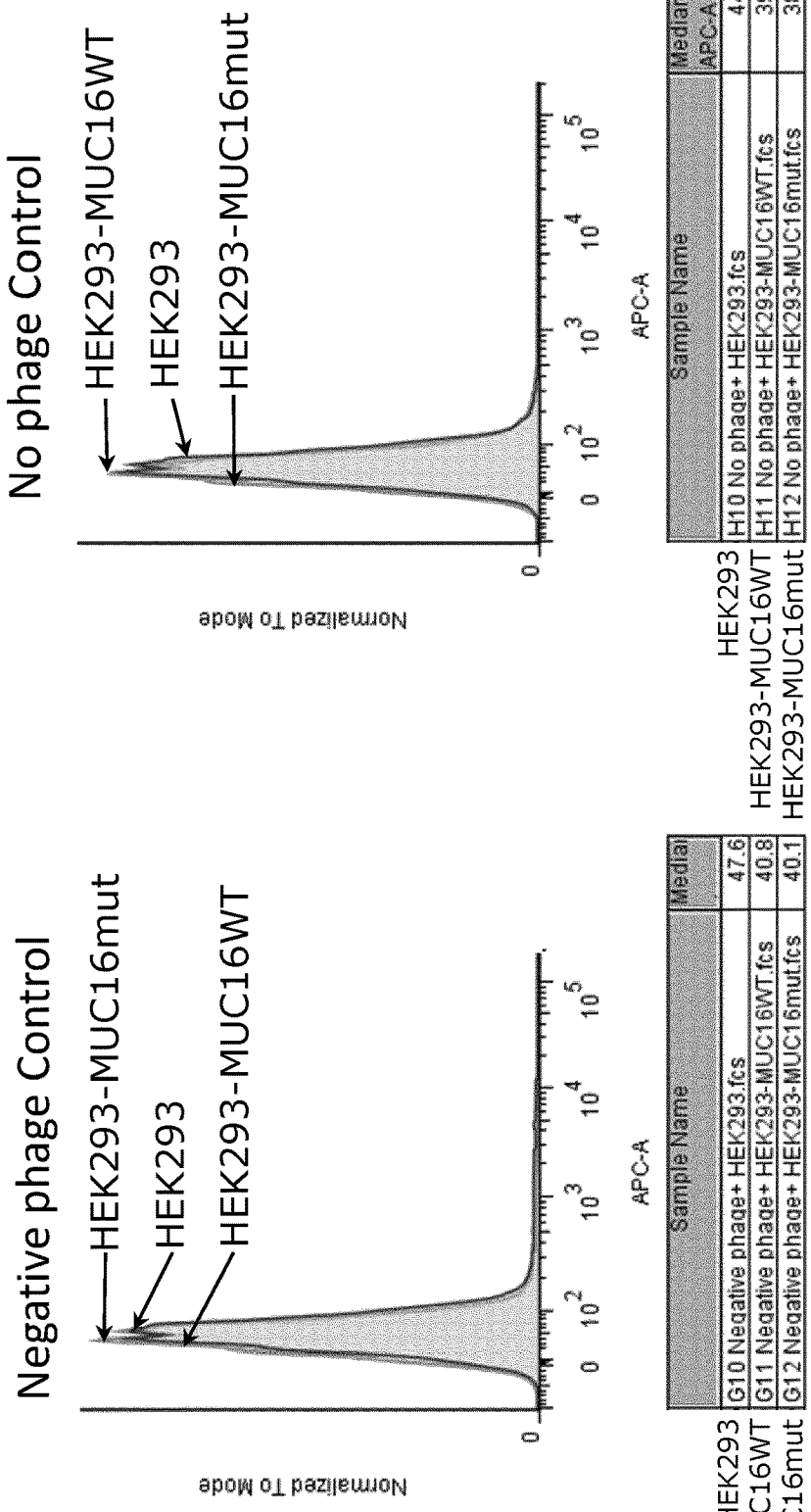
FIG. 4 illustrates results of a FACS analysis wild-type MUC16-C114 (HEK293-MUC16WT) or N30 mutant MUC16-C114 (HEK293-MUC16mut) cells incubated with a negative phage control and a no phage control for all three cell lines.
Figure 5:
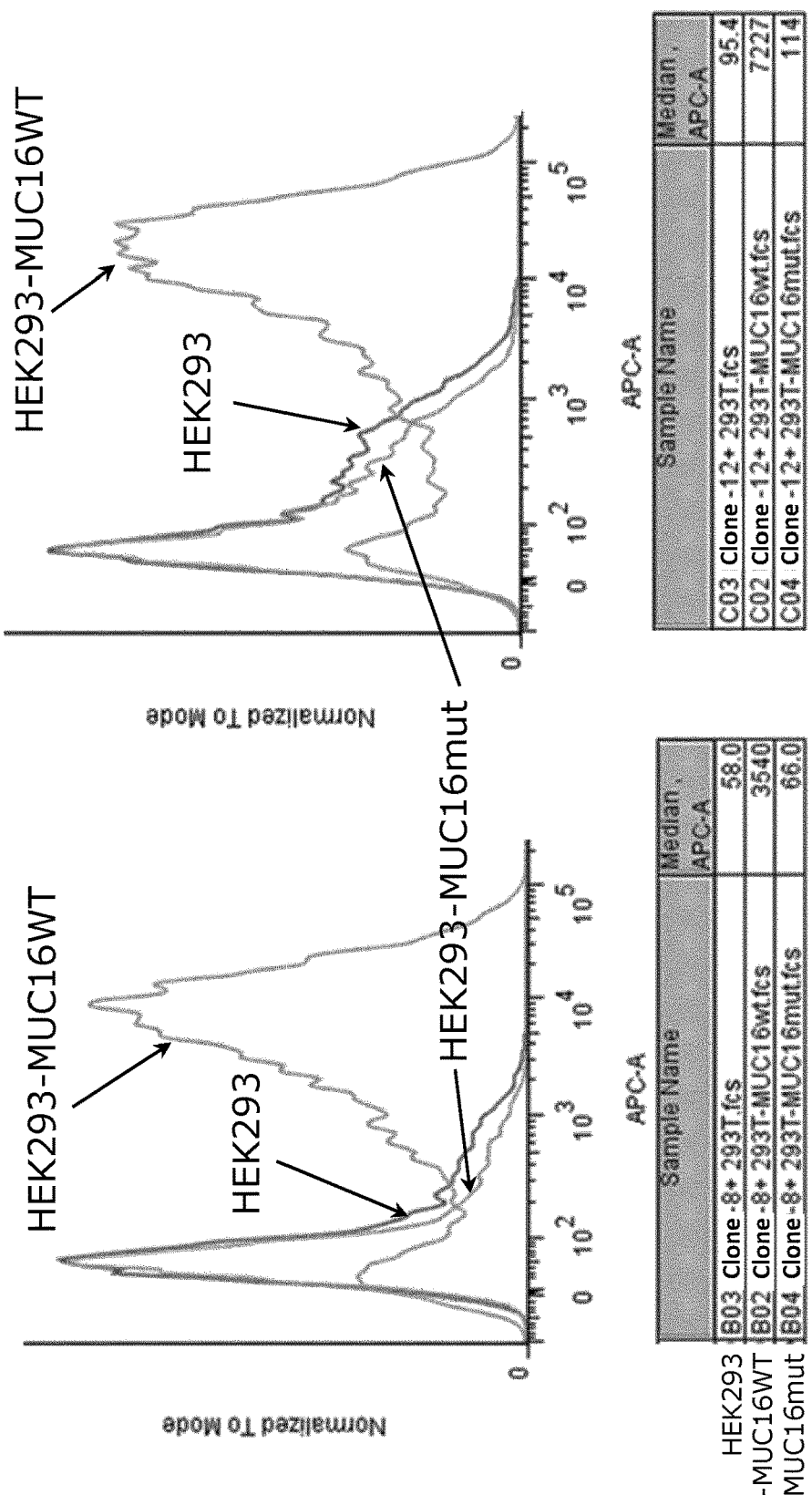
FIG. 5 illustrates exemplary results of a FACS analysis wild-type MUC16-C114 (HEK293-MUC16WT) or N30 mutant MUC16-C114 (HEK293-MUC16mut) cells incubated with two exemplary antibody phage clones, clone 8 and clone 12. Antibody clones that bound to wild-type MUC16-C114 and not N30 mutant MUC16-C114 were selected for sequencing and further development.

The 40 MUC16 specific clones were tested for their binding to HEK293-MUC16WT, HEK293-MUC16mut, and parental HEK293 cells. FIG. 4 shows the results of FACS analysis with a negative phage control and a no phage control for all three cell lines. FACS analysis with each of the 40 clones showed that all of the 40 clones showed binding towards HEK293-MUC16WT while 16 of the 40 clones showed minimum binding towards HEK293-MUC16mut. These clones were thus specific for the N-glycosylation site (N30). FIG. 5 shows the results for two exemplary clones, clone 8 and clone 12.

Figure 7:
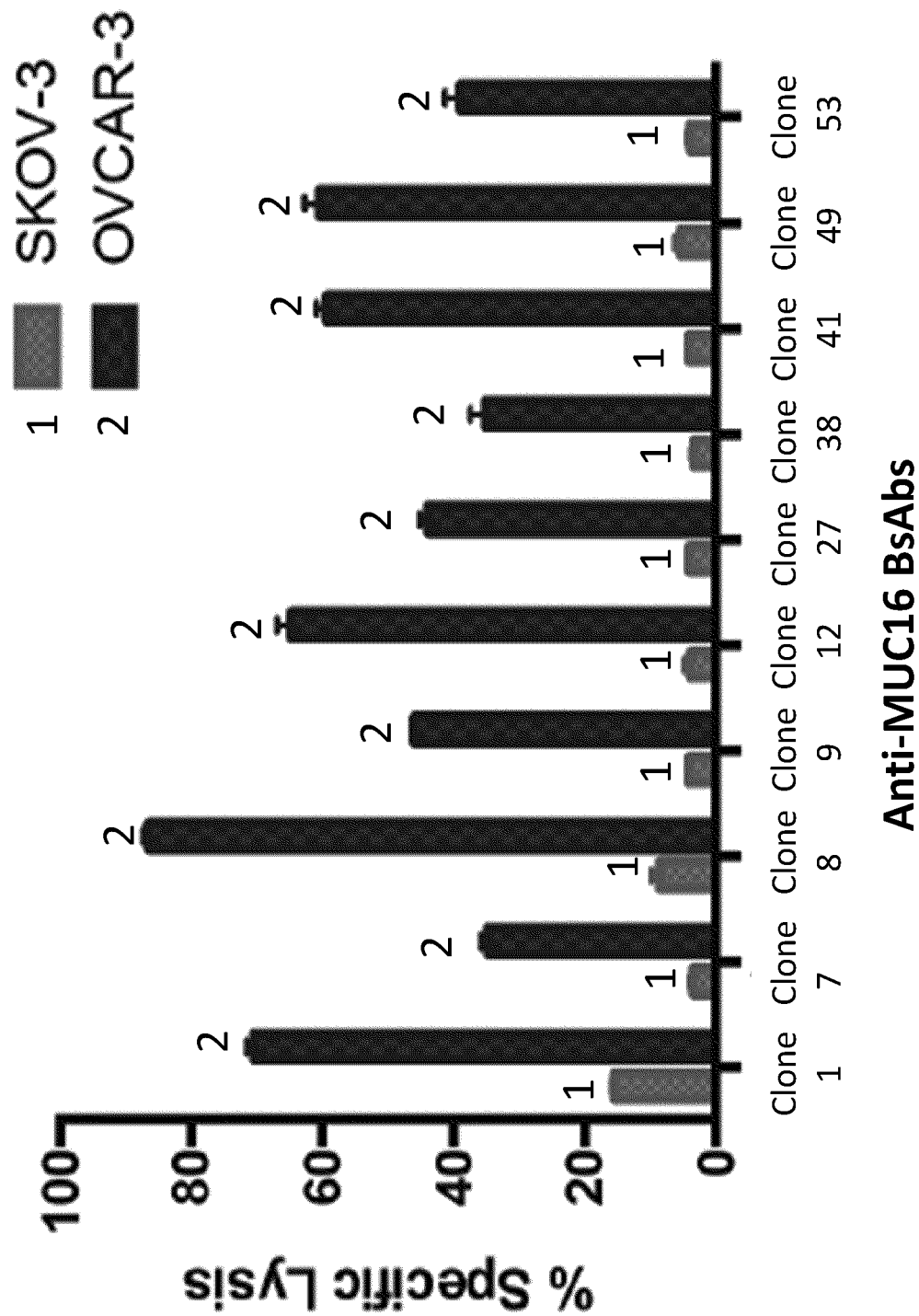
FIG. 7 illustrates exemplary results of a cell cytotoxicity assay using selected anti-MUC16 BsAbs, including anti-MUC16 clone 8 BsAb and anti-MUC16 clone 12 BsAb, incubated with a MUC16+ OVCAR3 cell line compared to a MUC16⁻ SKOV3 cell line. The clone 8 and clone 12 BsAbs were able to induce target specific cell lysis of a MUC16+ OVCAR3 cell line as compared to a MUC16⁻ SKOV3 cell line.
Figure 8:
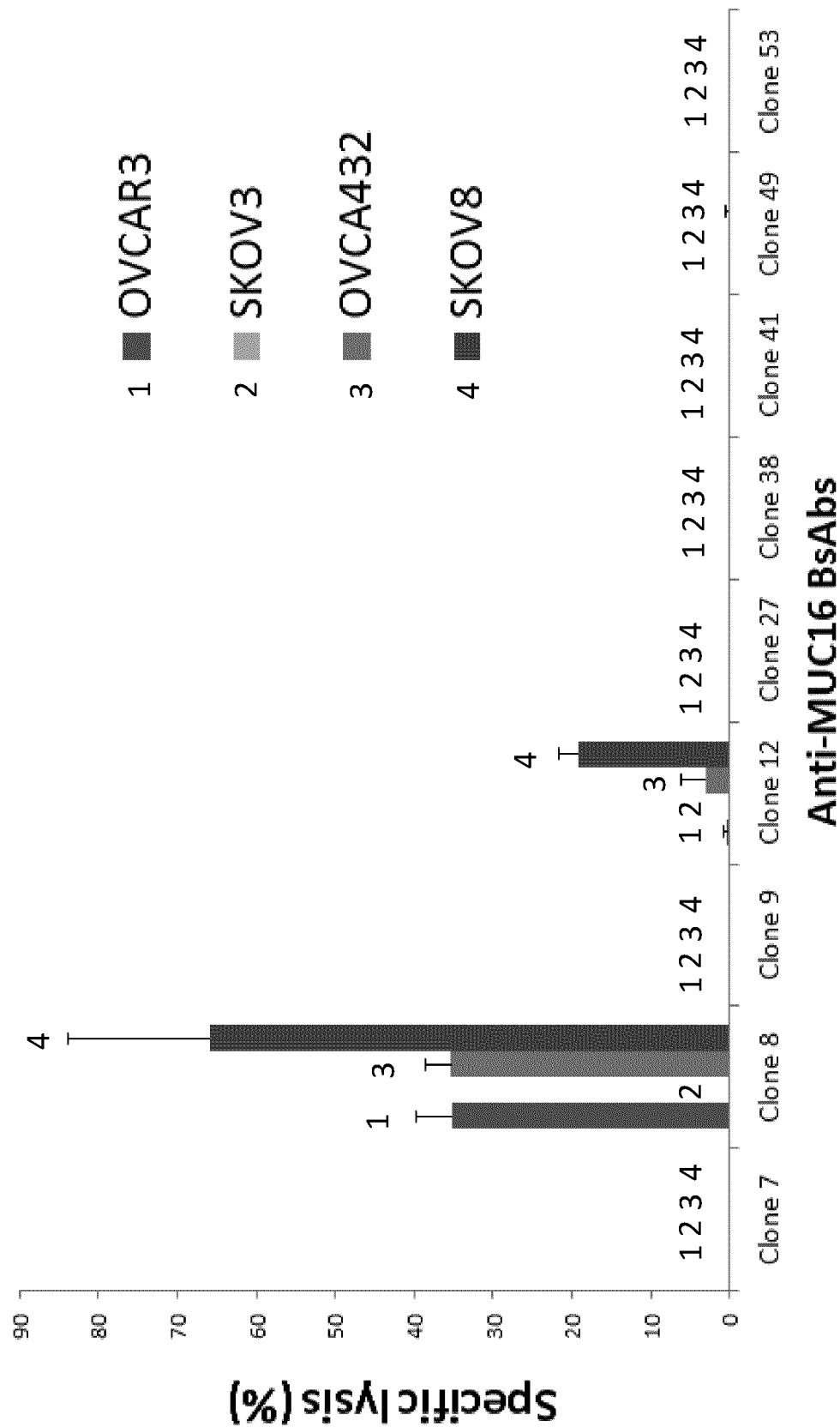
FIG. 8 illustrates exemplary results of a cell cytotoxicity assay using selected anti-MUC16 BsAbs, including anti-MUC16 clone 8 BsAb and anti-MUC16 clone 12 BsAb, incubated with a MUC16+ OVCAR3 cell line, a MUC16+ SKOV8 cell line, and a MUC16+ OVCA432 cell line compared to a MUC16− SKOV3 cell line. The anti-MUC16 clone 8 BsAb was able to induce target specific cell lysis of the MUC16+ OVCAR3, SKOV8, and OVCA432 cell lines. The anti-MUC16 clone 12 BsAb also induced cell lysis of the MUC16+, though to a lesser extent.

The top 9 clones among the 16 were then tested for binding to MUC16⁺ cancer cell lines OVCAR3, SKOV8, and OVCA432. Anti-MUC16 clones 8 and 12 bound most specifically to MUC16+ cancer cell lines but not to a MUC16⁻ cancer cell line SKOV3 (FIG. 8). Several other clones bound specifically to MUC16+ cancer cell lines as well, although at lower specificities (FIG. 7).

Example 2: Generation of Anti-MUC16 Bispecific Antibodies

The example describes the generation of anti-MUC16 bi-specific antibodies (BsAbs) from the anti-MUC16 scFvs identified in Example 1. In this example, a single-chain BsAb comprising anti-MUC16 scFv at the N-terminal end and an anti-human CD3ε scFv of a mouse monoclonal antibody at the C-terminal end was generated. An anti-MUC16 clone 8 BsAb and anti-MUC16 clone 12 BsAb were generated by cloning DNA fragments encoding the anti-MUC16 scFv and the anti-human CD3ε scFv antibody derived from parental clone L2K into an expression vector using standard DNA technology. A hexahistidine (His) tag (SEQ ID NO: 33) was inserted downstream of the anti-MUC16 BsAb at the C-terminal end for antibody purification and detection.

Chinese hamster ovary (CHO) cells were transfected with the anti-MUC16 BsAb expression vector and stable expression was achieved by standard drug selection with methionine sulfoximine (MSX), a glutamine synthetase (GS)-based method (Fan, et al., *Biotechnology Bioengineering*. 109 (4), 1007-1005 (2012)). CHO cell supernatants containing secreted anti-MUC16 BsAb molecules were collected. Anti-MUC16 BsAb was purified using HISTRAP™ HP column (GE healthcare) by FPLC AKTA system. Briefly, CHO cell culture was clarified and loaded onto the column with low imidazole concentration (20 mM), and then an isocratic high imidazole concentration elution buffer (500 mM) was used to elute the bound anti-MUC16 bi-specific antibody protein. The major bands for the clone 8 BsAb and clone 12 BsAb were observed around 50 kDa by SDS-PAGE, indicating that the BsAbs were successfully purified.

Example 3: Anti-MUC16 BsAb—MUC16+ Cell Specificity

Figure 6:
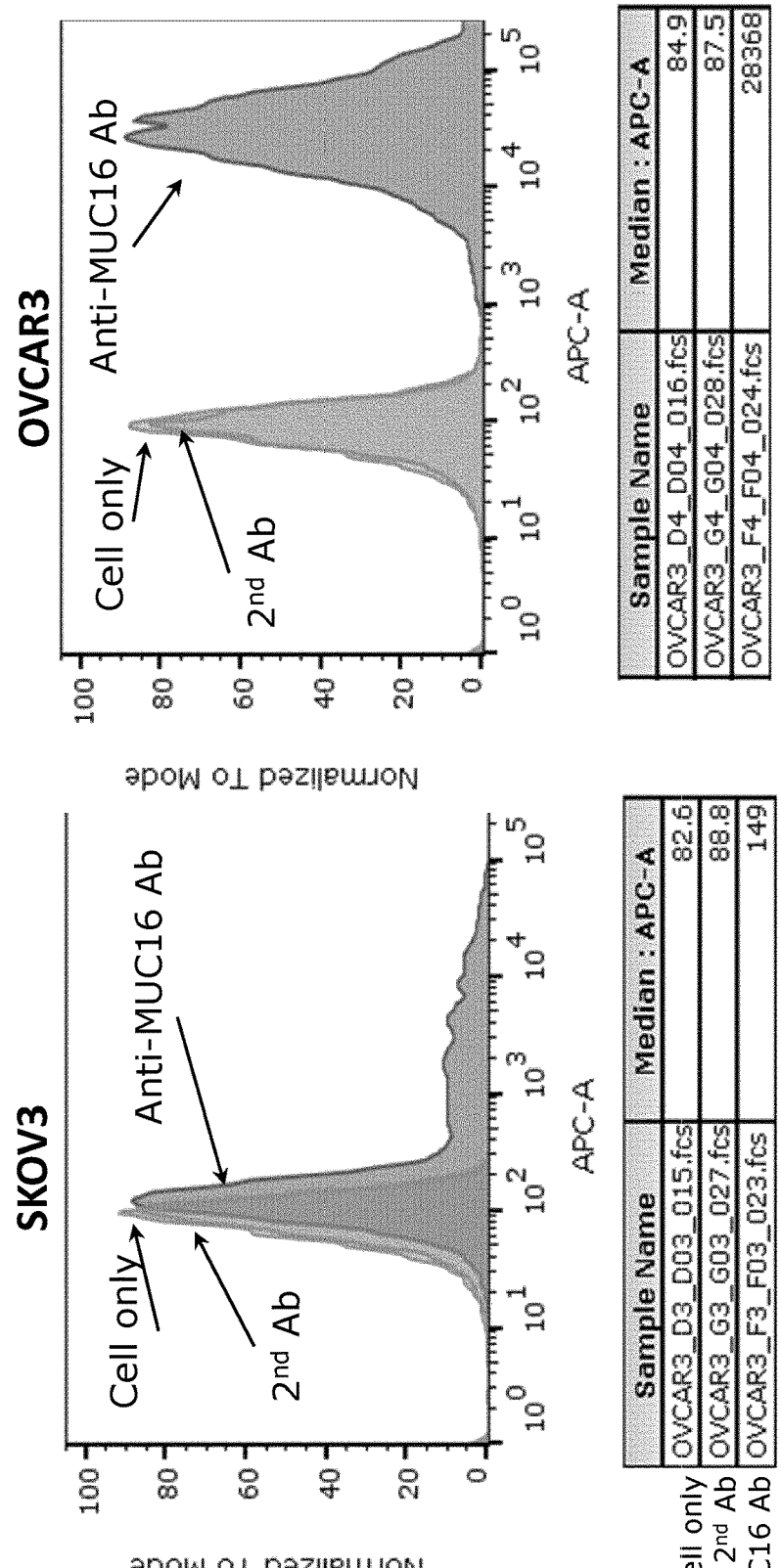
FIG. 6 illustrates the binding of the clone 8 bispecific antibody (BsAb), comprising the anti-MUC16 scFv at the N-terminal end and an anti-human CD3ε scFv of a mouse monoclonal antibody at the C-terminal end, to a MUC16+ OVCAR3 cell line, but not a control MUC16⁻ SKOV3 cell line.

In this example, the specificity of the anti-MUC16 BsAbs for binding to cancer cells that express MUC16 was assessed. In one study, two target cell lines were employed, a MUC16$^+$ OVCAR3 cell line and a MUC16$^-$ SKOV3 cell line. OVCAR3 and SKOV3 cell lines were obtained through the American Type Culture Collection (ATCC, Manassas, V$_H$.) and sustained in culture according to the ATCC literature. FACS analysis of anti-MUC16 antibody binding to the two target cell lines was performed to confirm that antibody binding was observed only with the MUC16+ OVCAR3 cell line. SKOV3 or OVCAR3 cell lines were incubated with the anti-MUC16 Ab followed by a secondary antibody or with a secondary antibody alone as a control. Data for the anti-MUC16 clone 8 BsAb is shown in FIG. 6. The MUC16+ OVCAR3 cell line showed about a 300×MFI increase in binding over the control cells while SKOV3 exhibited only a minimum signal.

Example 4: Anti-MUC16 BsAb—Directed Cell Cytotoxicity

In this example, the ability of the anti-MUC16 BsAbs to induce MUC16-specific cell toxicity was assessed. Anti-MUC16 clone 8 BsAb and anti-MUC16 clone 12 BsAb were incubated at a concentration of 0.2 µg/ml with either the MUC16$^+$ OVCAR3 target cell line or the MUC16$^-$ SKOV3 target cell line and human activated T cells at an effector: target (E:T) ratio of 5:1 for 16 hours. The cytotoxicity was measured by lactate dehydrogenase (LDH) release assay. As shown in FIG. 7, the clone 8 and clone 12 BsAbs were able to induce cell lysis of OVCAR3 cells at a level of about 90% and 65%, respectively, while cell lysis of SKOV3 was minimal, indicating that the MUC16$^+$ target specificity is required for the T cell activation. Thus, both clone 8 BsAb and clone 12 BsAb induced potent and specific killing of a MUC16$^+$ cancer cell line.

In a separate study, four target cell lines were employed, a MUC16$^+$ OVCAR3 cell line, a MUC16$^-$ SKOV3 cell line, a MUC16$^+$ SKOV8 cell line, and a MUC16$^+$ OVCA432 cell line. Anti-MUC16 clone 8 BsAb and anti-MUC16 clone 12 BsAb were incubated at a concentration of 0.2 µg/ml with a target cell line and human activated T cells at an effector: target (E:T) ratio of 3:1 for 16 hours. The cytotoxicity was measured by LDH release assay. Lower percentages of cell lysis for the MUC16+ cell lines were observed at the lower E:T ratio of 3:1 (FIG. 8), compared to the E:T ratio of 5:1. Cell lysis of MUC16$^-$ SKOV3 was minimal in this study as well, further support that the MUC16+ target specificity of the BsAb is required for the T cell activation.

Example 5: Therapy of Human MUC16$^+$ Metastatic Ovarian Cancer in NSG Mice

Figure 9A:
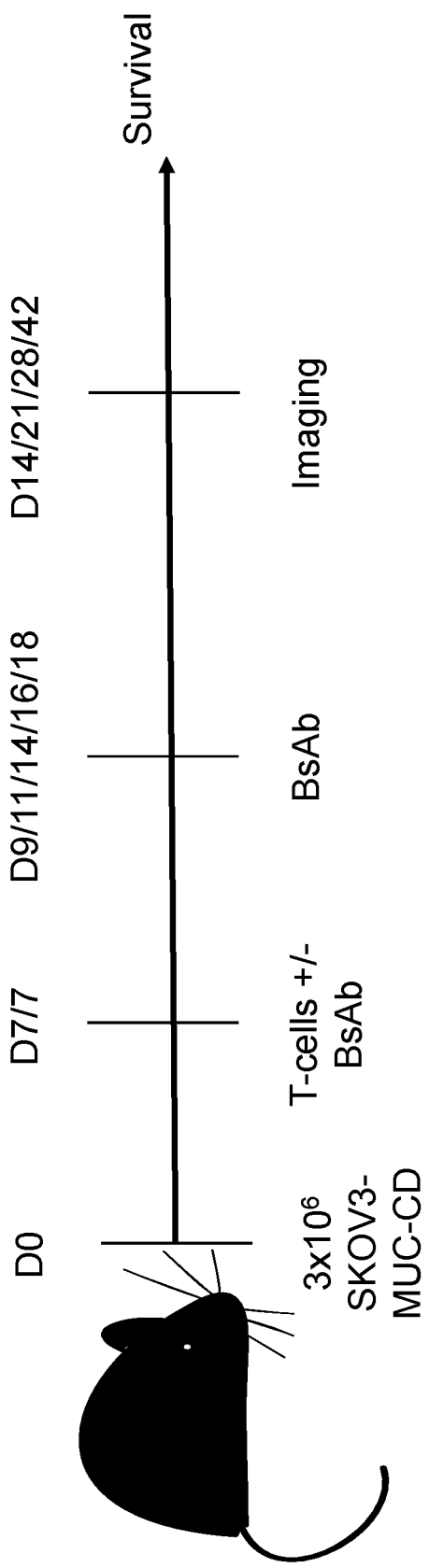
FIG. 9A illustrates an exemplary experimental schema of a ovarian xenograft study using injections of SKOV3-MUC-CD modified cells that express MUC16 to establish tumors and injections of the anti-MUC16 clone 8 BsAb for treatment.

In this example, the in vivo therapeutic efficacy of anti-MUC16 BsAb in a mouse xenograft model of metastatic ovarian cancer was assessed. Female NSG mice between 6-8 weeks old were injected on day 0 (D0) intraperitoneally (i.p.) with 3×10$^6$ SKOV3-MUC-CD tumor cells that are modified to express MUC16-C114 and GFP-LUC. These mice were then treated intravenously (i.v.) with 1×10$^7$ human T cells on day 7 (D7) and i.p with 5 µg of anti-MUC16 clone 8 BsAb. Additional treatments with 5 µg of the BsAb were administered i.p. on D9, D11, D14, D16, and D18 for a total of six BsAb treatments. Animals were imaged on D14, D21, D28, and D42. The experimental schema of the SKOV3-MUC-CD and BsAb injections is shown in FIG. 9A.

Figure 9B:
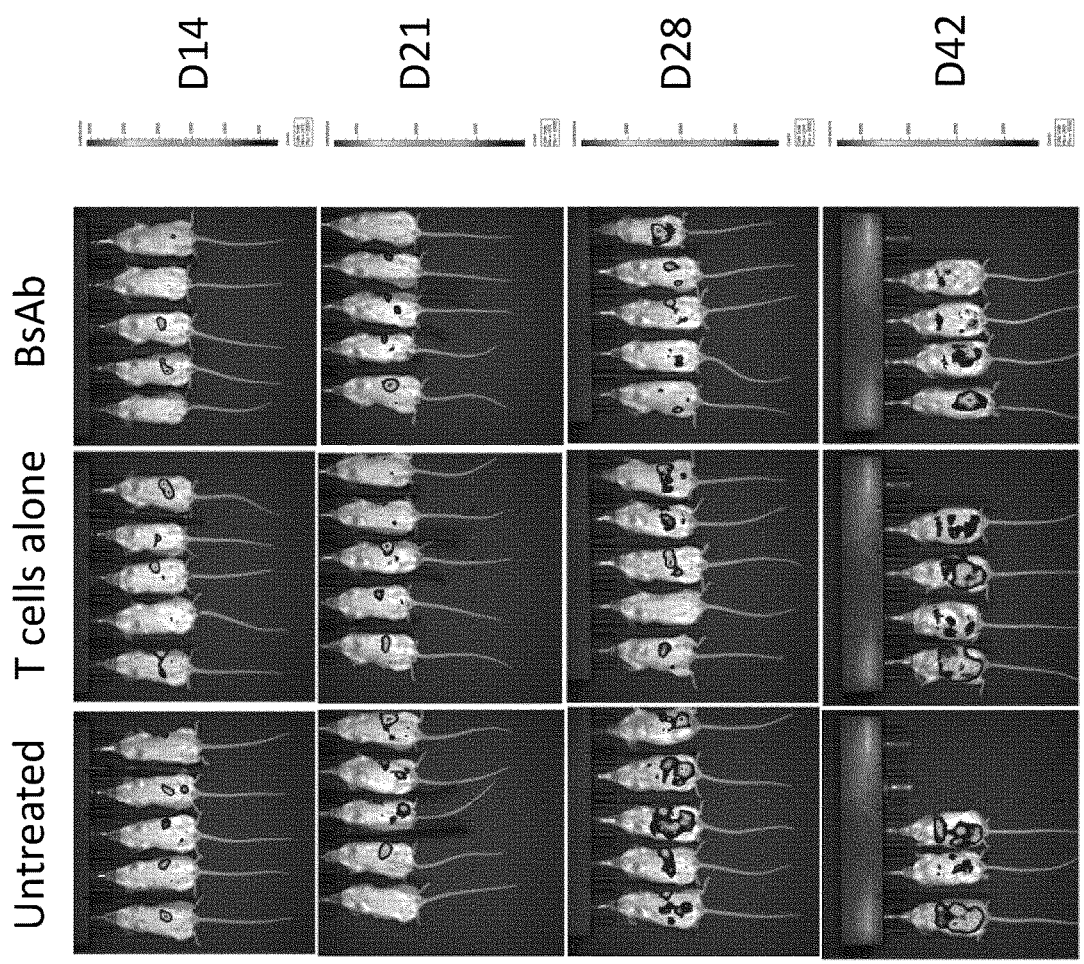
FIG. 9B illustrates exemplary visualization data show establishment and treatment of the tumors.
Figure 9C:
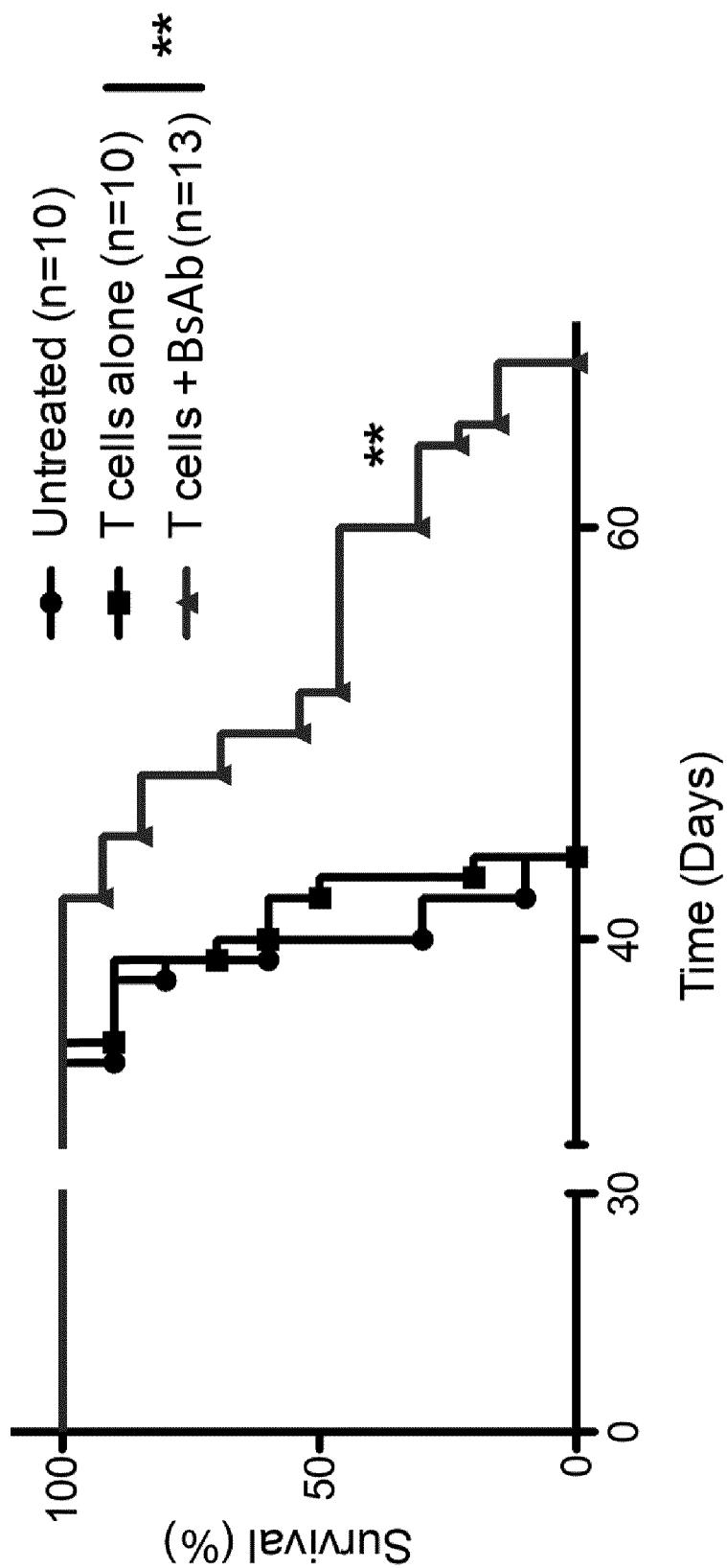
FIG. 9C illustrates exemplary survival curve data for the xenograft experiment.
Figure 9D:
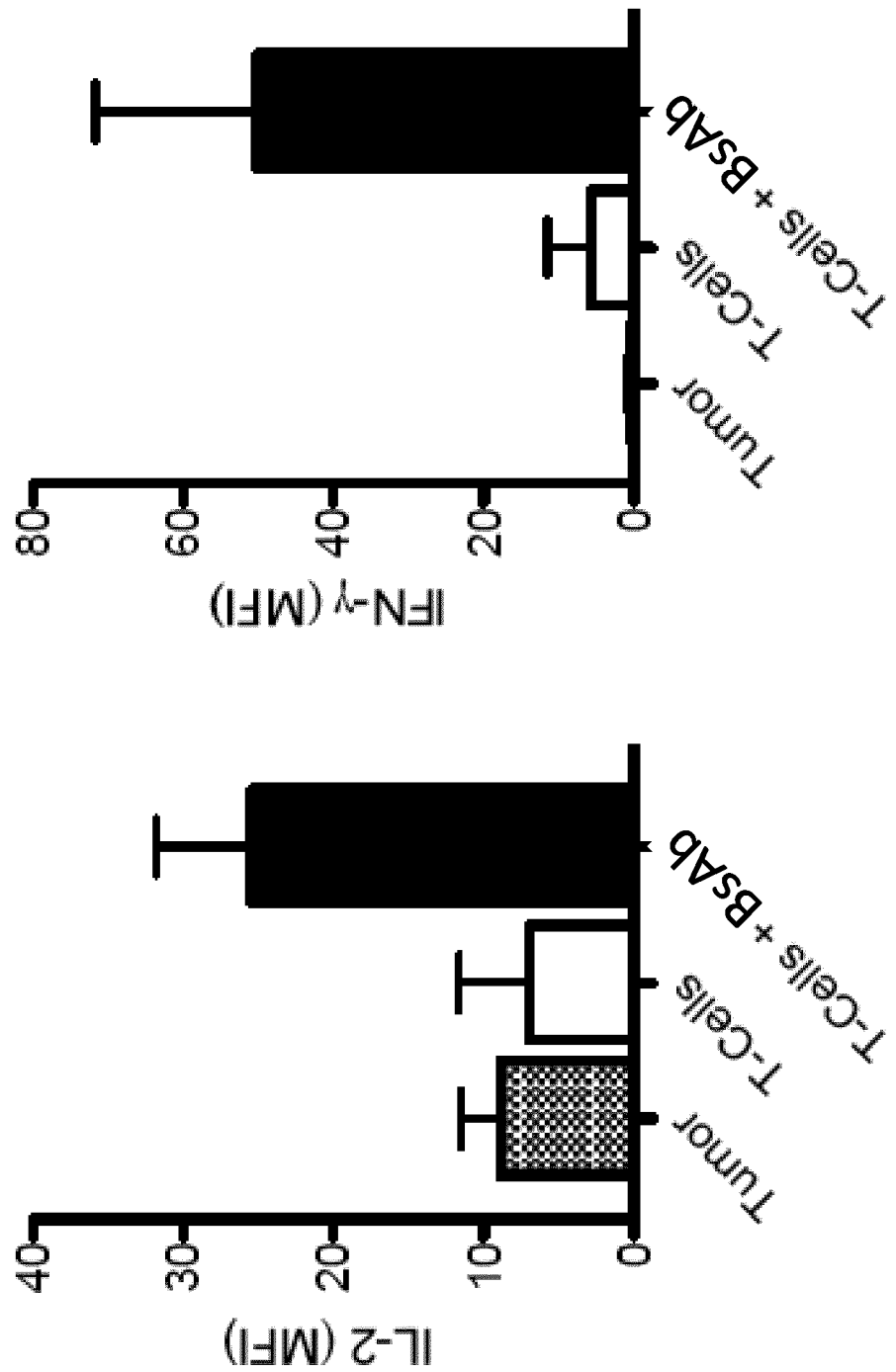
FIG. 9D illustrates exemplary data showing induction of cytokines IL-2 and IFN-γ following treatment of tumor bearing mice with anti-MUC16 clone 8 BsAb.

Animals treated with the anti-MUC16 clone 8 BsAb exhibited delayed disease progression compared to untreated mice or mice treated with T-cells alone (FIG. 9B). FIG. 9C shows the survival curves of the tumor-bearing mice. Treatment with the anti-MUC16 clone 8 BsAb significantly prolonged survival in tumor-bearing mice compared to T-cell therapy or no treatment. Tumor-bearing mice treated with T-cells and anti-MUC16 BsAbs also showed significantly elevated levels of systemic IL-2 and IFN-γ 7 days after treatment indicating an induction of an anti-tumor immune response (FIG. 9D). These results demonstrate that administration of anti-MUC16 BsAb delays disease progression and improves survival in a xenogeneic model of MUC16+ metastatic ovarian cancer.

Example 6: Generation of Full-Length Human IgG Anti-MUC16 Antibodies

Full-length human IgG1 of the selected phage clones are produced, for example, in HEK293 and CHO cell lines as described (Tomimatsu, K. et al., *Biosci. Biotechnol. Biochem.* 73(7):1465-1469, 2009). In brief, antibody variable regions from the phage clones are subcloned into mammalian expression vectors, with matching human lambda light chain constant region (SEQ ID NO: 31) and human IgG1 constant region (SEQ ID NO: 28) sequences (see Table 5). Molecular weight of the purified full-length IgG1 antibodies can be measured under both reducing and non-reducing conditions by electrophoresis. SDS-PAGE of purified IgG1 antibodies can be performed to determine protein purity.

TABLE 5

| Phage clone | HC Variable | HC Constant | LC Variable | LC Constant |
|---|---|---|---|---|
| 8 | SEQ ID NO: 2 | SEQ ID NO: 28 | SEQ ID NO: 3 | SEQ ID NO: 31 |
| 12 | SEQ ID NO: 10 | SEQ ID NO: 28 | SEQ ID NO: 11 | SEQ ID NO: 31 |

Example 7: Characterization of Full-Length Human IgG Anti-MUC16 Antibodies

Anti-MUC16 IgG antibodies are tested for binding to MUC16-expressing cells, such as HEK293-MUC16 wt cells or MUC16$^+$ cell lines such as OVCAR3, SKOV8 cell line, or OVCA432 cell line, by flow cytometry. Dose dependence of binding is tested. Briefly, MUC16-expressing cells are incubated with varying amounts of the anti-human MUC16 IgG antibodies, for example, at 10, 3.3, 1.1, 0.37, 0.12, 0.041, 0.014 or 0 µg/ml, on ice for 1 hour. The anti-MUC16 IgG antibodies are evaluated for their affinity towards the MUC16-expressing cells by EC50 of the dose dependence curve (MFI vs. antibody concentration). Furthermore, apparent $K_D$ is determined based on EC50 value. Binding affinity of the anti-MUC16 IgG antibodies can be determined, for example, by ForteBio.

Example 8: Characterization of Full-Length Human IgG Anti-MUC16 Antibodies

The ability of anti-MUC16 clone 8 and anti-MUC16 clone 12 to inhibit Matrigel invasion is evaluated. The anti-MUC16 monoclonal antibody 4H11 is used as a negative control Matrigel invasion assays are performed with SKOV3 ovarian cancer stable cell lines expressing phrGFP or phr-GFP-MUC16-C114 by incubating the cells in the presence or absence of 4H11, clone 8, or clone 12. Clone 8 and Clone 12 inhibit MUC16-C114-induced Matrigel invasion. In contrast, the monoclonal anti-MUC16 antibody 4H11 does not inhibit MUC16-C114-induced Matrigel invasion. These data demonstrate that, in contrast to the monoclonal antibody 4H11, clone 8 and clone 12 block MATRIGEL® invasion.

TABLE 6

Table of Sequences

| SEQ ID NO | Description | Sequence |
|---|---|---|
| 1 | hMUC16 (Immature) | MLKPSGLPGSSSPTRSLMTGSRSTKATPEMDSGLTGATLSPKTSTGA IVVTEHTLPFTSPDKTLASPTSSVVGRTTQSLGVMSSALPESTSRGM THSEQRTSPSLSPQVNGTPSRNYPATSMVSGLSSPRTRTSSTEGNFT KEASTYTLTVETTSGPVTEKYTVPTETSTTEGDSTETPWDTRYIPVK ITSPMKTFADSTASKENAPVSMTPAETTVTDSHTPGRTNPSFGTLYS SFLDLSPKGTPNSRGETSLELILSTTGYPFSSPEPGSAGHSRISTSAPL SSSASVLDNKISETSIFSGQSLTSPLSPGVPEARASTMPNSAIPFSMTL SNAETSAERVRSTISSLGTPSISTKQTAETILTFHAFAETMDIPSTHIA KTLASEWLGSPGTLGGTSTSALTTTSPSTTLVSEETNTHHSTSGKET EGTLNTSMTPLETSAPGEESEMTATLVPTLGFTTLDSKIRSPSQVSSS HPTRELRTTGSTSGRQSSSTAAHGSSDILRATTSSTSKASSWTSESTA QQFSEPQHTQWVETSPSMKTERPPASTSVAAPITTSVPSVVSGFTTL KTSSSTKGIWLEETSADTLIGESTAGPTTHQFAVPTGISMTGGSSTRG SQGTTHLLTRATASSETSADLTLATNGVPVSVSPAVSKTAAGSSPPG GTKPSYTMVSSVIPETSSLQSSAFREGTSLGLTPLNTRHPFSSPEPDS AGHTKISTSIPLLSSASVLEDKVSATSTFSHHKATSSITTGTPEISTKT KPSSAVLSSMTLSNAATSPERVRNATSPLTHPSPSGEETAGSVLTLS TSAETTDSPNIHPTGTLTSESSESPSTLSLPSVSGVKTTFSSSTPSTHLF TSGEETEETSNPSVSQPETSVSRVRTTLASTSVPTPVFPTMDTWPTR SAQFSSSHLVSELRATSSTSVINSTGSALPKISHLTGTATMSQTNRD TFNDSAAPQSTTWPETSPRFKTGLPSATTTVSTSATSLSATVMVSKF TSPATSSMEATSIREPSTTILTTETTNGPGSMAVASTNIPIGKYITEG RLDTSHLPIGTTASSETSMDFTMAKESVSMSVSPSQSMDAAGSSTP GRTSQFVDTFSDDVYHLTSREITIPRDGTSSALTPQMTATHPPSPDP GSARSTWLGILSSSPSSPTPKVTMSSTFSTQRVTTSMIMDTVETSRW NMPNLPSTTSLTPSNIPTSGAIGKSTLVPLDTPSPATSLEASEGGLPTL STYPESTNTPSIHLGAHASSESPSTIKLTMASVVKPGSYTPLTFPSIET HIHVSTARMAYSSGSSPEMTAPGETNTGSTWDPTTYITTTDPKDTSS AQVSTPHSVRTLRTTENHPKTESATPAAYSGSPKISSSPNLTSPATK AWTITDTTEHSTQLHYTKLAEKSSGFETQSAPGPVSVVIPTSPTIGSS TLELTSDVPGEPLVLAPSEQTTITLPMATWLSTSLTEEMASTDLDISS PSSPMSTFAIFPPMSTPSHELSKSEADTSAIRNTDSTTLDQHLGIRSLG RTGDLTTVPITPLTTTWTSVIEHSTQAQDTLSATMSPTHVTQSLKDQ TSIPASASPSHLTEVYPELGTQGRSSSEATTFWKPSTDTLSREIETGP TNIQSTPPMDNTTTGSSSSGVTLGIAHLPIGTSSPAETSTNMALERRS STATVSMAGTMGLLVTSAPGRSISQSLGRVSSVLSESTTEGVTDSSK GSSPRLNTQGNTALSSSLEPSYAEGSQMSTSIPLTSSPTTPDVEFIGGS TFWTKEVTTVMTSDISKSSARTESSSATLMSTALGSTENTGKEKLR TASMDLPSPTPSMEVTPWISLTLSNAPNTTDSLDLSHGVHTSSAGTL ATDRSLNTGVTRASRLENGSDTSSKSLSMGNSTHTSMTYTEKSEVS SSIHPRPETSAPGAETTLTSTPGNRAISLTLPFSSIPVEEVISTGITSGPD INSAPMTHSPITPPTIVWTSTGTIEQSTQPLHAVSSEKVSVQTQSTPY VNSVAVSASPTHENSVSSGSSTSSPYSSASLESLDSTISRRNAITSWL WDLTTSLPTTTWPSTSLSEALSSGHSGVSNPSSTTTEFPLFSAASTSA AKQRNPETETHGPQNTAASTLNTDASSVTGLSETPVGASISSEVPLP MAITSRSDVSGLTSESTANPSLGTASSSAGTKLTRTISLPTSESLVSFR MNKDPWTVSIPLGSHPTTNTETSIPVNSAGPPGLSTVASDVIDTPSD GAESIPTVSFSPSPDTEVTTISHFPEKTTHSFRTISSLTHELTSRVTPIP GDWMSSAMSTKPTGASPSITLGERRTITSAAPTTSPIVLTASFTETST VSLDNETTVKTSDILDARKTNELPSDSSSSSDLINTSIASSTMDVTKT ASISPTSISGMTASSSPSLFSSDRPQVPTSTTETNTATSPSVSSNTYSL DGGSNVGGTPSTLPPFTITHPVETSSALLAWSRPVRTFSTMVSTDTA SGENPTSSNSVVTSVPAPGTWTSVGSTTDLPAMGFLKTSPAGEAHS LLASTIEPATAFTPHLSAAVVTGSSATSEASLLTTSESKAIHSSPQTPT TPTSGANWETSATPESLLVVTETSDTTLTSKILVTDTILFSTVSTPPS KFPSTGTLSGASFPTLLPDTPAIPLTATEPTSSLATSFDSTPLVTIASDS LGTVPETTLTMSETSNGDALVLKTVSNPDRSIPGITIQGVTESPLHPS STSPSKIVAPRNTTYEGSITVALSTLPAGTTGSLVFSQSSENSETTAL VDSSAGLERASVMPLTTGSQGMASSGGIRSGSTHSTGTKTFSSLPLT MNPGEVTAMSEITTNRLTATQSTAPKGIPVKPTSAESGLLTPVSASS SPSKAFASLTTAPPTWGIPQSTLTFEFSEVPSLDTKSASLPTPGQSLN TIPDSDASTASSSLSKSPEKNPRARMMTSTKAISASSFQSTGFTETPE GSASPSMAGHEPRVPTSGTGDPRYASESMSYPDPSKASSAMTSTSL ASKLTTLFSTGQAARSGSSSSPISLSTEKETSFLSPTASTSRKTSLFLG PSMARQPNILVHLQTSALTLSPTTSTLNMSQEEPPELTSSQTIAEEEGT TAETQTLTFTPSETPTSLLPVSSPTEPTARRKSSPETWASSISVPAKTS |

TABLE 6-continued

Table of Sequences

| SEQ ID NO | Description | Sequence |
|---|---|---|
| | | LVETTDGTLVTTIKMSSQAAQGNSTWPAPAEETGSSPAGTSPGSPE
MSTTLKIMSSKEPSISPEIRSTVRNSPWKTPETTVPMETTVEPVTLQS
TALGSGSTSISHLPTGTTSPTKSPTENMLATERVSLSPSPPEAWTNLY
SGTPGGTRQSLATMSSVSLESPTARSITGTGQQSSPELVSKTTGMEF
SMWHGSTGGTTGDTHVSLSTSSNILEDPVTSPNSVSSLTDKSKHKT
ETWVSTTAIPSTVLNNKIMAAEQQTSRSVDEAYSSTSSWSDQTSGS
DITLGASPDVTNTLYITSTAQTTSLVSLPSGDQGITSLTNPSGGKTSS
ASSVTSPSIGLETLRANVSAVKSDIAPTAGHLSQTSSPAEVSILDVTT
APTPGISTTITTMGTNSISTTTPNPEVGMSTMDSTPATERRTTSTEHP
STWSSTAASDSWTVTDMTSNLKVARSPGTISTMHTTSFLASSTELD
SMSTPHGRITVIGTSLVTPSSDASAVKTETSTSERTLSPSDTTASTPIS
TFSRVQRMSISVPDILSTSWTPSSTEAEDVPVSMVSTDHASTKTDPN
TPLSTFLFDSLSTLDWDTGRSLSSATATTSAPQGATTPQELTLETMIS
PATSQLPFSIGHITSAVTPAAMARSSGVTFSRPDPTSKKAEQTSQLP
TTTSAHPGQVPRSAATTLDVIPHTAKTPDATFQRQGQTALTTEARA
TSDSWNEKEKSTPSAPWITEMMNSVSEDTIKEVTSSSSVLRTLNTLD
INLESGTTSSPSWKSSPYERIAPSESTTDKEAIHPSTNTVETTGWVTS
SEHASHSTIPAHSASSKLTSPVVTTSTREQAIVSMSTTTWPESTRART
EPNSFLTIELRDVSPYMDTSSTTQTSIISSPGSTAITKGPRTEITSSKRIS
SSFLAQSMRSSDSPSEAITRLSNFPAMTESGGMILAMQTSPPGATSL
SAPTLDTSATASWTGTPLATTQRFTYSEKTTLFSKGPEDTSQPSPPS
VEETSSSSSLVPIHATTSPSNILLTSQGHSPSSTPPVTSVFLSETSGLG
KTTDMSRISLEPGTSLPPNLSSTAGEALSTYEASRDTKAIHHSADTA
VTNMEATSSEYSPIPGHTKPSKATSPLVTSHIMGDITSSTSVFGSSET
TEIETVSSVNQGLQERSTSQVASSATETSTVITHVSSGDATTHVTKT
QATFSSGTSISSPHQFITSTNTFTDVSTNPSTSLIMTESSGVTITTQTGP
TGAATQGPYLLDTSTMPYLTETPLAVTPDFMQSEKTTLISKGPKDV
SWTSPPSVAETSYPSSLTPFLVTTIPPATSTLQGQHTSSPVSATSVLTS
GLVKTTDMLNTSMEPVTNSPQNLNNPSNEILATLAATTDIETIHPSI
NKAVTNMGTASSAHVLHSTLPVSSEPSTATSPMVPASSMGDALASI
SIPGSETTDIEGEPTSSLTAGRKENSTLQEMNSTTESNIILSNVSVGAI
TEATKMEVPSFDATFIPTPAQSTKFPDIFSVASSRLSNSPPMTISTHM
TTTQTGSSGATSKIPLALDTSTLETSAGTPSVVTEGFAHSKITTAMN
NDVKDVSQTNPPFQDEASSPSSQAPVLVTTLPSSVAFTPQWHSTSSP
VSMSSVLTSSLVKTAGKVDTSLETVTSSPQSMSNTLDDISVTSAATT
DIETTHPSINTVVTNVGTTGSAFESHSTVSAYPEPSKVTSPNVTTST
MEDTTISRSIPKSSKTTRTETETTSSLTPKLRETSISQEITSSTETSVP
YKELTGATTEVSRTDVTSSSSTSFPGPDQSTVSLDISTETNTRLSTSPI
MTESAEITITTQTGPHGATSQDTFTMDPSNTTPQAGIHSAMTHGFSQ
LDVTTLMSRIPQDVSWTSPPSVDKTSSPSSFLSSPAMTTPSLISSTLPE
DKLSSPMTSLLTSGLVKITDILRTRLEPVTSSLPNFSSTSDKILATSKD
SKDTKEIFPSINTEETNVKANNSGHESHSPALADSETPKATTQMVIT
TTVGDPAPSTSMPVHGSSETTNIKREPTYFLTPRLRETSTSQESSFPT
DTSFLLSKVPTGTITEVSSTGVNSSSKISTPDHDKSTVPPDTFTGEIPR
VFTSSIKTKSAEMTITTQASPPESASHSTLPLDTSTTLSQGGTHSTVT
QGFPYSEVTTLMGMGPGNVSWMTTPPVEETSSVSSLMSSPAMTSPS
PVSSTSPQSIPSSPLPVTALPTSVLVTTTDVLGTTSPESVTSSPPNLSSI
THERPATYKDTAHTEAAMHHSTNTAVTNVGTSGSGHKSQSSVLAD
SETSKATPLMSTTSTLGDTSVSTSTPNISQTNQIQTEPTASLSPRLRES
STSEKTSSTTETNTAFSYVPTGAITQASRTEISSSRTSISDLDRPTIAPD
ISTGMITRLFTSPIMTKSAEMTVTTQTTTPGATSQGILPWDTSTTLFQ
GGTHSTVSQGFPHSEITTLRSRTPGDVSWMTTPPVEETSSGFSLMSP
SMTSPSPVSSTSPESIPSSPLPVTALLTSVLVTTTNVLGTTSPEPVTSS
PPNLSSPTQERLTTYKDTAHTEAMHASMHTNTAVANVGTSISGHES
QSSVPADSHTSKATSPMGITFAMGDTSVSTSTPAFFETRIQTESTSSL
IPGLRDTRTSEEINTVTETSTVLSEVPTTTTTEVSRTEVITSSRTTISGP
DHSKMSPYISTETITRLSTFPFVTGSTEMAITNQTGPIGTISQATLTLD
TSSTASWEGTHSPVTQRFPHSEETTTMSRSTKGVSWQSPPSVEETSS
PSSPVPLPAITSHSSLYSAVSGSSPTSALPVTSLLTSGRRKTIDMLDT
HSELVTSSLPSASSFSGEILTSEASTNTETIHFSENTAETNMGTTNSM
HKLHSSVSIHSQPSGHTPPKVTGSMMEDAIVSTSTPGSPETKNVDRD
STSPLTPELKEDSTALVMNSTTESNTVFSSVSLDAATEVSRAEVTYY
DPTFMPASAQSTKSPDISPEASSSHSNSPPLTISTHKTIATQTGPSGVT
SLGQLTLDTSTIATSAGTPSARTQDFVDSETTSVMNNDLNDVLKTS
PFSAEEANSLSSQAPLLVTTSPSPVTSTLQEHSTSSLVSVTSVPTPTL
AKITDMDTNLEPVTRSPQNLRNTLATSEATTDTHTMHPSINTAVAN
VGTTSSPNEFYFTVSPDSDPYKATSAVVITSTSGDSIVSTSMPRSSAM
KKIESETTFSLIFRLRETSTSQKIGSSSDTSTVFDKAFTAATTEVSRTE
LTSSSRTSIQGTEKPTMSPDTSTRSVTMLSTFAGLTKSEERTIATQTG
PHRATSQGTLTWDTSITTSQAGTHSAMTHGFSQLDLSTLTSRVPEYI
SGTSPPSVEKTSSSSSLLLSLPAITSPSPVPTTLPESRPSSPVHLTSLPTS
GLVKTTDMLASVASLPPNLGSTSHKIPTTSEDIKDTEKMYPSTNIAV
TNVGTTTSEKESYSSVPAYSEPPKVTSPMVTSFNIRDTIVSTSMPGSS
EITRIEMESTFSLAHGLKGTSTSQDPIVSTEKSAVLHKLTTGATETSR |

TABLE 6-continued

Table of Sequences

| SEQ ID NO | Description | Sequence |
|---|---|---|
| | | TEVASSRRTSIPGPDHSTESPDISTEVIPSLPISLGITESSNMTIITRTGP
PLGSTSQGTFTLDTPTTSSRAGTHSMATQEFPHSEMTTVMNKDPEIL
SWTIPPSIEKTSFSSSLMPSPAMTSPPVSSTLPKTIHTTPSPMTSLLTPS
LVMTTDTLGTSPEPTTSSPPNLSSTSHEILTTDEDTTAIEAMHPSTST
AATNVETTSSGHGSQSSVLADSEKTKATAPMDTTSTMGHTTVSTS
MSVSSETTKIKRESTYSLTPGLRETSISQNASFSTDTSIVLSEVPTGTT
AEVSRTEVTSSGRTSIPGPSQSTVLPEISTRTMTRLFASPTMTESAEM
TIPTQTGPSGSTSQDTLTLDTSTTKSQAKTHSTLTQRFPHSEMTTLM
SRGPGDMSWQSSPSLENPSSLPSLLSLPATTSPPPISSTLPVTISSSPLP
VTSLLTSSPVTTTDMLHTSPELVTSSPPKLSHTSDERLTTGKDTTNT
EAVHPSTNTAASNVEIPSSGHESPSSALADSETSKATSPMFITSTQED
TTVAISTPHFLETSRIQKESISSLSPKLRETGSSVETSSAIETSAVLSEV
SIGATTEISRTEVTSSSRTSISGSAESTMLPEISTTRKIIKFPTSPILAESS
EMTIKTQTSPPGSTSESTFTLDTSTTPSLVITHSTMTQRLPHSEITTLV
SRGAGDVPRPSSLPVEETSPPSSQLSLSAMISPSPVSSTLPASSHSSSA
SVTSLLTPGQVKTTEVLDASAEPETSSPPSLSSTSVEILATSEVTTDT
EKIHPFSNTAVTKVGTSSSGHESPSSVLPDSETTKATSAMGTISIMGD
TSVSTLTPALSNTRKIQSEPASSLTTRLRETSTSEETSLATEANTVLS
KVSTGATTEVSRTEAISFSRTSMSGPEQSTMSQDISIGTIPRISASSVL
TESAKMTITTQTGPSESTLESTLNLNTATTPSWVETHSIVIQGFPHPE
MTTSMGRGPGGVSWPSPPFVKETSPPSSPLSLPAVTSPHPVSTTFLA
HIPPSPLPVTSLLTSGPATTTDILGTSTEPGTSSSSSLSTTSHERLTTYK
DTAHTEAVHPSTNTGGTNVATTSSGYKSQSSVLADSSPMCTTSTM
GDTSVLTSTPAFLETRRIQTELASSLTPGLRESSGSEGTSSGTKMSTV
LSKVPTGATTEISKEDVTSIPGPAQSTISPDISTRTVSWFSTSPVMTES
AEITMNTHTSPLGATTQGTSTLDTSSTTSLTMTHSTISQGFSHSQMS
TLMRRGPEDVSWMSPPLLEKTRPSFSLMSSPATTSPSPVSSTLPESIS
SSPLPVTSLLTSGLAKTTDMLHKSSEPVTNSPANLSSTSVEILATSEV
TTDTEKTHPSSNRTVTDVGTSSSGHESTSFVLADSQTSKVTSPMVIT
STMEDTSVSTSTPGFFETSRIQTEPTSSLTLGLRKTSSSEGTSLATEM
STVLSGVPTGATAEVSRTEVTSSSRTSISGFAQLTVSPETSTETITRLP
TSSIMTESAEMMIKTQTDPPGSTPESTHTVDISTTPNWVETHSTVTQ
RFSHSEMTTLVSRSPGDMLWPSQSSVEETSSASSLLLSLPATTSPSPVS
STLVEDFPSASLPVTSLLNPGLVITTDRMGISREPGTSSTSNLSSTSHE
RLTTLEDTVDTEDMQPSTHTAVTNVRTSISGHESQSSVLSDSETPKA
TSPMGTTYTMGETSVSISTSDFFETSRIQIEPTSSLTSGLRETSSSERIS
SATEGSTVLSEVPSGATTEVSRTEVISSRGTSMSGPDQFTISPDISTEA
ITRLSTSPIMTESAESAITIETGSPGATSEGTLTLDTSTTTFWSGTHST
ASPGFSHSEMTTLMSRTPGDVPWPSLPSVEEASSVSSSLSSPAMTST
SFFSTLPESISSSPHPVTALLTLGPVKTTDMLRTSSEPETSSPPNLSSTS
AEILATSEVTKDREKIHPSSNTPVVNVGTVIYKHLSPSSVLADLVTT
KPTSPMATTSTLGNTSVSTSTPAFPETMMTQPTSSLTSGLREISTSQE
TSSSATERSASLSGMPTGATTKVSRTEALSLGRTSTPGPAQSTISPEIS
TETITRISTPLTTTGSAEMTITPKTGHSGASSQGTFTLDTSSSRASWPG
THSAATHRSPHSGMTTPMSRGPEDVSWPSRPSVEKTSPPSSLVSLSA
VTSPSPLYSTPSESSHSSPLRVTSLFTPVMMKTTDMLDTSLEPVTTSP
PSMNITSDESLATSKATMETEAIQLSENTAVTQMGTISARQEFYSSY
PGLPEPSKVTSPVVTSSTIKDIVSTTIPASSEITRIEMESTSTLTPTPRET
STSQEIHSATKPSTVPYKALTSATIEDSMTQVMSSSRGPSPDQSTMS
QDISTEVITRLSTSPIKTESTEMTITTQTGSPGATSRGTLTLDTSTTFM
SGTHSTASQGFSHSQMTALMSRTPGDVPWLSHPSVEEASSASFSLSS
PVMTSSSPVSSTLPDSIHSSSLPVTSLLTSGLVKTTELLGTSSEPETSS
PPNLSSTSAEILAITEVTTDTEKLEMTNVVTSGYTHESPSSVLADSVT
TKATSSMGITYPTGDTNVLTSTPAFSDTSRIQTKSKLSLTPGLMETSI
SEETSSATEKSTVLSSVPTGATTEVSRTEAISSSRTSIPGPAQSTMSSD
TSMETITRISTPLTRKESTDMAITPKTGPSGATSQGTFTLDSSSTASW
PGTHSATTQRFPQSVVTTPMSRGPEDVSWPSPLSVEKNSPPSLVSS
SSVTSPSPLYSTPSGSSHSSPVPVTSLFTSIMMKATDMLDASLEPETT
SAPNMNITSDESLAASKATTETEAIHVFENTAASHVETTSATEELYS
SSPGFSEPTKVISPVVTSSSIRDNMVSTTMPGSSGITRIEIESMSSLTPG
LRETRTSQDITSSSTETSTVLYKMPSGATPEVSRTEVMPSSRTSIPGPA
QSTMSLDISDEVVTRLSTSPIMTESAEITITTQTGYSLATSQVTLPLG
TSMTFLSGTHSTMSQGLSHSEMTNLMSRGPESLSWTSPRFVETTRS
SSSLTSLPLTTSLSPVSSTLLDSSPSSPLPVTSLILPGLVKTTEVLDTSS
EPKTSSSPNLSSTSVEIPATSEIMTDTEKIHPSSNTAVAKVRTSSSVHE
SHSSVLADSETTITIPSMGITSAVDDTTVFTSNPAFSETRRIPTEPTFSL
TPGFRETSTSEETTSITETSAVLYGVPTSATTEVSMTEIMSSNRIHIPD
SDQSTMSPDIITEVITRLSSSMMSESTQMTITTQKSSPGATAQSTLT
LATTTAPLARTHSTVPPRFLHSEMTTLMSRSPENPSWKSSLFVEKTS
SSSSLLSLPVTTSPSVSSTLPQSIPSSSFSVTSLLTPGMVKTTDTSTEPG
TSLSPNLSGTSVEILAASEVTTDTEKIHPSSSMAVTNVGTTSSGHELY
SSVSIHSEPSKATYPVGTPSSMAETSISTSMPANFETTGFEAEPFSHL
TSGFRKTNMSLDTSSVTPTNTPSSPGSTHLLQSSKTDFTSSAKTSSPD
WPPASQYTEIPVDIITPFNASPSITESTGITSFPESRFTMSVTESTHHLS |

TABLE 6-continued

Table of Sequences

| SEQ ID NO | Description | Sequence |
|---|---|---|

```
TDLLPSAETISTGTVMPSLSEAMTSFATTGVPRAISGSGSPFSRTESG
PGDATLSTIAESLPSSTPVPFSSSTFTTTDSSTIPALHEITSSSATPYRV
DTSLGTESSTTEGRLVMVSTLDTSSQPGRTSSSPILDTRMTESVELG
TVTSAYQVPSLSTRLTRTDGIMEHITKIPNEAAHRGTIRPVKGPQTST
SPASPKGLHTGGTKRMETTTTALKTTTTALKTTSRATLTTSVYTPTL
GTLTPLNASMQMASTIPTEMMITTPYVFPDVPETTSSLATSLGAETS
TALPRTTPSVFNRESETTASLVSRSGAERSPVIQTLDVSSSEPDTTAS
WVIHPAETIPTVSKTTPNFFHSELDTVSSTATSHGADVSSAIPTNISPS
ELDALTPLVTISGTDTSTTFPTLTKSPHETETRTTWLTHPAETSSTIPR
TIPNFSHHESDATPSIATSPGAETSSAIPIMTVSPGAEDLVTSQVTSSG
TDRNMTIPTLTLSPGEPKTIASLVTHPEAQTSSAIPTSTISPAVSRLVT
SMVTSLAAKTSTTNRALTNSPGEPATTVSLVTHPAQTSPTVPWTTSI
FFHSKSDTTPSMTTSHGAESSSAVPTPTVSTEVPGVVTPLVTSSRAVI
STTIPILTLSPGEPETTPSMATSHGEEASSAIPTPTVSPGVPGVVTSLV
TSSRAVTSTTIPILTFSLGEPETTPSMATSHGTEAGSAVPTVLPEVPG
MVTSLVASSRAVTSTTLPTLTLSPGEPETTPSMATSHGAEASSTVPT
VSPEVPGVVTSLVTSSSGVNSTSIPTLILSPGELETTPSMATSHGAEA
SSAVPTPTVSPGVSGVVTPLVTSSRAVTSTTIPILTLSSSEPETTPSMA
TSHGVEASSAVLTVSPEVPGMVTSLVTSSRAVTSTTIPTLTISSDEPE
TTTSLVTHSEAKMISAIPTLAVSPTVQGLVTSLVTSSGSETSAFSNLT
VASSQPETIDSWVAHPGTEASSVVPTLTVSTGEPFTNISLVTHPAESS
STLPRTTSRFSHSELDTMPSTVTSPEAESSSAISTTISPGIPGVLTSLVT
SSGRDISATFPTVPESPHESEATASWVTHPAVTSTTVPRTTPNYSHSE
PDTTPSIATSPGAEATSDFPTITVSPDVPDMVTSQVTSSGTDTSITIPT
LTLSSGEPETTTSFITYSETHTSSAIPTLPVSPGASKMLTSLVISSGTDS
TTTFPTLTETPYEPETTAIQLIHPAETNTMVPRTTPKFSHSKSDTTLP
VAITSPGPEASSAVSTTTISPDMSDLVTSLVPSSGTDTSTTFPTLSETP
YEPETTATWLTHPAETSTTVSGTIPNFSHRGSDTAPSMVTSPGVDTR
SGVPTTTIPPSIPGVVTSQVTSSATDTSTAIPTLTPSPGEPETTASSAT
HPGTQTGFTVPIRTVPSSEPDTMASWVTHPPQTSTPVSRTTSSFSHSS
PDATPVMATSPRTEASSAVLTTISPGAPEMVTSQITSSGAATSTTVPT
LTHSPGMPETTALLSTHPRTETSTRSVTFFPASTVFPQVSETTASLTIRPGA
ETSTALPTQTTSSLFTLLVTGTSRVDLSPTASPGVSAKTAPLSTHPGT
ETSTMIPTSTLSLGLLETTGLLATSSSAETSTSTLTLTVSPAVSGLSSA
SITTDKPQTVTSWNTETSPSVTSVGPPEFSRTVTGTTMTLIPSEMPTP
PKTSHGEGVSPTTILRTTMVEATNLATTGSSPTVAKTTTTFNTLAGS
LFTPLTTPGMSTLASESVTSRTSYNHRSWISTTSSYNRRYWTPATST
PVTSTFSPGISTSSIPSSTAATVPFMVPFTLNFTITNLQYEEDMRHPGS
RKFNATERELQGLLKPLFRNSSLEYLYSGCRLASLRPEKDSSATAV
DAICTHRPDPEDLGLDRERLYWELSNLTNGIQELGPYTLDRNSLYV
NGFTHRSSMPTTSTPGTSTVDVGTSGTPSSSPSPTTAGPLLMPFTLNF
TITNLQYEEDMRRTGSRKFNTMESVLQGLLKPLFKNTSVGPLYSGC
RLTLLRPEKDGAATGVDAICTHRLDPKSPGLNREQLYWELSKLIND
IEELGPYTLDRNSLYVNGFTHQSSVSTTSTPGTSTVDLRTSGTPSSLS
SPTIMAAGPLLVPFTLNFTITNLQYGEDMGHPGSRKFNTTERVLQG
LLGPIFKNTSVGPLYSGCRLTSLRSEKDGAATGVDAICIHHLDPKSP
GLNRERLYWELSQLTNGIKELGPYTLDRNSLYVNGFTHRTSVPTSS
TPGTSTVDLGTSGTPFSLPSPATAGPLLVLFTLNFTITNLKYEEDMH
RPGSRKFNTTERVLQTLLGPMFKNTSVGLLYSGCRLTLLRSEKDGA
ATGVDAICTHRLDPKSPGVDREQLYWELSQLTNGIKELGPYTLDRN
SLYVNGFTHWIPVPTSSTPGTSTVDLGSGTPSSLPSTTAGPLLVPFT
LNFTITNLKYEEDMHCPGSRKFNTTERVLQSLLGPMFKNTSVGPLY
SGCRLTLLRSEKDGAATGVDAICTHRLDPKSPGVDREQLYWELSQL
TNGIKELGPYTLDRNSLYVNGFTHQTSAPNTSTPGTSTVDLGTSGTP
SSLPSPTSAGPLLVPFTLNFTITNLQYEEDMHHPGSRKENTTERVLQ
GLLGPMFKNTSVGLLYSGCRLTLLRPEKNGAATGMDAICSHRLDP
KSPGLNREQLYWELSQLTHGIKELGPYTLDRNSLYVNGFTHRSSVA
PTSTPGTSTVDLGTSGTPSSLPSTTAVPLLVPFTLNFTITNLQYGED
MRHPGSRKFNTTERVLQGLLGPLFKNSSVGPLYSGCRLISLRSEKD
GAATGVDAICTHHLNPQSPGLDREQLYWQLSQMTNGIKELGPYTL
DRNSLYVNGFTHRSSGLTTSTPWTSTVDLGTSGTPSPVPSPTTTGPL
LVPFTLNFTITNLQYEENMGHPGSRKFNITESVLQGLLKPLFKSTSV
GPLYSGCRLTLLRPEKDGVATRVDAICTHRPDPKIPGLDRQQLYWE
LSQLTHSITELGPYTLDRDSLYVNGFTQRSSVPTTSTPGTFTVQPETS
ETPSSLPGPATGPVLLPFTLNFTITNLQYEEDMRRPGSRKENTTER
VLQGLLMPLFKNTSVSSLYSGCRLTLLRPEKDGAATRVDAVCTHRP
DPKSPGLDRERLYWKLSQLTHGITELGPYTLDRHSLYVNGFTHQSS
MTTTRTPDTSTMHLATSRTPASLSGPMTASPLLVLFTINFTITNLRYE
ENMHHPGSRKFNTTERVLQGLLRPVFKNTSVGPLYSGCRLTLLRPK
KDGAATKVDAICTYRPDPKSPGLDREQLYWELSQLTHSITELGPYT
LDRDSLYVNGFTQRSSVPTTSIPGTPTVDLGTSGTPVSKPGPSAASPL
LVLFTLNFTITNLRYEENMQHPGSRKFNTTERVLQGLLRSLFKSTSV
GPLYSGCRLTLLRPEKDGTATGVDAICTHHPDPKSPRLDREQLYWE
LSQLTHNITELGPYALDNDSLFVNGFTHRSSVSTTSTPGTPTVYLGA
```

TABLE 6-continued

Table of Sequences

| SEQ ID NO | Description | Sequence |
|---|---|---|
|  |  | SKTPASIFGPSAASHLLILFTLNFTITNLRYEENMWPGSRKENTTERV LQGLLRPLFKNTSVGPLYSGCRLTLLRPEKDGEATGVDAICTHRPD PTGPGLDREQLYLELSQLTHSITELGPYTLDRDSLYVNGFTHRSSVP TTSTGVVSEEPPFTLNFTINNLRYMADMGQPGSLKFNITDNVMQHLL SPLFQRSSLGARYTGCRVIALRSVKNGAETRVDLLCTYLQPLSGPG LPIKQVFHELSQQTHGITRLGPYSLDKDSLYLNGYNEPGPDEPPTTP KPATTFLPPLSEATTAMGYHLKTLTLNFTISNLQYSPDMGKGSATF NSTEGVLQHLLRPLFQKSSMGPFYLGCQLISLRPEKDGAATGVDTT CTYHPDPVGPGLDIQQLYWELSQLTHGVTQLGFYVLDRDSLFINGY APQNLSIRGEYQINFHIVNWNLSNPDPTSSEYITLLRDIQDKVTTLYK GSQLHDTFRFCLVTNLTMDSVLVTVKALFSSNLDPSLEQVFLDKT LNASFHWLGSTYQLVDIHVTEMESSVYQPTSSSSTQHFYLNFTITNL PYSQDKAQPGTTNYQRNKRNIEDALNQLFRNSSIKSYFSDCQVSTF RSVPNRHHTGVDSLCNFSPLARRVDRVAIYEEFLRMTRNGTQLQNF TLDRSSVLVDGYSPNRNEPLTGNSDLPFWAVILIGLAGLLGVITCLI CGVLVTTRRRKKEGEYNVQQQCPGYYQSHLDLEDLQ |
| 2 | Clone 8 VH | QVQLQQWGAGLLKPSETLSLTCAVYGGSFSGYYWSWIRQPPGKGL EWIGEINHSGSTNYNPSLKSRVTISVDTSKNQFSLKLSSVTAADTAV YYCARQSYITDSWGQGTLVTVSS |
| 3 | Clone 8 VL | DIQLTQSPSAVSASVGDRVTITCRASQDVSKWLAWYQQKPGKAPR LLISAASGLQSWVPSRFSGSGSGTEFTLSISSLQPEDFATYYCQQANS FPWTFGQGTKVEIKR |
| 4 | Clone 8 HC-CDR1 | GGSFSGYY |
| 5 | Clone 8 HC-CDR2 | INHSGST |
| 6 | Clone 8 HC-CDR3 | ARQSYITDS |
| 7 | Clone 8 LC-CDR1 | QDVSKW |
| 8 | Clone 8 LC-CDR2 | AAS |
| 9 | Clone 8 LC-CDR3 | QQANSFPWT |
| 10 | Clone 12 VH | QVQLQQWGAGLLKPSETLSLTCAVYGGSFSGYYWSWIRQPPGKGL EWIGEINHSGSTNYNPSLKSRIIMSVDTSKRQFSLKLRSATAADTAV YYCARWSPFSYKQMYDYWGQGTLVTVSS |
| 11 | Clone 12 VL | NFMLTQPHSVSESPGKTVTISCTRSRGSIASAYVQWYQQRPGSAPIT VIYEDYERPSEIPDRFSGSIDSSSNSASLTISGLKTEDEADYYCQSYD DNDHVIFGGGTKVTVLG |
| 12 | Clone 12 HC-CDR1 | GGSFSGYY |
| 13 | Clone 12 HC-CDR2 | INHSGST |
| 14 | Clone 12 HC-CDR3 | ARWSPFSYKQMYDY |
| 15 | Clone 12 LC-CDR1 | RGSIASAY |
| 16 | Clone 12 LC-CDR2 | EDY |
| 17 | Clone 12 LC-CDR3 | QSYDDNDHVI |
| 18 | Signal peptide | METDTLLLWVLLLWVPGSTG |

TABLE 6-continued

Table of Sequences

| SEQ ID NO | Description | Sequence |
|---|---|---|
| 19 | Clone 8 scFv | DIQLTQSPSAVSASVGDRVTITCRASQDVSKWLAWYQQKPGKAPR LLISAASGLQSWVPSRFSGSGSGTEFTLSISSLQPEDFATYYCQQANS FPWTFGQGTKVEIKRSRGGGGSGGGGSGGGGSLEMAQVQLQQWG AGLLKPSETLSLTCAVYGGSFSGYYWSWIRQPPGKGLEWIGEINHS GSTNYNPSLKSRVTISVDTSKNQFSLKLSSVTAADTAVYYCARQSYI TDSWGQGTLVTVSS |
| 20 | Clone 12 scFv | NFMLTQPHSVSESPGKTVTISCTRSRGSIASAYVQWYQQRPGSAPIT VIYEDYERPSEIPDRFSGSIDSSSNSASLTISGLKTEDEADYYCQSYD DNDHVIFGGGTKVTVLGSRGGGGSGGGGSGGGGSLEMAQVQLQQ WGAGLLKPSETLSLTCAVYGGSFSGYYWSWIRQPPGKGLEWIGEIN HSGSTNYNPSLKSRIIMSVDTSKRQFSLKLRSATAADTAVYYCARW SPFSYKQMYDYWGQGTLVTVSS |
| 21 | Anti-CD3 scFv | DVQLVQSGAEVKKPGASVKVSCKASGYTFTRYTMHWVRQAPGQG LEWIGYINPSRGYTNYADSVKGRFTITTDKSTSTAYMELSSLRSEDT ATYYCARYYDDHYCLDYWGQGTTVTVSSGEGTSTGSGGSGGSGG ADDIVLTQSPATLSLSPGERATLSCRASQSVSYMNWYQQKPGKAP KRWIYDTSKVASGVPARFSGSGSGTDYSLTINSLEAEDAATYYCQQ WSSNPLTFGGGTKVEIK |
| 22 | Clone 8/anti-CD3 bispecific antibody | METDTLLLWVLLLWVPGSTGDIQLTQSPSAVSASVGDRVTITCRAS QDVSKWLAWYQQKPGKAPRLLISAASGLQSWVPSRFSGSGSGTEF TLSISSLQPEDFATYYCQQANSFPWTFGQGTKVEIKRSRGGGGSGG GGSGGGGSLEMAQVQLQQWGAGLLKPSETLSLTCAVYGGSFSGY YWSWIRQPPGKGLEWIGEINHSGSTNYNPSLKSRVTISVDTSKNQFS LKLSSVTAADTAVYYCARQSYITDSWGQGTLVTVSSTSGGGGSDV QLVQSGAEVKKPGASVKVSCKASGYTFTRYTMHWVRQAPGQGLE WIGYINPSRGYTNYADSVKGRFTITTDKSTSTAYMELSSLRSEDTAT YYCARYYDDHYCLDYWGQGTTVTVSSGEGTSTGSGGSGGSGGAD DIVLTQSPATLSLSPGERATLSCRASQSVSYMNWYQQKPGKAPKR WIYDTSKVASGVPARFSGSGSGTDYSLTINSLEAEDAATYYCQQWS SNPLTFGGGTKVEIKHHHHHH |
| 23 | Clone 12/anti-CD3 bispecific antibody | METDTLLLWVLLLWVPGSTGNFMLTQPHSVSESPGKTVTISCTRSR GSIASAYVQWYQQRPGSAPITVIYEDYERPSEIPDRFSGSIDSSSNSA SLTISGLKTEDEADYYCQSYDDNDHVIFGGGTKVTVLGSRGGGGS GGGGSGGGGSLEMAQVQLQQWGAGLLKPSETLSLTCAVYGGSFS GYYWSWIRQPPGKGLEWIGEINHSGSTNYNPSLKSRIIMSVDTSKR QFSLKLRSATAADTAVYYCARWSPFSYKQMYDYWGQGTLVTVSS TSGGGGSDVQLVQSGAEVKKPGASVKVSCKASGYTFTRYTMHWV RQAPGQGLEWIGYINPSRGYTNYADSVKGRFTITTDKSTSTAYMEL SSLRSEDTATYYCARYYDDHYCLDYWGQGTTVTVSSGEGTSTGSG GSGGSGGADDIVLTQSPATLSLSPGERATLSCRASQSVSYMNWYQ QKPGKAPKRWIYDTSKVASGVPARFSGSGSGTDYSLTINSLEAEDA ATYYCQQWSSNPLTFGGGTKVEIKHHHHHH |
| 24 | MUC16c344 | WELSQLTHGVTQLGFYVLDRDSLFINGYAPQNLSIRGEYQINFHIVN QNLSNPDPTSSEYITLLRDIQDKVTTLYKGSQLHDTFRFCLVTNLTM DSVLVTVKALFSSNLDPSLVEQVFLDKTLNASFHQLGSTYQLVDIH VTEMESSVYQPTSSSSTQHFYLNFTITNLPYSQDKAQPGTTNYQRN KRNIEDALNQLFRNSSIKSYFSDCQVSTFRSVPNRHHTGVDSLCNFS PLARRVDRVAIYEEFLRMTRNGTQLQNFTLDRSSVLVDGYSPNRNE PLTGNSDLPFWAVILIGLAGLLGLITCLICGVLVTTRRRKKEGEYNV QQQCPGYYQSHLDLEDLQ |
| 25 | MUC16c114 | NFSPLARRVDRVAIYEEFLRMTRNGTQLQNFTLDRSSVLVDGYSPN RNEPLTGNSDLPFWAVILIGLAGLLGLITCLICGVLVTTRRRKKEGE YNVQQQCPGYYQSHLDLEDLQ |
| 26 | MUC16c86 | NFSPLARRVDRVAIYEEFLRMDLPFWAVILIGLAGLLGLITCLICGV LVTTRRRKKEGEYNVQQQCPGYYQSHLDLEDLQ |
| 27 | MUC16c80 | NFSPLARRVDRVAIYEEFLRMTRNGTQLQNFTLDRSSVLVDGYSPN RNEPLTGNSDLPFWAVILIGLAGLLGLITCLICGDLEDLQ |

TABLE 6-continued

Table of Sequences

| SEQ ID NO | Description | Sequence |
|---|---|---|
| 28 | IgG1 heavy chain constant region | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNTK VDKKVEPKSCDKTHTCPPCPAPELLGGPSVFLFPPKPKDTLMISRTP EVTCVVVDVSHEDPEVKFNWYVDGVEVHNAKTKPREEQYNSTYR VVSVLTVLHQDWLNGKEYKCKVSNKALPAPIEKTISKAKGQPREP QVYTLPPSREEMTKNQVSLTCLVKGFYPSDIAVEWESNGQPENNY KTTPPVLDSDGSFFLYSKLTVDKSRWQQGNVFSCSVMHEALHNHY TQKSLSLSPGK |
| 29 | IgG4 heavy chain constant region | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTK VDKRVESKYGPPCPSCPAPEFLGGPSVFLFPPKPKDTLMISRTPEVT CVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHNHYTQKSL SLSLGK |
| 30 | Light chain constant region | QPKANPTVTLFPPSSEELQANKATLVCLISDFYPGAVTVAWKADGS PVKAGVETTKPSKQSNNKYAASSYLSLTPEQWKSHRSYSCQVTHE GSTVEKTVAPTECS |
| 31 | MUC16c114 N30A | NFSPLARRVDRVAIYEEFLRMTRNGTQLQAFTLDRSSVLVDGYSPN RNEPLTGNSDLPFWAVILIGLAGLLGLITCLICGVLVTTRRRKKEGE YNVQQQCPGYYQSHLDLEDLQ |
| 32 | hMUC16 (mature) | DKTLASPTSSVVGRTTQSLGVMSSALPESTSRGMTHSEQRTSPSLSP QVNGTPSRNYPATSMVSGLSSPRTRTSSTEGNFTKEASTYTLTVETT SGPVTEKYTVPTETSTTEGDSTETPWDTRYIPVKITSPMKTFADSTA SKENAPVSMTPAETTVTDSHTPGRTNPSFGTLYSSFLDLSPKGTPNS RGETSLELILSTTGYPFSSPEPGSAGHSRISTSAPLSSSASVLDNKISET SIFSGQSLTSPLSPGVPEARASTMPNSAIPFSMTLSNAETSAERVRSTI SSLGTPSISTKQTAETILTFHAFAETMDIPSTHIAKTLASEWLGSPGT LGGTSTSALTTTSPSTTLVSEETNTHHSTSGKETEGTLNTSMTPLETS APGEESEMTATLVPTLGFTTLDSKIRSPSQVSSSHPTRELRTTGSTSG RQSSSTAAHGSSDILRATTSSTSKASSWTSESTAQQFSEPQHTQWVE TSPSMKTERPPASTSVAAPITTSVPSVVSGFTTLKTSSTKGIWLEETS ADTLIGESTAGPTTHQFAVPTGISMTGGSSTRGSQGTTHLLTRATAS SETSADLTLATNGVPVSVSPAVSKTAAGSSPPGGTKPSYTMVSSVIP ETSSLQSSAFREGTSLGLTPLNTRHPFSSPEPDSAGHTKISTSIPLLSS ASVLEDKVSATSTFSHHKATSSITTGTPEISTKTKPSSAVLSSMTLSN AATSPERVRNATSPLTHPSPSGEETAGSVLTLSTSAETTDSPNIHPTG TLTSESSESPSTLSLPSVSGVKTTFSSSTPSTHLFTSGEETEETSNPSVS QPETSVSRVRTTLASTSVPTPVFPTMDTWPTRSAQFSSSHLVSELRA TSSTSVTNSTGSALPKISHLTGTATMSQTNRDTFNDSAAPQSTTWPE TSPRFKTGLPSATTTVSTSATSLSATVMVSKFTSPATSSMEATSIREP STTILTTETTNGPGSMAVASTNIPIGKGYITEGRLDTSHLPIGTTASSE TSMDFTMAKESVSMSVSPSQSMDAAGSSTPGRTSQFVDTFSDDVY HLTSREITIPRDGTSSALTPQMTATHPPSPDPGSARSTWLGILSSSPSS PTPKVTMSSTFSTQRVTTSMIMDTVETSRWNMPNLPSTTSLTPSNIP TSGAIGKSTLVPLDTPSPATSLEASEGGLPTLSTYPESTNTPSIHLGA HASSESPSTIKLTMASVVKPGSYTPLTFPSIETHIHVSTARMAYSSGS SPEMTAPGETNTGSTWDPTTYITTTDPKDTSSAQVSTPHSVRTLRTT ENHPKTESATPAAYSGSPKISSSPNLTSPATKAWTITDTTEHSTQLH YTKLAEKSSGFETQSAPGPVSVVIPTSPTIGSSTLELTSDVPGEPLVL APSEQTTITLPMATWLSTSLTEEMASTDLDISSPSSPMSTFAIFPPMS TPSHELSKSEADTSAIRNTDSTTLDQHLGIRSLGRTGDLTTVPITPLT TTWTSVIEHSTQAQDTLSATMSPTHVTQSLKDQTSIPASASPSHLTE VYPELGTQGRSSSEATTFWKPSTDTLSREIETGPTNIQSTPPMDNTTT GSSSSGVTLGIAHLPIGTSSPAETSTNMALERRSSTATVSMAGTMGL LVTSAPGRSISQSLGRVSSVLSESTTEGVTDSSKGSSPRLNTQGNTA LSSSLEPSYAEGSQMSTSIPLTSSPTTPDVEFIGGSTFWTKEVTTVMT SDISKSSARTESSSATLMSTALGSTENTGKEKLRTASMDLPSPTPSM EVTPWISLTLSNAPNTTDSLDLSHGVHTSSAGTLATDRSLNTGVTR ASRLENGSDTSSKSLSMGNSTHTSMTYTEKSEVSSSIHPRPETSAPG AETTLTSTPGNRAISLTLPFSSIPVEEVISTGITSGPDINSAPMTHSPITP PTIVWTSTGTIEQSTQPLHAVSSEKVSVQTQSTPYVNSVAVSASPTH ENSVSSGSSTSSPYSSASLESLDSTISRRNAITSWLWDLTTSLPTTTW PSTSLSEALSSGHSGVSNPSSTTTEFPLFSAASTSAAKQRNPETETHG PQNTAASTLNTDASSVTGLSETPVGASISSEVPLPMAITSRSDVSGLT SESTANPSLGTASSAGTKLTRTISLPTSESLVSFRMNKDPWTVSIPLG SHPTTNTETSIPVNSAGPPGLSTVASDVIDTPSDGAESIPTVSFSPSPD TEVTTISHFPEKTTHSFRTISSSLTHELTSRVTPIPGDWMSSAMSTKPT |

TABLE 6-continued

Table of Sequences

| SEQ ID NO | Description | Sequence |
|---|---|---|
| | | GASPSITLGERRTITSAAPTTSPIVLTASFTETSTVSLDNETTVKTSDI
LDARKTNELPSDSSSSSDLINTSIASSTMDVTKTASISPTSISGMTASS
SPSLFSSDRPQVPTSTTETNTATSPSVSSNTYSLDGGSNVGGTPSTLP
PFTITHPVETSSALLAWSRPVRTFSTMVSTDTASGENPTSSNSVVTS
VPAPGTWTSVGSTTDLPAMGFLKTSPAGEAHSLLASTIEPATAFTPH
LSAAVVTGSSATSEASLLTTSESKAIHSSPQTPTTPTSGANWETSATP
ESLLVVTETSDTTLTSKILVTDTILFSTVSTPPSKFPSTGTLSGASFPT
LLPDTPAIPLTATEPTSSLATSFDSTPLVTIASDSLGTVPETTLTMSET
SNGDALVLKTVSNPDRSIPGITIQGVTESPLHPSSTSPSKIVAPRNTTY
EGSITVALSTLPAGTTGSLVFSQSSENSETTALVDSSAGLERASVMP
LTTGSQGMASSGGIRSGSTHSTGTKTFSSLPLTMNPGEVTAMSEITT
NRLTATQSTAPKGIPVKPTSAESGLLTPVSASSSPSKAFASLTTAPPT
WGIPQSTLTFEFSEVPSLDTKSASLPTPGQSLNTIPDSDASTASSSLSK
SPEKNPRARMMTSTKAISASSFQSTGFTETPEGSASPSMAGHEPRVP
TSGTGDPRYASESMSYPDPSKASSAMTSTSLASKLTTLFSTGQAARS
GSSSSPISLSTEKETSFLSPTASTSRKTSLFLGPSMARQPNILVHLQTS
ALTLSPTSTLNMSQEEPPELTSSQTIAEEEGTTAETQTLTFTPSETPTS
LLPVSSPTEPTARRKSSPETWASSISVPAKTSLVETTDGTLVTTIKMS
SQAAQGNSTWPAPAEETGSSPAGTSPGSPEMSTTLKIMSSKEPSISPE
IRSTVRNSPWKTPETTVPMETTVEPVTLQSTALGSGSTSISHLPTGTT
SPTKSPTENMLATERVSLSPSPPEAWTNLYSGTPGGTRQSLATMSS
VSLESPTARSITGTGQQSSPELVSKTTGMEFSMWHGSTGGTTGDTH
VSLSTSSNILEDPVTSPNSVSSLTDKSKHKTETWVSTTAIPSTVLNNK
IMAAEQQTSRSVDEAYSSTSSWSDQTSGSDITLGASPDVTNTLYITS
TAQTTSLVSLPSGDQGITSLTNPSGGKTSSASSVTSPSIGLETLRANV
SAVKSDIAPTAGHLSQTSSPAEVSILDVTTAPTPGISTTITTMGTNSIS
TTTPNPEVGMSTMDSTPATERRTTSTEHPSTWSSTAASDSWTVTDM
TSNLKVARSPGTISTMHTTSFLASSTELDSMSTPHGRITVIGTSLVTP
SSDASAVKTETSTSERTLSPSDTTASTPISTFSRVQRMSISVPDILSTS
WTPSSTEAEDVPVSMVSTDHASTKTDPNTPLSTFLFDSLSTLDWDT
GRSLSSATATTSAPQGATTPQELTLETMISPATSQLPFSIGHITSAVTP
AAMARSSGVTFSRPDPTSKKAEQTSTQLPTTTSAHPGQVPRSAATT
LDVIPHTAKTPDATFQRQGQTALTTEARATSDSWNEKEKSTPSAPW
ITEMMNSVSEDTIKEVTSSSSVLRTLNTLDINLESGTTSSPSWKSSPY
ERIAPSESTTDKEAIHPSTNTVETTGWVTSSEHASHSTIPAHSASSKL
TSPVVTTSTREQAIVSMSTTTWPESTRARTEPNSFLTIELRDVSPYM
DTSSTTQTSIISSPGSTAITKGPRTEITSSKRISSSFLAQSMRSSDSPSE
AITRLSNFPAMTESGGMILAMQTSPPGATSLSAPTLDTSATASWTGT
PLATTQRFTYSEKTTLFSKGPEDTSQPSPPSVEETSSSSSLVPIHATTS
PSNILLTSQGHSPSSTPPVTSVFLSETSGLGKTTDMSRISLEPGTSLPP
NLSSTAGEALSTYEASRDTKAIHHSADTAVTNMEATSSEYSPIPGHT
KPSKATSPLVTSHIMGDITSSTSVFGSSETTEIETVSSVNQGLQERSTS
QVASSATETSTVITHVSSGDATTHVTKTQATFSSGTSISSPHQFITST
NTFTDVSTNPSTSLIMTESSGVTITTQTGPTGAATQGPYLLDTSTMP
YLTETPLAVTPDFMQSEKTTLISKGPKDVSWTSPPSVAETSYPSSLT
PFLVTTIPPATSTLQGQHTSSPVSATSVLTSGLVKTTDMLNTSMEPV
TNSPQNLNNPSNEILATLAATTDIETIHPSINKAVINMGTASSAHVL
HSTLPVSSEPSTATSPMVPASSMGDALASISIPGSETTDIEGEPTSSLT
AGRKENSTLQEMNSTTESNIILSNVSVGAITEATKMEVPSFDATFIPT
PAQSTKFPDIFSVASSRLSNSPPMTISTHMTTTQTGSSGATSKIPLAL
DTSTLETSAGTPSVVTEGFAHSKITTAMNNDVKDVSQTNPPFQDEA
SSPSSQAPVLVTTLPSSVAFTPQWHSTSSPVSMSSVLTSSLVKTAGK
VDTSLETVTSSPQSMSNTLDDISVTSAATTDIETTHPSINTVVTNVGT
TGSAFESHSTVSAYPEPSKVTSPNVTTSTMEDTTISRSIPKSSKTTRT
ETETTSSLTPKLRETSISQEITSSTETSTVPYKELTGATTEVSRTDVTS
SSSTSFPGPDQSTVSLDISTETNTRLSTSPIMTESAEITITTQTGPHGAT
SQDTFTMDPSNTTPQAGIHSAMTHGFSQLDVTTLMSRIPQDVSWTS
PPSVDKTSSPSSFLSSPAMTTPSLISSTLPEDKLSSPMTSLLTSGLVKI
TDILRTRLEPVTSSLPNFSSTSDKILATSKDSKDTKEIFPSINTEETNV
KANNSGHESHSPALADSETPKATTQMVITTTVGDPAPSTSMPVHGS
SETTNIKREPTYFLTPRLRETSTSQESSFPTDTSFLLSKVPTGTITEVSS
TGVNSSSKISTPDHDKSTVPPDTFTGEIPRVFTSSIKTKSAEMTITTQA
SPPESASHSTLPLDTSTTLSQGGTHSTVTQGFPYSEVTTLMGMGPGN
VSWMTTPPVEETSSVSSLMSSPAMTSPSPVSSTSPQSIPSSPLPVTAL
PTSVLVTTTDVLGTTSPESVTSSPPNLSSITHERPATYKDTAHTEAA
MHHSTNTAVTNVGTSGSGHKSQSSVLADSETSKATPLMSTTSTLGD
TSVSTSTPNISQTNQIQTEPTASLSPRLRESSTSEKTSSTTETNTAFSY
VPTGAITQASRTEISSSRTSISDLDRPTIAPDISTGMITRLFTSPIMTKS
AEMTVTTQTTTPGATSQGILPWDTSTTLFQGGTHSTVSQGFPHSEIT
TLRSRTPGDVSWMTTPPVEETSSGFSLMSPSMTSPSPVSSTSPESIPSS
PLPVTALLTSVLVTTTNVLGTTSPEPVTSSPPNLSSPTQERLTTYKDT
AHTEAMHASMHTNTAVANVGTSISGHESQSSVPADSHTSKATSPM
GITFAMGDTSVSTSTPAFFETRIQTESTSSLIPGLRDTRTSEEINTVTE
TSTVLSEVPTTTTTEVSRTEVITSSRTTISGPDHSKMSPYISTETITRLS |

TABLE 6-continued

Table of Sequences

| SEQ ID NO | Description | Sequence |
|---|---|---|

TFPFVTGSTEMAITNQTGPIGTISQATLTLDTSSTASWEGTHSPVTQR
FPHSEETTTMSRSTKGVSWQSPPSVEETSSPSSPVPLPAITSHSSLYS
AVSGSSPTSALPVTSLLTSGRRKTIDMLDTHSELVTSSLPSASSFSGEI
LTSEASTNTETIHFSENTAETNMGTTNSMHKLHSSVSIHSQPSGHTP
PKVTGSMMEDAIVSTSTPGSPETKNVDRDSTSPLTPELKEDSTALV
MNSTTESNTVFSSVSLDAATEVSRAEVTYYDPTFMPASAQSTKSPDI
SPEASSSHSNSPPLTISTHKTIATQTGPSGVTSLGQLTLDTSTIATSAG
TPSARTQDFVDSETTSVMNNDLNDVLKTSPFSAEEANSLSSQAPLL
VTTSPSPVTSTLQEHSTSSLVSVTSVPTPTLAKITDMDTNLEPVTRSP
QNLRNTLATSEATTDHTMHPSINTAVANVGTTSSPNEFYFTVSPDS
DPYKATSAVVITSTSGDSIVSTSMPRSSAMKKIESETTFSLIFRLRETS
TSQKIGSSSDTSTVFDKAFTAATTEVSRTELTSSSRTSIQGTEKPTMS
PDTSTRSVTMLSTFAGLTKSEERTIATQTGPHRATSQGTLTWDTSIT
TSQAGTHSAMTHGFSQLDLSTLTSRVPEYISGTSPPSVEKTSSSSSLL
SLPAITSPSPVPTTLPESRPSSPVHLTSLPTSGLVKTTDMLASVASLPP
NLGSTSHKIPTTSEDIKDTEKMYPSTNIAVTNVGTTTSEKESYSSVPA
YSEPPKVTSPMVTSFNIRDTIVSTSMPGSSEITRIEMESTFSLAHGLK
GTSTSQDPIVSTEKSAVLHKLTTGATETSRTEVASSRRTSIPGPDHST
ESPDISTEVIPSLPISLGITESSNMTIITRTGPPLGSTSQGTFTLDTPTTS
SRAGTHSMATQEFPHSEMTTVMNKDPEILSWTIPPSIEKTSFSSSLM
PSPAMTSPPVSSTLPKTIHTTPSPMTSLLTPSLVMTTDTLGTSPEPTTS
SPPNLSSTSHEILTTDEDTTAIEAMHPSTSTAATNVETTSSGHGSQSS
VLADSEKTKATAPMDTTSTMGHTTVSTSMSVSSETTKIKRESTYSL
TPGLRETSISQNASFSTDTSIVLSEVPTGTTAEVSRTEVTSSGRTSIPG
PSQSTVLPEISTRTMTRLFASPTMTESAEMTIPTQTGPSGSTSQDTLT
LDTSTTKSQAKTHSTLTQRFPHSEMTTLMSRGPGDMSWQSSPSLEN
PSSLPSLLSLPATTSPPPISSTLPVTISSSPLPVTSLLTSSPVTTTDMLHT
SPELVTSSPPKLSHTSDERLTTGKDTTNTEAVHPSTNTAASNVEIPSS
GHESPSSALADSETSKATSPMFITSTQEDTTVAISTPHFLETSRIQKES
ISSLSPKLRETGSSVETSSAIETSAVLSEVSIGATTEISRTEVTSSSRTSI
SGSSAESTMLPEISTTRKIIKFPTSPILAESSEMTIKTQTSPPGSTSESTFT
LDTSTTPSLVITHSTMTQRLPHSEITTLVSRGAGDVPRPSSLPVEETS
PPSSQLSLSAMISPSPVSSTLPASSHSSSASVTSLLTPGQVKTTEVLD
ASAEPETSSPPSLSSTSVEILATSEVTTDTEKIHPFSNTAVTKVGTSSS
GHESPSSVLPDSETTKATSAMGTISIMGDTSVSTLTPALSNTRKIQSE
PASSLTTRLRETSTSEETSLATEANTVLSKVSTGATTEVSRTEAISFS
RTSMSGPEQSTMSQDISIGTIPRISASSVLTESAKMTITTQTGPSESTL
ESTLNLNTATTPSWVETHSIVIQGFPHPEMTTSMGRGPGGVSWPSPP
FVKETSPPSSPLSLPAVTSPHPVSTTFLAHIPPSPLPVTSLLTSGPATTT
DILGTSTEPGTSSSSSLSTTSHERLTTYKDTAHTEAVHPSTNTGGTN
VATTSSGYKSQSSVLADSSPMCTTSTMGDTSVLTSTPAFLETRRIQT
ELASSLTPGLRESSGSEGTSSSGTKMSTVLSKVPTGATTEISKEDVTSI
PGPAQSTISPDISTRTVSWFSTSPVMTESAEITMNTHTSPLGATTQGT
STLDTSSTTSLTMTHSTISQGFSHSQMSTLMRRGPEDVSWMSPPLLE
KTRPSFSLMSSPATTSPSPVSSTLPESISSSPLPVTSLLTSGLAKTTDM
LHKSSEPVTNSPANLSSTSVEILATSEVTTDTEKTHPSSNRTVTDVG
TSSSGHESTSFVLADSQTKSVTSPMVITSTMEDTSVSTSTPGFFETSR
IQTEPTSSLTLGLRKTSSSEGTSLATEMSTVLSGVPTGATAEVSRTEV
TSSSRTSISGFAQLTVSPETSTETITRLPTSSIMTESAEMMIKTQTDPP
GSTPESTHTVDISTTPNWVETHSTVTQRFSHSEMTTLVSRSPGDML
WPSQSSVEETSSASSLLSLPATTSPSPVSSTLVEDFPSASLPVTSLLNP
GLVITTDRMGISREPGTSSTSNLSSTSHERLTTLEDTVDTEDMQPST
HTAVTNVRTSISGHESQSSVLSDSETPKATSPMGTTYTMGETSVSIS
TSDFFETSRIQIEPTSSLTSGLRETSSSERISSATEGSTVLSEVPSGATT
EVSRTEVISSRGTSMSGPDQFTISPDISTEAITRLSTSPIMTESAESAITI
ETGSPGATSEGTLTLDTSTTTFWSGTHSTASPGFSHSEMTTLMSRTP
GDVPWPSLPSVEEASSVSSSLSSPAMTSTSFFSTLPESISSSPHPVTAL
LTLGPVKTTDMLRTSSEPETSSPPNLSSTSAEILATSEVTKDREKIHP
SSNTPVVNVGTVIYKHLSPSSVLADLVTTKPTSPMATTSTLGNTSVS
TSTPAFPETMMTQPTSSLTSGLREISTSQETSSATERSASLSGMPTGA
TTKVSRTEALSLGRTSTPGPAQSTISPEISTETITRISTPLTTTGSAEMT
ITPKTGHSGASSQGTFTLDTSSRASWPGTHSAATHRSPHSGMTTPM
SRGPEDVSWPSRPSVEKTSPPSSLVSLSAVTSPSPLYSTPSESSHSSPL
RVTSLFTPVMMKTTDMLDTSLEPVTTSPPSMNITSDESLATSKATM
ETEAIQLSENTAVTQMGTISARQEFYSSYPGLPEPSKVTSPVVTSSTI
KDIVSTTIPASSEITRIEMESTSTLTPTPRETSTSQEIHSATKPSTVPYK
ALTSATIEDSMTQVMSSSRGPSPDQSTMSQDISTEVITRLSTSPIKTES
TEMTITTQTGSPGATSRGTLTLDTSTTFMSGTHSTASQGFSHSQMTA
LMSRTPGDVPWLSHPSVEEASSASFSLSSPVMTSSSPVSSTLPDSIHS
SSLPVTSLLTSGLVKTTELLGTSSEPETSSPPNLSSTSAEILAITEVTTD
TEKLEMTNVVTSGYTHESPSSVLADSVTTKATSSMGITYPTGDTNV
LTSTPAFSDTSRIQTKSKLSLTPGLMETSISEETSSATEKSTVLSSVPT
GATTEVSRTEAISSSRTSIPGPAQSTMSSDTSMETITRISTPLTRKEST
DMAITPKTGPSATSQGTFTLDSSSTASWPGTHSATTQRFPQSVVTT

TABLE 6-continued

Table of Sequences

| SEQ ID NO | Description | Sequence |
|---|---|---|

PMSRGPEDVSWPSPLSVEKNSPPSSLVSSSSVTSPSPLYSTPSGSSHSS
PVPVTSLFTSIMMKATDMLDASLEPETTSAPNMNITSDESLAASKAT
TETEAIHVFENTAASHVETTSATEELYSSSPGFSEPTKVISPVVTSSSI
RDNMVSTTMPGSSGITRIEIESMSSLTPGLRETRTSQDITSSTETSTVL
YKMPSGATPEVSRTEVMPSSRTSIPGPAQSTMSLDISDEVVTRLSTS
PIMTESAEITITTQTGYSLATSQVTLPLGTSMTFLSGTHSTMSQGLSH
SEMTNLMSRGPESLSWTSPRFVETTRSSSSLTSLPLTTSLSPVSSTLL
DSSPSSPLPVTSLILPGLVKTTEVLDTSSEPKTSSSPNLSSTSVEIPATS
EIMTDTEKIHPSSNTAVAKVRTSSSVHESHSSVLADSETTITIPSMGIT
SAVDDTTVFTSNPAFSETRRIPTEPTFSLTPGFRETSTSEETTSITETSA
VLYGVPTSATTEVSMTEIMSSNRIHIPDSDQSTMSPDIITEVITRLSSS
SMMSESTQMTITTQKSSPGATAQSTLTLATTTAPLARTHSTVPPRFL
HSEMTTLMSRSPENPSWKSSLFVEKTSSSSSLLSLPVTTSPSVSSTLP
QSIPSSSFSVTSLLTPGMVKTTDTSTEPGTSLSPNLSGTSVEILAASEV
TTDTEKIHPSSSMAVTNVGTTSSGHELYSSVSIHSEPSKATYPVGTPS
SMAETSISTSMPANFETTGFEAEPFSHLTSGFRKTNMSLDTSSVTPT
NTPSSPGSTHLLQSSKTDFTSSAKTSSPDWPPASQYTEIPVDIITPFNA
SPSITESTGITSFPESRFTMSVTESTHHLSTDLLPSAETISTGTVMPSLS
EAMTSFATTGVPRAISGSGSPFSRTESGPGDATLSTIAESLPSSTPVPF
SSSTFTTTDSSTIPALHEITSSSATPYRVDTSLGTESSTTEGRLVMVST
LDTSSQPGRTSSSPILDTRMTESVELGTVTSAYQVPSLSTRLTRTDGI
MEHITKIPNEAAHRGTIRPVKGPQTSTSPASPKGLHTGGTKRMETTT
TALKTTTTALKTTSRATLTTSVYTPTLGTLTPLNASMQMASTIPTEM
MITTPYVFPDVPETTSSLATSLGAETSTALPRTTPSVFNRESETTASL
VSRSGAERSPVIQTLDVSSSEPDTTASWVIHPAETIPTVSKTTPNFFH
SELDTVSSTATSHGADVSSAIPTNISPSELDALTPLVTISGTDTSTTFP
TLTKSPHETETRTTWLTHPAETSSTIPRTIPNFSHHESDATPSIATSPG
AETSSAIPIMTVSPGAEDLVTSQVTSSGTDRNMTIPTLTLSPGEPKTI
ASLVTHPEAQTSSAIPTSTISPAVSRLVTSMVTSLAAKTSTTNRALTN
SPGEPATTVSLVTHPAQTSPTVPWTTSIFFHSKSDTTPSMTTSHGAES
SSAVPTPTVSTEVPGVVTPLVTSSSRAVISTTIPILTLSPGEPETTPSMA
TSHGEEASSAIPTPTVSPGVPGVVTSLVTSSRAVTSTTIPILTFSLGEP
ETTPSMATSHGTEAGSAVPTVLPEVPGMVTSLVASSRAVTSTTLPT
LTLSPGEPETTPSMATSHGAEASSTVPTVSPEVPGVVTSLVTSSSGV
NSTSIPTLILSPGELETTPSMATSHGAEASSAVPTPTVSPGVSGVVTP
LVTSSRAVTSTTIPILTLSSSEPETTPSMATSHGVEASSAVLTVSPEVP
GMVTSLVTSSRAVTSTTIPTLTISSDEPETTTSLVTHSEAKMISAIPTL
AVSPTVQGLVTSLVTSSGSETSAFSNLTVASSQPETIDSWVAHPGTE
ASSVVPTLTVSTGEPFTNISLVTHPAESSSTLPRTTSRFSHSELDTMPS
TVTSPEAESSSAISTTISPGIPGVLTSLVTSSGRDISATFPTVPESPHES
EATASWVTHPAVTSTTVPRTTPNYSHSEPDTTPSIATSPGAEATSDF
PTITVSPDVPDMVTSQVTSSGTDTSITIPTLTLSSGEPETTTSFITYSET
HTSSAIPTLPVSPGASKMLTSLVISSGTDSTTTFPTLTETPYEPETTAI
QLIHPAETNTMVPRTTPKFSHSKSDTTLPVAITSPGPEASSAVSTTTIS
PDMSDLVTSLVPSSGTDTSTTFPTLSETPYEPETTATWLTHPAETSTT
VSGTIPNFSHRGSDTAPSMVTSPGVDTRSGVPTTTIPPSIPGVVTSQV
TSSATDTSTAIPTLTPSPGEPETTASSATHPGTQTGFTVPIRTVPSSEP
DTMASWVTHPPQTSTPVSRTTSSFSHSSPDATPVMATSPRTEASSAV
LTTISPGAPEMVTSQITSSGAATSTTVPTLTHSPGMPETTALLSTHPR
TETSKTFPASTVFPQVSETTASLTIRPGAETSTALPTQTTSSLFTLLVT
GTSRVDLSPTASPGVSAKTAPLSTHPGTETSTMIPTSTLSLGLLETTG
LLATSSSAETSTSTLTLTVSPAVSGLSSASITTDKPQTVTSWNTETSP
SVTSVGPPEFSRTVTGTTMTLIPSEMPTPPKTSHGEGVSPTTILRTTM
VEATNLATTGSSPTVAKTTTTFNTLAGSLFTPLTTPGMSTLASESVT
SRTSYNHRSWISTTSSYNRRYWTPATSTPVTSTFSPGISTSSIPSSTAA
TVPFMVPFTLNFTITNLQYEEDMRHPGSRKFNATERELQGLLKPLF
RNSSLEYLYSGCRLASLRPEKDSSATAVDAICTHRPDPEDLGLDRER
LYWELSNLTNGIQELGPYTLDRNSLYVNGFTHRSSMPTTSTPGTST
VDVGTSGTPSSSPSPTTAGPLLMPFTLNFTITNLQYEEDMRRTGSRK
FNTMESVLQGLLKPLFKNTSVGPLYSGCRLTLLRPEKDGAATGVD
AICTHRLDPKSPGLNREQLYWELSKLINDIEELGPYTLDRNSLYVN
GFTHQSSVSTTSTPGTSTVDLRTSGTPSSLSSPTIMAAGPLLVPFTLN
FTITNLQYGEDMGHPGSRKFNTTERVLQGLLGPIFKNTSVGPLYSG
CRLTSLRSEKDGAATGVDAICIHHLDPKSPGLNRERLYWELSQLTN
GIKELGPYTLDRNSLYVNGFTHRTSVPTSSTPGTSTVDLGTSGTPFS
LPSPATAGPLLVLFTLNFTITNLKYEEDMHRPGSRKFNTTERVLQTL
LGPMFKNTSVGLLYSGCRLTLLRSEKDGAATGVDAICTHRLDPKSP
GVDREQLYWELSQLTNGIKELGPYTLDRNSLYVNGFTHWIPVPTSS
TPGTSTVDLGSGTPSSLPSPTTAGPLLVPFTLNFTITNLKYEEDMHCP
GSRKFNTTERVLQSLLGPMFKNTSVGPLYSGCRLTLLRSEKDGAAT
GVDAICTHRLDPKSPGVDREQLYWELSQLTNGIKELGPYTLDRNSL
YVNGFTHQSAPNTSTPGTSTVDLGTSGTPSSLPSPTSAGPLLVPFTL
NFTITNLQYEEDMHHPGSRKFNTTERVLQGLLGPMFKNTSVGLLYS
GCRLTLLRPEKNGAATGMDAICSHRLDPKSPGLNREQLYWELSQL

TABLE 6-continued

Table of Sequences

| SEQ ID NO | Description | Sequence |
|---|---|---|
| | | THGIKELGPYTLDRNSLYVNGFTHRSSVAPTSTPGTSTVDLGTSGTP SSLPSPTTAVPLLVPFTLNFTITNLQYGEDMRHPGSRKFNTTERVLQ GLLGPLFKNSSVGPLYSGCRLISLRSEKDGAATGVDAICTHHLNPQS PGLDREQLYWQLSQMTNGIKELGPYTLDRNSLYVNGFTHRSSGLT TSTPWTSTVDLGTSGTPSPVPSPTTTGPLLVPFTLNFTITNLQYEENM GHPGSRKFNITESVLQGLLKPLFKSTSVGPLYSGCRLTLLRPEKDGV ATRVDAICTHRPDPKIPGLDRQQLYWELSQLTHSITELGPYTLDRDS LYVNGFTQRSSVPTTSTPGTFTVQPETSETPSSLPGPTATGPVLLPFT LNFTITNLQYEEDMRRPGSRKFNTTERVLQGLLMPLFKNTSVSSLY SGCRLTLLRPEKDGAATRVDAVCTHRPDPKSPGLDRERLYWKLSQ LTHGITELGPYTLDRHSLYVNGFTHQSSMTTTRTPDTSTMHLATSR TPASLSGPMTASPLLVLFTINFTITNLRYEENMHHPGSRKENTTERV LQGLLRPVFKNTSVGPLYSGCRLTLLRPKKDGAATKVDAICTYRPD PKSPGLDREQLYWELSQLTHSITELGPYTLDRDSLYVNGFTQRSSVP TTSIPGTPTVDLGTSGTPVSKPGPSAASPLLVLFTLNFTITNLRYEEN MQHPGSRKFNTTERVLQGLLRSLFKSTSVGPLYSGCRLTLLRPEKD GTATGVDAICTHHPDPKSPRLDREQLYWELSQLTHNITELGPYALD NDSLFVNGFTHRSSVSTTSTPGTPTVYLGASKTPASIFGPSAASHLLI LFTLNFTITNLRYEENMWPGSRKFNTTERVLQGLLRPLFKNTSVGP LYSGCRLTLLRPEKDGEATGVDAICTHRPDPTGPGLDREQLYLELS QLTHSITELGPYTLDRDSLYVNGFTHRSSVPTTSTGVVSEEPFTLNFT INNLRYMADMGQPGSLKFNITDNVMQHLLSPLFQRSSLGARYTGC RVIALRSVKNGAETRVDLLCTYLQPLSGPGLPIKQVFHELSQQTHGI TRLGPYSLDKDSLYLNGYNEPGPDEPPTTPKPATTFLPPLSEATTAM GYHLKTLTLNFTISNLQYSPDMGKGSATFNSTEGVLQHLLRPLFQK SSMGPFYLGCQLISLRPEKDGAATGVDTTCTYHPDPVGPGLDIQQL YWELSQLTHGVTQLGFYVLDRDSLFINGYAPQNLSIRGEYQINFHIV NWNLSNPDPTSSEYITLLRDIQDKVTTLYKGSQLHDTFRFCLVTNLT MDSVLVTVKALFSSNLDPSLVEQVFLDKTLNASFHWLGSTYQLVDI HVTEMESSVYQPTSSSSTQHFYLNFTITNLPYSQDKAQPGTTNYQR NKRNIEDALNQLFRNSSIKSYFSDCQVSTFRSVPNRHHTGVDSLCNF SPLARRVDRVAIYEEFLRMTRNGTQLQNFTLDRSSVLVDGYSPNRN EPLTGNSDLPFWAVILIGLAGLLGVITCLICGVLVTTRRRKKEGEYN VQQQCPGYYQSHLDLEDLQ |

The present disclosure may be described in terms of the following non-limiting embodiments:

Embodiment 1

An anti-mucin 16 (MUC16) construct comprising an antibody moiety that immunospecifically recognizes a mucin 16 (MUC16) polypeptide, wherein the antibody moiety comprises: a) (i) a variable heavy (VH) chain comprising a heavy chain complementarity determining region (HC-CDR) 1, an HC-CDR2, and an HC-CDR3 of the heavy chain variable domain of SEQ ID NO: 2; and (ii) a variable light (VL) chain comprising a light chain complementarity determining region (LC-CDR) 1, an LC-CDR2, and an LC-CDR3 of the light chain variable domain of SEQ ID NO: 3; or (b) (i) a variable heavy (VH) chain comprising a heavy chain complementarity determining region (HC-CDR) 1, an HC-CDR2, and an HC-CDR3 of the heavy chain variable domain of SEQ ID NO: 10; and ii) a variable light (VL) chain comprising a light chain complementarity determining region (LC-CDR) 1, an LC-CDR2, and an LC-CDR3 of the light chain variable domain of SEQ ID NO: 11.

Embodiment 2

The anti-mucin 16 (MUC16) construct of Embodiment 1 wherein the antibody moiety comprises: (a) (i) a variable heavy (VH) chain comprising a heavy chain complementarity determining region (HC-CDR) 1 comprising the amino acid sequence of SEQ ID NO: 4; a HC-CDR2 comprising the amino acid sequence of SEQ ID NO: 5; and a HC-CDR3 comprising the amino acid sequence of SEQ ID NO: 6; and (ii) a variable light (VL) chain comprising: a light chain complementarity determining region (LC-CDR) 1 comprising the amino acid sequence of SEQ ID NO: 7; a LC-CDR2 comprising the amino acid sequence of SEQ ID NO: 8; and a LC-CDR3 comprising the amino acid sequence of SEQ ID NO: 9; or (b) (i) a variable heavy (VH) chain comprising a HC-CDR1 comprising the amino acid sequence of SEQ ID NO: 12; a HC-CDR2 comprising the amino acid sequence of SEQ ID NO: 13; and a HC-CDR3 comprising the amino acid sequence of SEQ ID NO: 14; and (ii) a variable light (VL) chain comprising: a LC-CDR1 comprising the amino acid sequence of SEQ ID NO: 15; a LC-CDR2 comprising the amino acid sequence of SEQ ID NO: 16; and a LC-CDR3 comprising the amino acid sequence of SEQ ID NO: 17.

Embodiment 3

The anti-MUC16 construct of Embodiment 1 or Embodiment 2, wherein the antibody moiety immunospecifically binds to the ectodomain of MUC16.

Embodiment 4

The anti-MUC16 construct of any one of Embodiments 1-3, wherein the antibody moiety is a full-length antibody, a Fab, a Fab', a F(ab')2, an Fv, or a single chain Fv (scFv).

Embodiment 5

The anti-MUC16 construct of any one of Embodiments 1-4, wherein the MUC16 is a human MUC16.

Embodiment 6 the anti-MUC16 construct of any one of Embodiments 1-5, wherein the VH chain and the VL chain are human VH chain and VL chain.

Embodiment 7

The anti-MUC16 construct of any one of Embodiments 1-6, wherein the antibody moiety immunospecifically binds to a MUC16 c114 polypeptide comprising the amino acid sequence of SEQ ID NO: 25.

Embodiment 8

The anti-MUC16 construct of any one of Embodiments 1-6, wherein the anti-MUC16 construct inhibits in vitro invasion of a tumor cell that expresses MUC16 in a Matrigel invasion assay.

Embodiment 9

The anti-MUC16 construct of Embodiment 8, wherein the tumor cell is an ovarian tumor cell.

Embodiment 10

The anti-MUC16 construct of Embodiment 8 or Embodiment 9, wherein the MUC16 is glycosylated.

Embodiment 11

The anti-MUC16 construct of Embodiment 10, wherein the MUC16 is N-glycosylated at N24 or N30 relative to SEQ ID NO: 25.

Embodiment 12

The anti-MUC16 construct of any one of Embodiments 1-11, wherein the antibody moiety is a monoclonal antibody.

Embodiment 13

The anti-MUC16 construct of any one of Embodiments 1-12, wherein the antibody moiety comprises a VH comprising the amino acid sequence of SEQ ID NO: 2.

Embodiment 14

The anti-MUC16 construct of any one of Embodiments 1-13, wherein the antibody moiety comprises a VL comprising the amino acid sequence of SEQ ID NO: 3.

Embodiment 15

The anti-MUC16 construct of any one of Embodiments 1-12, wherein the antibody moiety comprises a VH comprising the amino acid sequence of SEQ ID NO: 10.

Embodiment 16

The anti-MUC16 construct of any one of Embodiments 1-12 or 15, wherein the antibody moiety comprises a VL comprising the amino acid sequence of SEQ ID NO: 11.

Embodiment 17

The anti-MUC16 construct of any one of Embodiments 1-12, wherein the antibody moiety comprises a VH comprising the amino acid sequence of SEQ ID NO: 2 and a VL comprising the amino acid sequence of SEQ ID NO: 3.

Embodiment 18

The anti-MUC16 construct of any one of Embodiments 1-12, wherein the antibody moiety comprises a VH comprising the amino acid sequence of SEQ ID NO: 10 and a VL comprising the amino acid sequence of SEQ ID NO: 11.

Embodiment 19

The anti-MUC16 construct of any one of Embodiments 1-18, wherein the antibody moiety comprises human-derived heavy and light chain constant regions.

Embodiment 20

The anti-MUC16 construct of Embodiment 19, wherein the heavy chain constant region has an isotype selected from the group consisting of gamma 1, gamma 2, gamma 3, and gamma 4.

Embodiment 21

The anti-MUC16 construct of Embodiment 19 or 20, wherein the light chain constant region has an isotype selected from the group consisting of kappa and lambda.

Embodiment 22

The anti-MUC16 construct of any one of Embodiments 1-21, wherein the antibody moiety is an immunoglobulin comprising two identical heavy chains and two identical light chains.

Embodiment 23

The anti-MUC16 construct of Embodiment 22, wherein the immunoglobulin is an IgG.

Embodiment 24

The anti-MUC16 construct of any one of Embodiments 1-22, wherein the anti-MUC16 construct is monospecific.

Embodiment 25

The anti-MUC16 construct of any one of Embodiments 1-22, wherein the anti-MUC16 construct is multispecific.

Embodiment 26

The anti-MUC16 construct of any one of Embodiments 1-22, wherein the anti-MUC16 construct is bispecific.

Embodiment 27

The anti-MUC16 construct of any one of Embodiments 1-22, wherein the anti-MUC16 construct is a tandem scFv, a diabody (Db), a single chain diabody (scDb), a dual-affinity retargeting (DART) antibody, a F(ab')2, a dual variable domain (DVD) antibody, a knob-into-hole (KiH) antibody, a dock and lock (DNL) antibody, a chemically cross-linked antibody, a heteromultimeric antibody, or a heteroconjugate antibody.

Embodiment 28

The anti-MUC16 construct of Embodiment 27, wherein the construct is a tandem scFv comprising two scFvs linked by a peptide linker.

Embodiment 29

The anti-MUC16 construct of any one of Embodiments 25-28, wherein the antibody moiety that immunospecifically recognizes MUC16 is a first antibody moiety, and wherein the anti-MUC16 construct further comprises a second antibody moiety that immunospecifically recognizes a second antigen.

Embodiment 30

The anti-MUC16 construct of Embodiment 29, wherein the second antigen is an antigen on the surface of a T cell.

Embodiment 31

The anti-MUC16 construct of Embodiment 30, wherein the second antigen is a CD3.

Embodiment 32

The anti-MUC16 construct of Embodiment 31, wherein the second antigen is selected from the group consisting of CD3γ, CD3δ, CD3ε, and CD3ζ.

Embodiment 33

The anti-MUC16 construct of Embodiment 32, wherein the second antigen is CD3ε.

Embodiment 34

The anti-MUC16 construct of any one of Embodiments 1-19 or 24-26, wherein the anti-MUC16 construct is a chimeric antigen receptor (CAR).

Embodiment 35

The anti-MUC16 construct of Embodiment 34, wherein the CAR comprises a co-stimulatory domain.

Embodiment 36

The anti-MUC16 construct of Embodiment 34 or 35, wherein the CAR comprises a CD3 zeta (ζ) chain cytoplasmic signaling domain.

Embodiment 37

The anti-MUC16 construct of any one of Embodiments 1-36 further conjugated to a peptide agent, a detection agent, an imaging agent, a therapeutic agent, or a cytotoxic agent.

Embodiment 38

A polypeptide comprising an amino acid sequence of one or more of SEQ ID NOs: 2-17 or an amino acid of the anti-MUC16 construct of any one of Embodiments 1-37.

Embodiment 39

A polynucleotide comprising a nucleic acid sequence encoding one or more polypeptides of Embodiment 38.

Embodiment 40

A vector comprising the polynucleotide of Embodiment 39 operably linked to a promoter.

Embodiment 41

A cell comprising the anti-MUC16 construct of any one of Embodiments 1-37, the polypeptide of Embodiment 38, the polynucleotide of Embodiment 39, or the vector of Embodiment 40.

Embodiment 42

The cell of Embodiment 41, wherein the cell is a mammalian cell.

Embodiment 43

The cell of Embodiment 42, wherein the cell is an immune cell.

Embodiment 44

The cell of Embodiment 43, wherein the cell is a lymphocyte.

Embodiment 45

The cell of Embodiment 44, wherein the cell is a T cell or a B cell.

Embodiment 46

A pharmaceutical composition comprising: a therapeutically effective amount of the anti-MUC16 construct of any one of Embodiments 1-37, the polynucleotide of Embodiment 39, the vector of Embodiment 40, or the cell of any one of Embodiments 41-45; and a pharmaceutically acceptable carrier.

Embodiment 47

A method of treating a MUC16-associated disease or disorder in a patient in need thereof, comprising administering to said patient the pharmaceutical composition of Embodiment 46.

Embodiment 48

The method of Embodiment 47, wherein said MUC16-associated disease or disorder is a cancer.

Embodiment 49

The method of Embodiment 47, wherein said cancer is a cancer of the ovary, lung, pancreas, breast, uterine, fallopian tube, or primary peritoneum.

Embodiment 50

The method of Embodiment 47 or 48, wherein said cancer is a metastatic cancer.

Embodiment 51

The method of any one of Embodiments 47-49, wherein the pharmaceutical composition inhibits metastasis in the patient.

Embodiment 52

The method of any one of Embodiments 47-50, wherein said patient is a human patient.

Embodiment 53

A method of producing an effector cell, comprising genetically modifying a cell with one or more nucleic acids encoding the anti-MUC16 construct of any one of Embodiments 1-37.

Embodiment 54

A method of treatment comprising introducing one or more nucleic acids encoding the anti-MUC16 construct of any one of Embodiments 1-37 into one or more primary cells isolated from a patient and administering cells comprising the one or more nucleic acids to the patient.

Embodiment 55

The method of Embodiment 52, further comprising expanding the cells prior to administering the cells to the patient.

Embodiment 56

The method Embodiment 52 or 53, wherein the primary cells are lymphocytes.

Embodiment 57

The method of Embodiment 54, wherein the primary cells are T cells.

Embodiment 58

The method of any one of Embodiments 47-55, wherein the method further comprises administering a therapeutically effective amount of an additional therapeutic agent to the patient.

Embodiment 59

The method of any of any one of Embodiments 53-58, wherein the anti-MUC16 construct is the anti-MUC16 construct of any one of Embodiments 34-36.

Embodiment 60

A method of detecting MUC16 in a sample, comprising: (a) contacting the sample with the anti-MUC16 construct of any one of Embodiments 1-24 and 37; and (b) detecting the binding, directly or indirectly, between the anti-MUC16 construct and any MUC16 in the sample.

Embodiment 61

The method of Embodiment 60, wherein the anti-MUC16 construct is conjugated to a detectable label.

Embodiment 62

The method of Embodiment 61, wherein the detectable label is a chromogenic, enzymatic, radioisotopic, isotopic, fluorescent, toxic, chemiluminescent, nuclear magnetic resonance contrast agent.

Embodiment 63

The method of Embodiment 61 or 62, wherein the binding between the anti-MUC16 construct and any MUC16 in the sample is detected directly by detecting the detectable label.

Embodiment 64

The method of Embodiment 60, wherein the binding between the anti-MUC16 construct and any MUC16 in the sample is detected indirectly using a secondary antibody.

Embodiment 65

A method of diagnosing an individual suspected of having a MUC16-associated disease or disorder, comprising: a) administering an effective amount of the anti-MUC16 construct of any one of Embodiments 1-24 and 37 to the individual; and b) determining the level of the binding, directly or indirectly, between the anti-MUC16 construct and any MUC16 in the individual, wherein a level of the binding above a threshold level indicates that the individual has the MUC16-associated disease or disorder.

Embodiment 66

A method of diagnosing an individual suspected of having a MUC16-associated disease or disorder, comprising: a) contacting a sample comprising cells derived from the individual with the anti-MUC16 construct of any one of Embodiments 1-24 and 37; and b) determining the number of cells in the sample bound to the anti-MUC16 construct, wherein a value for the number of cells bound to the anti-MUC16 construct above a threshold level indicates that the individual has the MUC16-associated disease or disorder.

Embodiment 67

Use of the anti-MUC16 construct of any one of Embodiments 1-37, the polynucleotide of Embodiment 39, the vector of Embodiment 40, or the cell of any one of Embodiments 41-45 for the treatment of a disease or disorder associated with positive MUC16 expression.

Embodiment 68

Use of the anti-MUC16 construct of any one of Embodiments 1-37, the polynucleotide of Embodiment 39, the vector of Embodiment 40, or the cell of any one of Embodiments 41-45 in the manufacture of a medicament for the treatment of a disease or disorder associated with positive MUC16 expression.

Embodiment 69

Use of the anti-MUC16 construct of any one of Embodiments 1-37, the polynucleotide of Embodiment 39, the vector of Embodiment 40, or the cell of any one of Embodiments 41-45 for the diagnosis of a disease or disorder associated with positive MUC16 expression.

Embodiment 70

The use of any one of Embodiments 62-64, wherein the disease or disorder associated with positive MUC16 expression is a cancer.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

What is claimed is:

1. An anti-mucin 16 (MUC16) construct comprising an antibody moiety that immunospecifically recognizes a mucin 16 (MUC16) polypeptide, wherein the antibody moiety comprises:

(a) (i) a variable heavy (VH) chain comprising a heavy chain complementarity determining region (HC-CDR) 1, a HC-CDR2, and a HC-CDR3 of the heavy chain variable domain of SEQ ID NO: 2; and (ii) a variable light (VL) chain comprising a light chain complementarity determining region (LC-CDR) 1, a LC-CDR2, and a LC-CDR3 of the light chain variable domain of SEQ ID NO: 3;

or (b) (i) a variable heavy (VH) chain comprising a heavy chain complementarity determining region (HC-CDR) 1, a HC-CDR2, and a HC-CDR3 of the heavy chain variable domain of SEQ ID NO: 10; and (ii) a variable light (VL) chain comprising a light chain complementarity determining region (LC-CDR) 1, a LC-CDR2, and a LC-CDR3 of the light chain variable domain of SEQ ID NO: 11, optionally wherein the antibody moiety immunospecifically binds to the ectodomain of MUC16; or comprises human-derived heavy and light chain constant regions; or is an immunoglobulin comprising two identical heavy chains and two identical light chains, optionally wherein the immunoglobulin is an IgG, or is a full-length antibody, a monoclonal antibody, a Fab, a Fab', a F(ab')2, an Fv, or a single chain Fv (scFv).

2. The anti-MUC16 construct of claim 1, wherein the antibody moiety comprises:
(a) (i) a variable heavy (VH) chain comprising a heavy chain complementarity determining region (HC-CDR) 1 comprising the amino acid sequence of SEQ ID NO: 4; a HC-CDR2 comprising the amino acid sequence of SEQ ID NO: 5; and a HC-CDR3 comprising the amino acid sequence of SEQ ID NO: 6; and
(ii) a variable light (VL) chain comprising: a light chain complementarity determining region (LC-CDR) 1 comprising the amino acid sequence of SEQ ID NO: 7; a LC-CDR2 comprising the amino acid sequence of SEQ ID NO: 8; and a LC-CDR3 comprising the amino acid sequence of SEQ ID NO: 9;
or
(b) (i) a variable heavy (VH) chain comprising a HC-CDR1 comprising the amino acid sequence of SEQ ID NO: 12; a HC-CDR2 comprising the amino acid sequence of SEQ ID NO: 13; and a HC-CDR3 comprising the amino acid sequence of SEQ ID NO: 14; and
(ii) a variable light (VL) chain comprising: a LC-CDR1 comprising the amino acid sequence of SEQ ID NO: 15; a LC-CDR2 comprising the amino acid sequence of SEQ ID NO: 16; and a LC-CDR3 comprising the amino acid sequence of SEQ ID NO: 17.

3. The anti-MUC16 construct of claim 1, wherein the VH chain is a human VH chain and/or the VL chain is a human VL chain.

4. The anti-MUC16 construct of claim 1, wherein the antibody moiety comprises: (a) a VH comprising the amino acid sequence of SEQ ID NO: 2 and/or a VL comprising the amino acid sequence of SEQ ID NO: 3; or (b) a VH comprising the amino acid sequence of SEQ ID NO: 10 and/or a VL comprising the amino acid sequence of SEQ ID NO: 11.

5. The anti-MUC16 construct of claim 1, wherein the anti-MUC16 construct is monospecific, bispecific or multispecific.

6. The anti-MUC16 construct of claim 1, wherein the anti-MUC16 construct is a tandem scFv, a diabody (Db), a single chain diabody (scDb), a dual-affinity retargeting (DART) antibody, a F(ab')2, a dual variable domain (DVD) antibody, a knob-into-hole (KiH) antibody, a dock and lock (DNL) antibody, a chemically cross-linked antibody, a heteromultimeric antibody, a chimeric antigen receptor (CAR) or a heteroconjugate antibody.

7. The anti-MUC16 construct of claim 5, wherein the antibody moiety that immunospecifically recognizes MUC16 is a first antibody moiety, and wherein the anti-MUC16 construct further comprises a second antibody moiety that immunospecifically recognizes a second antigen, optionally wherein the second antigen is a CD3 antigen.

8. The anti-MUC16 construct of claim 1 further conjugated to a peptide agent, a detection agent, an imaging agent, a therapeutic agent, or a cytotoxic agent.

9. A polypeptide of the anti-MUC16 construct of claim 1 having an amino acid sequence of one or more of SEQ ID NOs: 2-17.

10. A polynucleotide or cell comprising a nucleic acid having a sequence encoding the polypeptide of claim 9.

11. A vector or cell comprising the polynucleotide of claim 10 operably linked to a promoter.

12. An isolated cell comprising the vector of claim 11.

13. A pharmaceutical composition comprising: a therapeutically effective amount of the anti-MUC16 construct of claim 1, or a polypeptide, a polynucleotide, or vector comprising the anti-MUC16 construct; and a pharmaceutically acceptable carrier.

14. A method of treating a MUC16-positive cancer in a patient in need thereof, comprising administering to said patient the pharmaceutical composition of claim 13.

15. The method of claim 14, wherein the MUC16-positive cancer is a cancer of the ovary, lung, pancreas, breast, uterine, fallopian tube, or primary peritoneum.

\* \* \* \* \*